United States Patent
Sonntag et al.

(10) Patent No.: US 10,344,057 B2
(45) Date of Patent: Jul. 9, 2019

(54) ASSEMBLY ACTIVATING PROTEIN (AAP) AND ITS USE FOR THE MANUFACTURE OF PARVOVIRUS PARTICLES ESSENTIALLY CONSISTING OF VP3

(71) Applicants: Deutsches Krebsforschungszentrum, Heidelberg (DE); Medigene AG, Planegg/Martinsried (DE)

(72) Inventors: Florian Sonntag, Heidelberg (DE); Juergen Kleinschmidt, Bammental (DE); Markus Hoerer, Planegg (DE); Kerstin Pino Tossi, Munich (DE)

(73) Assignees: Deutsches Krebsforschungszentrum, Heidelberg (DE); Medigene AG, Planegg/Martinsried (DE)

( * ) Notice: Subject to any disclaimer, the term of this patent is extended or adjusted under 35 U.S.C. 154(b) by 0 days.

(21) Appl. No.: 15/263,072

(22) Filed: Sep. 12, 2016

(65) Prior Publication Data

US 2017/0226160 A1    Aug. 10, 2017

Related U.S. Application Data

(62) Division of application No. 13/203,442, filed as application No. PCT/EP2010/001343 on Mar. 4, 2010, now Pat. No. 9,464,119.

(Continued)

(51) Int. Cl.
*A61K 39/23* (2006.01)
*C12N 7/00* (2006.01)
(Continued)

(52) U.S. Cl.
CPC ........ *C07K 14/005* (2013.01); *A61K 39/0005* (2013.01); *C12N 7/00* (2013.01);
(Continued)

(58) Field of Classification Search
None
See application file for complete search history.

(56) References Cited

U.S. PATENT DOCUMENTS

| | | | |
|---|---|---|---|
| 4,168,062 A | 9/1979 | McCarthy et al. | |
| 6,846,665 B1 | 1/2005 | Horer et al. | |

(Continued)

FOREIGN PATENT DOCUMENTS

| | | | |
|---|---|---|---|
| JP | 2001/169777 A | 6/2001 | |
| WO | WO 01/05991 A1 | 1/2001 | |

(Continued)

OTHER PUBLICATIONS

Gall-Recule et al., "Expression of muscovy duck parvovirus capsid proteins (VP2 and VP3) in a baculovirus expression system and demonstration of immunity induced by the recombinant proteins," Journal of General Virology 77: 2159-2163 (Year: 1996).*

(Continued)

*Primary Examiner* — M Franco G Salvoza
(74) *Attorney, Agent, or Firm* — Clark & Elbing LLP; Karen L. Elbing

(57) ABSTRACT

The present invention relates to nucleic acids encoding the novel parvoviral protein "assembly activating protein" (AAP), the encoded polypeptides, methods of producing the polypeptides, antibodies specific for AAP, the use of the nucleic acids for the preparation of the polypeptides, the use of the nucleic acids or the polypeptides for the preparation of the parvoviral particle and methods of producing parvoviral particles essentially consisting of VP3 by providing in addition to the coding sequence of the parvoviral structural protein VP3 a sequence fragment Z/a nucleic acid encoding AAP in the cell and expressing VP3 and fragment Z under control of a rep-independent promoter. Furthermore, the present invention relates to parvoviral particles essentially consisting of VP3 and/oror obtainable by the above method (Continued)

Figure 1:
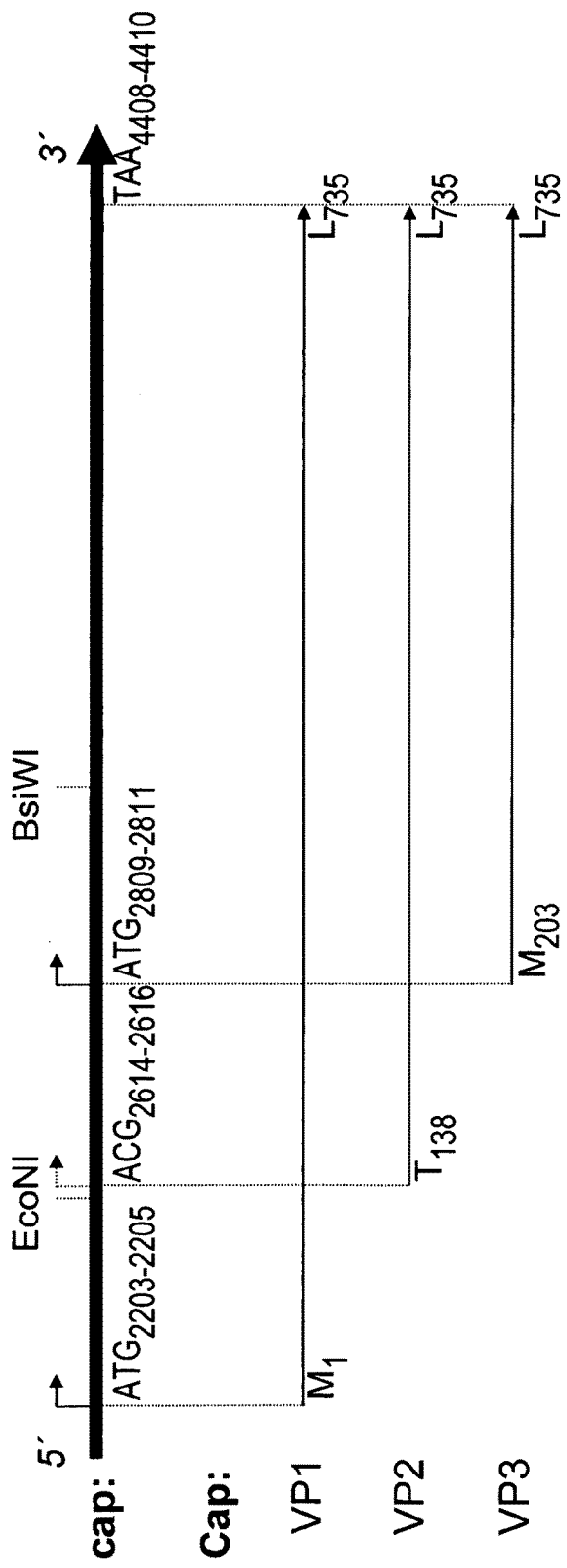

as well as expression cassettes comprising (i) a heterologous promoter and (ii) VP3 coding sequence and/oror fragment Z. The present invention further relates to a medicament, particularly a vaccine, comprising the parvoviral particles or expression cassettes and their use.

8 Claims, 45 Drawing Sheets

Specification includes a Sequence Listing.

Related U.S. Application Data

(60) Provisional application No. 61/306,205, filed on Feb. 19, 2010, provisional application No. 61/157,436, filed on Mar. 4, 2009.

(51) Int. Cl.
C07K 14/005 (2006.01)
A61K 39/00 (2006.01)

(52) U.S. Cl.
CPC .............. A61K 2039/5256 (2013.01); A61K 2039/5258 (2013.01); C12N 2750/14122 (2013.01); C12N 2750/14123 (2013.01); C12N 2750/14143 (2013.01)

(56) References Cited

U.S. PATENT DOCUMENTS

| | | | |
|---|---|---|---|
| 2002/0052040 A1 | 5/2002 | Hunt | |
| 2004/0053410 A1 | 3/2004 | Horer et al. | |
| 2004/0101514 A1 | 5/2004 | Liu et al. | |
| 2005/0287122 A1 | 12/2005 | Bartlett et al. | |
| 2006/0093589 A1* | 5/2006 | Warrington | C12N 15/86 424/93.21 |

FOREIGN PATENT DOCUMENTS

| | | |
|---|---|---|
| WO | WO-01/05991 A1 | 1/2001 |
| WO | WO-02/053703 A2 | 7/2002 |
| WO | WO-04/000220 A2 | 12/2003 |
| WO | WO-2004/027019 A2 | 4/2004 |
| WO | WO-2008/145400 A2 | 12/2008 |
| WO | WO-2008/145401 A2 | 12/2008 |
| WO | WO-10/099960 A2 | 9/2010 |

OTHER PUBLICATIONS

Arnold et al., "Metabolic biotinylation provides a unique platform for the purification and targeting of multiple AAV vector serotypes," Mol Ther. 14(1):97-106 (2006).
Asokan et al., "AAV does the shuffle," Nat Biotechnol. 24:158-60 (2006).
Bachmann et al., "The influence of antigen organization on B cell responsiveness," Science 262:1448-1451 (1993).
Becerra et al., "Synthesis of adeno-associated virus structural proteins requires both alternative mRNA splicing and alternative initiations from a single transcript," J. Virol. 62:2745-2754 (1988).
Becerra et al., "Direct mapping of adeno-associated virus capsid proteins B and C: a possible ACG initiation codon," Proc. Natl. Acad. Sci. USA 82:7919-7923 (1985).
Corpet, "Multiple sequence alignment with hierarchical clustering," Nucleic Acids Res. 16(22):10881-90 (1988).
Girod et al., "Genetic capsid modifications allow efficient retargeting of adeno-associated virus type 2," Nat Med. 5:1052-1056 (1999).
Grieger et al., "Surface-exposed adeno-associated virus Vp1-NLS capsid fusion protein rescues infectivity of noninfectious wild-type Vp2/Vp3 and Vp3-only capsids but not that of fivefold pore mutant virions," J. Virol. 81:7833-7843 (2007).
Grieger et al., "Adeno-associated virus as a gene therapy vector: vector development, production and clinical applications," Engin/ Biotechnol. 99:119-145 (2005).
Grifman et al., "Incorporation of tumor-targeting peptides into recombinant adeno-associated virus capsids," Mol Ther. 3(6):964-75 (2001).
Grimm, "Production methods for gene transfer vectors based on adeno-associated virus serotypes," Methods 28:146-157 (2002).
Grimm et al., "Titration of AAV-2 particles via a novel capsid ELISA: packaging of genomes can limit production of recombinant AAV-2," Gene Ther. 6:1322-1330 (1999).
Grimm et al., "Progress in adeno-associated virus type 2 vector production: promises and prospects for clinical use," Hum Gene Ther. 10:2445-2450 (1999).
Heilbronn et al., "The adeno-associated virus rep gene suppresses herpes simplex virus-induced DNA amplification," J. Virol. 64:3012-3018 (1990).
Hoque et al., "Chimeric virus-like particle formation of adeno-associated virus," Biochem Biophys Res Commun. 266:371-376 (1999).
Huttner et al., "Genetic modifications of the adeno-associated virus type 2 capsid reduce the affinity and the neutralizing effects of human serum antibodies," Gene Ther. 10:2139-2147 (2003).
King et al., "DNA helicase-mediated packaging of adeno-associated virus type 2 genomes into preformed capsids," EMBO J. 20:3282-3291 (2001).
"DNA shuffling of adeno-associated virus yields functionally diverse viral progeny," available in PMC May 18, 2009, published in final edited form as: Mol Ther. 16:1703-1709 (2008) (17 pages).
Kozak, "Pushing the limits of the scanning mechanism for initiation of translation," Gene 299:1-34 (2002).
Kronenberg et al., "Electron cryo-microscopy and image reconstruction of adeno-associated virus type 2 empty capsids," EMBO Rep. 2:997-1002 (2001).
Laughlin et al., "Cloning of infectious adeno-associated virus genomes in bacterial plasmids," Gene. 23:65-73 (1983).
"Engineering and selection of shuffled AAV genomes: a new strategy for producing targeted biological nanoparticles," available in PMC Jan. 29, 2009, published in final edited form as: Mol Ther. 16(7):1252-1260 (2008).
Maheshri et al., "Directed evolution of adeno-associated virus yields enhanced gene delivery vectors," Nat Biotechnol. 24:198-204 (2006).
Mittereder et al., "Evaluation of the concentration and bioactivity of adenovirus vectors for gene therapy," J. Virol. 70:7498-7509 (1996).
Moskalenko et al., "Epitope mapping of human anti-adeno-associated virus type 2 neutralizing antibodies: implications for gene therapy and virus structure," J. Virol. 74:1761-1766 (2000).
Nicklin et al., "Efficient and selective AAV2-mediated gene transfer directed to human vascular endothelial cells," Mol Ther. 4:174-181 (2001).
Nygren et al., "Binding proteins from alternative scaffolds," J Immunol Methods. 290:3-28 (2004).
Rabinowitz et al., "Insertional mutagenesis of AAV2 capsid and the production of recombinant virus," Virology 265:274-285 (1999).
Ried et al., "Adeno-associated virus capsids displaying immunoglobulin-binding domains permit antibody-mediated vector retargeting to specific cell surface receptors," J. Virol. 76:4559-4566 (2002).
Shi et al., "Insertional mutagenesis of the adeno-associated virus type 2 (AAV2) capsid gene and generation of AAV2 vectors targeted to alternative cell-surface receptors," Hum Gene Ther. 12:1697-1711 (2001).
Shi et al., "RGD inclusion in VP3 provides adeno-associated virus type 2 (AAV2)-based vectors with a heparan sulfate-independent cell entry mechanism," Mol Ther. 7:515-525 (2003).
Stachler et al., "Mosaic vectors comprised of modified AAV1 capsid proteins for efficient vector purification and targeting to vascular endothelial cells," Gene Ther. 13:926-931 (2006).
Szomolanyi-Tsuda et al., "Antiviral T-cell-independent type 2 antibody responses induced in vivo in the absence of T and NK cells," Virology 280:160-168 (2001).

(56) References Cited

OTHER PUBLICATIONS

Szomolanyi-Tsuda et al., "The role of CD40-CD154 interaction in antiviral T cell-independent IgG responses," *J Immunol.* 164:5877-5882 (2000).
Szomolanyi-Tsuda et al., "T-Cell-independent immunoglobulin G responses in vivo are elicited by live-virus infection but not by immunization with viral proteins or virus-like particles," *J. Virol.* 72:6665-6670 (1998).
Szomolanyi-Tsuda et al., "T-cell-independent antiviral antibody responses," *Curr Opin Immunol.* 10:431-435 (1998).
Ward et al., "Chimeric AAV Cap sequences alter gene transduction," *Virology* 386:237-248 (2009).
Wistuba et al., "Subcellular compartmentalization of adeno-associated virus type 2 assembly," *J. Virol.* 71:1341-1352 (1997).
Wistuba et al., "Intermediates of adeno-associated virus type 2 assembly: identification of soluble complexes containing Rep and Cap proteins," *J. Virol.* 69:5311-5319 (1995).
Xie et al., "The atomic structure of adeno-associated virus (AAV-2), a vector for human gene therapy," *Proc. Natl. Acad. Sci. USA* 99:10405-10410 (2002).
Xie et al., "Large-scale production, purification and crystallization of wild-type adeno-associated virus-2," *J Virol Methods.* 122:17-27 (2004).
Zinkernagel, "Uncertainties—discrepancies in immunology," *Immunol Rev.* 185:103-125 (2002).
NCBI Blast for Accession No. NC_001401. Retrieved on Feb. 17, 2012 (5 pages).
NCBI Blast for Accession No. AF043303. Retrieved on Feb. 17, 2012 (5 pages).
NCBI Blast for Accession No. AVU89790. Retrieved on Feb. 17, 2012 (3 pages).
NCBI Blast for Accession No. AF028704. Retrieved on Feb. 17, 2012 (3 pages).
NCBI Blast for Accession No. AF513851. Retrieved on Feb. 17, 2012 (3 pages).
NCBI Blast for Accession No. AF513852. Retrieved on Feb. 17, 2012 (3 pages).
NCBI Blast for Accession No. NC_002077. Retrieved on Feb. 17, 2012 (3 pages).
NCBI Blast for Accession No. AF028705. Retrieved on Feb. 17, 2012 (3 pages).
NCBI Blast for Accession No. NC_001829. Retrieved on Feb. 17, 2012 (3 pages).
NCBI Blast for Accession No. NC_006152. Retrieved on Feb. 20, 2012 (3 pages).
NCBI Blast for Accession No. NC_006260. Retrieved on Feb. 17, 2012 (3 pages).
NCBI Blast for Accession No. NC_006261. Retrieved on Feb. 17, 2012 (3 pages).
NCBI Blast for Accession No. AY530579. Retrieved on Feb. 17, 2012 (2 pages).
NCBI Blast for Accession No. AY631965. Retrieved on Feb. 17, 2012 (3 pages).
NCBI Blast for Accession No. AY631966. Retrieved on Feb. 17, 2012 (3 pages).
NCBI Blast for Accession No. DQ813647. Retrieved on Feb. 17, 2012 (3 pages).
NCBI Blast for Accession No. NC_005889. Retrieved on Feb. 17, 2012 (3 pages).
NCBI Blast for Accession No. AY186198. Retrieved on Feb. 17, 2012 (3 pages).
NCBI Blast for Accession No. AY629583. Retrieved on Feb. 17, 2012 (3 pages).
NCBI Blast for Accession No. EU285562. Retrieved on Feb. 17, 2012 (3 pages).
NCBI Blast for Accession No. AY724675. Retrieved on Feb. 17, 2012 (2 pages).
NCBI Blast for Accession No. DQ100363. Retrieved on Feb. 17, 2012 (3 pages).
NCBI Blast for Accession No. EU088102. Retrieved on Feb. 17, 2012 (3 pages).
NCBI Blast for Accession No. AY382892. Retrieved on Feb. 17, 2012 (2 pages).
NCBI Blast for Accession No. AY349010. Retrieved on Feb. 17, 2012 (3 pages).
NCBI Blast for Accession No. DQ100362. Retrieved on May 15, 2013 (3 pages).
Mathakia, "The Parvovirus Family," <http://virus.stanford.edu/parvo/parvovirus.html>, Winter 1998, retrieved on Nov. 21, 2016 (5 pages).
Muramatsu et al., "Nucleotide sequencing and generation of an infectious clone of adeno-associated virus 3," Virology. 221(1):208-17 (1996).
Vincent et al., "Analysis of recombinant adeno-associated virus packaging and requirements for rep and cap gene products," *J Virol.* 71(3):1897-905 (1997).
Hoque et al., "Nuclear transport of the major capsid protein is essential for adeno-associated virus capsid formation," J. Virol. 73: 7912-7915 (1999).
Ruffing et al., "Assembly of viruslike particles by recombinant structural proteins of adeno-associated virus type 2 in insect cells," J. Virol. 66: 6922-6930 (1992).
Ruffing et al., "Mutations in the carboxy terminus of adeno-associated virus 2 capsid proteins affect viral infectivity: lack of an RGD integrin-binding motif," J. Gen. Virol. 75: 3385-3392 (1994).
Sonntag et al., "A viral assembly factor promotes AAV2 capsid formation in the nucleolus," Proc. Natl. Acad. Sci. USA 107: 10220-10225 (2010).
Steinbach et al., "Assembly of adeno-associated virus type 2 capsids in vitro," J. Gen. Virol. 78: 1453-1462 (1997).
Warrington et al., "Adeno-associated virus type 2 VP2 capsid protein is nonessential and can tolerate large peptide insertions at its N terminus," J. Virol. 78: 6595-6609 (2004).
Wu et al., "Mutational analysis of the adeno-associated virus type 2 (AAV2) capsid gene and construction of AAV2 vectors with altered tropism," J. Virol. 74: 8635-8647 (2000).
International Preliminary Report on Patentability for PCT/EP2010/001343 dated Sep. 6, 2011.

\* cited by examiner

Fig. 2A

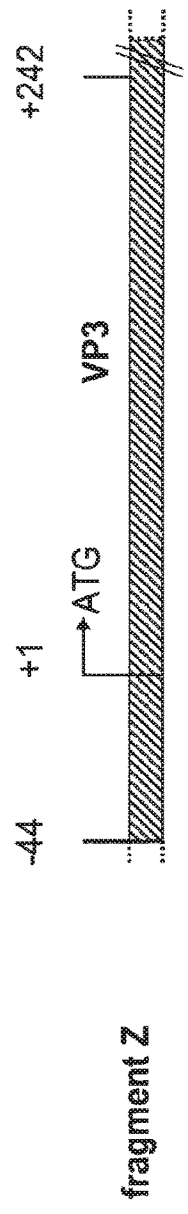

```
fragment Z                    -44    +1         +242
                                     →ATG        VP3

AAV2   1 tcggacagcc accagcagcc ccctctgtc tgggaactaa tacgatggct acaggcagtg
      61 gcgcaccaat ggcagacaat aacgagggcg ccgacggagt gggtaattcc tgggaaatt
     121 ggcattgcga ttccacatgg atgggcgaca gagtcatcac caccagcacc cgaacctggg
     181 ccctgcccac ctacaacaac cacctctaca aacaaatttc cagccaatca ggagcctcga
     241 acgacaatca ctactttggc tacagcaccc ctggggta ttttga (SEQ ID NO: 144)

AAV1   1 tcggagaacc tccagcaacc cccgctgctg tgggacctac tacaatggct tcaggcggtg
      61 gcgcaccaat ggcagacaat aacgaaggcg ccgacggagt gggtaatgcc tcaggaaatt
     121 ggcattgcga ttccacatgg ctgggcgaca gagtcatcac caccagcacc cgcacctggg
     181 ccttgcccac ctacaataac cacctctaca agcaaatctc cagtgcttca acggggcca
     241 gcaacgacaa ccactacttc ggctacagca cccctgggg gtattt (SEQ ID NO: 47)
```

Fig. 2B

```
AAV3b   1 tcggagaacc accagcagcc cccacaagtt tggatctaa tacaatggct tcaggcggtg
       61 gcgcaccaat ggcagacaat aacgagggtg ccgatggagt gggtaattcc tcaggaaatt
      121 ggcattgcga ttcccaatgg ctgggcgaca gagtcatcac caccagcacc agaacctggg
      181 ccctgcccac ttacaacaac catctctaca agcaaatctc cagccaatca ggagcttcaa
      241 acgacaacca ctactttggc tacagcaccc cttgggggta tttga (SEQ ID NO: 48)

AAV4    1 cccctgaggg atcaacttcc ggagccatgt ctgatgacag tgagatgcgt gcagcagctg
       61 gcggagctgc agtcgagggc ggacaaggtg ccgatggagt gggtaatgcc tcgggtgatt
      121 ggcattgcga ttccacctgg tctgagggcc acgtcacgac accagcacc agaacctggg
      181 tcttgcccac ctacaacaaa cacctctaca agcgactcgg agagagcctg cagtccaaca
      241 cctacaacgg atttctccacc ccctggggat actttgactt caaccg (SEQ ID NO: 49)

AAV5    1 tgcaaatccc agcccaacca gcctcaagtt tgggagctga tacaatgtct gcggaggtg
       61 gcgccaacatt gggcgacaat aaccaaggtg ccgatggagt gggcaatgcc tcgggagatt
      121 ggcattgcga ttccacgtgg atgggggaca gagtcgtcac caagtccacc cgaacctggg
      181 tgctgcccag ctacaacaac caccagtacc gagagatcaa aagcggctcc gtcgacggaa
      241 gcaacgccaa cgcctacttt ggatacagca cccctgggg gtactt (SEQ ID NO: 50)

AAV6    1 tcggagaacc tccagcaacc ccgctgctg tgggacctac tacaatggct tcaggcggtg
       61 gcgcaccaat ggcagacaat aacgaaggcg ccgacggagt gggtaatgcc tcaggaaatt
      121 ggcattgcga ttccacatgg ctgggcgaca gagtcatcac caccagcacc cgaacatggg
      181 cctgtgccac ctataacaac cacctctaca agcaaatctc cagtgcttca acggggccca
      241 gcaacgacaa ccactactc ggctacttc cccctgggg gtatt (SEQ ID NO: 51)
```

Fig. 2C

```
AAV7    1 ctagtgtggg atctggtaca gtggctgcag gcggtggcgc accaatggca gacaataacg
       61 aaggtgccga cggagtgggt aatgcctcag gaaattggca ttgcgattcc acatggctgg
      121 gcgacagagt cattaccacc agcaccacgg cctgggccct gccacctac aacaaccacc
      181 tctacaagca aatctccagt gaaactgcag gtagtaccaa cgacaacacc tacttcggct
      241 acagcacccc ctggggtat tttgacttta acagattcca ctgcca (SEQ ID NO: 52)

AAV8    1 tcggagaacc tccagcagcg ccctctggtg tgggacctaa tacaatggct gcaggcggtg
       61 gcgcaccaat ggcagacaat aacgaaggcg ccgacggagt gggtagttcc tcgggaaatt
      121 ggcattgcga ttccacatgg ctgggcgaca gagtcatcac caccagcacc cgaacctggg
      181 ccctgcccac ctacaacaac cacctctaca agcaaatctc caacgggaca tcggaggag
      241 ccaccaacga caacacctac ttcggctaca gcacccctg ggggta (SEQ ID NO: 53)

AAV10   1 tcggagaacc accagcaggc ccctctggtc tgggatctgg tacaatggct gcaggcggtg
       61 gcgctccaat ggcagacaat aacgaaggcg ccgacggagt gggtagttcc tcaggaaatt
      121 ggcattgcga ttccacatgg ctgggcgaca gagtcatcac caccagcacc cgaacctggg
      181 ccctgcccac ctacaacaac cacctctaca agcaaatctc caacgggaca tcggaggaa
      241 gcaccaacga caacacctac ttcggctaca gcaccccctg ggggta (SEQ ID NO: 54)

AAV11   1 cccctgaagg atcagatacc agcgccatgt cttcagacat tgaaatgcgt gcagcaccgg
       61 gcggaaatgc tgtcgatgcg ggacaaggtt ccgatggagt gggtaatgcc tcggtgatt
      121 ggcattgcga ttccaccctgg tctgagggca aggtcacaac aacctcgacc agaacctggg
      181 tcttgccac cactgtacc cacttgtacc tgcgtctcgg aacaacatca agcagcaaca
      241 cctacaacgg attctccacc ccctggggat attttgactt caacag (SEQ ID NO: 55)
```

Fig. 2D

```
b-AAV   1 cccagaagg accatcttcc ggagctatgt ctactgagac tgaaatgcgt gcagcagctg
       61 gcggaaatgg tggcgatgcg ggacaaggtg ccgagggagt gggtaatgcc tccggtgatt
      121 ggcattgcga ttccacttgg tcagagagcc acgtcaccac cacctcaaac cgcacctggg
      181 tcctgccgac ctacaacaac cacctgtacc cacggctcgg tgcggctcgg ctcgagcaac gccagcgaca
      241 ccttcaacgg attctccacc ccctggggat actttgactt taaccg (SEQ ID NO: 56)
```

Fig. 8A

```
=========================================================
Aligned_sequences:
1: pVP2N-gfp
2: pVP2Ncm-gfp
(from VP2 translation initation codon to BsiWI restriction site)
Identity DNA Sequence: 459/646 (71.1%)
Identity Codon Usage: 60/215 (27.9%)
Identity Protein Sequence: 215/215 (100%)
=========================================================

10         20         30         40         50
VP2N    ACGGCTCCGGGAAAAAGAGGCCGGTAGAGCACTCTCCTGTGGAGCCAGA
        :::::  :: :::::: :::: ::  :: ::::::  :: :: :: ::
VP2Ncm  ACGGCCCCTGGCAAGAAACGGCCCCGTGGAGCACAGCCCCGTGGAGCCCGA
                10         20         30         40         50
         T  A  P  G  K  K  R  P  V  E  H  S  P  V  E  P 60         70         80         90        100
VP2N    CTCCTCCTGGAACCGGAAAGGCGCAGCCTGCAGCCCGCCAAGAAAAAGAT
        :  ::::::: ::: ::::::  :: :::: ::::::: :: :: :: :
VP2Ncm  CAGCAGCAGCGGCACCGGCAAGGCCGGACAGCAGCCCGCCAGAAAGCGGC
                60         70         80         90        100
         D  S  S  G  T  G  K  A  G  Q  Q  P  A  R  K  R 110        120        130        140        150
VP2N    TGAATTTTGGTCAGACTGGAGACGCAGACTCAGTACCTGACCCCCAGCCT
        :::: ::: ::::::: :::::  :::: ::::: :: :::  :::::
VP2Ncm  TGAACTTCGGCCAGACCGGCGACGCTGATAGCGTGCCCGACCCTCAGCCC
               110        120        130        140        150
         L  N  F  G  Q  T  G  D  A  D  S  V  P  D  P  Q  P
```

Fig. 8B

```
                 160        170        180        190        200
VP2N     CTCGGACACAGCCACCAGCAGCCCCCTCTGTCTGGAACTAATACGATGGC
         :::::::::: ::::::: :::::::::::::::::: ::::::::::
VP2Ncm   CTGGGCCAGCTCCTGCTGCTCCTAGCGGGCCTCGGCACCAACACCATGGC
                 160        170        180        190        200
          L  G  Q  P  P  A  A  P  S  G  L  G  T  N  T  M 210        220        230        240        250
VP2N     TACAGGCAGTGGGCGCACCAGCAGACAATGGCAGACAATAACGAGGGCCGACGGAG
         :::::::::::::::::::::::::::::::::::::::: :::::::::
VP2Ncm   CACCGGCAGCGGAGCCCCCATGGCCGATAACAACGAAGGGCAGACGGCG
                 210        220        230        240        250
          A  T  G  S  G  A  P  M  A  D  N  N  E  G  A  D  G 260        270        280        290        300
VP2N     TGGGTAATTCCTCGGGAAATTGGCATTGCGATTCCACATGGGATGGGCGAC
         :::  :  :::::::::  ::::: :::::::: ::: :::::::::::
VP2Ncm   TGGGCAACAGTCCGGCAACTGGCACTGGACAGCACCTGGATGGGAGAGAT
                 260        270        280        290        300
          V  G  N  S  S  G  N  W  H  C  D  S  T  W  M  G  D 310        320        330        340        350
VP2N     AGAGTCATCACCACCAGCACCCGAACCTGGGCCACATGGGCCACTACAACAA
         :::::::::::::: ::::::::: ::::::::::::::::: :::: ::
VP2Ncm   CGGGTGATCACAACCTCCACCCGGACATGGACAGCCCTCTCCCTACTTATATAA
                 310        320        330        340        350
          R  V  I  T  T  S  T  R  T  W  A  L  P  T  Y  N 360        370        380        390        400
VP2N     CCACCTCTACAACAAATTCCAGCCAATCAGGAGCCTCGAACGACAATC
         :::::::  ::::::: :::::::::::::::: :::::::::::::::
VP2Ncm   TCACCTGTACAAGCAGATCAGCAGCCAGAGCGGCGCCAGCAATGATAACC
                 360        370        380        390        400
          N  H  L  Y  K  Q  I  S  S  Q  S  G  A  S  N  D  N
```

Fig. 8C

```
              410         420         430         440         450
VP2N    ACTACTTTGGCTACAGCACCCCTTGGGGTATTTTGACTTCAACAGATTC
        :::: ::::::  ::: ::  ::::::  :: :::::: ::::::  ::
VP2Ncm  ACTACTTCGGGTACTCTACACCCTGGGGCTACTTCGATTTCAATCGGTTT
              410         420         430         440         450
         H  Y  F  G  Y  S  T  P  W  G  Y  F  D  F  N  R  F
              460         470         480         490         500
VP2N    CACTGCCACTTTTCACCACGTGACTGGCAAAGACTCATCAACAACAACTG
        ::::  ::::::::: :::  :: ::::::::  ::: ::    :: ::
VP2Ncm  CACTGTCACTTCAGCCCCCAGAGACTGGCAGCGGCTGATTAATAATAATTG
              460         470         480         490         500
         H  C  H  F  S  P  R  D  W  Q  R  L  I  N  N  N
              510         520         530         540         550
VP2N    GGGATTCCGACCCAAGACTCAACTTCAAGCTCTTTAACATTCAAGTCA
        :::  ::::: :::::::  :: :::::::::   ::::: :::: ::
VP2Ncm  GGGCTTCCGGCCCAAGCTGGCCAAGCTGGCCAAGCTGTTCAATATCCAGGTGA
              510         520         530         540         550
         W  G  F  R  P  K  R  L  N  F  K  L  F  N  I  Q  V
              560         570         580         590         600
VP2N    AAGAGGTCACGCAGAATGACGGTTACTGACGACGATTGCCAATAACCTTACC
        :::   ::::::::::: : ::: :::   :::   :: ::::::::::
VP2Ncm  AGGAAGTGACCCAGAACGATGCCACCACCATCGCCAACAACCTGACC
              560         570         580         590         600
         K  E  V  T  Q  N  D  G  T  T  I  A  N  N  L  T
              610         620         630         640
VP2N    AGCACGGTTCAGGTGTTTACTGACTCGGAGTACCAGCTCCCGTACG
         :: ::::::::::::::::: ::: ::::::::::::::::: :
VP2Ncm  TCAACCGTGCAGGTGTTCACCGACAGCGAGTACCAGCTGCCGTACG
              610         620         630         640
         S  T  V  Q  V  F  T  D  S  E  Y  Q  L  P  Y
```

Figs. 8D - 8F

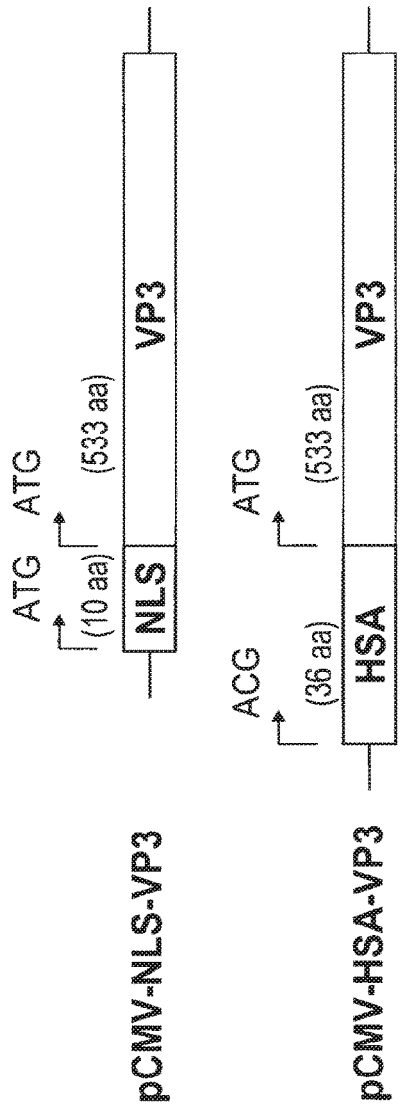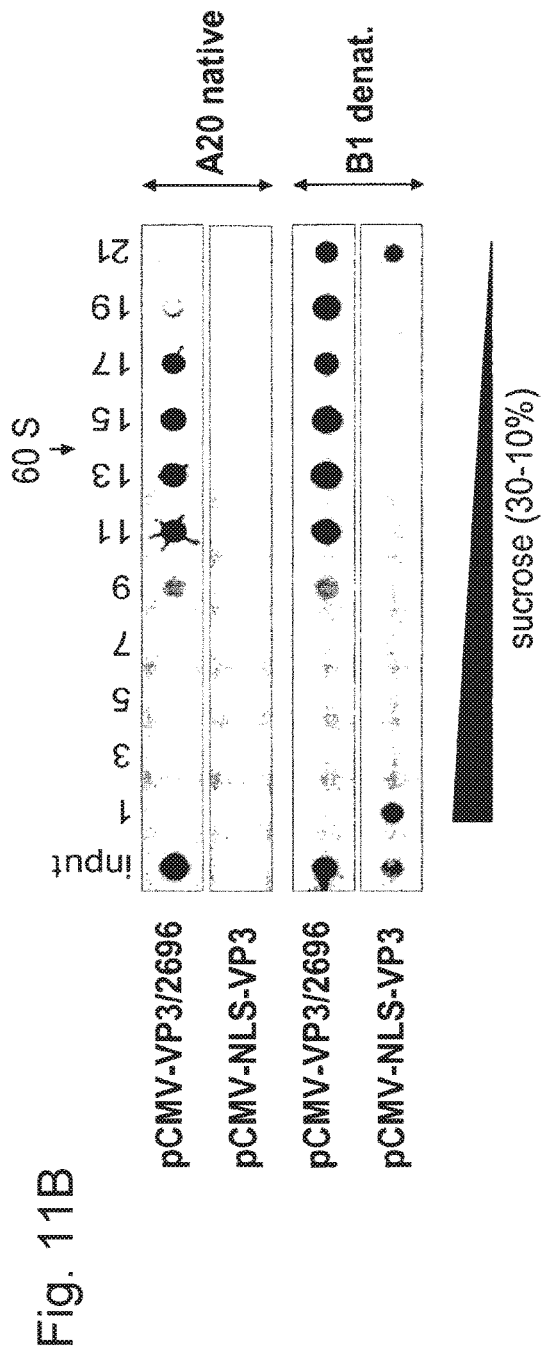
Fig. 11A
Fig. 11B

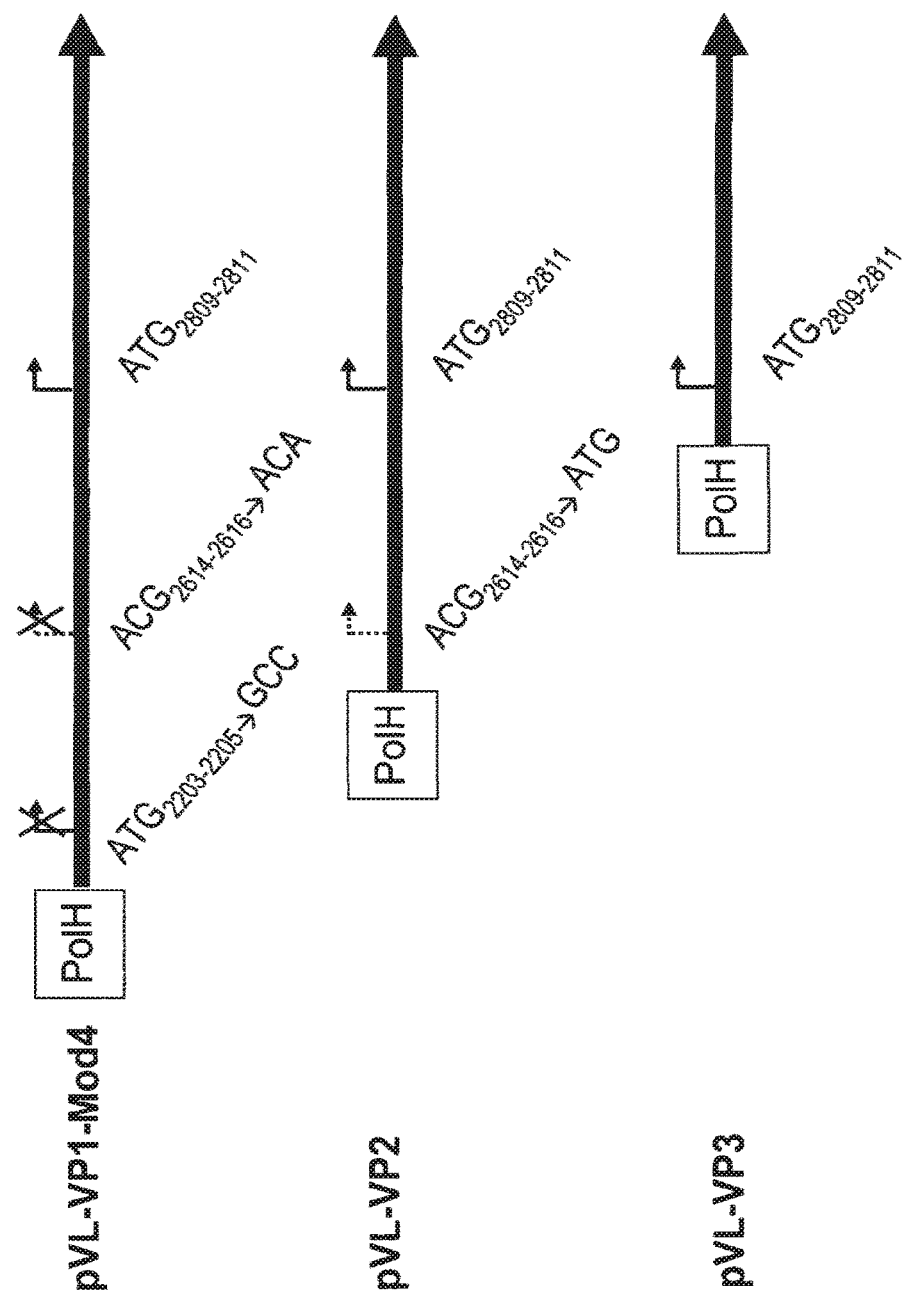

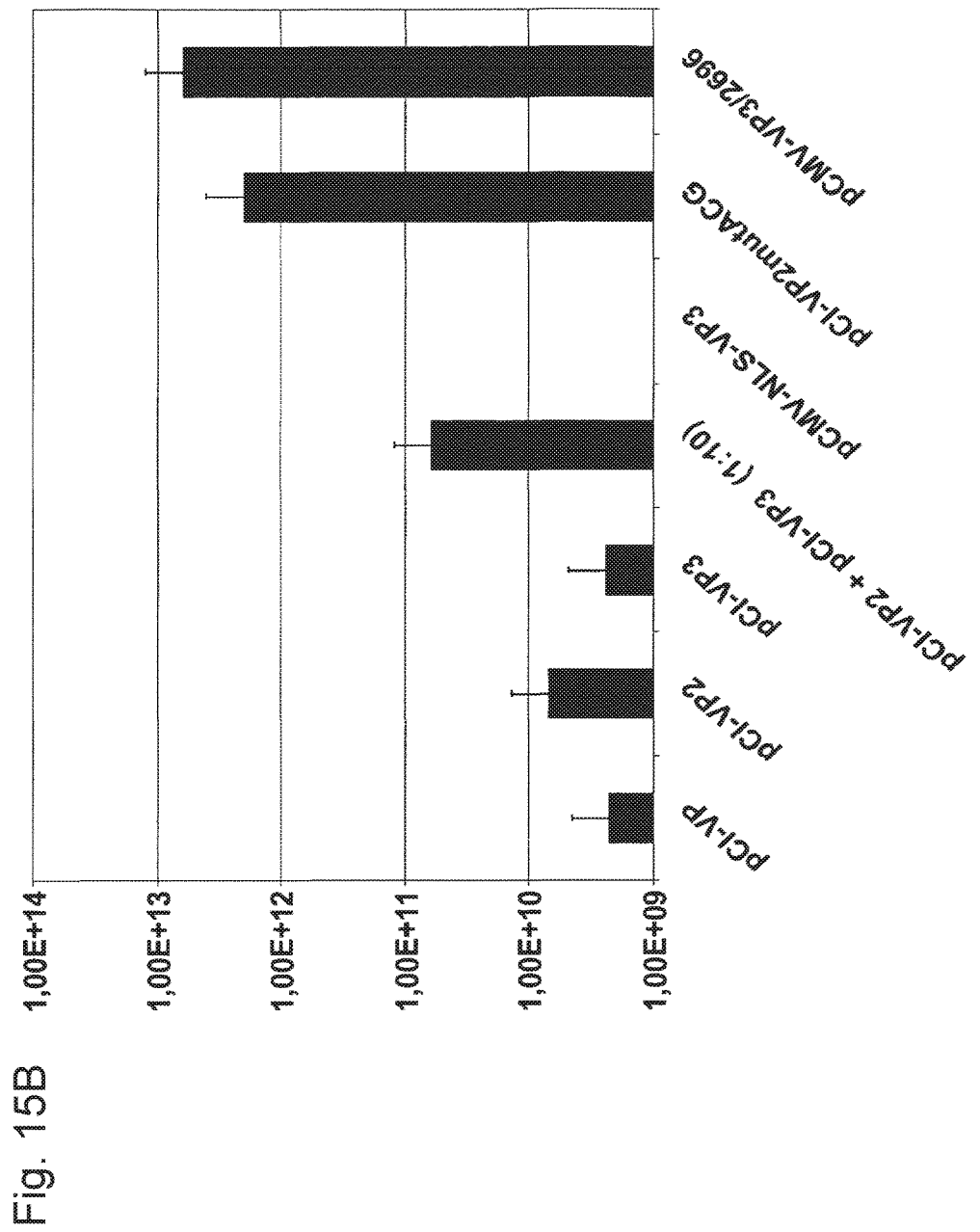

Fig. 17

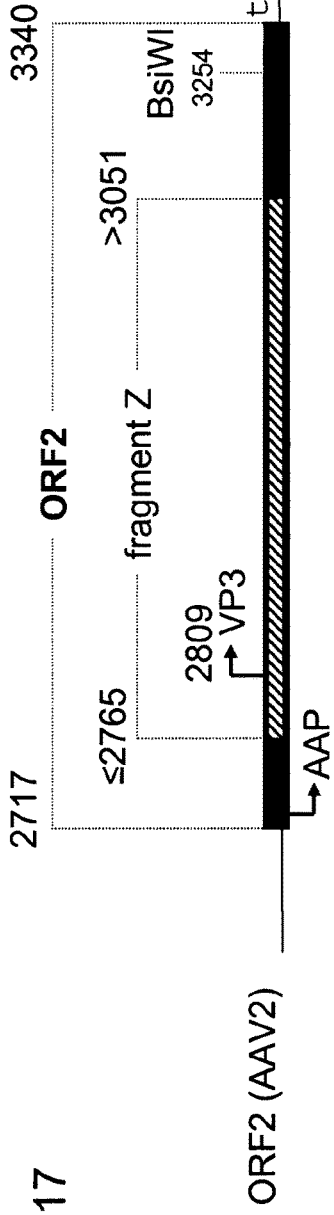

ORF2 (AAV2)

```
DNA 2717                                             attt tggtcagact ggagacgcag actcagtacc tgaccccag
    2761 cctctcggac agccaccagc caataacgag gtctgggaa ggcgccacg ctaatacgat ggctacaggc
    2821 agtggcgcac caatggcaga caataacgag atggatgggc gacagagtca tcaccaccag cacccgaacc
    2881 aattggcatt gcgattccac ccactacaa caaccactc tggctacagc acccctggg ggtatttga cttcaacaga
    2941 tgggccctgc ccactacaa caccactc tggctacagc acccctggg ggtatttga cttcaacaga
    3001 tcgaacgaca atcactactt actttcacc acgtgactgg caaagactca tcaaacaca ctggggattc
    3061 ttccactgcc actttcacc gactcaactt caagtctttt aacattcaag tcaaagaggt cacgcagaat
    3121 cgaccaaga gactcaactt caataacctt accagcacgg ttcaggtgtt tactgactcg
    3181 gacggtacga cgacgattgc caataacctt accagcacgg ttcaggtgtt tactgactcg
    3241 gagtaccagc tcccgtacgt cctcggctcg gcgcatcaag atgcctccc gccgttccca
    3301 gcagacgtct tcatggtgcc acagtatgga tacctccacc tga (SEQ ID NO: 23)

AAP    1  ILVRLETQTQ  YLTPSLSDSH  QQPPLVWELI  RWLQAVAHQW  QTITRAPTEW
      51  VIPREIGIAI  PHGWATESSP  PAPEPGPCPP  TTTTSTNKFP  ANQEPRTTIT
     101  TLATAPLGGI  LTSTDSTATF  HHVTGKDSST  TTGDSDPRDS  TSSSLTFKSK
     151  RSRRMTVRRR  LPITLPARFR  CLLTRSTSSR  TSSARRIKDA  SRRSQQTSSW
     201  CHSMDTSP  (SEQ ID NO: 1)
```

Fig. 18A

```
ORF1cm    1  TTGAGGAACC TGTTAAGACG GCCCCCTGGCA AGAAACGGCC CGTTGGAGCAC
         51  AGCCCCGTGG AGCCCGACAG CAGCAGCGGC ACCGGCAAGG CCGACACAGCA
        101  GCCCGCCAGA AAGCGGCTGA ACTTCGGCCA GACCGGCGAC GCTGATAGCG
        151  TGCCCGACCC TCAGCCCCTG GGCCAGCCTC CTGCTGCTCC TAGCGGCCTC
        201  GGCACCAACA CCATGGCCAC CGGCAGCGGA GCCCCCATGG CCGATAACAA
        251  TGAAGGGGCA GACGGCGTGG GCAACAGCTC CGGCAACTGG CACTGCGACA
        301  GCACCTGGAT GGGAGATCGG GTGATCACAA CCTCCACCCG GACATGGGCT
        351  CTCCCTACTT ATAATAATCA CCTGTACAAG CAGATCAGCA GCCAGAGCGG
        401  CGCCAGCAAT GATAACCACT ACTTCGGGTA CTCTACACCC TGGGGCTACT
        451  TCGATTTCAA TCGGTTTCAC TGTCACTTCA GCCCCAGAGA CTGGCAGCGG
        501  CTGATTAATA ATAATTGGGG CTTCCGGCCC AAGCGGCTGA ATTTCAAGCT
        551  GTTCAATATC CAGGTGAAGG AAGTGACCCA GAACGATGGC ACCACCACCA
        601  TCGCCAACAA CCTGACCTCA ACCGTGCAGG TGTTCACCGA CAGCGAGTAC
        651  CAGCTGCCGT AC (SEQ ID NO: 57)
```

Fig. 18B

```
ORF2cm
   1 TTGAGGAACC TGTTAAGACG GCTCCGGGAA AAAAGAGGCC GGTAGAGCAC
  51 TCTCCTGTGG AGCCAGACTC CTCCTCGGGA ACCGGAAAGG CGGGCCAGCA
 101 GCCTGCAAGA AAAGATTGA↓ATTTTGGTCA GA CTG GAGAC GCAGACTCAG
 151 TACCTGACCC CCAGCCTCTC GGACAGCCAC CAGCAGCCCC CTCTGGTCTG
 201 GGAACTAATA CGATGGCTGC AGGCCGTGGC CCACCAGTGG CAGACCATCA
 251 CCAGAGCCCC CACCGAGTGG GTGATCCCTC GGGAGATCGG CATTGCCATC
 301 CCTCACGGCT GGGCCACAGA GTCTAGCCCT CCAGCCCCTG AGCCTGGCCC
 351 TTGTCCCCCT ACCACCACCA CCTCCACCAA CAAGTTCCCC GCCAACCAGG
 401 AACCCCGGAC CACCATCACC ACACTGGCCA CAGCCCCTCT GGGCGGCATC
 451 CTGACCAGCA CCGACAGCAC CGCCACCTTT CACCACGTGA CCGGCAAGGA
 501 CAGCAGCACC ACCACCGGCG ACAGGACCC CAGAGACAGC ACCAGCTCCA
 551 GCCTGACCTT CAAGAGCAAG CGGAGCAGAC GGATGACCGT GCGGGGGAGA
 601 CTGCCTATCA CCCTGCCCGC CAGATTCCGG TGCCTGCTGA CCAGAAGCAC
 651 CAGCAGCCGT AC (SEQ ID NO: 58)
```

Figs. 21A-21C
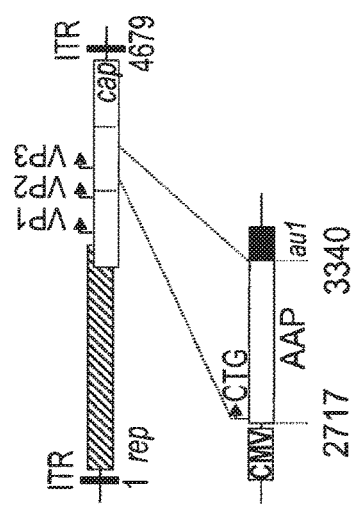
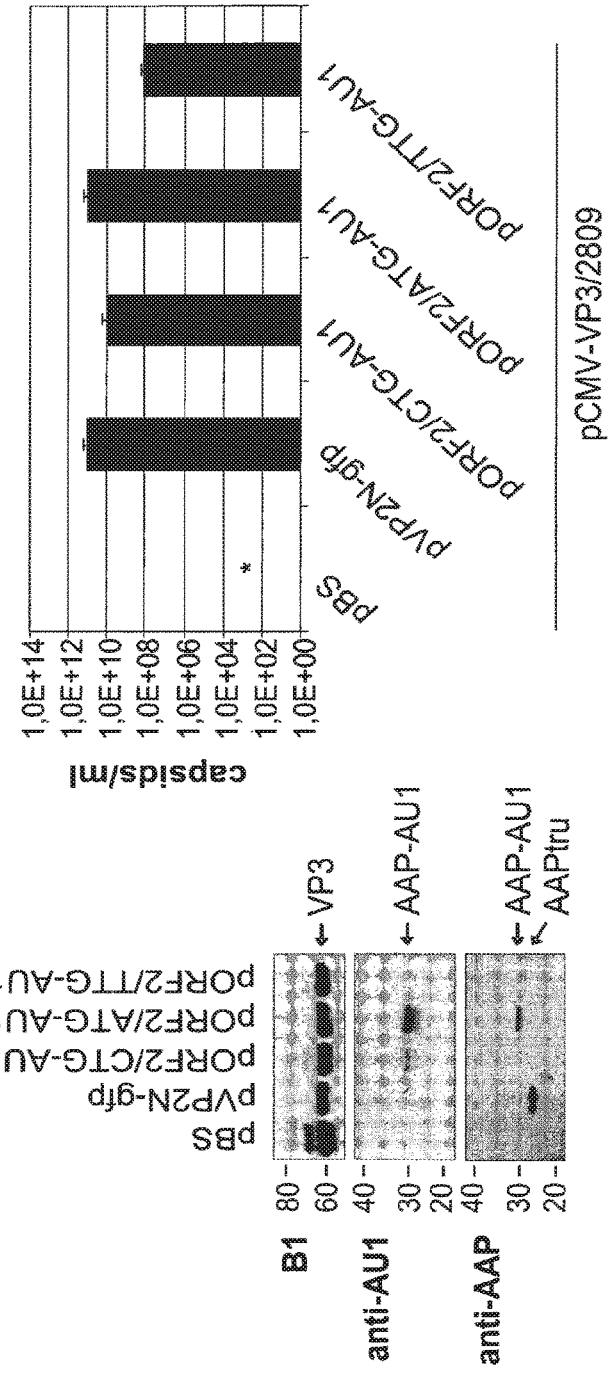

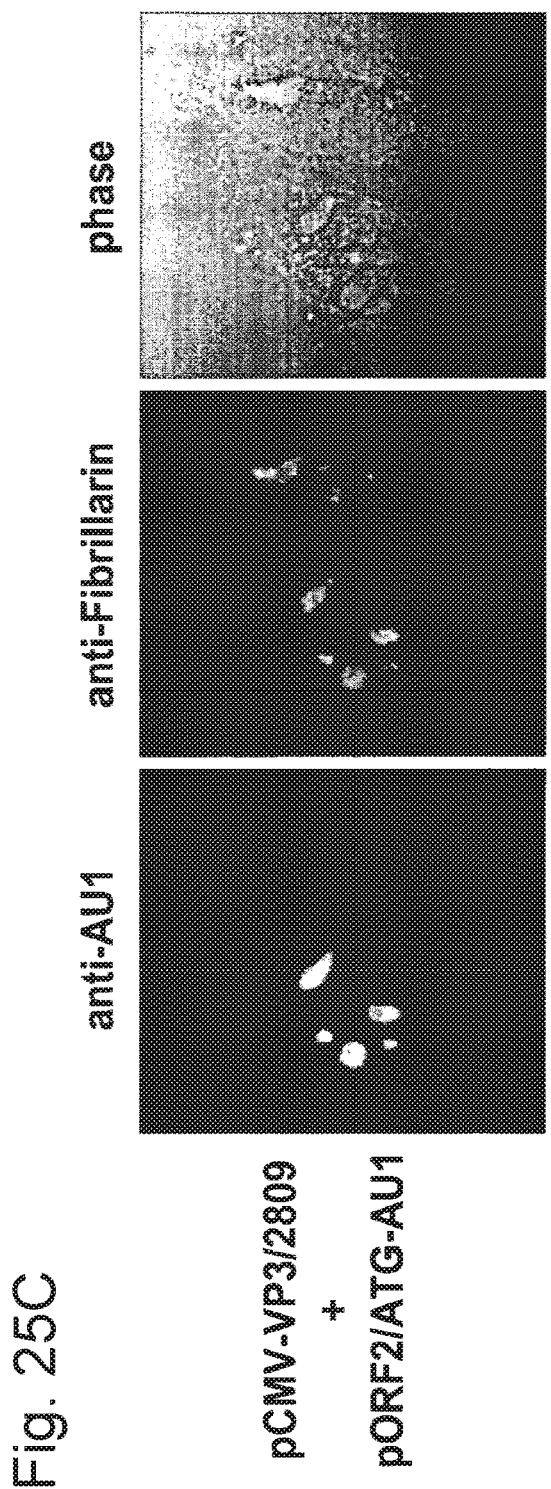

Fig. 27A

```
AAV2              -----------------------------------------------------------------
AAV10             MVLETQVLTPSLSDSHQQPP--LV-------------------------WELIRWL--------
mouse_AAV1        TLGRLASQSQSPTLNQSENHQQAP--LV-------------------------WDLVQWL-------
Avian_AAV         TRRTVSSLPLQRRPKLEALPPP--AI-------------------------WDLVRWL-------
caprine_AA        LNNPTTRPGPGRSVPNASTTFSRKRRRPPSKAKPLLKRAKTPEKEPLPTLDQAPPLV------WDHLSWL-------
Rat_AAV1          TTFQKERRLGPKRTPSLPPRQTPKLDPADPSSCKSQHNQPQVWELIQCL----------------
Goose_PV          ASRSRSWLLQSSVHTRPRKPQRTRRVSRDRIPGRRPRRGSSSPISLDLQQTYLHPHNSPSLPQGFPVWFLVRCL------
Duck_PV                                     KTEE---PPRRAPNL------------------WQHLKWQ---
b-AAV             KSLNYLKKTLLHPVIVEEKQVQ--LPPKAPNL------------------WQHLTWQ---
Snake_PV1         SRVLKSQTPRAELARKANSLPERDSTLTTNLEPETGLPQKDHLPELCLLRLKCV
conserved         TNTILKKRPNKACRYQLHLKAEKKKLHRHNLEGAQQVPILAAHL----SWL AAV2              QAVAHQWQTITRAPTEWVIPREIGIAIPHGWATESSPPAPEPGPCPPTTTTTSTNKFPANQ--EPRTTITTLATAPLGGILTSTDSTATF
AAV10             QAVALQWQTITKAPTEWVVPQEIGIAIPHGWATESSPPAPEPGPCPPTTTTTSTSKSPTGHREEAPTTTPTSATAPPGGILTSTDSTATS
mouse_AAV1        EAVARQSTTARMVPMEWAMPREIGIAIPHGWTTVSSPEPLGPGICQPTTTTSTN----DSTERPETKATSDSAPPGDTLTSTASTVIS
Avian_AAV         KEVAVQWAMQAKVPTEWAIPREIGIAIPNGWTTESLPEPLBPGSCPATTTTCT--SGSKDREEPTFTINSLDSAPPGGTLTTTDSTATS
caprine_AA        REVAAHWATITKVPMEWAMPREIGIAIPRGWGTESSPSPPAPGCCPATTTTSTERSKAAPSTEATFTP-TLDTAPPGGTLTLTASTATG
Rat_AAV1          QEERALQWTMLNKVPTEWAMPREIGIAIPNGWATEFSPDPPGPGCCPATTTTCTSRSQTPPACTASPGADTLATAPPGGTSTSIASTATS
Goose_PV          REEAELNATLQGVPMEWVMPEWVMPREIGIAIPNGWETQSSQRPPEPGSCQATTTTSTKQLPVE--PLKMQMSSMQDTVPPGGTLTSTASTATS
Duck_PV           REEAELNATLQGVPMEWVMPEWVMPQEIGIAIPNGWETQSLPRLQBPGSCQATTTTSKPSQAE--QTQTQIPNMLDTAPPGGTLISTDSTAIS
b-AAV             QQLAEMVAMRDKVPREWVMPPVIGIAIPLGQRATSPPPQPAPGSCRPTTTTCCGS-----ARATPATPSTDSPPPGDTLTLTASTATS
Snake_PV1         QEEAVRWQTITRAPREWVIPQVIGIAIPSGWETTSLQSQPELGCSPLTGIISTGLSTLTAPQVRVLMQPMQDTRLPGGTLTSIDSIATS
conserved AAV2              HHVTGKDSTTTGDSDPRDSTSSSLTFKKSRSRRMTVRRRLPITLPARFRCLITRSTSSRTSSAARRIKDASRRSQQTSSWCHSMDTSP
AAV10             HHVTGSDSSTTTGDSGQKDSASSSSTSRSRRSRRMKAPRPSPITLPARFRYLRTRNTSCRTSSAPRTRAACLRSRRMSS
mouse_AAV1        PLETGKDSSTITGDSDQRAYGSKLSLTFKLKKSRRKTQRRSSPITLPARFRYLRTRSTSSRT
Avian_AAV         PPETGNDSSTTTGASDFKKRCALDSLITSRLKKSLSKTPTTPPSPTTSPARSKSLRTRITSCRTSSDRLQAPSRRSQRISTRSRSMVTAR
caprine_AA        APETGKDSSTTTIGASDPGLSESKSSTSKSKRSRCRTPPPSPTTSPPPSKCLRTTTTNSRTSSATGPRDACRPSPRRSLRCRSTATRR
Rat_AAV1          RPETGSASSITTGASDPRDCESNSSTSRSRRSRLLIRRPRSPTTSRARSRSSQTTSTSCRTSAATPPRDACRRSPRTSSRCRSTATRR
Goose_PV          PLRTGRDLSTTIGESDPNILNSRSSMSKKSQRRIKQRPLQTISPQRFKSLRMMSINSRMSWARLRKAPCRRSRRMSMPCRSTGTAQC
Duck_PV           LQETGRDSSTTIGGLDRKHSNSRYSMCKLKKSRRKTRQRLLLTTLPLQSRYSRIMNTSCPMFWARPRRGRCHRSPQMCWPCPSTATAQC
b-AAV             RQETGKGSSTTTGDCAPKACKSASSTSKLRRSRRLTGRRPYPTTSPARSRSLRTARTSSRT
Snake_PV1         PPETGKDSSTTTQASGRKDSKSKSLITSKSKKLQHKIQRKQLPTISPAPYRSLRTRTTTYHMY
conserved
```

Fig. 27B

| | | |
|---|---|---|
| AAV2 | | (SEQ ID NO: 1) |
| AAV10 | | (SEQ ID NO: 10) |
| mouse_AAV1 | | (SEQ ID NO: 16) |
| Avian_AAV | | (SEQ ID NO: 143) |
| caprine_AA | | (SEQ ID NO: 18) |
| Rat_AAV1 | | (SEQ ID NO: 19) |
| Goose_PV | TPTRMEHGSMTVVHSTA | (SEQ ID NO: 20) |
| Duck_PV | TPTRVELDSMTEVPSIA | (SEQ ID NO: 21) |
| b-AAV | | (SEQ ID NO: 13) |
| Snake_PV1 | | (SEQ ID NO: 22) |
| conserved | | |

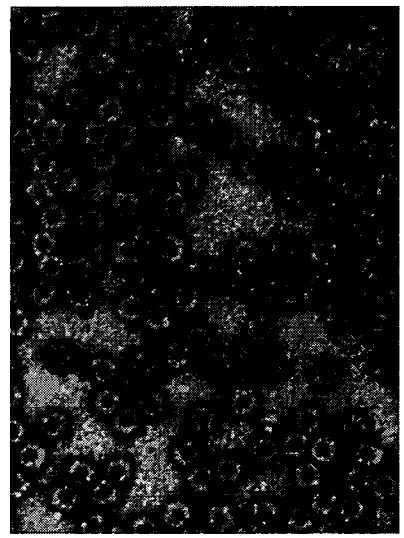
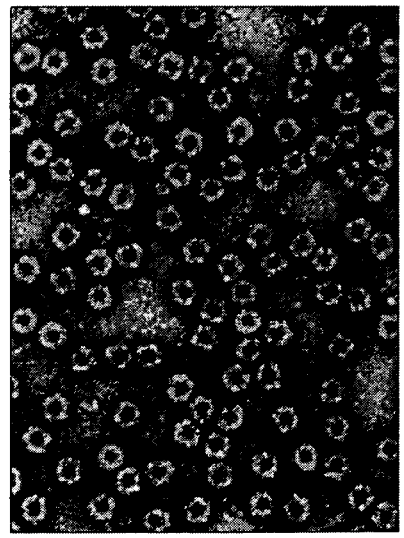
Fig. 28

SEQUENCE LISTING

<160> NUMBER OF SEQ ID NOS: 188

<210> SEQ ID NO 1
<211> LENGTH: 208

<212> TYPE: PRT
<213> ORGANISM: adeno-associated virus 2

<400> SEQUENCE: 1

```
Ile Leu Val Arg Leu Glu Thr Gln Thr Gln Tyr Leu Thr Pro Ser Leu
1               5                   10                  15

Ser Asp Ser His Gln Gln Pro Pro Leu Val Trp Glu Leu Ile Arg Trp
            20                  25                  30

Leu Gln Ala Val Ala His Gln Trp Gln Thr Ile Thr Arg Ala Pro Thr
        35                  40                  45

Glu Trp Val Ile Pro Arg Glu Ile Gly Ile Ala Ile Pro His Gly Trp
50                  55                  60

Ala Thr Glu Ser Ser Pro Pro Ala Pro Glu Pro Gly Pro Cys Pro Pro
65                  70                  75                  80

Thr Thr Thr Thr Ser Thr Asn Lys Phe Pro Ala Asn Gln Glu Pro Arg
                85                  90                  95

Thr Thr Ile Thr Thr Leu Ala Thr Ala Pro Leu Gly Gly Ile Leu Thr
            100                 105                 110

Ser Thr Asp Ser Thr Ala Thr Phe His His Val Thr Gly Lys Asp Ser
        115                 120                 125

Ser Thr Thr Thr Gly Asp Ser Asp Pro Arg Asp Ser Thr Ser Ser Ser
130                 135                 140

Leu Thr Phe Lys Ser Lys Arg Ser Arg Arg Met Thr Val Arg Arg Arg
145                 150                 155                 160

Leu Pro Ile Thr Leu Pro Ala Arg Phe Arg Cys Leu Leu Thr Arg Ser
                165                 170                 175

Thr Ser Ser Arg Thr Ser Ser Ala Arg Arg Ile Lys Asp Ala Ser Arg
            180                 185                 190

Arg Ser Gln Gln Thr Ser Ser Trp Cys His Ser Met Thr Ser Pro
        195                 200                 205
```

<210> SEQ ID NO 2
<211> LENGTH: 225
<212> TYPE: PRT
<213> ORGANISM: adeno-associated virus 1

<400> SEQUENCE: 2

```
Ser Ser Arg His Lys Ser Gln Thr Pro Pro Arg Ala Ser Ala Arg Gln
1               5                   10                  15

Ala Ser Ser Pro Leu Lys Arg Asp Ser Ile Leu Val Arg Leu Ala Thr
            20                  25                  30

Gln Ser Gln Ser Pro Ile His Asn Leu Ser Glu Asn Leu Gln Gln Pro
        35                  40                  45

Pro Leu Leu Trp Asp Leu Leu Gln Trp Leu Gln Ala Val Ala His Gln
50                  55                  60

Trp Gln Thr Ile Thr Lys Ala Pro Thr Glu Trp Val Met Pro Gln Glu
65                  70                  75                  80

Ile Gly Ile Ala Ile Pro His Gly Trp Ala Thr Glu Ser Ser Pro Pro
                85                  90                  95

Ala Pro Ala Pro Gly Pro Cys Pro Pro Thr Ile Thr Thr Ser Thr Ser
            100                 105                 110

Lys Ser Pro Val Leu Gln Arg Gly Pro Ala Thr Thr Thr Thr Thr Ser
        115                 120                 125

Ala Thr Ala Pro Pro Gly Gly Ile Leu Ile Ser Thr Asp Ser Thr Ala
130                 135                 140
```

```
Thr Phe His His Val Thr Gly Ser Asp Ser Thr Thr Ile Gly Asp
145                 150                 155                 160

Ser Gly Pro Arg Asp Ser Thr Asn Ser Ser Thr Ser Lys Ser Arg
            165                 170                 175

Arg Ser Arg Arg Met Met Ala Ser Gln Pro Ser Leu Ile Thr Leu Pro
        180                 185                 190

Ala Arg Phe Lys Ser Ser Arg Thr Arg Ser Thr Ser Phe Arg Thr Ser
        195                 200                 205

Ser Ala Leu Arg Thr Arg Ala Ser Leu Arg Ser Arg Arg Thr Cys
210                 215                 220

Ser
225

<210> SEQ ID NO 3
<211> LENGTH: 208
<212> TYPE: PRT
<213> ORGANISM: adeno-associated virus 3b

<400> SEQUENCE: 3

Ile Ser Val Arg Leu Ala Thr Gln Ser Gln Ser Gln Thr Leu Asn Leu
1               5                   10                  15

Ser Glu Asn His Gln Gln Pro Pro Gln Val Trp Asp Leu Ile Gln Trp
                20                  25                  30

Leu Gln Ala Val Ala His Gln Trp Gln Thr Ile Thr Arg Val Pro Met
            35                  40                  45

Glu Trp Val Ile Pro Gln Glu Ile Gly Ile Ala Ile Pro Asn Gly Trp
        50                  55                  60

Ala Thr Glu Ser Ser Pro Pro Ala Pro Glu Pro Gly Pro Cys Pro Leu
65                  70                  75                  80

Thr Thr Thr Ile Ser Thr Ser Lys Ser Pro Ala Asn Gln Glu Leu Gln
                85                  90                  95

Thr Thr Thr Thr Thr Leu Ala Thr Ala Pro Leu Gly Gly Ile Leu Thr
            100                 105                 110

Leu Thr Asp Ser Thr Ala Thr Ser His His Val Thr Gly Ser Asp Ser
        115                 120                 125

Leu Thr Thr Thr Gly Asp Ser Gly Pro Arg Asn Ser Ala Ser Ser Ser
130                 135                 140

Ser Thr Ser Lys Leu Lys Arg Ser Arg Arg Thr Met Ala Arg Arg Leu
145                 150                 155                 160

Leu Pro Ile Thr Leu Pro Ala Arg Phe Lys Cys Leu Arg Thr Arg Ser
                165                 170                 175

Ile Ser Ser Arg Thr Cys Ser Gly Arg Arg Thr Lys Ala Val Ser Arg
            180                 185                 190

Arg Phe Gln Arg Thr Ser Ser Trp Ser Leu Ser Met Asp Thr Ser Pro
        195                 200                 205

<210> SEQ ID NO 4
<211> LENGTH: 198
<212> TYPE: PRT
<213> ORGANISM: adeno-associated virus 4

<400> SEQUENCE: 4

Leu Asn Pro Pro Ser Ser Pro Thr Pro Pro Arg Val Ser Ala Lys Lys
1               5                   10                  15

Ala Ser Ser Arg Leu Lys Arg Ser Arg Ser Phe Ser Lys Thr Lys Leu Glu
                20                  25                  30
```

Gln Ala Thr Asp Pro Leu Arg Asp Gln Leu Pro Glu Pro Cys Leu Met
            35                  40                  45

Thr Val Arg Cys Val Gln Gln Leu Ala Glu Leu Gln Ser Arg Ala Asp
 50                  55                  60

Lys Val Pro Met Glu Trp Val Met Pro Arg Val Ile Gly Ile Ala Ile
 65                  70                  75                  80

Pro Pro Gly Leu Arg Ala Thr Ser Arg Pro Pro Ala Pro Glu Pro Gly
                85                  90                  95

Ser Cys Pro Pro Thr Thr Thr Thr Ser Thr Ser Asp Ser Glu Arg Ala
            100                 105                 110

Cys Ser Pro Thr Pro Thr Thr Asp Ser Pro Pro Gly Asp Thr Leu
            115                 120                 125

Thr Ser Thr Ala Ser Thr Ala Thr Ser His His Val Thr Gly Ser Asp
130                 135                 140

Ser Ser Thr Thr Thr Gly Ala Cys Asp Pro Lys Pro Cys Gly Ser Lys
145                 150                 155                 160

Ser Ser Thr Ser Arg Ser Arg Arg Ser Arg Arg Thr Ala Arg Gln
                165                 170                 175

Arg Trp Leu Ile Thr Leu Pro Ala Arg Phe Arg Ser Leu Arg Thr Arg
            180                 185                 190

Arg Thr Asn Cys Arg Thr
            195

<210> SEQ ID NO 5
<211> LENGTH: 226
<212> TYPE: PRT
<213> ORGANISM: adeno-associated virus 5

<400> SEQUENCE: 5

Thr Thr Thr Phe Gln Lys Glu Arg Arg Leu Gly Pro Lys Arg Thr Pro
 1               5                  10                  15

Ser Leu Pro Pro Arg Gln Thr Pro Lys Leu Asp Pro Ala Asp Pro Ser
                20                  25                  30

Ser Cys Lys Ser Gln Pro Asn Gln Pro Gln Val Trp Glu Leu Ile Gln
            35                  40                  45

Cys Leu Arg Glu Val Ala Ala His Trp Ala Thr Ile Thr Lys Val Pro
 50                  55                  60

Met Glu Trp Ala Met Pro Arg Glu Ile Gly Ile Ala Ile Pro Arg Gly
 65                  70                  75                  80

Trp Gly Thr Glu Ser Ser Pro Ser Pro Glu Pro Gly Cys Cys Pro
                85                  90                  95

Ala Thr Thr Thr Thr Ser Thr Glu Arg Ser Lys Ala Ala Pro Ser Thr
            100                 105                 110

Glu Ala Thr Pro Thr Pro Thr Leu Asp Thr Ala Pro Pro Gly Gly Thr
            115                 120                 125

Leu Thr Leu Thr Ala Ser Thr Ala Thr Gly Ala Pro Glu Thr Gly Lys
130                 135                 140

Asp Ser Ser Thr Thr Thr Gly Ala Ser Asp Pro Gly Pro Ser Glu Ser
145                 150                 155                 160

Lys Ser Ser Thr Phe Lys Ser Lys Arg Ser Arg Cys Arg Thr Pro Pro
                165                 170                 175

Pro Pro Ser Pro Thr Ser Pro Pro Ser Lys Cys Leu Arg Thr
            180                 185                 190

Thr Thr Thr Ser Cys Pro Thr Ser Ser Ala Thr Gly Pro Arg Asp Ala
            195                 200                 205

```
Cys Arg Pro Ser Leu Arg Arg Ser Leu Arg Cys Arg Ser Thr Val Thr
        210                 215                 220

Arg Arg
225

<210> SEQ ID NO 6
<211> LENGTH: 225
<212> TYPE: PRT
<213> ORGANISM: adeno-associated virus 6

<400> SEQUENCE: 6

Ser Ser Arg His Lys Ser Gln Thr Pro Pro Arg Ala Leu Ala Arg Gln
1               5                   10                  15

Ala Ser Ser Pro Leu Lys Arg Asp Ser Ile Leu Val Arg Leu Ala Thr
            20                  25                  30

Gln Ser Gln Ser Pro Thr His Asn Leu Ser Glu Asn Leu Gln Gln Pro
        35                  40                  45

Pro Leu Leu Trp Asp Leu Leu Gln Trp Leu Gln Ala Val Ala His Gln
    50                  55                  60

Trp Gln Thr Ile Thr Lys Ala Pro Thr Glu Trp Val Met Pro Gln Glu
65                  70                  75                  80

Ile Gly Ile Ala Ile Pro His Gly Trp Ala Thr Glu Ser Ser Pro Pro
                85                  90                  95

Ala Pro Glu His Gly Pro Cys Pro Pro Ile Thr Thr Thr Ser Thr Ser
            100                 105                 110

Lys Ser Pro Val Leu Gln Arg Gly Pro Ala Thr Thr Thr Thr Thr Ser
        115                 120                 125

Ala Thr Ala Pro Pro Gly Gly Ile Leu Ile Ser Thr Asp Ser Thr Ala
    130                 135                 140

Ile Ser His His Val Thr Gly Ser Asp Ser Ser Thr Thr Ile Gly Asp
145                 150                 155                 160

Ser Gly Pro Arg Asp Ser Thr Ser Ser Ser Thr Ser Lys Ser Arg
                165                 170                 175

Arg Ser Arg Arg Met Met Ala Ser Arg Pro Ser Leu Ile Thr Leu Pro
            180                 185                 190

Ala Arg Phe Lys Ser Ser Arg Thr Arg Ser Thr Ser Cys Arg Thr Ser
        195                 200                 205

Ser Ala Leu Arg Thr Arg Ala Ala Ser Leu Arg Ser Arg Arg Thr Cys
    210                 215                 220

Ser
225

<210> SEQ ID NO 7
<211> LENGTH: 226
<212> TYPE: PRT
<213> ORGANISM: adeno-associated virus 7

<400> SEQUENCE: 7

Ser Arg His Leu Ser Val Pro Pro Thr Pro Arg Ala Ser Ala Arg
1               5                   10                  15

Lys Ala Ser Ser Pro Pro Glu Arg Asp Ser Ile Ser Val Arg Leu Ala
            20                  25                  30

Thr Gln Ser Gln Ser Pro Thr Leu Asn Leu Ser Glu Asn Leu Gln Gln
        35                  40                  45

Arg Pro Leu Val Trp Asp Leu Val Gln Trp Leu Gln Ala Val Ala His
    50                  55                  60
```

```
Gln Trp Gln Thr Ile Thr Lys Val Pro Thr Glu Trp Val Met Pro Gln
 65                  70                  75                  80

Glu Ile Gly Ile Ala Ile Pro His Gly Trp Ala Thr Glu Ser Leu Pro
                 85                  90                  95

Pro Ala Pro Glu Pro Gly Pro Cys Pro Pro Thr Thr Thr Ser Thr
            100                 105                 110

Ser Lys Ser Pro Val Lys Leu Gln Val Val Pro Thr Thr Thr Pro Thr
        115                 120                 125

Ser Ala Thr Ala Pro Pro Gly Gly Ile Leu Thr Leu Thr Asp Ser Thr
    130                 135                 140

Ala Thr Ser His His Val Thr Gly Ser Asp Ser Ser Thr Thr Thr Gly
145                 150                 155                 160

Asp Ser Gly Pro Arg Ser Cys Gly Ser Ser Ser Thr Ser Arg Ser
                165                 170                 175

Arg Arg Ser Arg Arg Met Thr Ala Leu Arg Pro Ser Leu Ile Thr Leu
            180                 185                 190

Pro Ala Arg Phe Arg Tyr Ser Arg Thr Arg Asn Thr Ser Cys Arg Thr
            195                 200                 205

Ser Ser Ala Leu Arg Thr Arg Ala Ala Cys Leu Arg Ser Arg Arg Thr
    210                 215                 220

Ser Ser
225

<210> SEQ ID NO 8
<211> LENGTH: 227
<212> TYPE: PRT
<213> ORGANISM: adeno-associated virus 8

<400> SEQUENCE: 8

Ser His His Pro Ser Val Leu Gln Thr Pro Leu Arg Ala Ser Ala Arg
 1               5                  10                  15

Lys Ala Asn Ser Pro Pro Glu Lys Asp Ser Ile Leu Val Arg Leu Ala
             20                  25                  30

Thr Gln Ser Gln Phe Gln Thr Leu Asn Leu Ser Glu Asn Leu Gln Gln
         35                  40                  45

Arg Pro Leu Val Trp Asp Leu Ile Gln Trp Leu Gln Ala Val Ala His
     50                  55                  60

Gln Trp Gln Thr Ile Thr Lys Ala Pro Thr Glu Trp Val Val Pro Arg
 65                  70                  75                  80

Glu Ile Gly Ile Ala Ile Pro His Gly Trp Ala Thr Glu Ser Ser Pro
                 85                  90                  95

Pro Ala Pro Glu Pro Gly Pro Cys Pro Pro Thr Thr Thr Ser Thr
            100                 105                 110

Ser Lys Ser Pro Thr Gly His Arg Glu Glu Pro Pro Thr Thr Pro
        115                 120                 125

Thr Ser Ala Thr Ala Pro Pro Gly Gly Ile Leu Thr Leu Thr Asp Ser
    130                 135                 140

Thr Ala Thr Phe His His Val Thr Gly Ser Asp Ser Ser Thr Thr Thr
145                 150                 155                 160

Gly Asp Ser Gly Pro Arg Asp Ser Ala Ser Ser Ser Thr Ser Arg
                165                 170                 175

Ser Arg Arg Ser Arg Arg Met Lys Ala Pro Arg Pro Ser Pro Ile Thr
            180                 185                 190

Ser Pro Ala Pro Ser Arg Cys Leu Arg Thr Arg Ser Thr Ser Cys Arg
```

```
            195                 200                 205
Thr Phe Ser Ala Leu Pro Thr Arg Ala Ala Cys Leu Arg Ser Arg Arg
    210                 215                 220

Thr Cys Ser
225

<210> SEQ ID NO 9
<211> LENGTH: 226
<212> TYPE: PRT
<213> ORGANISM: adeno-associated virus 9

<400> SEQUENCE: 9

Ser Ser Leu Leu Arg Asn Arg Thr Pro Pro Arg Val Leu Ala Asn Arg
1               5                   10                  15

Val His Ser Pro Leu Lys Arg Asp Ser Ile Ser Val Arg Leu Ala Thr
            20                  25                  30

Gln Ser Gln Ser Gln Thr Leu Asn Gln Ser Glu Asn Leu Pro Gln Pro
        35                  40                  45

Pro Gln Val Trp Asp Leu Leu Gln Trp Leu Gln Val Ala His Gln
    50                  55                  60

Trp Gln Thr Ile Thr Lys Val Pro Met Glu Trp Val Pro Arg Glu
65                  70                  75                  80

Ile Gly Ile Ala Ile Pro Asn Gly Trp Gly Thr Glu Ser Ser Pro Pro
                85                  90                  95

Ala Pro Glu Pro Gly Pro Cys Pro Pro Thr Thr Ile Thr Ser Thr Ser
            100                 105                 110

Lys Ser Pro Thr Ala His Leu Glu Asp Leu Gln Met Thr Thr Pro Thr
        115                 120                 125

Ser Ala Thr Ala Pro Pro Gly Gly Ile Leu Thr Ser Thr Asp Ser Thr
    130                 135                 140

Ala Thr Ser His His Val Thr Gly Ser Asp Ser Ser Thr Thr Thr Gly
145                 150                 155                 160

Asp Ser Gly Leu Ser Asp Ser Thr Ser Ser Ser Ser Thr Phe Arg Ser
                165                 170                 175

Lys Arg Leu Arg Thr Thr Met Glu Ser Arg Pro Ser Pro Ile Thr Leu
            180                 185                 190

Pro Ala Arg Ser Arg Ser Ser Arg Thr Gln Thr Ile Ser Ser Arg Thr
        195                 200                 205

Cys Ser Gly Arg Leu Thr Arg Ala Ala Ser Arg Arg Ser Gln Arg Thr
    210                 215                 220

Phe Ser
225

<210> SEQ ID NO 10
<211> LENGTH: 201
<212> TYPE: PRT
<213> ORGANISM: adeno-associated virus 10

<400> SEQUENCE: 10

Thr Leu Gly Arg Leu Ala Ser Gln Ser Gln Ser Pro Thr Leu Asn Gln
1               5                   10                  15

Ser Glu Asn His Gln Gln Ala Pro Leu Val Trp Asp Leu Val Gln Trp
            20                  25                  30

Leu Gln Ala Val Ala Leu Gln Trp Gln Thr Ile Thr Lys Ala Pro Thr
        35                  40                  45

Glu Trp Val Val Pro Gln Glu Ile Gly Ile Ala Ile Pro His Gly Trp
```

```
                    50                  55                  60
Ala Thr Glu Ser Ser Pro Pro Ala Pro Glu Pro Gly Pro Cys Pro Pro
 65                  70                  75                  80

Thr Thr Thr Thr Ser Thr Ser Lys Ser Pro Thr Gly His Arg Glu Glu
                     85                  90                  95

Ala Pro Thr Thr Thr Pro Thr Ser Ala Thr Ala Pro Pro Gly Gly Ile
                    100                 105                 110

Leu Thr Ser Thr Asp Ser Thr Ala Thr Ser His His Val Thr Gly Ser
                115                 120                 125

Asp Ser Ser Thr Thr Thr Gly Asp Ser Gly Gln Lys Asp Ser Ala Ser
            130                 135                 140

Ser Ser Ser Thr Ser Arg Ser Arg Arg Ser Arg Arg Met Lys Ala Pro
145                 150                 155                 160

Arg Pro Ser Pro Ile Thr Leu Pro Ala Arg Phe Arg Tyr Leu Arg Thr
                165                 170                 175

Arg Asn Thr Ser Cys Arg Thr Ser Ser Ala Pro Arg Thr Arg Ala Ala
            180                 185                 190

Cys Leu Arg Ser Arg Arg Met Ser Ser
        195                 200

<210> SEQ ID NO 11
<211> LENGTH: 197
<212> TYPE: PRT
<213> ORGANISM: adeno-associated virus 11

<400> SEQUENCE: 11

Ser His His Lys Ser Pro Thr Pro Pro Arg Ala Ser Ala Lys Lys Ala
  1               5                  10                  15

Asn Asn Gln Pro Glu Arg Gly Ser Thr Leu Lys Arg Thr Leu Glu Pro
                 20                  25                  30

Glu Thr Asp Pro Leu Lys Asp Gln Ile Pro Ala Pro Cys Leu Gln Thr
             35                  40                  45

Leu Lys Cys Val Gln His Arg Ala Glu Met Leu Ser Met Arg Asp Lys
 50                  55                  60

Val Pro Met Glu Trp Val Met Pro Arg Val Ile Gly Ile Ala Ile Pro
 65                  70                  75                  80

Pro Gly Leu Arg Ala Arg Ser Gln Gln Pro Arg Pro Glu Pro Gly Ser
                 85                  90                  95

Cys Pro Pro Thr Thr Thr Cys Thr Cys Val Ser Glu Gln His Gln
                100                 105                 110

Ala Ala Thr Pro Thr Thr Asp Ser Pro Pro Gly Asp Ile Leu Thr
             115                 120                 125

Ser Thr Asp Ser Thr Val Thr Ser His His Val Thr Gly Lys Asp Ser
            130                 135                 140

Ser Thr Thr Thr Gly Asp Tyr Asp Gln Lys Pro Cys Ala Leu Lys Ser
145                 150                 155                 160

Ser Ile Ser Lys Leu Arg Arg Ser Gln Arg Arg Thr Ala Arg Leu Arg
                165                 170                 175

Ser Leu Ile Thr Leu Pro Ala Arg Phe Arg Tyr Leu Arg Thr Arg Arg
            180                 185                 190

Met Ser Ser Arg Thr
            195

<210> SEQ ID NO 12
<211> LENGTH: 206
```

<212> TYPE: PRT
<213> ORGANISM: adeno-associated virus 12

<400> SEQUENCE: 12

```
Lys Arg Leu Gln Ile Gly Arg Pro Thr Arg Thr Leu Gly Arg Pro Arg
1               5                   10                  15

Pro Arg Lys Ser Lys Lys Thr Ala Asn Gln Pro Thr Leu Leu Glu Gly
            20                  25                  30

His Ser Thr Leu Lys Thr Leu Glu Gln Glu Thr Asp Pro Leu Arg Asp
        35                  40                  45

His Leu Pro Glu Lys Cys Leu Met Met Leu Arg Cys Val Arg Arg Gln
    50                  55                  60

Ala Glu Met Leu Ser Arg Arg Asp Lys Val Pro Met Glu Trp Val Met
65                  70                  75                  80

Pro Pro Val Ile Gly Ile Ala Ile Pro Pro Gly Gln Arg Ala Glu Ser
                85                  90                  95

Pro Pro Pro Ala Pro Glu Pro Gly Ser Tyr Pro Arg Thr Thr Thr Thr
            100                 105                 110

Cys Thr Cys Glu Ser Glu Gln Arg Pro Thr Ala Thr Pro Thr Thr Asp
        115                 120                 125

Ser Pro Pro Gly Asp Thr Leu Thr Leu Thr Ala Ser Thr Ala Thr
130                 135                 140

Phe Pro His Ala Thr Gly Ser Asp Ser Ser Thr Thr Gly Asp Ser
145                 150                 155                 160

Gly Arg Asn Arg Cys Val Leu Lys Ser Ser Thr Tyr Arg Ser Arg Arg
                165                 170                 175

Ser Arg Arg Gln Thr Ala Arg Leu Arg Ser Leu Ile Thr Leu Pro Ala
            180                 185                 190

Arg Phe Arg Ser Leu Arg Ile Arg Met Asn Ser His Thr
            195                 200                 205
```

<210> SEQ ID NO 13
<211> LENGTH: 199
<212> TYPE: PRT
<213> ORGANISM: bovine adeno-associated virus

<400> SEQUENCE: 13

```
Ser Arg Val Leu Lys Ser Gln Thr Pro Arg Ala Glu Leu Ala Arg Lys
1               5                   10                  15

Ala Asn Ser Leu Pro Glu Arg Asp Ser Thr Leu Thr Thr Asn Leu Glu
            20                  25                  30

Pro Glu Thr Gly Leu Pro Gln Lys Asp His Leu Pro Glu Leu Cys Leu
        35                  40                  45

Leu Arg Leu Lys Cys Val Gln Gln Leu Ala Glu Met Val Ala Met Arg
    50                  55                  60

Asp Lys Val Pro Arg Glu Trp Val Met Pro Val Ile Gly Ile Ala
65                  70                  75                  80

Ile Pro Leu Gly Gln Arg Ala Thr Ser Pro Pro Gln Pro Ala Pro
                85                  90                  95

Gly Ser Cys Arg Pro Thr Thr Thr Cys Thr Cys Gly Ser Ala Arg
            100                 105                 110

Ala Thr Pro Ala Thr Pro Ser Thr Asp Ser Pro Pro Gly Asp Thr
        115                 120                 125

Leu Thr Leu Thr Ala Ser Thr Ala Thr Ser Arg Gln Glu Thr Gly Lys
    130                 135                 140
```

Gly Ser Ser Thr Thr Thr Gly Asp Cys Ala Pro Lys Ala Cys Lys Ser
145                 150                 155                 160

Ala Ser Ser Thr Ser Lys Leu Arg Arg Ser Arg Arg Leu Thr Gly Arg
            165                 170                 175

Arg Pro Tyr Pro Thr Thr Ser Pro Ala Arg Ser Arg Ser Leu Arg Thr
            180                 185                 190

Ala Arg Thr Ser Ser Arg Thr
            195

<210> SEQ ID NO 14
<211> LENGTH: 262
<212> TYPE: PRT
<213> ORGANISM: avian adeno-associated virus ATCC VR-865

<400> SEQUENCE: 14

Val Lys Pro Ser Ser Arg Pro Lys Arg Gly Phe Ser Asn Pro Leu Val
1               5                   10                  15

Trp Trp Lys Thr Gln Arg Arg Leu Arg Pro Glu Thr Ser Gly Lys Ala
            20                  25                  30

Lys Thr Asn Leu Val Cys Pro Thr Leu Leu His Arg Leu Pro Arg Lys
        35                  40                  45

Thr Arg Ser Leu Ala Arg Lys Asp Leu Pro Ala Gly Gln Lys Ile Arg
    50                  55                  60

Ala Lys Ala Pro Leu Pro Thr Leu Glu Gln Gln His Pro Pro Leu Val
65                  70                  75                  80

Trp Asp His Leu Ser Trp Leu Lys Glu Val Ala Ala Gln Trp Ala Met
                85                  90                  95

Gln Ala Arg Val Pro Met Glu Trp Ala Ile Pro Pro Glu Ile Gly Ile
            100                 105                 110

Ala Ile Pro Asn Gly Trp Lys Thr Glu Ser Ser Leu Glu Pro Pro Glu
        115                 120                 125

Pro Gly Ser Cys Pro Ala Thr Thr Thr Cys Thr Asn Glu Ser Lys
    130                 135                 140

Asp Pro Ala Glu Ala Thr Thr Thr Asn Ser Leu Asp Ser Ala Pro
145                 150                 155                 160

Pro Gly Asp Thr Leu Thr Thr Ile Asp Ser Thr Ala Thr Phe Pro Arg
                165                 170                 175

Glu Thr Gly Asn Asp Ser Ser Thr Thr Gly Ala Ser Val Pro Lys
            180                 185                 190

Arg Cys Ala Leu Asp Ser Leu Thr Ser Arg Leu Lys Arg Ser Arg Ser
        195                 200                 205

Lys Thr Ser Thr Pro Pro Ser Ala Thr Thr Ser Pro Val Arg Ser Arg
    210                 215                 220

Ser Leu Arg Thr Arg Thr Thr Asn Cys Arg Thr Ser Ser Asp Arg Leu
225                 230                 235                 240

Pro Lys Ala Pro Ser Arg Arg Ser Gln Arg Ile Ser Thr Arg Ser Arg
                245                 250                 255

Ser Thr Gly Thr Ala Arg
            260

<210> SEQ ID NO 15
<211> LENGTH: 208
<212> TYPE: PRT
<213> ORGANISM: adeno-associated virus 13

<400> SEQUENCE: 15

Ile Leu Val Arg Leu Ala Thr Gln Ser Gln Ser Gln Thr Leu Asn His
1               5                  10                  15

Ser Asp Asn Leu Pro Gln Pro Pro Leu Val Trp Asp Leu Leu Gln Trp
            20                  25                  30

Leu Gln Ala Val Ala His Gln Trp Gln Thr Ile Thr Arg Val Pro Met
        35                  40                  45

Glu Trp Val Ile Pro Gln Glu Ile Gly Ile Ala Ile Pro Asn Gly Trp
50                  55                  60

Ala Thr Glu Ser Ser Pro Ala Pro Ala Pro Gly Pro Cys Pro Pro
65                  70                  75                  80

Thr Thr Ile Thr Ser Thr Ser Lys Ser Pro Ala Asn Gln Glu Pro Pro
            85                  90                  95

Thr Thr Thr Thr Thr Leu Ala Thr Ala Pro Pro Gly Gly Ile Leu Thr
        100                 105                 110

Ser Thr Asp Ser Thr Ala Thr Phe His His Val Thr Gly Lys Asp Ser
        115                 120                 125

Ser Thr Thr Thr Gly Asp Ser Asp Pro Arg Asp Ser Thr Ser Ser Ser
        130                 135                 140

Leu Thr Phe Lys Ser Lys Arg Ser Arg Arg Met Thr Val Arg Arg Arg
145                 150                 155                 160

Leu Pro Ile Thr Leu Pro Ala Arg Phe Arg Cys Leu Leu Thr Pro Ser
            165                 170                 175

Thr Ser Ser Arg Thr Ser Ser Ala Arg Arg Ile Arg Asp Ala Ser Arg
        180                 185                 190

Arg Ser Gln Gln Thr Ser Ser Trp Ser His Ser Met Asp Thr Ser Pro
        195                 200                 205

<210> SEQ ID NO 16
<211> LENGTH: 177
<212> TYPE: PRT
<213> ORGANISM: mouse adeno-associated virus 1

<400> SEQUENCE: 16

Thr Arg Arg Thr Val Ser Ser Leu Pro Leu Gln Arg Arg Pro Lys Leu
1               5                   10                  15

Glu Ala Leu Pro Pro Ala Ile Trp Asp Leu Val Arg Trp Leu Glu
            20                  25                  30

Ala Val Ala Arg Gln Ser Thr Thr Ala Arg Met Val Pro Met Glu Trp
        35                  40                  45

Ala Met Pro Arg Glu Ile Gly Ile Ala Ile Pro His Gly Trp Thr Thr
50                  55                  60

Val Ser Ser Pro Glu Pro Leu Gly Pro Gly Ile Cys Gln Pro Thr Thr
65                  70                  75                  80

Thr Thr Ser Thr Asn Asp Ser Thr Glu Arg Pro Pro Glu Thr Lys Ala
            85                  90                  95

Thr Ser Asp Ser Ala Pro Pro Gly Asp Thr Leu Thr Ser Thr Ala Ser
        100                 105                 110

Thr Val Ile Ser Pro Leu Glu Thr Gly Lys Asp Ser Ser Thr Ile Thr
        115                 120                 125

Gly Asp Ser Asp Gln Arg Ala Tyr Gly Ser Lys Ser Leu Thr Phe Lys
        130                 135                 140

Leu Lys Lys Ser Arg Arg Lys Thr Gln Arg Arg Ser Ser Pro Ile Thr
145                 150                 155                 160

Leu Pro Ala Arg Phe Arg Tyr Leu Arg Thr Arg Ser Thr Ser Ser Arg
            165                 170                 175

Thr

<210> SEQ ID NO 17
<211> LENGTH: 240
<212> TYPE: PRT
<213> ORGANISM: avian adeno-associated virus strain DA-1

<400> SEQUENCE: 17

```
Leu Asn Asn Pro Thr Thr Arg Pro Gly Pro Gly Arg Ser Val Pro Asn
1               5                   10                  15

Ala Ser Thr Thr Phe Ser Arg Lys Arg Arg Pro Arg Pro Ser Lys
            20                  25                  30

Ala Lys Pro Leu Leu Lys Arg Ala Lys Thr Pro Glu Lys Glu Pro Leu
            35                  40                  45

Pro Thr Leu Asp Gln Ala Pro Pro Leu Val Trp Asp His Leu Ser Trp
        50                  55                  60

Leu Lys Glu Val Ala Val Gln Trp Ala Met Gln Ala Lys Val Pro Thr
65                  70                  75                  80

Glu Trp Ala Ile Pro Arg Glu Ile Gly Ile Ala Ile Pro Asn Gly Trp
                    85                  90                  95

Thr Thr Glu Ser Leu Pro Glu Pro Leu Glu Pro Gly Ser Cys Pro Ala
                100                 105                 110

Thr Thr Thr Thr Cys Thr Ser Gly Ser Lys Asp Arg Glu Glu Pro Thr
            115                 120                 125

Pro Thr Ile Asn Ser Leu Asp Ser Ala Pro Pro Gly Gly Thr Leu Thr
        130                 135                 140

Thr Thr Asp Ser Thr Ala Thr Ser Pro Pro Glu Thr Gly Asn Asp Ser
145                 150                 155                 160

Ser Thr Thr Thr Gly Ala Ser Asp Pro Lys Arg Cys Ala Leu Asp Ser
                    165                 170                 175

Leu Thr Ser Arg Leu Lys Lys Ser Leu Ser Lys Thr Pro Thr Pro Pro
                180                 185                 190

Ser Pro Thr Thr Ser Pro Ala Arg Ser Lys Ser Leu Arg Thr Arg Thr
            195                 200                 205

Thr Ser Cys Arg Thr Ser Ser Asp Arg Leu Gln Arg Ala Pro Ser Arg
        210                 215                 220

Arg Ser Gln Arg Ile Ser Thr Arg Ser Arg Ser Met Val Thr Ala Arg
225                 230                 235                 240
```

<210> SEQ ID NO 18
<211> LENGTH: 226
<212> TYPE: PRT
<213> ORGANISM: caprine adeno-associated virus 1 isolate adeno-associated virus Go.1

<400> SEQUENCE: 18

```
Thr Thr Thr Phe Gln Lys Glu Arg Arg Leu Gly Pro Lys Arg Thr Pro
1               5                   10                  15

Ser Leu Pro Pro Arg Gln Thr Pro Lys Leu Asp Pro Ala Asp Pro Ser
            20                  25                  30

Ser Cys Lys Ser Gln His Asn Gln Pro Gln Val Trp Glu Leu Ile Gln
            35                  40                  45

Cys Leu Arg Glu Val Ala Ala His Trp Ala Thr Ile Thr Lys Val Pro
        50                  55                  60

Met Glu Trp Ala Met Pro Arg Glu Ile Gly Ile Ala Ile Pro Arg Gly
65                  70                  75                  80
```

```
Trp Gly Thr Glu Ser Ser Pro Ser Pro Pro Ala Pro Gly Cys Cys Pro
                85                  90                  95

Ala Thr Thr Thr Thr Ser Thr Glu Arg Ser Lys Ala Ala Pro Ser Thr
            100                 105                 110

Glu Ala Thr Pro Thr Pro Thr Leu Asp Thr Ala Pro Pro Gly Gly Thr
        115                 120                 125

Leu Thr Leu Thr Ala Ser Thr Ala Thr Gly Ala Pro Glu Thr Gly Lys
    130                 135                 140

Asp Ser Ser Thr Thr Ile Gly Ala Ser Asp Pro Gly Leu Ser Glu Ser
145                 150                 155                 160

Lys Ser Ser Thr Ser Lys Ser Lys Arg Ser Arg Cys Arg Thr Pro Pro
                165                 170                 175

Pro Pro Ser Pro Thr Thr Ser Pro Pro Ser Lys Cys Leu Arg Thr
            180                 185                 190

Thr Thr Thr Asn Ser Arg Thr Ser Ser Ala Thr Gly Pro Arg Asp Ala
            195                 200                 205

Cys Arg Pro Ser Pro Arg Arg Ser Leu Arg Cys Arg Ser Thr Ala Thr
    210                 215                 220

Arg Arg
225

<210> SEQ ID NO 19
<211> LENGTH: 251
<212> TYPE: PRT
<213> ORGANISM: rat adeno-associated virus 1

<400> SEQUENCE: 19

Ala Ser Arg Ser Arg Ser Trp Leu Leu Gln Ser Ser Val His Thr Arg
1               5                   10                  15

Pro Arg Lys Pro Gln Arg Thr Arg Arg Val Ser Arg Asp Arg Ile Pro
            20                  25                  30

Gly Arg Arg Pro Arg Arg Gly Ser Ser Pro Ile Ser Leu Asp Leu
        35                  40                  45

Gln Gln Thr Tyr Leu His Pro His Asn Ser Pro Ser Leu Pro Gln Gly
    50                  55                  60

Phe Pro Val Trp Phe Leu Val Arg Cys Leu Gln Glu Glu Ala Leu Gln
65                  70                  75                  80

Trp Thr Met Leu Asn Lys Val Pro Thr Glu Trp Ala Met Pro Arg Glu
                85                  90                  95

Ile Gly Ile Ala Ile Pro Asn Gly Trp Ala Thr Glu Phe Ser Pro Asp
            100                 105                 110

Pro Pro Gly Pro Gly Cys Cys Pro Ala Thr Thr Thr Cys Thr Ser
        115                 120                 125

Arg Ser Gln Thr Pro Pro Ala Cys Thr Ala Ser Pro Gly Ala Asp Thr
    130                 135                 140

Leu Ala Thr Ala Pro Pro Gly Gly Thr Ser Thr Ser Ile Ala Ser Thr
145                 150                 155                 160

Ala Thr Ser Arg Pro Glu Thr Gly Ser Ala Ser Ser Ile Thr Thr Gly
                165                 170                 175

Ala Ser Asp Pro Arg Asp Cys Glu Ser Asn Ser Ser Thr Ser Arg Ser
            180                 185                 190

Arg Arg Ser Arg Leu Leu Ile Arg Arg Pro Arg Ser Pro Thr Thr Ser
        195                 200                 205

Arg Ala Arg Ser Arg Ser Ser Gln Thr Thr Ser Thr Ser Cys Arg Thr
```

Ser Ala Ala Thr Pro Arg Asp Ala Cys Arg Arg Ser Pro Arg Thr
225                 230                 235                 240

Ser Ser Arg Cys Arg Ser Thr Ala Thr Arg Arg
            245                 250

<210> SEQ ID NO 20
<211> LENGTH: 212
<212> TYPE: PRT
<213> ORGANISM: goose parvovirus strain DB3

<400> SEQUENCE: 20

Lys Thr Glu Glu Pro Pro Arg Arg Ala Pro Asn Leu Trp Gln His Leu
1               5                   10                  15

Lys Trp Gln Arg Glu Glu Ala Glu Leu Trp Ala Thr Leu Gln Gly Val
            20                  25                  30

Pro Met Glu Trp Val Met Pro Arg Glu Ile Gly Ile Ala Ile Pro Asn
        35                  40                  45

Gly Trp Glu Thr Gln Ser Ser Gln Arg Pro Glu Pro Gly Ser Cys
    50                  55                  60

Gln Ala Thr Thr Thr Thr Ser Thr Lys Gln Leu Pro Val Glu Pro Leu
65                  70                  75                  80

Lys Met Gln Met Ser Ser Met Gln Asp Thr Val Pro Pro Gly Gly Thr
                85                  90                  95

Leu Ile Ser Thr Ala Ser Thr Ala Thr Ser Pro Leu Glu Thr Gly Arg
            100                 105                 110

Asp Leu Ser Thr Thr Ile Gly Glu Ser Asp Pro Asn Leu Leu Asn Ser
        115                 120                 125

Arg Ser Ser Met Ser Lys Ser Lys Ser Gln Arg Arg Ile Lys Gln
    130                 135                 140

Arg Pro Leu Gln Thr Ile Ser Pro Gln Arg Phe Lys Ser Leu Arg Met
145                 150                 155                 160

Met Ser Ile Asn Ser Arg Met Ser Trp Ala Arg Leu Arg Lys Ala Pro
                165                 170                 175

Cys Arg Arg Ser Arg Arg Met Ser Met Pro Cys Arg Ser Thr Gly Thr
            180                 185                 190

Ala Gln Cys Thr Pro Thr Arg Met Glu His Gly Ser Met Thr Val Val
        195                 200                 205

His Ser Thr Ala
    210

<210> SEQ ID NO 21
<211> LENGTH: 230
<212> TYPE: PRT
<213> ORGANISM: duck parvovirus strain 90-0219

<400> SEQUENCE: 21

Lys Ser Leu Asn Tyr Leu Lys Lys Thr Leu His Pro Val Ile Val
1               5                   10                  15

Glu Glu Lys Gln Val Gln Leu Pro Pro Lys Ala Pro Asn Leu Trp Gln
            20                  25                  30

His Leu Thr Trp Gln Arg Glu Ala Glu Leu Trp Ala Thr Leu Gln
        35                  40                  45

Gly Val Pro Met Glu Trp Val Met Pro Gln Glu Ile Gly Ile Ala Ile
    50                  55                  60

Pro Asn Gly Trp Glu Thr Gln Ser Leu Pro Arg Leu Gln Glu Pro Gly

```
        65                  70                  75                  80
Ser Cys Gln Ala Thr Thr Thr Ser Thr Lys Pro Ser Gln Ala Glu
                    85                  90                  95

Gln Thr Gln Thr Gln Ile Pro Asn Met Leu Asp Thr Ala Pro Pro Gly
                100                 105                 110

Gly Thr Leu Ile Ser Thr Asp Ser Thr Ala Ile Ser Leu Gln Glu Thr
                115                 120                 125

Gly Arg Asp Ser Ser Thr Thr Ile Gly Gly Leu Asp Arg Lys His Ser
                130                 135                 140

Asn Ser Arg Tyr Ser Met Cys Lys Leu Lys Ser Arg Arg Lys Thr
145                 150                 155                 160

Arg Gln Arg Leu Leu Leu Thr Thr Leu Pro Leu Gln Ser Arg Tyr Ser
                165                 170                 175

Arg Ile Met Asn Thr Ser Cys Pro Met Phe Trp Ala Arg Pro Arg Arg
                180                 185                 190

Gly Arg Cys His Arg Ser Pro Gln Met Cys Met Pro Cys Pro Ser Thr
                195                 200                 205

Ala Thr Ala Gln Cys Thr Pro Thr Arg Val Glu Leu Asp Ser Met Thr
                210                 215                 220

Glu Val Pro Ser Ile Ala
225                 230

<210> SEQ ID NO 22
<211> LENGTH: 199
<212> TYPE: PRT
<213> ORGANISM: snake parvovirus 1

<400> SEQUENCE: 22

Thr Asn Thr Ile Leu Lys Leu Lys Arg Pro Asn Lys Ala Cys Arg Tyr
1               5                   10                  15

Gln Leu His Leu Lys Ala Glu Lys Lys Lys Leu His Arg His Asn Leu
                20                  25                  30

Glu Gly Ala Gln Gln Val Pro Ile Leu Ala Ala His Leu Ser Trp Leu
                35                  40                  45

Gln Glu Glu Ala Val Arg Trp Gln Thr Ile Thr Arg Ala Pro Arg Glu
                50                  55                  60

Trp Val Ile Pro Gln Val Ile Gly Ile Ala Ile Pro Ser Gly Trp Glu
65                  70                  75                  80

Thr Thr Ser Leu Gln Ser Gln Pro Glu Leu Gly Cys Ser Pro Leu Thr
                85                  90                  95

Gly Ile Ile Ser Thr Gly Leu Ser Thr Leu Thr Ala Pro Gln Val Arg
                100                 105                 110

Val Leu Met Gln Pro Met Gln Asp Thr Arg Leu Pro Gly Gly Thr Leu
                115                 120                 125

Thr Ser Ile Asp Ser Ile Ala Thr Ser Pro Pro Glu Thr Gly Lys Asp
                130                 135                 140

Ser Ser Thr Thr Thr Gln Ala Ser Gly Arg Lys Asp Ser Lys Ser Lys
145                 150                 155                 160

Ser Leu Thr Ser Lys Ser Lys Lys Leu Gln His Lys Ile Gln Arg Lys
                165                 170                 175

Gln Leu Pro Thr Ile Ser Pro Ala Pro Tyr Arg Ser Leu Arg Thr Arg
                180                 185                 190

Thr Thr Thr Tyr His Met Tyr
                195
```

<210> SEQ ID NO 23
<211> LENGTH: 627
<212> TYPE: DNA
<213> ORGANISM: adeno-associated virus 2

<400> SEQUENCE: 23

```
attttggtca gactggagac gcagactcag tacctgaccc ccagcctctc ggacagccac    60
cagcagcccc ctctggtctg ggaactaata cgatggctac aggcagtggc gcaccaatgg   120
cagacaataa cgagggcgcc gacggagtgg gtaattcctc gggaaattgg cattgcgatt   180
ccacatggat gggcgacaga gtcatcacca ccagcacccg aacctgggcc ctgcccacct   240
acaacaacca cctctacaaa caaatttcca gccaatcagg agcctcgaac gacaatcact   300
actttggcta cagcaccccct tggggtatt ttgacttcaa cagattccac tgccactttt   360
caccacgtga ctggcaaaga ctcatcaaca acaactgggg attccgaccc aagagactca   420
acttcaagct ctttaacatt caagtcaaag aggtcacgca gaatgacggt acgacgacga   480
ttgccaataa ccttaccagc acggttcagg tgtttactga ctcggagtac cagctcccgt   540
acgtcctcgg ctcggcgcat caaggatgcc tcccgccgtt cccagcagac gtcttcatgg   600
tgccacagta tggataccte accctga                                       627
```

<210> SEQ ID NO 24
<211> LENGTH: 678
<212> TYPE: DNA
<213> ORGANISM: adeno-associated virus 1

<400> SEQUENCE: 24

```
agcagtcgcc acaagagcca gactcctcct cgggcatcgg caagacaggc cagcagcccg    60
ctaaaaagag actcaatttt ggtcagactg gcgactcaga gtcagtcccc gatccacaac   120
ctctcggaga acctccagca accccgctg ctgtgggacc tactacaatg gcttcaggcg   180
gtggcgcacc aatggcagac aataacgaag gcgccgacgg agtgggtaat gcctcaggaa   240
attggcattg cgattccaca tggctgggcg acagagtcat caccaccagc acccgcacct   300
gggccttgcc cacctacaat aaccactct acaagcaaat ctccagtgct tcaacggggg   360
ccagcaacga caaccactac ttcggctaca gcacccctg ggggtatttt gatttcaaca   420
gattccactg ccacttttca ccacgtgact ggcagcgact catcaacaac aattggggat   480
tccggcccaa gagactcaac ttcaaactct tcaacatcca agtcaaggag gtcacgacga   540
atgatggcgt cacaaccatc gctaataacc ttaccagcac ggttcaagtc ttctcggact   600
cggagtacca gcttccgtac gtcctcggct ctgcgcacca gggctgcctc cctccgttcc   660
cggcggacgt gttcatga                                                 678
```

<210> SEQ ID NO 25
<211> LENGTH: 627
<212> TYPE: DNA
<213> ORGANISM: adeno-associated virus 3

<400> SEQUENCE: 25

```
atttcggtca gactggcgac tcagagtcag tcccagaccc tcaacctctc ggagaaccac    60
cagcagcccc cacaagtttg ggatctaata caatggcttc aggcggtggc gcaccaatgg   120
cagacaataa cgagggtgcc gatggagtgg gtaattcctc aggaaattgg cattgcgatt   180
cccaatggct gggcgacaga gtcatcacca ccagcaccag aacctgggcc ctgcccactt   240
acaacaacca tctctacaag caaatctcca gccaatcagg agcttcaaac gacaaccact   300
```

```
actttggcta cagcacccct tgggggtatt ttgactttaa cagattccac tgccacttct    360
caccacgtga ctggcagcga ctcattaaca acaactgggg attccggccc aagaaactca    420
gcttcaagct cttcaacatc caagttaaag aggtcacgca gaacgatggc acgacgacta    480
ttgccaataa ccttaccagc acggttcaag tgtttacgga ctcggagtat cagctcccgt    540
acgtgctcgg gtcggcgcac caaggctgtc tcccgccgtt ccagcggac gtcttcatgg     600 tccctcagta tggatacctc accctga                                        627

<210> SEQ ID NO 26
<211> LENGTH: 597
<212> TYPE: DNA
<213> ORGANISM: adeno-associated virus 4

<400> SEQUENCE: 26
ttgaatcccc ccagcagccc gactcctcca cgggtatcgg caaaaaaggc aagcagccgg     60
ctaaaaagaa gctcgttttc gaagacgaaa ctggagcagg cgacggaccc cctgagggat    120
caacttccgg agccatgtct gatgacagtg agatgcgtgc agcagctggc ggagctgcag    180
tcgagggcgg acaaggtgcc gatggagtgg gtaatgcctc gggtgattgg cattgcgatt    240
ccacctggtc tgagggccac gtcacgacca ccagcaccag aacctgggtc ttgcccacct    300
acaacaacca cctctacaag cgactcggag agagcctgca gtccaacacc tacaacggat    360
tctccacccc ctggggatac tttgacttca accgcttcca ctgccacttc tcaccacgtg    420
actggcagcg actcatcaac aacaactggg gcatgcgacc caaagccatg cgggtcaaaa    480
tcttcaacat ccaggtcaag gaggtcacga cgtcgaacgg cgagacaacg gtggctaata    540
accttaccag cacggttcag atctttgcgg actcgtcgta cgaactgccg tacgtga       597

<210> SEQ ID NO 27
<211> LENGTH: 681
<212> TYPE: DNA
<213> ORGANISM: adeno-associated virus 5

<400> SEQUENCE: 27
acgaccactt tccaaaaaga aagaaggctc ggaccgaaga ggactccaag ccttccacct     60
cgtcagacgc cgaagctgga cccagcggat cccagcagct gcaaatccca gcccaaccag    120
cctcaagttt gggagctgat acaatgtctg cgggaggtgg cggccattg ggcgacaata     180 accaaggtgc cgatggagtg ggcaatgcct cgggagattg gcattgcgat tccacgtgga    240
tgggggacag agtcgtcacc aagtccaccc gaacctgggt gctgcccagc tacaacaacc    300
accagtaccg agagatcaaa agcggctccg tcgacggaag caacgccaac gcctactttg    360
gatacagcac cccctggggg tactttgact ttaaccgctt ccacagccac tggagccccc    420
gagactggca aagactcatc aacaactact ggggcttcag accccggtcc ctcagagtca    480
aaatcttcaa cattcaagtc aaagaggtca cggtgcagga ctccaccacc atcgcca      540 acaacctcac ctccaccgtc caagtgttta cggacgacga ctaccagctg ccctacgtcg    600
tcggcaacgg gaccgaggga tgcctgccgg ccttccctcc gcaggtcttt acgctgccgc    660
agtacggtta cgcgacgctg a                                              681

<210> SEQ ID NO 28
<211> LENGTH: 678
<212> TYPE: DNA
<213> ORGANISM: adeno-associated virus 6
```

<400> SEQUENCE: 28

```
agcagtcgcc acaagagcca gactcctcct cgggcattgg caagacaggc cagcagcccg    60
ctaaaaagag actcaatttt ggtcagactg gcgactcaga gtcagtcccc gacccacaac   120
ctctcggaga acctccagca accccgctg ctgtgggacc tactacaatg gcttcaggcg    180
gtggcgcacc aatggcagac aataacgaag gcgccgacgg agtgggtaat gcctcaggaa   240
attggcattg cgattccaca tggctgggcg acagagtcat caccaccagc acccgaacat   300
gggccttgcc cacctataac aaccacctct acaagcaaat ctccagtgct caacggggg    360
ccagcaacga caaccactac ttcggctaca gcaccccctg ggggtatttt gatttcaaca   420
gattccactg ccatttctca ccacgtgact ggcagcgact catcaacaac aattggggat   480
tccggcccaa gagactcaac ttcaagtctc tcaacatcca gtcaaggag gtcacgacga   540
atgatggcgt cacgaccatc gctaataacc ttaccagcac ggttcaagtc ttctcggact   600
cggagtacca gttgccgtac gtcctcggct ctgcgcacca gggctgcctc cctccgttcc   660
cggcggacgt gttcatga                                                  678
```

<210> SEQ ID NO 29
<211> LENGTH: 681
<212> TYPE: DNA
<213> ORGANISM: adeno-associated virus 7

<400> SEQUENCE: 29

```
agccgtcacc tcagcgttcc cccgactcct ccacgggcat cggcaagaaa ggccagcagc    60
ccgccagaaa gagactcaat ttcggtcaga ctggcgactc agagtcagtc cccgacccte   120
aacctctcgg agaacctcca gcagcgccct ctagtgtggg atctggtaca gtggctgcag   180
gcggtggcgc accaatggca gacaataacg aaggtgccga cggagtgggt aatgcctcag   240
gaaattggca ttgcgattcc acatggctgg gcgacagagt cattaccacc agcacccgaa   300
cctgggccct gcccacctac aacaaccacc tctacaagca atctccagt gaaactgcag    360
gtagtaccaa cgacaacacc tacttcggct acagcacccc ctgggggtat tttgacttta   420
acagattcca ctgccacttc tcaccacgtg actggcagcg actcatcaac aacaactggg   480
gattccggcc caagaagctg cggttcaagc tcttcaacat ccaggtcaag gaggtcacga   540
cgaatgacgg cgttacgacc atcgctaata accttaccag cacgattcag gtattctcgg   600
actcggaata ccagctgccg tacgtcctcg gctctgcgca cagggctgc ctgcctccgt     660
tcccggcgga cgtcttcatg a                                              681
```

<210> SEQ ID NO 30
<211> LENGTH: 684
<212> TYPE: DNA
<213> ORGANISM: adeno-associated virus 8

<400> SEQUENCE: 30

```
agccatcacc ccagcgttct ccagactcct ctacgggcat cggcaagaaa ggccaacagc    60
ccgccagaaa aagactcaat tttggtcaga ctggcgactc agagtcagtt ccagaccctc   120
aacctctcgg agaacctcca gcagcgccct ctggtgtggg acctaataca atggctgcag   180
gcggtggcgc accaatggca gacaataacg aaggcgccga cggagtgggt agttcctcgg   240
gaaattggca ttgcgattcc acatggctgg gcgacagagt catcaccacc agcacccgaa   300
cctgggccct gcccacctac aacaaccacc tctacaagca aatctccaac gggacatcgg   360
gaggagccac caacgacaac acctacttcg gctacagcac cccctggggg tattttgact   420
```

```
ttaacagatt ccactgccac ttttcaccac gtgactggca gcgactcatc aacaacaact    480
ggggattccg gcccaagaga ctcagcttca agctcttcaa catccaggtc aaggaggtca    540
cgcagaatga aggcaccaag accatcgcca ataacctcac cagcaccatc caggtgttta    600
cggactcgga gtaccagctg ccgtacgttc tcggctctgc ccaccagggc tgcctgcctc    660
cgttcccggc ggacgtgttc atga                                          684
```

```
<210> SEQ ID NO 31
<211> LENGTH: 681
<212> TYPE: DNA
<213> ORGANISM: adeno-associated virus 9

<400> SEQUENCE: 31
agcagtctcc tcaggaaccg gactcctccg cgggtattgg caaatcgggt gcacagcccg     60
ctaaaaagag actcaatttc ggtcagactg gcgacacaga gtcagtccca gaccctcaac    120
caatcggaga acctcccgca gcccctcag gtgtgggatc tcttacaatg gcttcaggtg    180
gtggcgcacc agtggcagac aataacgaag gtgccgatgg agtgggtagt tcctcgggaa    240
attggcattg cgattcccaa tggctggggg acagagtcat caccaccagc acccgaacct    300
gggccctgcc cacctacaac aatcacctct acaagcaaat ctccaacagc acatctggag    360
gatcttcaaa tgacaacgcc tacttcggct acagcacccc ctgggggtat tttgacttca    420
acagattcca ctgccacttc tcaccacgtg actggcagcg actcatcaac aacaactggg    480
gattccggcc taagcgactc aacttcaagc tcttcaacat tcaggtcaaa gaggttacgg    540
acaacaatgg agtcaagacc atcgccaata accttaccag cacggtccag gtcttcacgg    600
actcagacta tcagctcccg tacgtgctcg ggtcggctca cgagggctgc ctcccgccgt    660
tcccagcgga cgttttcatg a                                             681
```

```
<210> SEQ ID NO 32
<211> LENGTH: 606
<212> TYPE: DNA
<213> ORGANISM: adeno-associated virus 10

<400> SEQUENCE: 32
actttgggca gactggcgag tcagagtcag tccccgaccc tcaaccaatc ggagaaccac     60
cagcaggccc ctctggtctg ggatctggta caatggctgc aggcggtggc gctccaatgg    120
cagacaataa cgaaggcgcc gacggagtgg gtagttcctc aggaaattgg cattgcgatt    180
ccacatggct gggcgacaga gtcatcacca ccagcacccg aacctgggcc ctgcccacct    240
acaacaacca cctctacaag caaatctcca cgggacatc gggaggaagc accaacgaca    300
acacctactt cggctacagc accccctggg ggtattttga cttcaacaga ttccactgcc    360
acttctcacc acgtgactgg cagcgactca tcaacaacaa ctggggattc cggccaaaaa    420
gactcagctt caagctcttc aacatccagg tcaaggaggt cacgcagaat gaaggcacca    480
agaccatcgc caataacctt accagcacga ttcaggtatt acggactcg gaataccagc    540 tgccgtacgt cctcggctcc gcgcaccagg gctgcctgcc tccgttcccg gcggatgtct    600
tcatga                                                              606
```

```
<210> SEQ ID NO 33
<211> LENGTH: 594
<212> TYPE: DNA
<213> ORGANISM: adeno-associated virus 11
```

<400> SEQUENCE: 33

```
agtcaccaca agagcccgac tcctcctcgg gcatcggcaa aaaaggcaaa caaccagcca      60
gaaagaggct caactttgaa gaggacactg gagccggaga cggacccct gaaggatcag     120
ataccagcgc catgtcttca gacattgaaa tgcgtgcagc accgggcgga atgctgtcg     180
atgcgggaca aggttccgat ggagtgggta atgcctcggg tgattggcat tgcgattcca     240
cctggtctga gggcaaggtc acaacaacct cgaccagaac ctgggtcttg cccacctaca     300
acaaccactt gtacctgcgt ctcggaacaa catcaagcag caacacctac aacggattct     360
ccacccctg gggatatttt gacttcaaca gattccactg tcacttctca ccacgtgact      420
ggcaaagact catcaacaac aactggggac tacgaccaaa agccatgcgc gttaaaatct     480
tcaatatcca agttaaggag gtcacaacgt cgaacggcga gactacggtc gctaataacc     540
ttaccagcac ggttcagata tttgcggact cgtcgtatga gctcccgtac gtga           594
```

<210> SEQ ID NO 34
<211> LENGTH: 621
<212> TYPE: DNA
<213> ORGANISM: adeno-associated virus 12

<400> SEQUENCE: 34

```
aaaagactcc aaatcggccg accaacccgg actctgggaa ggccccggcc aagaaaaagc      60
aaaaagacgg cgaaccagcc gactctgcta aaggacact cgactttgaa gactctggag     120
caggagacgg accccctgag ggatcatctt ccggagaaat gtctcatgat gctgagatgc     180
gtgcggcgcc aggcggaaat gctgtcgagg cgggacaagg tgccgatgga gtgggtaatg     240
cctccggtga ttggcattgc gattccacct ggtcagaggg ccgagtcacc accaccagca     300
cccgaacctg gtcctacccc acgtacaaca accacctgta cctgcgaatc ggaacaacgg     360
ccaacagcaa cacctacaac ggattctcca cccctgggg atactttgac tttaaccgct     420
tccactgcca cttttcccca cgcgactggc agcgactcat caacaacaac tggggactca     480
ggccgaaatc gatgcgtgtt aaaatcttca acatacaggt caaggaggtc acgacgtcaa     540
acggcgagac tacggtcgct aataacctta ccagcacggt tcagatcttt gcggattcga     600
cgtatgaact cccatacgtg a                                               621
```

<210> SEQ ID NO 35
<211> LENGTH: 600
<212> TYPE: DNA
<213> ORGANISM: bovine adeno-associated virus

<400> SEQUENCE: 35

```
agcagagtcc tcaagagcca gactcctcga gcggagttgg caagaaaggc aaacagcctg      60
ccagaaagag actcaacttt gacgacgaac ctggagccgg agacgggcct cccccagaag     120
gaccatcttc cggagctatg tctactgaga ctgaaatgcg tgcagcagct ggcggaaatg     180
gtggcgatgc gggacaaggt gccgagggag tgggtaatgc ctccggtgat tggcattgcg     240
attccacttg gtcagagagc cacgtcacca ccacctcaac ccgcacctgg tcctgccga      300
cctacaacaa ccacctgtac ctgcggctcg gctcgagcaa cgccagcgac accttcaacg     360
gattctccac cccctgggga tactttgact ttaaccgctt ccactgccac ttctcgccaa     420
gagactggca aaggctcatc aacaaccact ggggactgcg ccccaaaagc atgcaagtcc     480
gcatcttcaa catccaagtt aaggaggtca cgacgtctaa cggggagacg accgtatcca     540
acaacctcac cagcacggtc cagatctttg cggacagcac gtacgagctc ccgtacgtga     600
```

<210> SEQ ID NO 36
<211> LENGTH: 789
<212> TYPE: DNA
<213> ORGANISM: avian adeno-associated virus ATCC VR-865

<400> SEQUENCE: 36

```
gtaaagccat cttccaggcc aaaaagaggg ttctcgaacc ctttggtctg gtggaagact      60
caaagacggc tccgaccgga gacaagcgga aaggcgaaga cgaacctcgt ttgcccgaca     120
cttcttcaca gactcccaag aaaaacaaga agcctcgcaa ggaaagacct ccggcgggg     180
cagaagatcc gggcgaaggc acctcttcca acgctggagc agcagcaccc gcctctagtg     240
tgggatcatc tatcatggct gaaggaggtg gcggcccagt gggcgatgca ggccagggtg     300
ccgatggagt gggcaattcc tccggaaatt ggcattgcga ttcccaatgg ctggaaaacg     360
gagtcgtcac tcgaaccacc cgaacctggg tcttgcccag ctacaacaac cacctgtaca     420
aacgaatcca aggacccagc ggaggcgaca caacaacaa attctttgga ttcagcaccc     480
cctggggata ctttgactac aatcgattcc actgccactt ttccccgcga gactggcaac     540
gactcatcaa caacaactgg ggcatccgtc ccaaagcgat gcgctttaga ctctttaaca     600
tccaggttaa agaggtcacg gtccaagact tcaacaccac catcggcaac aacctcacca     660
gtacggtcca ggtctttgcg acaaggact accaactgcc gtacgtcctc ggatcggcta     720
ccgaaggcac cttcccgccg ttcccagcgg atatctacac gatcccgcag tacgggtact     780
gcacgctaa                                                             789
```

<210> SEQ ID NO 37
<211> LENGTH: 627
<212> TYPE: DNA
<213> ORGANISM: adeno-associated virus 13

<400> SEQUENCE: 37

```
attttggtca gactggcgac acagagtcag tcccagaccc tcaaccactc ggacaacctc      60
ccgcagcccc ctctggtgtg ggatctacta caatggcttc aggcggtggc gcaccaatgg     120
cagacaataa cgagggtgcc gatggagtgg gtaattcctc aggaaattgg cattgcgatt     180
cccaatggct gggcgacaga gtcatcacca ccagcacccg cacctgggcc ctgcccacct     240
acaacaatca cctctacaag caaatctcca gccaatcagg agccaccaac gacaaccact     300
actttggcta cagcaccccc tgggggtatt ttgacttcaa cagattccac tgccactttt     360
caccacgtga ctggcaaaga ctcatcaaca acaactgggg attccgaccc aagagactca     420
acttcaagct ctttaacatt caagtcaaag aggtcacgca gaatgacggt acgacgacga     480
ttgccaataa ccttaccagc acggttcagg tgtttactga ctccgagtac cagctcccgt     540
acgtcctcgg ctcggcgcat cagggatgcc tcccgccgtt cccagcagac gtcttcatgg     600
tcccacagta tggataccte accctga                                        627
```

<210> SEQ ID NO 38
<211> LENGTH: 534
<212> TYPE: DNA
<213> ORGANISM: mouse adeno-associated virus 1

<400> SEQUENCE: 38

```
acgaggagga ccgtgagttc gctgccgctg cagcggagac cgaaactgga agcgctcccc      60
ccaccggcaa tttgggacct ggtacgatgg ctggaggcgg tagcgcgcca atcgacgacg     120
```

```
gctcgtatgg tgccgatgga gtgggcaatg cctcgggaga ttggcattgc gattccacat    180
ggctggacaa ctgtgtcatc acccgaacca ctcggacctg gaatctgcca acctacaaca    240
accacatcta caaacgactc aacggaacga cctccggaga ccaaagctac ttcggattca    300
gcacccsctg gggatacttt gacttcaacc gcttccactg tcatttctcc cctcgagact    360
ggcaaagact catcaacaat aactggggac tccgaccaaa gagcctacgg ttcaaaatct    420
ttaacattca agttaaagaa gtcacgacgc aagactcaac gaagatcatc tccaataacc    480
ttaccagcac ggttcaggta tttgcggaca cggagtacca gctcccgtac gtga           534

<210> SEQ ID NO 39
<211> LENGTH: 723
<212> TYPE: DNA
<213> ORGANISM: avian adeno-associated virus strain DA-1

<400> SEQUENCE: 39
ttgaacaacc cgacaacacg gccgggaccg gggagaagcg tcccgaacgc gtcgacgact     60
ttttcccgaa aagaagaag gccaagaccg agcaaggcaa agcccctgct caaacgggcg    120
aagaccccgg agaaggaacc tcttccaacg ctggatcaag cgcccccctct agtgtgggat    180 catctgtcat ggctgaagga ggtggcggtc aatgggcga tgcaggccaa ggtgccgacg    240
gagtgggcaa ttcctcggga aattggcatt gcgattccca atggctggac aacggagtcg    300
ttacccgaac cactcgaacc tgggtcctgc ccagctacaa caaccacttg tacaagcgga    360
tccaaggacc gggaggaacc gaccccaaca ataaattctt tggattcagc accccctggg    420
ggtactttga ctacaaccga ttccactgcc acttctcccc cgagactgg caacgactca    480 tcaacaacaa ctggggcatc cgacccaaag cgatgcgctt tagactcttt aacatccagg    540
ttaaagaagt cactgtccaa gactccaaca ccaccatcgc caacaacctc accagcacgg    600
tccaagtctt tgcggacaag gactaccagc tgccgtacgt cctcggatcg gctacagagg    660
gcaccttccc gccgttccca gcggatatct acacgatccc gcagtatggt tactgcacgc    720
taa                                                                     723

<210> SEQ ID NO 40
<211> LENGTH: 581
<212> TYPE: DNA
<213> ORGANISM: caprine adeno-associated virus 1 isolate adeno-
       associated virus Go.1

<400> SEQUENCE: 40
acgaccactt tccaaaaaga aagaaggctc ggaccgaaga ggactccaag ccttccacct     60
cgtcagacgc cgaagctgga cccagcggat cccagcagct gcaaatccca gcacaaccag    120
cctcaagttt gggagctgat acaatgtctg cggaggtgg cggccattg ggcgacaata    180 accaaggtgc cgatggagtg ggcaatgcct cgggagattg gcattgcgat tccacgtgga    240
tgggggacag agtcgtcacc aagtccaccg cacctgggt gctgcccagc tacaacaacc    300
accagtaccg agagatcaaa agcggctccg tcgacgaag caacgccaac gcctactttg    360
gatacagcac cccctggggg tactttgact taaccgctt ccacagccac tggagccccc    420
gagactggca aagactcatc aacaactatt ggggcttcag accccggtct ctcagagtca    480
aaatcttcaa catccaagtc aaagaggtca cggtgcagga ctccaccacc accatcgcca    540
acaacctcac ctccaccgtc caagtgttta cggacgacga c                         581

<210> SEQ ID NO 41
```

<211> LENGTH: 756
<212> TYPE: DNA
<213> ORGANISM: rat adeno-associated virus 1

<400> SEQUENCE: 41

```
gcgtcgagga gccggagctg gctcctccag tcaagcgtcc acactcgccc gagaaaaccc      60
cagagaacca gaagggtcag ccgcgaccgg atccccggac gccggccaag aagaggctcg     120
agttctccga tcagcctgga tcttcagcag acttacctgc atcctcacaa cagtcccagc     180
ctcccgcagg ggttcccggt gtggttcctg gtacgatgtc tgcaggagga ggcgctccag     240
tggacgatgc tcaacaaggt gccgacggag tgggcaatgc tcgggagat tggcattgcg      300
attccaaatg gctgggcaac cgagttctca cccgatccac ccggacctgg gtgctgccca     360
gctacaacaa ccacctgtac aagcagatct cagacgcctc cggcgtgcac agcctccccg     420
ggagccgata ctttggctac agcaccccct ggggggtactt cgacttcaat cgcttccact     480
gccacttctc gcccagagac tggcagcgcc tcgtcaataa ccactgggc ttccgaccca      540
agagactgcg agtcaaactc ttcaacatcc aggtcaagga ggtcacgact actgattcga     600
cgaccacggt ctccaacaac ctcacgagca cggtccaggt cttcacagac gacgagtacc     660
agctgccgta cgtctgcggc aacgccaccg agggatgcct gccgccgttc cccccggacg     720
tcttcacgct gccgcagtac ggctacgcga cgctga                               756
```

<210> SEQ ID NO 42
<211> LENGTH: 639
<212> TYPE: DNA
<213> ORGANISM: goose parvovirus strain DB3

<400> SEQUENCE: 42

```
aagacggagg agccaccgcg gagggcaccg aacctgtggc agcatctgaa atggcagagg      60
gaggaggcgg agctatgggc gactcttcag ggggtgccga tggagtgggt aatgcctcgg     120
gaaattggca ttgcgattcc caatggatgg gaaacacagt catcacaaag accaccagaa     180
cctgggtcct gccaagctac aacaaccaca tctacaaagc aattaccagt ggaacctctc     240
aagatgcaaa tgtccagtat gcaggataca gtaccccctg ggggtacttt gatttcaacc     300
gcttccactg ccacttctcc cctagagact ggcagagact tatcaacaac cattggggaa     360
tccgacccaa atctcttaaa ttcaagatct tcaatgtcca agtcaaagaa gtcacaacgc     420
aggatcaaac aaagaccatt gcaaacaatc tcacctcaac gattcaagtc tttacggatg     480
atgagcatca actcccgtat gtcctgggct cggctacgga aggcaccatg ccgccgttcc     540
cgtcggatgt ctatgccctg ccgcagtacg ggtactgcac aatgcacacc aaccagaatg     600
gagcacggtt caatgaccgt agtgcattct actgcttag                             639
```

<210> SEQ ID NO 43
<211> LENGTH: 693
<212> TYPE: DNA
<213> ORGANISM: duck parvovirus strain 90-0219

<400> SEQUENCE: 43

```
aaaagcctaa attatctgaa gaaaactctc cttcacccag taatagtgga ggagaagcaa      60
gtgcagctgc caccgaaggc tccgaacctg tggcagcacc taacatggca gagggaggaa     120
gcggagctat gggcgactct gcaggggtg ccgatggagt gggtaatgcc tcaggaaatt      180
ggcattgcga ttcccaatgg ctgggagaca cagtcattac caagactaca agaacctggg     240
tcctgccaag ctacaacaac cacatctaca agccatcac aagcggaaca aacccagaca     300
```

```
caaatacccca atatgctgga tacagcaccc cctgggggta ctttgatttc aacagattcc    360
actgccattt ctctccaaga gactggcaga gactcatcaa caaccattgg gggattagac    420
cgaaagcact caaattcaag atattcaatg tgcaagttaa agaagtcacg acgcaagacc    480
agacaaagac tattgctaac aaccttacct ctacaatcca gatattcacg ataatgaac    540 accagctgcc ctatgttctg ggctcggcca cggaggggac gatgccaccg ttcccctcag    600
atgtgtatgc cttgccccag tacggctact gcacaatgca caccaaccag agtggagcta    660
gattcaatga cagaagtgcc ttctattgct tag                                  693
```

```
<210> SEQ ID NO 44
<211> LENGTH: 600
<212> TYPE: DNA
<213> ORGANISM: snake parvovirus 1

<400> SEQUENCE: 44
acgaatacta tcctaaagct aaaaaggcca aacaaggctt gcagatacca gctccaccta     60
aaggcggaga agaagaagct acatcgtcac aatctggagg gagcccagca ggttccgata    120
ctagcggcac atctgtcatg gctacaggag gaggcggtcc gatggcagac gataaccagg    180
gcgccgaggg agtgggtaat tcctcaggtg attggcattg cgataccaag tggatgggag    240
accacgtcat tacaaagtca accagaactt gggtgctccc cacttacggg aatcatctct    300
acgggcctat caactttgac ggcaccacag gttcgggtgc taatgcagcc tatgcaggat    360
acaagactcc ctgggggtac tttgacttca atcgattcca ttgccacttc tccccccgag    420
actggcaaag actcatcaac aaccacacag gcatcaggcc gaaaggactc aaaatcaaag    480
tctttaacgt ccaagtcaaa gaagttacaa cacaagattc aacgaaaaca attgccaaca    540
atctcaccag caccgtacag atctttgcgg acgagaacta cgacttacca tatgtattag    600
```

```
<210> SEQ ID NO 45
<211> LENGTH: 287
<212> TYPE: DNA
<213> ORGANISM: Artificial
<220> FEATURE:
<223> OTHER INFORMATION: fragment Z derived from adeno-associated virus
      2

<400> SEQUENCE: 45
tcggacagcc accagcagcc ccctctggtc tgggaactaa tacgatggct acaggcagtg     60
gcgcaccaat ggcagacaat aacgagggcg ccgacggagt gggtaattcc tcgggaaatt    120
ggcattgcga ttccacatgg atgggcgaca gagtcatcac caccagcacc cgaacctggg    180
ccctgcccac ctacaacaac cacctctaca aacaaatttc cagccaatca ggagcctcga    240
acgacaatca ctactttggc tacagcaccc cttggggta ttttgac                   287
```

```
<210> SEQ ID NO 46
<211> LENGTH: 287
<212> TYPE: DNA
<213> ORGANISM: Unknown
<220> FEATURE:
<223> OTHER INFORMATION: unknown DNA fragment as fragment Z of adeno-
      associated virus

<400> SEQUENCE: 46
gtcaaaatac ccccaagggg tgctgtagcc aaagtagtga ttgtcgttcg aggctcctga     60
ttggctggaa atttgtttgt agaggtggtt gttgtaggtg gcagggccc aggttcgggt    120
```

```
gctggtggtg atgactctgt cgcccatcca tgtggaatcg caatgccaat ttcccgagga    180 attaccccact ccgtcggcgc cctcgttatt gtctgccatt ggtgcgccac tgcctgtagc    240
catcgtatta gttcccagac cagagggggc tgctggtggc tgtccga                  287
```

```
<210> SEQ ID NO 47
<211> LENGTH: 286
<212> TYPE: DNA
<213> ORGANISM: adeno-associated virus 1

<400> SEQUENCE: 47
tcggagaacc tccagcaacc cccgctgctg tgggacctac tacaatggct tcaggcggtg    60
gcgcaccaat ggcagacaat aacgaaggcg ccgacggagt gggtaatgcc tcaggaaatt    120
ggcattgcga ttcccacatgg ctgggcgaca gagtcatcac caccagcacc cgcacctggg    180
ccttgcccac ctacaataac cacctctaca agcaaatctc cagtgcttca acgggggcca    240
gcaacgacaa ccactacttc ggctacagca ccccctgggg gtattt                   286
```

```
<210> SEQ ID NO 48
<211> LENGTH: 286
<212> TYPE: DNA
<213> ORGANISM: adeno-associated virus 3b

<400> SEQUENCE: 48
tcggagaacc accagcagcc cccacaagtt tgggatctaa tacaatggct tcaggcggtg    60
gcgcaccaat ggcagacaat aacgagggtg ccgatggagt gggtaattcc tcaggaaatt    120
ggcattgcga ttcccaatgg ctgggcgaca gagtcatcac caccagcacc agaacctggg    180
ccctgcccac ttacaacaac catctctaca agcaaatctc cagccaatca ggagcttcaa    240
acgacaacca ctactttggc tacagcaccc cttgggggta ttttga                   286
```

```
<210> SEQ ID NO 49
<211> LENGTH: 286
<212> TYPE: DNA
<213> ORGANISM: adeno-associated virus 4

<400> SEQUENCE: 49
cccctgaggg atcaacttcc ggagccatgt ctgatgacag tgagatgcgt gcagcagctg    60
gcggagctgc agtcgagggc ggacaaggtg ccgatggagt gggtaatgcc tcgggtgatt    120
ggcattgcga ttccacctgg tctgagggcc acgtcacgac caccagcacc agaacctggg    180
tcttgcccac ctacaacaac cacctctaca agcgactcgg agagagcctg cagtccaaca    240
cctacaacgg attctccacc ccctggggat actttgactt caaccg                   286
```

```
<210> SEQ ID NO 50
<211> LENGTH: 286
<212> TYPE: DNA
<213> ORGANISM: adeno-associated virus 5

<400> SEQUENCE: 50
tgcaaatccc agcccaacca gcctcaagtt tgggagctga tacaatgtct gcgggaggtg    60
gcggcccatt gggcgacaat aaccaaggtg ccgatggagt gggcaatgcc tcgggagatt    120
ggcattgcga ttccacgtgg atgggggaca gagtcgtcac caagtccacc cgaacctggg    180
tgctgcccag ctacaacaac caccagtacc gagagatcaa aagcggctcc gtcgacggaa    240
gcaacgccaa cgcctacttt ggatacagca ccccctgggg gtactt                   286
```

<210> SEQ ID NO 51
<211> LENGTH: 286
<212> TYPE: DNA
<213> ORGANISM: adeno-associated virus 6

<400> SEQUENCE: 51

```
tcggagaacc tccagcaacc cccgctgctg tgggacctac tacaatggct tcaggcggtg      60
gcgcaccaat ggcagacaat aacgaaggcg ccgacggagt gggtaatgcc tcaggaaatt     120
ggcattgcga ttccacatgg ctgggcgaca gagtcatcac caccagcacc cgaacatggg     180
ccttgcccac ctataacaac cacctctaca agcaaatctc cagtgcttca acgggggcca     240
gcaacgacaa ccactacttc ggctacagca ccccctgggg gtattt                    286
```

<210> SEQ ID NO 52
<211> LENGTH: 286
<212> TYPE: DNA
<213> ORGANISM: adeno-associated virus 7

<400> SEQUENCE: 52

```
ctagtgtggg atctggtaca gtggctgcag gcggtggcgc accaatggca gacaataacg      60
aaggtgccga cggagtgggt aatgcctcag gaaattggca ttgcgattcc acatggctgg     120
gcgacagagt cattaccacc agcacccgaa cctgggccct gcccacctac aacaaccacc     180
tctacaagca aatctccagt gaaactgcag gtagtaccaa cgacaacacc tacttcggct     240
acagcacccc ctgggggtat tttgacttta acagattcca ctgcca                    286
```

<210> SEQ ID NO 53
<211> LENGTH: 286
<212> TYPE: DNA
<213> ORGANISM: adeno-associated virus 8

<400> SEQUENCE: 53

```
tcggagaacc tccagcagcg ccctctggtg tgggacctaa tacaatggct gcaggcggtg      60
gcgcaccaat ggcagacaat aacgaaggcg ccgacggagt gggtagttcc tcgggaaatt     120
ggcattgcga ttccacatgg ctgggcgaca gagtcatcac caccagcacc cgaacctggg     180
ccctgcccac ctacaacaac cacctctaca agcaaatctc caacgggaca tcgggaggag     240
ccaccaacga caacacctac ttcggctaca gcaccccctg ggggta                    286
```

<210> SEQ ID NO 54
<211> LENGTH: 286
<212> TYPE: DNA
<213> ORGANISM: adeno-associated virus 10

<400> SEQUENCE: 54

```
tcggagaacc accagcaggc ccctctggtc tgggatctgg tacaatggct gcaggcggtg      60
gcgctccaat ggcagacaat aacgaaggcg ccgacggagt gggtagttcc tcaggaaatt     120
ggcattgcga ttccacatgg ctgggcgaca gagtcatcac caccagcacc cgaacctggg     180
ccctgcccac ctacaacaac cacctctaca agcaaatctc caacgggaca tcgggaggaa     240
gcaccaacga caacacctac ttcggctaca gcaccccctg ggggta                    286
```

<210> SEQ ID NO 55
<211> LENGTH: 286
<212> TYPE: DNA
<213> ORGANISM: adeno-associated virus 11

<400> SEQUENCE: 55

```
cccctgaagg atcagatacc agcgccatgt cttcagacat tgaaatgcgt gcagcaccgg    60
gcggaaatgc tgtcgatgcg ggacaaggtt ccgatggagt gggtaatgcc tcgggtgatt   120
ggcattgcga ttccacctgg tctgagggca aggtcacaac aacctcgacc agaacctggg   180
tcttgcccac ctacaacaac cacttgtacc tgcgtctcgg aacaacatca agcagcaaca   240
cctacaacgg attctccacc ccctggggat attttgactt caacag                  286

<210> SEQ ID NO 56
<211> LENGTH: 286
<212> TYPE: DNA
<213> ORGANISM: bovine adeno-associated virus 1

<400> SEQUENCE: 56
ccccagaagg accatcttcc ggagctatgt ctactgagac tgaaatgcgt gcagcagctg    60
gcggaaatgg tggcgatgcg ggacaaggtg ccgagggagt gggtaatgcc tccggtgatt   120
ggcattgcga ttccacttgg tcagagagcc acgtcaccac cacctcaacc cgcacctggg   180
tcctgccgac ctacaacaac cacctgtacc tgcggctcgg ctcgagcaac gccagcgaca   240
ccttcaacgg attctccacc ccctggggat actttgactt taaccg                  286

<210> SEQ ID NO 57
<211> LENGTH: 662
<212> TYPE: DNA
<213> ORGANISM: Artificial
<220> FEATURE:
<223> OTHER INFORMATION: ORF1cm

<400> SEQUENCE: 57
ttgaggaacc tgttaagacg gcccctggca agaaacggcc cgtggagcac agccccgtgg    60
agcccgacag cagcagcggc accggcaagg ccggacagca gcccgccaga aagcggctga   120
acttcggcca gaccggcgac gctgatagcg tgcccgaccc tcagcccctg gccagcctc    180 ctgctgctcc tagcggcctc ggcaccaaca ccatggccac cggcagcgga gccccatgg    240 ccgataacaa tgaaggggca gacggcgtgg caacagctc cggcaactgg cactgcgaca    300
gcacctggat gggagatcgg gtgatcacaa cctccacccg gacatgggct ctccctactt   360
ataataatca cctgtacaag cagatcagca gccagagcgg cgccagcaat gataaccact   420
acttcgggta ctctacaccc tggggctact cgatttcaa tcggtttcac tgtcacttca    480
gccccagaga ctggcagcgg ctgattaata ataattgggg cttccggccc aagcggctga   540
atttcaagct gttcaatatc caggtgaagg aagtgaccca gaacgatggc accaccacaa   600
tcgccaacaa cctgacctca accgtgcagg tgttcaccga cagcgagtac cagctgccgt   660
ac                                                                  662

<210> SEQ ID NO 58
<211> LENGTH: 662
<212> TYPE: DNA
<213> ORGANISM: Artificial
<220> FEATURE:
<223> OTHER INFORMATION: ORF2cm

<400> SEQUENCE: 58
ttgaggaacc tgttaagacg gctccgggaa aaaagaggcc ggtagagcac tctcctgtgg    60
agccagactc ctcctcggga accggaaagg cgggccagca gcctgcaaga aaagattga    120 attttggtca gactggagac gcagactcag tacctgaccc ccagcctctc ggacagccac   180
cagcagcccc ctctggtctg gaactaata cgatggctgc aggccgtggc ccaccagtgg   240
```

```
cagaccatca ccagagcccc caccgagtgg gtgatccctc gggagatcgg cattgccatc    300
cctcacggct gggccacaga gtctagccct ccagcccctg agcctggccc ttgtccccct    360
accaccacca cctccaccaa caagttcccc gccaaccagg aaccccggac caccatcacc    420
acactggcca cagcccctct gggcggcatc ctgaccagca ccgacagcac cgccaccttt    480
caccacgtga ccggcaagga cagcagcacc accaccggcg acagcgaccc cagagacagc    540
accagctcca gcctgacctt caagagcaag cggagcagac ggatgaccgt gcggcggaga    600
ctgcctatca ccctgcccgc cagattccgg tgcctgctga ccagaagcac cagcagccgt    660
ac                                                                   662
```

```
<210> SEQ ID NO 59
<211> LENGTH: 30
<212> TYPE: DNA
<213> ORGANISM: Artificial
<220> FEATURE:
<223> OTHER INFORMATION: XbaI-VAI-780-3' primer for the VAI-VAII
      fragment from pAdVAntage

<400> SEQUENCE: 59
tctagagggc actcttccgt ggtctggtgg                                     30
```

```
<210> SEQ ID NO 60
<211> LENGTH: 33
<212> TYPE: DNA
<213> ORGANISM: Artificial
<220> FEATURE:
<223> OTHER INFORMATION: XbaI-VAII-1200-5' primer VAI-VAII fragment from
      pAdVAntage

<400> SEQUENCE: 60
tctagagcaa aaaggggct cgtccctgtt tcc                                  33
```

```
<210> SEQ ID NO 61
<211> LENGTH: 18
<212> TYPE: PRT
<213> ORGANISM: Artificial
<220> FEATURE:
<223> OTHER INFORMATION: peptide for the generation of polyclonal AAP
      antiserum (anti-AAP)

<400> SEQUENCE: 61

Gly Lys Asp Ser Ser Thr Thr Thr Gly Asp Ser Asp Pro Arg Asp Ser
1               5                   10                  15

Thr Ser
```

```
<210> SEQ ID NO 62
<211> LENGTH: 42
<212> TYPE: DNA
<213> ORGANISM: Artificial
<220> FEATURE:
<223> OTHER INFORMATION: primer for the generation of a novel HindIII
      restriction site

<400> SEQUENCE: 62
cctctggtct gggaactaag cttatggcta caggcagtgg cg                       42
```

```
<210> SEQ ID NO 63
<211> LENGTH: 42
<212> TYPE: DNA
<213> ORGANISM: Artificial
<220> FEATURE:
<223> OTHER INFORMATION: primer for the generation of a novel HindIII
``` restriction site

<400> SEQUENCE: 63
cgccactgcc tgtagccata agcttagttc ccagaccaga gg                           42

<210> SEQ ID NO 64
<211> LENGTH: 28
<212> TYPE: DNA
<213> ORGANISM: Artificial
<220> FEATURE:
<223> OTHER INFORMATION: primer for StopA in pVP2N-gfp

<400> SEQUENCE: 64
ccagcctctc ggatagccac cagcagcc                                          28

<210> SEQ ID NO 65
<211> LENGTH: 28
<212> TYPE: DNA
<213> ORGANISM: Artificial
<220> FEATURE:
<223> OTHER INFORMATION: primer for i-StopA in pVP2N-gfp

<400> SEQUENCE: 65
ggctgctggt ggctatccga gaggctgg                                          28

<210> SEQ ID NO 66
<211> LENGTH: 32
<212> TYPE: DNA
<213> ORGANISM: Artificial
<220> FEATURE:
<223> OTHER INFORMATION: primer for StopB in pVP2N-gfp

<400> SEQUENCE: 66 gcccctctg gtctgtgaac taatacgatg gc                                      32

<210> SEQ ID NO 67
<211> LENGTH: 32
<212> TYPE: DNA
<213> ORGANISM: Artificial
<220> FEATURE:
<223> OTHER INFORMATION: primer for i-StopB in pVP2N-gfp

<400> SEQUENCE: 67
gccatcgtat tagttcacag accagagggg gc                                     32

<210> SEQ ID NO 68
<211> LENGTH: 31
<212> TYPE: DNA
<213> ORGANISM: Artificial
<220> FEATURE:
<223> OTHER INFORMATION: primer for StopC in pVP2N-gfp

<400> SEQUENCE: 68
cgatggctac aggctgaggc gcaccaatgg c                                      31

<210> SEQ ID NO 69
<211> LENGTH: 31
<212> TYPE: DNA
<213> ORGANISM: Artificial
<220> FEATURE:
<223> OTHER INFORMATION: primer for i-StopC in pVP2N-gfp

<400> SEQUENCE: 69
gccattggtg cgcctcagcc tgtagccatc g                                      31

-continued

```
<210> SEQ ID NO 70
<211> LENGTH: 34
<212> TYPE: DNA
<213> ORGANISM: Artificial
<220> FEATURE:
<223> OTHER INFORMATION: primer for StopD in pVP2N-gfp

<400> SEQUENCE: 70
ggagtgggta attcctcgtg aaattggcat tgcg                              34

<210> SEQ ID NO 71
<211> LENGTH: 34
<212> TYPE: DNA
<213> ORGANISM: Artificial
<220> FEATURE:
<223> OTHER INFORMATION: primer for i-StopD in pVP2N-gfp

<400> SEQUENCE: 71
cgcaatgcca atttcacgag gaattaccca ctcc                              34

<210> SEQ ID NO 72
<211> LENGTH: 48
<212> TYPE: DNA
<213> ORGANISM: Artificial
<220> FEATURE:
<223> OTHER INFORMATION: BC3-ala forward primer

<400> SEQUENCE: 72
ggcgggccag cagcctgcag cagcagcatt gaattttggt cagactgg               48

<210> SEQ ID NO 73
<211> LENGTH: 48
<212> TYPE: DNA
<213> ORGANISM: Artificial
<220> FEATURE:
<223> OTHER INFORMATION: BC3-ala reverse prime

<400> SEQUENCE: 73
ccagtctgac caaaattcaa tgctgctgct gcaggctgct ggcccgcc               48

<210> SEQ ID NO 74
<211> LENGTH: 69
<212> TYPE: DNA
<213> ORGANISM: Artificial
<220> FEATURE:
<223> OTHER INFORMATION: primer for pCMV-NLS-VP3 of pCMV-VP3/2809 as
      template

<400> SEQUENCE: 74
ggaattcgat atcaagcttg ccatggcacc accaaagaag aagcgaaagg ttatggctac   60
aggcagtgg                                                          69

<210> SEQ ID NO 75
<211> LENGTH: 69
<212> TYPE: DNA
<213> ORGANISM: Artificial
<220> FEATURE:
<223> OTHER INFORMATION: primer for pCMV-NLS-VP3 of pCMV-VP3/2809 as
      template

<400> SEQUENCE: 75
ccactgcctg tagccataac ctttcgcttc ttctttggtg gtgccatggc aagcttgata   60
tcgaattcc                                                          69

<210> SEQ ID NO 76
```

-continued

<211> LENGTH: 129
<212> TYPE: DNA
<213> ORGANISM: Artificial
<220> FEATURE:
<223> OTHER INFORMATION: fragment of human serum albumin (HSA) directly upstream of the VP3 cds

<400> SEQUENCE: 76
ggtaccaagc ttacggacgc ccacaagagc gaggtggccc accggttcaa ggacctgggc 60
gaggaaaact tcaaggccct ggtgctgatc gccttcgccc agtacctgca gcagtgcaag 120
cttgagctc 129

<210> SEQ ID NO 77
<211> LENGTH: 48
<212> TYPE: DNA
<213> ORGANISM: Artificial
<220> FEATURE:
<223> OTHER INFORMATION: primer Insect_mod_4_s for VP1

<400> SEQUENCE: 77
cacccgcggg gatccgccgc tgccgacggt tatctacccg attggctc 48

<210> SEQ ID NO 78
<211> LENGTH: 31
<212> TYPE: DNA
<213> ORGANISM: Artificial
<220> FEATURE:
<223> OTHER INFORMATION: primer E_VP2_rev for VP1

<400> SEQUENCE: 78
cgcgaattcc tattacagat tacgagtcag g 31

<210> SEQ ID NO 79
<211> LENGTH: 28
<212> TYPE: DNA
<213> ORGANISM: Artificial
<220> FEATURE:
<223> OTHER INFORMATION: primer Insect-muta_4_s for site directed mutagenesis of VP2

<400> SEQUENCE: 79
acctgttaag acagctccgg gaaaaaag 28

<210> SEQ ID NO 80
<211> LENGTH: 28
<212> TYPE: DNA
<213> ORGANISM: Artificial
<220> FEATURE:
<223> OTHER INFORMATION: primer Insect-muta_4_as for site-directed mutagenesis of VP2

<400> SEQUENCE: 80 ctttttttccc ggagctgtct taacaggt 28

<210> SEQ ID NO 81
<211> LENGTH: 39
<212> TYPE: DNA
<213> ORGANISM: Artificial
<220> FEATURE:
<223> OTHER INFORMATION: primer E_VP2_for for adeno-associated virus2 VP2

<400> SEQUENCE: 81
cacccgcggg gatccactat ggctccggga aaaaagagg 39

```
<210> SEQ ID NO 82
<211> LENGTH: 31
<212> TYPE: DNA
<213> ORGANISM: Artificial
<220> FEATURE:
<223> OTHER INFORMATION: primer E_VP2_rev for adeno-associated virus 2
      VP2

<400> SEQUENCE: 82
cgcgaattcc tattacagat tacgagtcag g                                31

<210> SEQ ID NO 83
<211> LENGTH: 40
<212> TYPE: DNA
<213> ORGANISM: Artificial
<220> FEATURE:
<223> OTHER INFORMATION: primer E_VP3_for for adeno-associated virus 2
      VP3

<400> SEQUENCE: 83
cacccgcggg gatccactat ggctacaggc agtggcgcac                       40

<210> SEQ ID NO 84
<211> LENGTH: 31
<212> TYPE: DNA
<213> ORGANISM: Artificial
<220> FEATURE:
<223> OTHER INFORMATION: primer E_VP2_rev for adeno-associated virus 2
      VP3

<400> SEQUENCE: 84
cgcgaattcc tattacagat tacgagtcag g                                31

<210> SEQ ID NO 85
<211> LENGTH: 71
<212> TYPE: DNA
<213> ORGANISM: Artificial
<220> FEATURE:
<223> OTHER INFORMATION: rabbit CETP epitope TP18 sense oligonucleotide
      for cloning of epitope sequences into I-587

<400> SEQUENCE: 85
ggccggcgga ggtgacatca gcgtgaccgg tgcacccgtg atcaccgcca cctacctggg    60
gggtggcggt g                                                         71

<210> SEQ ID NO 86
<211> LENGTH: 71
<212> TYPE: DNA
<213> ORGANISM: Artificial
<220> FEATURE:
<223> OTHER INFORMATION: rabbit CETP epitope TP18 anti-sense nucleotide
      for cloning of epitope sequences into I-587

<400> SEQUENCE: 86
cgcgcaccgc cacccccag gtaggtggcg gtgatcacgg gtgcaccggt cacgctgatg    60
tcacctccgc c                                                        71

<210> SEQ ID NO 87
<211> LENGTH: 68
<212> TYPE: DNA
<213> ORGANISM: Artificial
<220> FEATURE:
<223> OTHER INFORMATION: human IgE epitope 3Depi-3 sense oligonucleotide
      for cloning of epitope sequences into I-587

<400> SEQUENCE: 87
```
ggccggcgga ggtggtgaca gcaaccctag aggcgtgagc gcctacctga gcagagggggg    60 tggcggtg    68

<210> SEQ ID NO 88
<211> LENGTH: 68
<212> TYPE: DNA
<213> ORGANISM: Artificial
<220> FEATURE:
<223> OTHER INFORMATION: human IgE epitope 3Depi-3 anti-sense
      oligonucleotide for cloning of epitope sequences into I-587

<400> SEQUENCE: 88
cgcgcaccgc cacccctct gctcaggtag gcgctcacgc ctctagggtt gctgtcacca    60
cctccgcc    68

<210> SEQ ID NO 89
<211> LENGTH: 56
<212> TYPE: DNA
<213> ORGANISM: Artificial
<220> FEATURE:
<223> OTHER INFORMATION: human IgE epitope Kricek sense oligonucleotide
      for cloning of epitope sequences into I-587

<400> SEQUENCE: 89
ggccgcagcg gcggtgaacc tgacctggag cagagcctcc ggcgcggcgg cggcgg    56

<210> SEQ ID NO 90
<211> LENGTH: 56
<212> TYPE: DNA
<213> ORGANISM: Artificial
<220> FEATURE:
<223> OTHER INFORMATION: human IgE epitope Kricek antisense
      oligonucleotide for cloning of epitope sequences into I-587

<400> SEQUENCE: 90
cgcgccgccg ccgccgcgcc ggaggctctg ctccaggtca ggttcaccgc cgctgc    56

<210> SEQ ID NO 91
<211> LENGTH: 86
<212> TYPE: DNA
<213> ORGANISM: Artificial
<220> FEATURE:
<223> OTHER INFORMATION: murine TNFalpha epitope TNFalpha-V1 sense
      oligonucleotide for cloning of epitope sequences into I-587

<400> SEQUENCE: 91
ggccggcgga ggtagcagcc agaacagcag cgacaagccc gtggcccacg tggtggctaa    60
ccaccaggtg gagggggggtg gcggtg    86

<210> SEQ ID NO 92
<211> LENGTH: 86
<212> TYPE: DNA
<213> ORGANISM: Artificial
<220> FEATURE:
<223> OTHER INFORMATION: murine TNFalpha epitope TNFalpha-V1 anti-sense
      oligonucleotide for cloning of epitope sequences into I-587

<400> SEQUENCE: 92
cgcgcaccgc cacccccctc cacctggtgg ttagccacca cgtgggccac gggcttgtcg    60
ctgctgttct ggctgctacc tccgcc    86

<210> SEQ ID NO 93
<211> LENGTH: 68
<212> TYPE: DNA

<213> ORGANISM: Artificial
<220> FEATURE:
<223> OTHER INFORMATION: murine IL-17 epitope IL-17-V1 sense
      oligonucleotide for cloning of epitope sequences into I-587

<400> SEQUENCE: 93
ggccggcgga ggtaacgccg agggcaagct tgaccaccac atgaacagcg tgctgggggg    60
tggcggtg                                                              68

<210> SEQ ID NO 94
<211> LENGTH: 68
<212> TYPE: DNA
<213> ORGANISM: Artificial
<220> FEATURE:
<223> OTHER INFORMATION: murine IL-17 epitope IL-17-V1 anti-sense
      oligonucleotide for cloning of epitope sequences into I-587

<400> SEQUENCE: 94
cgcgcaccgc caccccccag cacgctgttc atgtggtggt caagcttgcc ctcggcgtta    60
cctccgcc                                                              68

<210> SEQ ID NO 95
<211> LENGTH: 59
<212> TYPE: DNA
<213> ORGANISM: Artificial
<220> FEATURE:
<223> OTHER INFORMATION: murine IL-6 epitope IL-6-V2 sense
      oligonucleotide for cloning of epitope sequences into I-587

<400> SEQUENCE: 95
ggccggcgga ggtctggagg aattcctgaa ggtgaccctg agaagcgggg gtggcggtg     59

<210> SEQ ID NO 96
<211> LENGTH: 59
<212> TYPE: DNA
<213> ORGANISM: Artificial
<220> FEATURE:
<223> OTHER INFORMATION: murine IL-6 epitope IL-6-V2 anti-sense
      oligonucleotide for cloning of epitope sequences into I-587

<400> SEQUENCE: 96
cgcgcaccgc caccccgct tctcagggtc accttcagga attcctccag acctccgcc      59

<210> SEQ ID NO 97
<211> LENGTH: 68
<212> TYPE: DNA
<213> ORGANISM: Artificial
<220> FEATURE:
<223> OTHER INFORMATION: human amyloid-beta epitope Abeta(1-9) sense
      oligonucleotide

<400> SEQUENCE: 97
ggccgcaggc ggaggggag gcgacgccga gttcagacac gacagcggcg gcggaggggg     60
aggcgcgg                                                              68

<210> SEQ ID NO 98
<211> LENGTH: 68
<212> TYPE: DNA
<213> ORGANISM: Artificial
<220> FEATURE:
<223> OTHER INFORMATION: human amyloid-beta epitope Abeta(1-9) anti-
      sense oligonucleotide for cloning of epitope sequences into I-587

<400> SEQUENCE: 98
cgcgccgcgc ctccccctcc gccgccgctg tcgtgtctga actcggcgtc gcctcccct     60 ccgcctgc                                                          68

<210> SEQ ID NO 99
<211> LENGTH: 15
<212> TYPE: PRT
<213> ORGANISM: Artificial
<220> FEATURE:
<223> OTHER INFORMATION: CETP TP18 epitope at I-587

<400> SEQUENCE: 99

Asp Ile Ser Val Thr Gly Ala Pro Val Ile Thr Ala Thr Tyr Leu
1               5                   10                  15

<210> SEQ ID NO 100
<211> LENGTH: 13
<212> TYPE: PRT
<213> ORGANISM: Artificial
<220> FEATURE:
<223> OTHER INFORMATION: 3Depi-3 epitope at I-587

<400> SEQUENCE: 100

Asp Ser Asn Pro Arg Gly Val Ser Ala Tyr Leu Ser Arg
1               5                   10

<210> SEQ ID NO 101
<211> LENGTH: 10
<212> TYPE: PRT
<213> ORGANISM: Artificial
<220> FEATURE:
<223> OTHER INFORMATION: Kricek epitope at I-587

<400> SEQUENCE: 101

Val Asn Leu Thr Trp Ser Arg Ala Ser Gly
1               5                   10

<210> SEQ ID NO 102
<211> LENGTH: 20
<212> TYPE: PRT
<213> ORGANISM: Artificial
<220> FEATURE:
<223> OTHER INFORMATION: TNFalpha-V1 epitope at I-587

<400> SEQUENCE: 102

Ser Ser Gln Asn Ser Ser Asp Lys Pro Val Ala His Val Val Ala Asn
1               5                   10                  15

His Gln Val Glu
            20

<210> SEQ ID NO 103
<211> LENGTH: 14
<212> TYPE: PRT
<213> ORGANISM: Artificial
<220> FEATURE:
<223> OTHER INFORMATION: IL-17-V1 epitope at I-587

<400> SEQUENCE: 103

Asn Ala Glu Gly Lys Leu Asp His His Met Asn Ser Val Leu
1               5                   10

<210> SEQ ID NO 104
<211> LENGTH: 11
<212> TYPE: PRT
<213> ORGANISM: Artificial
<220> FEATURE:
<223> OTHER INFORMATION: IL-6-V2 epitope at I-587

<400> SEQUENCE: 104

Leu Glu Glu Phe Leu Lys Val Thr Leu Arg Ser
1               5                   10

<210> SEQ ID NO 105
<211> LENGTH: 9
<212> TYPE: PRT
<213> ORGANISM: Artificial
<220> FEATURE:
<223> OTHER INFORMATION: A(1-9) epitope at I-587

<400> SEQUENCE: 105

Asp Ala Glu Phe Arg His Asp Ser Gly
1               5

<210> SEQ ID NO 106
<211> LENGTH: 88
<212> TYPE: DNA
<213> ORGANISM: Artificial
<220> FEATURE:
<223> OTHER INFORMATION: murine TNFalpha epitope TNFalpha-V1 sense
      oligonucleotide for cloning of epitope sequences into I-453

<400> SEQUENCE: 106
ggccgccggt ggaggcagca gccagaacag cagcgacaag cccgtggccc acgtggtggc    60
taaccaccag gtggagggcg gtggaggg                                      88

<210> SEQ ID NO 107
<211> LENGTH: 88
<212> TYPE: DNA
<213> ORGANISM: Artificial
<220> FEATURE:
<223> OTHER INFORMATION: murine TNFalpha epitope TNFalpha-V1 anti-sense
      oligonucleotide for cloning of epitope sequences into I-453

<400> SEQUENCE: 107
cgcgccctcc accgccctcc acctggtggt tagccaccac gtgggccacg ggcttgtcgc    60
tgctgttctg gctgctgcct ccaccggc                                      88

<210> SEQ ID NO 108
<211> LENGTH: 70
<212> TYPE: DNA
<213> ORGANISM: Artificial
<220> FEATURE:
<223> OTHER INFORMATION: murine IL-17 epitope IL-17-V1 sense
      oligonucleotide for cloning of epitope sequences into I-453

<400> SEQUENCE: 108
ggccgccggt ggaggcaacg ccgagggcaa gcttgaccac cacatgaaca gcgtgctggg    60
cggtggaggg                                                          70

<210> SEQ ID NO 109
<211> LENGTH: 70
<212> TYPE: DNA
<213> ORGANISM: Artificial
<220> FEATURE:
<223> OTHER INFORMATION: murine IL-17 epitope IL-17-V1 anti-sense
      oligonucleotide for cloning of epitope sequences into I-453

<400> SEQUENCE: 109
cgcgccctcc accgcccagc acgctgttca tgtggtggtc aagcttgccc tcggcgttgc    60
ctccaccggc                                                          70

```
<210> SEQ ID NO 110
<211> LENGTH: 61
<212> TYPE: DNA
<213> ORGANISM: Artificial
<220> FEATURE:
<223> OTHER INFORMATION: murine IL-6 epitope IL-6-V2 sense
      oligonucleotide for cloning of epitope sequences into I-453

<400> SEQUENCE: 110
ggccgccggt ggaggcctgg aggaattcct gaaggtgacc ctgagaagcg gcggtggagg      60
g                                                                      61

<210> SEQ ID NO 111
<211> LENGTH: 61
<212> TYPE: DNA
<213> ORGANISM: Artificial
<220> FEATURE:
<223> OTHER INFORMATION: murine IL-6 epitope IL-6-V2 anti-sense
      oligonucleotide for cloning of epitope sequences into I-453

<400> SEQUENCE: 111
cgcgccctcc accgccgctt ctcagggtca ccttcaggaa ttcctccagg cctccaccgg      60
c                                                                      61

<210> SEQ ID NO 112
<211> LENGTH: 20
<212> TYPE: PRT
<213> ORGANISM: Artificial
<220> FEATURE:
<223> OTHER INFORMATION: TNFalpha-V1 epitope at I-453

<400> SEQUENCE: 112

Ser Ser Gln Asn Ser Ser Asp Lys Pro Val Ala His Val Val Ala Asn
1               5                   10                  15

His Gln Val Glu
            20

<210> SEQ ID NO 113
<211> LENGTH: 14
<212> TYPE: PRT
<213> ORGANISM: Artificial
<220> FEATURE:
<223> OTHER INFORMATION: IL-17-V1 epitope at I-587

<400> SEQUENCE: 113

Asn Ala Glu Gly Lys Leu Asp His His Met Asn Ser Val Leu
1               5                   10

<210> SEQ ID NO 114
<211> LENGTH: 20
<212> TYPE: PRT
<213> ORGANISM: Artificial
<220> FEATURE:
<223> OTHER INFORMATION: TNFalpha-V1 epitope at I-453

<400> SEQUENCE: 114

Ser Ser Gln Asn Ser Ser Asp Lys Pro Val Ala His Val Val Ala Asn
1               5                   10                  15

His Gln Val Glu
            20

<210> SEQ ID NO 115
<211> LENGTH: 11
<212> TYPE: PRT
<213> ORGANISM: Artificial
```

```
<220> FEATURE:
<223> OTHER INFORMATION: IL-6-V2 epitope at I-587

<400> SEQUENCE: 115

Leu Glu Glu Phe Leu Lys Val Thr Leu Arg Ser
1               5                   10

<210> SEQ ID NO 116
<211> LENGTH: 14
<212> TYPE: PRT
<213> ORGANISM: Artificial
<220> FEATURE:
<223> OTHER INFORMATION: IL-17-V1 epitope at I-453

<400> SEQUENCE: 116

Asn Ala Glu Gly Lys Leu Asp His His Met Asn Ser Val Leu
1               5                   10

<210> SEQ ID NO 117
<211> LENGTH: 20
<212> TYPE: PRT
<213> ORGANISM: Artificial
<220> FEATURE:
<223> OTHER INFORMATION: TNFa-V1 epitope at I-587

<400> SEQUENCE: 117

Ser Ser Gln Asn Ser Ser Asp Lys Pro Val Ala His Val Val Ala Asn
1               5                   10                  15

His Gln Val Glu
            20

<210> SEQ ID NO 118
<211> LENGTH: 11
<212> TYPE: PRT
<213> ORGANISM: Artificial
<220> FEATURE:
<223> OTHER INFORMATION: IL-6-V2 epitope at I-453

<400> SEQUENCE: 118

Leu Glu Glu Phe Leu Lys Val Thr Leu Arg Ser
1               5                   10

<210> SEQ ID NO 119
<211> LENGTH: 20
<212> TYPE: PRT
<213> ORGANISM: Artificial
<220> FEATURE:
<223> OTHER INFORMATION: TNFalpha-V1 epitope at I-587

<400> SEQUENCE: 119

Ser Ser Gln Asn Ser Ser Asp Lys Pro Val Ala His Val Val Ala Asn
1               5                   10                  15

His Gln Val Glu
            20

<210> SEQ ID NO 120
<211> LENGTH: 14
<212> TYPE: PRT
<213> ORGANISM: Artificial
<220> FEATURE:
<223> OTHER INFORMATION: IL-17-V1 epitope at I-453

<400> SEQUENCE: 120

Asn Ala Glu Gly Lys Leu Asp His His Met Asn Ser Val Leu
1               5                   10
```

<210> SEQ ID NO 121
<211> LENGTH: 11
<212> TYPE: PRT
<213> ORGANISM: Artificial
<220> FEATURE:
<223> OTHER INFORMATION: IL-6-V2 epitope at I-587

<400> SEQUENCE: 121

Leu Glu Glu Phe Leu Lys Val Thr Leu Arg Ser
1               5                   10

<210> SEQ ID NO 122
<211> LENGTH: 11
<212> TYPE: PRT
<213> ORGANISM: Artificial
<220> FEATURE:
<223> OTHER INFORMATION: IL-6-V2 epitope at 453

<400> SEQUENCE: 122

Leu Glu Glu Phe Leu Lys Val Thr Leu Arg Ser
1               5                   10

<210> SEQ ID NO 123
<211> LENGTH: 14
<212> TYPE: PRT
<213> ORGANISM: Artificial
<220> FEATURE:
<223> OTHER INFORMATION: IL-17-V1 epitope at I-587

<400> SEQUENCE: 123

Asn Ala Glu Gly Lys Leu Asp His His Met Asn Ser Val Leu
1               5                   10

<210> SEQ ID NO 124
<211> LENGTH: 31
<212> TYPE: DNA
<213> ORGANISM: Artificial
<220> FEATURE:
<223> OTHER INFORMATION: adeno-associated virus 1 NheI VP2plus95bp
      primer

<400> SEQUENCE: 124
gagcgtctgc tagcagatac ctcttttggg g                              31

<210> SEQ ID NO 125
<211> LENGTH: 29
<212> TYPE: DNA
<213> ORGANISM: Artificial
<220> FEATURE:
<223> OTHER INFORMATION: adeno-associated virus 1 VP3 Xma rev primer

<400> SEQUENCE: 125
gaaacgaatc acccgggtta ttgattaac                                 29

<210> SEQ ID NO 126
<211> LENGTH: 24
<212> TYPE: DNA
<213> ORGANISM: Artificial
<220> FEATURE:
<223> OTHER INFORMATION: adeno-associated virus 1 VP2ko for primer

<400> SEQUENCE: 126
ggcgctaaga ccgctcctgg aaag                                      24

<210> SEQ ID NO 127
<211> LENGTH: 24

```
<212> TYPE: DNA
<213> ORGANISM: Artificial
<220> FEATURE:
<223> OTHER INFORMATION: adeno-associated virus 1 VP2ko rev primer

<400> SEQUENCE: 127
ctttccagga gcggtcttag cgcc                                      24

<210> SEQ ID NO 128
<211> LENGTH: 45
<212> TYPE: DNA
<213> ORGANISM: Artificial
<220> FEATURE:
<223> OTHER INFORMATION: adeno-associated virus 1 VP2ko_VP1del for
      primer

<400> SEQUENCE: 128
acgactcact ataggctagc aggcgctaag accgctcctg gaaag               45

<210> SEQ ID NO 129
<211> LENGTH: 45
<212> TYPE: DNA
<213> ORGANISM: Artificial
<220> FEATURE:
<223> OTHER INFORMATION: adeno-associated virus 1 VP2ko_VP1del rev
      primer

<400> SEQUENCE: 129
ctttccagga gcggtcttag cgcctgctag cctatagtga gtcgt               45

<210> SEQ ID NO 130
<211> LENGTH: 41
<212> TYPE: DNA
<213> ORGANISM: Artificial
<220> FEATURE:
<223> OTHER INFORMATION: forward primer for HindIII mutagenesis

<400> SEQUENCE: 130
cgctgctgtg ggacctaagc ttatggcttc aggcggtggc g                   41

<210> SEQ ID NO 131
<211> LENGTH: 41
<212> TYPE: DNA
<213> ORGANISM: Artificial
<220> FEATURE:
<223> OTHER INFORMATION: reverse primer for HindIII mutagenesis

<400> SEQUENCE: 131
cgccaccgcc tgaagccata agcttaggtc ccacagcagc g                   41

<210> SEQ ID NO 132
<211> LENGTH: 58
<212> TYPE: DNA
<213> ORGANISM: Artificial
<220> FEATURE:
<223> OTHER INFORMATION: sense oligo for cloning the human IgE epitope
      "Kricek"

<400> SEQUENCE: 132
ggccgcagcc gcagtgaacc tgacctggag cagagcctcc ggcgcggcag ctgcagct  58

<210> SEQ ID NO 133
<211> LENGTH: 58
<212> TYPE: DNA
<213> ORGANISM: Artificial
<220> FEATURE:
<223> OTHER INFORMATION: anti-sense oligo for cloning the human IgE
```

-continued epitope "Kricek"

<400> SEQUENCE: 133
cgcgagctgc agctgccgcg ccggaggctc tgctccaggt caggttcact gcggctgc     58

<210> SEQ ID NO 134
<211> LENGTH: 73
<212> TYPE: DNA
<213> ORGANISM: Artificial
<220> FEATURE:
<223> OTHER INFORMATION: sense oligo for cloning the human IgE epitope
      "3Depi-3"

<400> SEQUENCE: 134
ggccggcggt ggaggcggtg acagcaaccc tagaggcgtg agcgcctacc tgagcagagg    60
aggcggtgga ggg                                                      73

<210> SEQ ID NO 135
<211> LENGTH: 73
<212> TYPE: DNA
<213> ORGANISM: Artificial
<220> FEATURE:
<223> OTHER INFORMATION: anti-sense oligo for cloning the human IgE
      epitope "3Depi-3"

<400> SEQUENCE: 135
cgcgccctcc accgcctcct ctgctcaggt aggcgctcac gcctctaggg ttgctgtcac    60
cgcctccacc gcc                                                      73

<210> SEQ ID NO 136
<211> LENGTH: 53
<212> TYPE: DNA
<213> ORGANISM: Artificial
<220> FEATURE:
<223> OTHER INFORMATION: forward primer I of ORF2 of the cap gene (AAV2
      nt 2717-3340) ORF2 of the cap gene (AAV2 nt 2717-3340) fused to
      sequences coding for an AU1-tag

<400> SEQUENCE: 136
ggatcgcaag cttattttgg tcagactgga gacgcagact cagtacctga ccc          53

<210> SEQ ID NO 137
<211> LENGTH: 43
<212> TYPE: DNA
<213> ORGANISM: Artificial
<220> FEATURE:
<223> OTHER INFORMATION: forward primer II of ORF2 of the cap gene (AAV2
      nt 2717-3340) ORF2 of the cap gene (AAV2 nt 2717-3340) fused to
      sequences coding for an AU1-tag

<400> SEQUENCE: 137
ggatcgcaag cttattttgg tcagaatgga gacgcagact cag                     43

<210> SEQ ID NO 138
<211> LENGTH: 43
<212> TYPE: DNA
<213> ORGANISM: Artificial
<220> FEATURE:
<223> OTHER INFORMATION: forward primer III of ORF2 of the cap gene
      (AAV2 nt 2717-3340) fused to sequences coding for an AU1-tag

<400> SEQUENCE: 138
ggatcgcaag cttattttgg tcagattgga gacgcagact cag                     43

<210> SEQ ID NO 139

```
<211> LENGTH: 68
<212> TYPE: DNA
<213> ORGANISM: Artificial
<220> FEATURE:
<223> OTHER INFORMATION: reverse primer of ORF2 of the cap gene (AAV2 nt
      2717-3340) fused to sequences coding for an AU1-tag

<400> SEQUENCE: 139
gcggtgtctc gagttatata tagcgatagg tgtcgggtga ggtatccata ctgtggcacc    60
atgaagac                                                             68

<210> SEQ ID NO 140
<211> LENGTH: 93
<212> TYPE: DNA
<213> ORGANISM: Artificial
<220> FEATURE:
<223> OTHER INFORMATION: primer I for cloning of pCMV-NLS-VP3

<400> SEQUENCE: 140
ggaattcgat atcaagcttg ccatggcacg gcaggcccgg cggaatagac ggagacggtg    60
gcgggaacgg cagcggatgg ctacaggcag tgg                                 93

<210> SEQ ID NO 141
<211> LENGTH: 93
<212> TYPE: DNA
<213> ORGANISM: Artificial
<220> FEATURE:
<223> OTHER INFORMATION: primer II for cloning of pCMV-NLS-VP3

<400> SEQUENCE: 141
ccactgcctg tagccatccg ctgccgttcc cgccaccgtc tccgtctatt ccgccgggcc    60
tgccgtgcca tggcaagctt gatatcgaat tcc                                 93

<210> SEQ ID NO 142
<211> LENGTH: 723
<212> TYPE: DNA
<213> ORGANISM: avian adeno-associated virus DA-1

<400> SEQUENCE: 142
ttgaacaacc cgacaacacg gccgggaccg gggagaagcg tcccgaacgc gtcgacgact    60
ttttcccgaa aaagaagaag gccaagaccg agcaaggcaa agcccctgct caaacgggcg   120
aagaccccgg agaaggaacc tcttccaacg ctggatcaag cgcccctct agtgtgggat    180 catctgtcat ggctgaagga ggtggcggtc caatgggcga tgcaggccaa ggtgccgacg   240
gagtgggcaa ttcctcggga aattggcatt gcgattccca atggctggac aacggagtcg   300
ttacccgaac cactcgaacc tgggtcctgc ccagctacaa caaccacttg tacaagcgga   360
tccaaggacc gggaggaacc gaccccaaca ataaattctt tggattcagc accccctggg   420
ggtactttga ctacaaccga ttccactgcc acttctcccc ccgagactgg caacgactca   480
tcaacaacaa ctggggcatc cgacccaaag cgatgcgctt tagactcttt aacatccagg   540
ttaaagaagt cactgtccaa gactccaaca ccaccatcgc caacaacctc accagcacgg   600
tccaagtctt tgcggacaag gactaccagc tgccgtacgt cctcggatcg gctacagagg   660
gcaccttccc gccgttccca gcggatatct acacgatccc gcagtatggt tactgcacgc   720
taa                                                                 723

<210> SEQ ID NO 143
<211> LENGTH: 240
<212> TYPE: PRT
```

<213> ORGANISM: avian adeno-associated virus DA-1

<400> SEQUENCE: 143

| | | | | | | | | | | | | | | |
|---|---|---|---|---|---|---|---|---|---|---|---|---|---|---|
| Leu | Asn | Asn | Pro | Thr | Thr | Arg | Pro | Gly | Pro | Gly | Arg | Ser | Val | Pro | Asn |
| 1 | | | | 5 | | | | | 10 | | | | | 15 | |
| Ala | Ser | Thr | Thr | Phe | Ser | Arg | Lys | Arg | Arg | Pro | Arg | Pro | Ser | Lys |
| | | | 20 | | | | | 25 | | | | | 30 | |
| Ala | Lys | Pro | Leu | Leu | Lys | Arg | Ala | Lys | Thr | Pro | Glu | Lys | Glu | Pro | Leu |
| | | | 35 | | | | 40 | | | | | 45 | | |
| Pro | Thr | Leu | Asp | Gln | Ala | Pro | Pro | Leu | Val | Trp | Asp | His | Leu | Ser | Trp |
| | 50 | | | | | 55 | | | | | 60 | | | | |
| Leu | Lys | Glu | Val | Ala | Val | Gln | Trp | Ala | Met | Gln | Ala | Lys | Val | Pro | Thr |
| 65 | | | | | 70 | | | | | 75 | | | | | 80 |
| Glu | Trp | Ala | Ile | Pro | Arg | Glu | Ile | Gly | Ile | Ala | Ile | Pro | Asn | Gly | Trp |
| | | | | 85 | | | | | 90 | | | | | 95 | |
| Thr | Thr | Glu | Ser | Leu | Pro | Glu | Pro | Leu | Glu | Pro | Gly | Ser | Cys | Pro | Ala |
| | | | 100 | | | | | 105 | | | | | 110 | | |
| Thr | Thr | Thr | Thr | Cys | Thr | Ser | Gly | Ser | Lys | Asp | Arg | Glu | Glu | Pro | Thr |
| | | | 115 | | | | | 120 | | | | | 125 | | |
| Pro | Thr | Ile | Asn | Ser | Leu | Asp | Ser | Ala | Pro | Pro | Gly | Gly | Thr | Leu | Thr |
| | 130 | | | | | 135 | | | | | 140 | | | | |
| Thr | Thr | Asp | Ser | Thr | Ala | Thr | Ser | Pro | Pro | Glu | Thr | Gly | Asn | Asp | Ser |
| 145 | | | | | 150 | | | | | 155 | | | | | 160 |
| Ser | Thr | Thr | Thr | Gly | Ala | Ser | Asp | Pro | Lys | Arg | Cys | Ala | Leu | Asp | Ser |
| | | | | 165 | | | | | 170 | | | | | 175 | |
| Leu | Thr | Ser | Arg | Leu | Lys | Lys | Ser | Leu | Ser | Lys | Thr | Pro | Thr | Pro | Pro |
| | | | 180 | | | | | 185 | | | | | 190 | | |
| Ser | Pro | Thr | Thr | Ser | Pro | Ala | Arg | Ser | Lys | Ser | Leu | Arg | Thr | Arg | Thr |
| | | | 195 | | | | | 200 | | | | | 205 | | |
| Thr | Ser | Cys | Arg | Thr | Ser | Ser | Asp | Arg | Leu | Gln | Arg | Ala | Pro | Ser | Arg |
| | | | 210 | | | | | 215 | | | | | 220 | | |
| Arg | Ser | Gln | Arg | Ile | Ser | Thr | Arg | Ser | Arg | Ser | Met | Val | Thr | Ala | Arg |
| 225 | | | | | 230 | | | | | 235 | | | | | 240 |

<210> SEQ ID NO 144
<211> LENGTH: 286
<212> TYPE: DNA
<213> ORGANISM: adeno-associated virus 2

<400> SEQUENCE: 144

```
tcggacagcc accagcagcc ccctctggtc tgggaactaa tacgatggct acaggcagtg    60
gcgcaccaat ggcagacaat aacgagggcg ccgacggagt gggtaattcc tcgggaaatt   120
ggcattgcga ttccacatgg atgggcgaca gagtcatcac caccagcacc cgaacctggg   180
ccctgcccac ctacaacaac cacctctaca acaaatttc cagccaatca ggagcctcga   240
acgacaatca ctactttggc tacagcaccc cttgggggta ttttga              286
```

<210> SEQ ID NO 145
<211> LENGTH: 646
<212> TYPE: DNA
<213> ORGANISM: Artificial
<220> FEATURE:
<223> OTHER INFORMATION: VP2N

<400> SEQUENCE: 145

```
acggctccgg gaaaaagag gccggtagag cactctcctg tggagccaga ctcctcctcg    60
```

```
ggaaccggaa aggcgggcca gcagcctgca agaaaaagat tgaattttgg tcagactgga    120
gacgcagact cagtacctga ccccagcct ctcggacagc caccagcagc ccctctggt      180 ctgggaacta atacgatggc tacaggcagt ggcgcaccaa tggcagacaa taacgagggc    240
gccgacggag tgggtaattc ctcgggaaat tggcattgcg attccacatg gatgggcgac    300
agagtcatca ccaccagcac ccgaacctgg gccctgccca cctacaacaa ccacctctac    360
aaacaaattt ccagccaatc aggagcctcg aacgacaatc actactttgg ctacagcacc    420 ccttggggt  attttgactt caacagattc cactgccact tttcaccacg tgactggcaa    480
agactcatca caacaactg  gggattccga cccaagagac tcaacttcaa gctctttaac    540
attcaagtca aagaggtcac gcagaatgac ggtacgacga cgattgccaa taaccttacc    600
agcacggttc aggtgtttac tgactcggag taccagctcc cgtacg                   646
```

<210> SEQ ID NO 146
<211> LENGTH: 646
<212> TYPE: DNA
<213> ORGANISM: Artificial
<220> FEATURE:
<223> OTHER INFORMATION: VP2Ncm

<400> SEQUENCE: 146

```
acggcccctg gcaagaaacg gcccgtggag cacagccccg tggagcccga cagcagcagc    60
ggcaccggca aggccggaca gcagcccgcc agaaagcggc tgaacttcgg ccagaccggc    120
gacgctgata gcgtgcccga ccctcagccc ctgggccagc tcctgctgc  tcctagcggc    180 ctcggcacca acaccatggc caccggcagc ggagccccca tggccgataa caatgaaggg    240
gcagacggcg tgggcaacag ctccggcaac tggcactgcg acagcacctg gatgggagat    300
cgggtgatca caacctccac ccggacatgg gctctcccta cttataataa tcacctgtac    360
aagcagatca gcagccagag cggcgccagc aatgataacc actacttcgg gtactctaca    420
ccctggggct acttcgattt caatcggttt cactgtcact tcagcccccag agactggcag    480 cggctgatta ataataattg gggcttccgg cccaagcggc tgaatttcaa gctgttcaat    540
atccaggtga aggaagtgac ccagaacgat ggcaccacca caatcgccaa caacctgacc    600
tcaaccgtgc aggtgttcac cgacagcgag taccagctgc cgtacg                   646
```

<210> SEQ ID NO 147
<211> LENGTH: 6
<212> TYPE: PRT
<213> ORGANISM: Artificial Sequence
<220> FEATURE:
<223> OTHER INFORMATION: Synthetic Construct

<400> SEQUENCE: 147

Pro Ala Arg Lys Arg Leu
1               5

<210> SEQ ID NO 148
<211> LENGTH: 10
<212> TYPE: PRT
<213> ORGANISM: Artificial Sequence
<220> FEATURE:
<223> OTHER INFORMATION: Synthetic Construct

<400> SEQUENCE: 148

Phe Gln Ser Ser Ser Thr Asp Pro Ala Thr
1               5                   10

```
<210> SEQ ID NO 149
<211> LENGTH: 10
<212> TYPE: PRT
<213> ORGANISM: Artificial Sequence
<220> FEATURE:
<223> OTHER INFORMATION: Synthetic Construct

<400> SEQUENCE: 149

Leu Gln Arg Gly Asn Arg Gln Ala Ala Thr
1               5                   10

<210> SEQ ID NO 150
<211> LENGTH: 10
<212> TYPE: PRT
<213> ORGANISM: Artificial Sequence
<220> FEATURE:
<223> OTHER INFORMATION: Synthetic Construct

<400> SEQUENCE: 150

Leu Gln Ser Ser Asn Thr Ala Pro Thr Thr
1               5                   10

<210> SEQ ID NO 151
<211> LENGTH: 10
<212> TYPE: PRT
<213> ORGANISM: Artificial Sequence
<220> FEATURE:
<223> OTHER INFORMATION: Synthetic Construct

<400> SEQUENCE: 151

Leu Gln Ser Ser Ser Thr Asp Pro Ala Thr
1               5                   10

<210> SEQ ID NO 152
<211> LENGTH: 10
<212> TYPE: PRT
<213> ORGANISM: Artificial Sequence
<220> FEATURE:
<223> OTHER INFORMATION: Synthetic Construct

<400> SEQUENCE: 152

Leu Gln Ala Ala Asn Thr Ala Ala Gln Thr
1               5                   10

<210> SEQ ID NO 153
<211> LENGTH: 10
<212> TYPE: PRT
<213> ORGANISM: Artificial Sequence
<220> FEATURE:
<223> OTHER INFORMATION: Synthetic Construct

<400> SEQUENCE: 153

Leu Gln Gln Gln Asn Thr Ala Pro Gln Ile
1               5                   10

<210> SEQ ID NO 154
<211> LENGTH: 10
<212> TYPE: PRT
<213> ORGANISM: Artificial Sequence
<220> FEATURE:
<223> OTHER INFORMATION: Synthetic Construct

<400> SEQUENCE: 154

Leu Gln Gln Ala Asn Thr Gly Pro Ile Val
1               5                   10

<210> SEQ ID NO 155
```

<211> LENGTH: 10
<212> TYPE: PRT
<213> ORGANISM: Artificial Sequence
<220> FEATURE:
<223> OTHER INFORMATION: Synthetic Construct

<400> SEQUENCE: 155

Asn Gln Asn Ala Thr Thr Ala Pro Ile Thr
1               5                   10

<210> SEQ ID NO 156
<211> LENGTH: 10
<212> TYPE: PRT
<213> ORGANISM: Artificial Sequence
<220> FEATURE:
<223> OTHER INFORMATION: Synthetic Construct

<400> SEQUENCE: 156

Asn Gln Ser Ser Thr Thr Ala Pro Ala Thr
1               5                   10

<210> SEQ ID NO 157
<211> LENGTH: 10
<212> TYPE: PRT
<213> ORGANISM: Artificial Sequence
<220> FEATURE:
<223> OTHER INFORMATION: Synthetic Construct

<400> SEQUENCE: 157

Gln Asn Gln Ser Gly Ser Ala Gln Asn Lys
1               5                   10

<210> SEQ ID NO 158
<211> LENGTH: 10
<212> TYPE: PRT
<213> ORGANISM: Artificial Sequence
<220> FEATURE:
<223> OTHER INFORMATION: Synthetic Construct

<400> SEQUENCE: 158

Asn Thr Pro Ser Gly Thr Thr Thr Gln Ser
1               5                   10

<210> SEQ ID NO 159
<211> LENGTH: 10
<212> TYPE: PRT
<213> ORGANISM: Artificial Sequence
<220> FEATURE:
<223> OTHER INFORMATION: Synthetic Construct

<400> SEQUENCE: 159

Gly Thr Thr Ser Gly Thr Thr Asn Gln Ser
1               5                   10

<210> SEQ ID NO 160
<211> LENGTH: 10
<212> TYPE: PRT
<213> ORGANISM: Artificial Sequence
<220> FEATURE:
<223> OTHER INFORMATION: Synthetic Construct

<400> SEQUENCE: 160

Gln Asn Gln Ser Gly Ser Ala Gln Asn Lys
1               5                   10

<210> SEQ ID NO 161
<211> LENGTH: 10

```
<212> TYPE: PRT
<213> ORGANISM: Artificial Sequence
<220> FEATURE:
<223> OTHER INFORMATION: Synthetic Construct

<400> SEQUENCE: 161

Ser Asn Pro Gly Gly Thr Ala Gly Asn Arg
1               5                   10

<210> SEQ ID NO 162
<211> LENGTH: 10
<212> TYPE: PRT
<213> ORGANISM: Artificial Sequence
<220> FEATURE:
<223> OTHER INFORMATION: Synthetic Construct

<400> SEQUENCE: 162

Gln Thr Thr Gly Gly Thr Ala Asn Thr Gln
1               5                   10

<210> SEQ ID NO 163
<211> LENGTH: 10
<212> TYPE: PRT
<213> ORGANISM: Artificial Sequence
<220> FEATURE:
<223> OTHER INFORMATION: Synthetic Construct

<400> SEQUENCE: 163

Gln Ser Thr Gly Gly Thr Gln Gly Thr Gln
1               5                   10

<210> SEQ ID NO 164
<211> LENGTH: 10
<212> TYPE: PRT
<213> ORGANISM: Artificial Sequence
<220> FEATURE:
<223> OTHER INFORMATION: Synthetic Construct

<400> SEQUENCE: 164

Ser Gly Glu Thr Leu Asn Gln Gly Asn Ala
1               5                   10

<210> SEQ ID NO 165
<211> LENGTH: 10
<212> TYPE: PRT
<213> ORGANISM: Artificial Sequence
<220> FEATURE:
<223> OTHER INFORMATION: Synthetic Construct

<400> SEQUENCE: 165

Phe Val Ser Thr Asn Asn Thr Gly Gly Val
1               5                   10

<210> SEQ ID NO 166
<211> LENGTH: 10
<212> TYPE: PRT
<213> ORGANISM: Artificial Sequence
<220> FEATURE:
<223> OTHER INFORMATION: Synthetic Construct

<400> SEQUENCE: 166

Tyr Lys Gln Ile Ser Ser Gln Ser Gly Ala
1               5                   10

<210> SEQ ID NO 167
<211> LENGTH: 10
<212> TYPE: PRT
```

```
<213> ORGANISM: Artificial Sequence
<220> FEATURE:
<223> OTHER INFORMATION: Synthetic Construct

<400> SEQUENCE: 167

Ser Gln Ser Gly Ala Ser Asn Asp Asn His
1               5                   10

<210> SEQ ID NO 168
<211> LENGTH: 10
<212> TYPE: PRT
<213> ORGANISM: Artificial Sequence
<220> FEATURE:
<223> OTHER INFORMATION: Synthetic Construct

<400> SEQUENCE: 168

Tyr Leu Thr Leu Asn Asn Gly Ser Gln Ala
1               5                   10

<210> SEQ ID NO 169
<211> LENGTH: 10
<212> TYPE: PRT
<213> ORGANISM: Artificial Sequence
<220> FEATURE:
<223> OTHER INFORMATION: Synthetic Construct

<400> SEQUENCE: 169

Tyr Tyr Leu Ser Arg Thr Asn Thr Pro Ser
1               5                   10

<210> SEQ ID NO 170
<211> LENGTH: 10
<212> TYPE: PRT
<213> ORGANISM: Artificial Sequence
<220> FEATURE:
<223> OTHER INFORMATION: Synthetic Construct

<400> SEQUENCE: 170

Tyr Leu Ser Arg Thr Asn Thr Pro Ser Gly
1               5                   10

<210> SEQ ID NO 171
<211> LENGTH: 10
<212> TYPE: PRT
<213> ORGANISM: Artificial Sequence
<220> FEATURE:
<223> OTHER INFORMATION: Synthetic Construct

<400> SEQUENCE: 171

Asn Thr Pro Ser Gly Thr Thr Thr Gln Ser
1               5                   10

<210> SEQ ID NO 172
<211> LENGTH: 10
<212> TYPE: PRT
<213> ORGANISM: Artificial Sequence
<220> FEATURE:
<223> OTHER INFORMATION: Synthetic Construct

<400> SEQUENCE: 172

Thr Thr Gln Ser Arg Leu Gln Phe Ser Gln
1               5                   10

<210> SEQ ID NO 173
<211> LENGTH: 10
<212> TYPE: PRT
<213> ORGANISM: Artificial Sequence
```

```
<220> FEATURE:
<223> OTHER INFORMATION: Synthetic Construct

<400> SEQUENCE: 173

Ala Ser Asp Ile Arg Asp Gln Ser Arg Asn
1               5                   10

<210> SEQ ID NO 174
<211> LENGTH: 10
<212> TYPE: PRT
<213> ORGANISM: Artificial Sequence
<220> FEATURE:
<223> OTHER INFORMATION: Synthetic Construct

<400> SEQUENCE: 174

Glu Glu Lys Phe Phe Pro Gln Ser Gly Val
1               5                   10

<210> SEQ ID NO 175
<211> LENGTH: 10
<212> TYPE: PRT
<213> ORGANISM: Artificial Sequence
<220> FEATURE:
<223> OTHER INFORMATION: Synthetic Construct

<400> SEQUENCE: 175

Arg Thr Thr Asn Pro Val Ala Thr Glu Gln
1               5                   10

<210> SEQ ID NO 176
<211> LENGTH: 10
<212> TYPE: PRT
<213> ORGANISM: Artificial Sequence
<220> FEATURE:
<223> OTHER INFORMATION: Synthetic Construct

<400> SEQUENCE: 176

Asn Pro Val Ala Thr Glu Gln Tyr Gly Ser
1               5                   10

<210> SEQ ID NO 177
<211> LENGTH: 10
<212> TYPE: PRT
<213> ORGANISM: Artificial Sequence
<220> FEATURE:
<223> OTHER INFORMATION: Synthetic Construct

<400> SEQUENCE: 177

Ser Thr Asn Leu Gln Arg Gly Asn Arg Gln
1               5                   10

<210> SEQ ID NO 178
<211> LENGTH: 10
<212> TYPE: PRT
<213> ORGANISM: Artificial Sequence
<220> FEATURE:
<223> OTHER INFORMATION: Synthetic Construct

<400> SEQUENCE: 178

Leu Gln Arg Gly Asn Arg Gln Ala Ala Thr
1               5                   10

<210> SEQ ID NO 179
<211> LENGTH: 10
<212> TYPE: PRT
<213> ORGANISM: Artificial Sequence
<220> FEATURE:
```

<223> OTHER INFORMATION: Synthetic Construct

<400> SEQUENCE: 179

Gln Arg Gly Asn Arg Gln Ala Ala Thr Ala
1               5                   10

<210> SEQ ID NO 180
<211> LENGTH: 10
<212> TYPE: PRT
<213> ORGANISM: Artificial Sequence
<220> FEATURE:
<223> OTHER INFORMATION: Synthetic Construct

<400> SEQUENCE: 180

Asn Arg Gln Ala Ala Thr Ala Asp Val Asn
1               5                   10

<210> SEQ ID NO 181
<211> LENGTH: 10
<212> TYPE: PRT
<213> ORGANISM: Artificial Sequence
<220> FEATURE:
<223> OTHER INFORMATION: Synthetic Construct

<400> SEQUENCE: 181

Val Pro Ala Asn Pro Ser Thr Thr Phe Ser
1               5                   10

<210> SEQ ID NO 182
<211> LENGTH: 10
<212> TYPE: PRT
<213> ORGANISM: Artificial Sequence
<220> FEATURE:
<223> OTHER INFORMATION: Synthetic Construct

<400> SEQUENCE: 182

Thr Phe Ser Ala Ala Lys Phe Ala Ser Phe
1               5                   10

<210> SEQ ID NO 183
<211> LENGTH: 10
<212> TYPE: PRT
<213> ORGANISM: Artificial Sequence
<220> FEATURE:
<223> OTHER INFORMATION: Synthetic Construct

<400> SEQUENCE: 183

Asn Val Asp Phe Thr Val Asp Thr Asn Gly
1               5                   10

<210> SEQ ID NO 184
<211> LENGTH: 10
<212> TYPE: PRT
<213> ORGANISM: Artificial Sequence
<220> FEATURE:
<223> OTHER INFORMATION: Synthetic Construct

<400> SEQUENCE: 184

Phe Thr Val Asp Thr Asn Gly Val Tyr Ser
1               5                   10

<210> SEQ ID NO 185
<211> LENGTH: 10
<212> TYPE: PRT
<213> ORGANISM: Artificial Sequence
<220> FEATURE:
<223> OTHER INFORMATION: Synthetic Construct

```
<400> SEQUENCE: 185

Ser Ser Ser Thr Asp Pro Ala Thr Gly Asp
1               5                   10

<210> SEQ ID NO 186
<211> LENGTH: 10
<212> TYPE: PRT
<213> ORGANISM: Artificial Sequence
<220> FEATURE:
<223> OTHER INFORMATION: Synthetic Construct

<400> SEQUENCE: 186

Asn Asn Leu Gln Ser Ser Asn Thr Ala Pro
1               5                   10

<210> SEQ ID NO 187
<211> LENGTH: 10
<212> TYPE: PRT
<213> ORGANISM: Artificial Sequence
<220> FEATURE:
<223> OTHER INFORMATION: Synthetic Construct

<400> SEQUENCE: 187

Gly Gly Asp Gln Ser Asn Ser Asn Leu Pro
1               5                   10

<210> SEQ ID NO 188
<211> LENGTH: 10
<212> TYPE: PRT
<213> ORGANISM: Artificial Sequence
<220> FEATURE:
<223> OTHER INFORMATION: Synthetic Construct

<400> SEQUENCE: 188

Thr Asn Asn Gln Ser Ser Thr Thr Ala Pro
1               5                   10
```

ASSEMBLY ACTIVATING PROTEIN (AAP) AND ITS USE FOR THE MANUFACTURE OF PARVOVIRUS PARTICLES ESSENTIALLY CONSISTING OF VP3

The present invention relates to nucleic acids encoding the novel parvoviral protein "assembly activating protein" (AAP), the encoded polypeptides, methods of producing the polypeptides, antibodies specific for AAP, the use of the nucleic acids for the preparation of the polypeptides, the use of the nucleic acids or the polypeptides for the preparation of the parvoviral particle and methods of producing parvoviral particles essentially consisting of VP3 by providing in addition to the coding sequence of the parvoviral structural protein VP3 a sequence fragment Z/a nucleic acid encoding AAP in the cell and expressing VP3 and fragment Z under control of a rep-independent promoter. Furthermore, the present invention relates to parvoviral particles essentially consisting of VP3 and/or obtainable by the above method as well as expression cassettes comprising (i) a heterologous promoter and (ii) VP3 coding sequence and/oror fragment Z. The present invention further relates to a medicament, particularly a vaccine, comprising the parvoviral particles or expression cassettes and their use.

Mutated parvovirus structural protein-based virus-like particles (VLPs) have been shown to be suitable vaccine candidates (WO 2008/145401, hereby incorporated by reference). Based on such mutated parvovirus structural proteins, VLPs were generated for the presentation of tolerogens or small antigens or even individual epitopes. These VLPs proved especially beneficial, where B cell tolerance has to be broken to have a therapeutic effect for the patient.

For the clinical development of vaccines based on VLPs it is generally necessary to generate a product which ideally is based on a single active compound/protein and which is as pure as possible. With respect of VLPs this is a problem in general as viruses are often composed of more than one protein and are capable of packaging specifically viral DNA or unspecifically DNA from the host cell. Accordingly it is desirable to obtain "pure" VLPs that contain as few different proteins as possible and preferably no nucleic acid. In the literature, several attempts have been made to efficiently produce those particles.

Rabinowitz et al. (e.g. Rabinowitz et al., 1999) have altered the structural genes of AAV2 by linker insertional mutagenesis in order to define critical components of virion assembly and infectivity. They generated the mutant H2634 that contains the rep and cap ORFs and an insertion at the HaeIII restriction site at position 2634. Importantly, due to the presence of the rep ORF this insertion mutant expressed the respective Rep protein. It assembled intact virions and the capsid appeared to be composed only of VP3. According to the authors the undetectable expression of VP1 and VP2 in either cell lysates or purified virions could have been a problem of detection limits.

Warrington et al. (2004) and WO 2004/027019 also addressed the question of the specific roles of the individual capsid proteins in capsid formation to define where full-length peptides can be inserted into the AAV capsid ORF without disruption of critical structural domains. Generating constructs containing the rep and cap ORF with mutations in the start codons of VP1, VP2 and/oror VP3 and thus expressing only a single or two capsid protein(s) in the presence of Rep, Warrington et al. showed that genome-containing particles were formed as long as the VP3 protein was present. Hence, mutants expressing VP1 and/oror VP2 as single capsid proteins or together did not form particles. Rather they concluded from their results that VP1 is necessary for viral infection but not essential for capsid assembly and particle formation whereas VP2 appears to be nonessential for viral infectivity. Moreover, they observed that expression of VP3 alone from constructs with mutated start codons for VP1 and VP2 is sufficient to form VLPs.

Just as well, Grieger et al. (2007) generated VP3-only particles using the AAV2 helper plasmid pXR2 (containing rep and cap genes, Li et al. (2008)) via mutagenesis of the VP1 and VP2 start codon. Expression of VP3- as well as VP2/VP3-only constructs in the presence of Rep resulted in noninfectious viral particles as long as they lacked the VP1 subunit.

From their results on the formation of genome-containing AAV-like particles from mutants expressing VP3 as only capsid protein in the presence of Rep it seemed that these particles can readily be obtained.

All the expression constructs described above expressed Rep proteins which should be omitted to assemble VLPs that are composed preferably of one protein and no DNA. Rep does not only represent a further protein that is attached to VLPs but also is held responsible for packaging of virus genomes and unspecific DNA into preformed capsids (King et al., 2001). Packaging of DNA is to be avoided as VLPs potentially can enter cells of a patient and thereby transfect such contaminating DNA, which may cause all sorts of unwanted effects.

To be sure that only VP3 is expressed, Hoque et al. (1999a, 1999b) and Handa et al. (JP 2001169777) generated expression constructs comprising the coding sequence (cds) of VP3 alone under control of a heterologous promoter in the absence of any Rep cds. Surprisingly, they could not produce viral particles from these expression constructs. By analyzing a series of deletion mutants of VP2 that started expression at different sites 5' of the VP3 start codon, they identified a region necessary for nuclear transfer of VP3 and found that the efficiency of nuclear localization of the capsid proteins and the efficiency of VLP formation correlated well. They observed that viral particles were formed as long as a region between amino acid 29 and 34 in the cds of VP2 or in other words in the 5' extension of VP3, was present. From the amino acid motif of this region which is PARKRL (SEQ ID NO:147) they concluded that it functions as a nuclear localization signal (NLS) which is important for the trans-location of VP3 into the nucleus.

Alternatively, capsids also could be obtained if the NLS of simian virus 40 (SV40) large T antigen was fused to the N-terminus of the VP3 protein ($NLS_{SV40}$-VP3). This fusion protein could form VLPs indicating that the VP2-specific region located on the N-terminal side of the protein is not structurally required. Due to this finding the authors reasoned that VP3 has sufficient information for VLP formation and that VP2 is necessary only for nuclear transfer of the capsid proteins, which again is a prerequisite for VLP formation.

Due to the method for mutant construction used by them, all constructs started with an ATG start codon directly at the 5' end of the coding sequence. Since in general the "position effect" (Kozak, 2002) will cause the first (most upstream) ATG start codon of a transcript to initiate translation, the main protein to be expressed and generating the particle will be N-terminally extended VP3. Only a minor part of translation will start at the further downstream ATG start codon of VP3.

In agreement with Hoque et al. (supra) and Handa et al. (supra) and using constructs described by them, we could not detect VLPs consisting of VP3 alone from expression constructs comprising the cds of VP3 alone under control of a constitutive promoter in neither mammalian cells nor insect cells in quantitative amounts (meaning that $<10^{10}$, particularly $<10^8$ capsids/ml were present) using the AAV2 Titration ELISA (quantified according to the instructions of the manufacturer Progen, Heidelberg, Germany, FIG. 15B). Nor could we detect AAV-like particles expressing VP1 or VP2 alone from expression constructs comprising the respective cds alone starting with an ATG codon under control of a constitutive promoter. The efficiency of capsid production of all constructs alone or in different combinations of different ratios in the presence or absence of Rep expression and in the presence or absence of co-delivery of adenoviral helper genes was at the lower detection limit of the AAV2 Titration ELISA ($<10^8$ capsids/ml, see above).

We could confirm that VLPs can be generated from expression constructs comprising some sequence 5' of the VP3 start codon together with the sequence coding for VP3, but in contrast to the results of Hoque et al., we could not quantify capsid assembly in detectable amounts ($\geq 10^8$ capsids/ml, see example 8) using the $NLS_{SV40}$-VP3 fusion construct. Accordingly, the method of Hoque et al. is not suitable for the generation of large amount of pure VLPs suitable for vaccination purposes for the market.

Taken together, the prior art techniques either use expression systems in the presence of Rep inevitably leading to the packaging of Rep and DNA or in the absence of Rep yields of VP3 VLPs are too low in order to generate a commercially viable process or product.

Accordingly, it was an object of the present invention to provide particles useful as a vaccine based on VLPs and methods of producing the same avoiding one or more of the above disadvantages. Particularly, it is desirable that the VLPs essentially consist of only one type of viral protein, contain no or only very little amounts of DNA and/oror that they may be produced in an economical manner, e.g. in high yields.

The problem is solved by providing parvoviral particles consisting essentially of VP3, with essentially no VP1, VP2 and Rep proteins. They may be produced by expressing in a cell VP3 from a VP3 coding sequence (cds) of the parvoviral structural protein VP3 (VP3 cds) under control of a rep-independent promoter. Additionally, in this method a DNA sequence fragment (fragment Z) (partially) encoding a newly identified polypeptide designated "assembly activating protein" (AAP) is expressed, which allows for high yields, e.g. approximately about $10^5$, preferably about $10^6$, and more preferably about $10^7$ virus particles to be formed per cell. The identification of this novel protein is a totally new concept with respect to the assembly of parvoviral capsids in general and especially for VP3 capsids, as no sequence motif within a VP2 protein such as the postulated "PARKRL" (SEQ ID NO:147) motif or a heterologous nuclear localization sequence for VP3 is required as postulated (Hoque et al., 1999a, 1999b).

In contrast to the state of the art these VLPs do not contain a heterologous NLS or a VP2 protein. Upon epitope insertion at one or several of the preferred sites in the VP3, particles could be successfully assembled that presented epitopes for vaccine development. With this method $10^{11}$, preferably about $10^{12}$, and more preferably about $10^{13}$ virus particles are formed per ml crude lysate and therefore yields are sufficient for a commercially viable product.

Surprisingly and in line with its function of encoding a polypeptide, the sequence fragment Z can be provided either in cis or in trans to assemble capsids consisting essentially of VP3.

Further, fragment Z and VP3 can be derived from the same or different species of parvovirus families, mutually trans-complementing each other regarding VP3 particle assembly.

The following definitions explain how the defined terms are to be interpreted in the context of the products, methods and uses of the present invention.

"AA" is used as abbreviation for amino acid(s), "nt" is used as abbreviation for nucleotide(s).

According to this invention a "parvovirus" or "parvoviral" relates to a member of the family of Parvoviridae wherein the wildtype expresses VP1, VP2 and VP3 as capsid proteins. The family of Parvoviridae contains several genera divided between 2 subfamilies Parvovirinae (Parvovirus, Erythrovirus, Dependovirus, Amdovirus and Bocavirus) and Densovirinae (Densovirus, Iteravirus, Brevidensovirus, Pefudensovirus and Contravirus) (Fields: Virology, fourth edition 2001, Volume 2, chapters 69 and 70, Lippincott Williams Wilkins, Philadelphia;). The wildtype capsid is assembled of the three structural proteins VP1, VP2 and VP3 that form the 60 subunits of the AAV capsid in a ratio of 1:1:8 (Kronenberg et al., 2001). Hence, the term "VP3" stands for virus protein 3. The naturally occurring parvoviral particle is composed of the icosahedral capsid that encloses the single stranded DNA genome. Preferred parvoviruses are the Dependoviruses, including AAV.

In the context of this invention the term "serotype" stands for the kind of virus of a group of closely related viruses distinguished by their characteristic set of antigens. Thus, the serotype is characterized by serologic typing (testing for recognizable antigens on the virus surface). Accordingly, the AAV can also be selected from a serotype evolved from AAV1, AAV2, AAV3, AAV4, AAV5, AAV6, AAV7, AAV8, AAV9, AAV10, AAV11 to AAV12 and AAV13, in particular from AAV2.

Parvoviral particles consisting "essentially of VP3" or "essentially only VP3" means that the capsid is assembled to at least 98%, preferably at least 99%, more preferably at least 99.6% and essentially at least 99.8% of VP3. This means that only $1/50$, preferably $1/100$, more preferably $1/250$ and essentially only $1/500$ or less of the proteins assembling the capsid are N-terminally extended versions of VP3 or completely different proteins. In a preferred embodiment the capsid is assembled to at least 98%, preferably at least 99%, more preferably at least 99.6% and essentially at least 99.8% of VP3, meaning that only $1/50$, preferably $1/100$, more preferably $1/250$ and essentially only $1/500$ or less of the proteins assembling the capsid are N-terminally extended versions of VP3 or different parvoviral proteins. It is especially preferred that the parvoviral capsid consists only of one protein, which is VP3 in its wildtype sequence or a mutated form of it.

A "coding sequence" or "cds" means that portion of a gene which directly specifies the amino acid (AA) sequence of its product. Hence, the "VP3 coding sequence" or "VP3 cds" defines that part of the cap gene from which the genetic code is translated into the amino acid (AA) sequence of a VP3, which can be wildtype or mutated as further defined in this invention. The VP3 cds is located at the 3' end of the cap ORF and starts with an ATG nucleotide triplet coding for a methionine. Depending from the individual parvovirus chosen, the VP3 cds is translated into about 533 Aas. E.g. for AAV2 the cds of the major coat protein VP3 can be obtained from the NCBI entree (ncbi.nlm.nih.gov) NC_001401 (nucleotides 2809-4410) according to Ruffing et al. (1994), the AA sequence from the corresponding NCBI entree YP_680428. A VP3 cds according to this invention encodes a VP3 protein which is capable of particle formation according to the methods of this invention. An N-terminally extended VP3 protein comprises one or more of the respective Aas of VP2. Accordingly, VP2 can be seen as an N-terminally extended VP3, in contrast to a VP3 which has an N-terminal insertion of a heterologous sequence thereto, such as a Tag or an epitope as further defined below.

The genetic code defines a mapping between tri-nucleotide sequences, called "codons", and Aas. A triplet codon in a nucleic acid sequence usually specifies a single AA.

A "reading frame" is a contiguous and non-overlapping set of tri-nucleotide codons in DNA or RNA. There are 3 possible reading frames in an mRNA strand and six in a double stranded DNA molecule due to the two strands from which transcription is possible. An "open reading frame" (ORF) is a reading frame that contains a start codon, the subsequent region which usually has a length which is a multiple of 3 nucleotides, and ends with a stop codon. An ORF could potentially encode a protein. Insertion of one or two nucleotides unambiguously results in a shift to a different reading frame (frameshift mutation). Usually, ATG is used as the start codon. However, as already known from VP2 of AAV non-canonical start codons are sometimes used.

"Mutations" are changes to the nucleotide sequence of the genetic material of an organism. Such mutations may lead to a change of the encoded protein and therefore may have varying effects depending on where they occur and whether they alter the structure and/oror function of the encoded protein. Structurally, mutations can be classified as point mutations, insertions adding one or more extra nt into the DNA/AA into the protein or deletions removing one or more nt/AA. An "insertion" of nt/AA is generally speaking an insertion of at least one heterologous nt/AA into the sequence of—for this invention—a parvovirus protein. 'Heterologous' in this context means heterologous as compared to the virus, from which the parvovirus protein is derived. Exemplified for a parvovirus structural protein, the inserted Aas can simply be inserted between two given Aas of the parvovirus structural protein. An insertion of Aas can also go along with a deletion of given Aas of the parvovirus structural protein at the site of insertion, leading to a complete substitution (e.g. 10 given Aas are substituted by 10 or more inserted Aas) or partial substitution (e.g. 10 given Aas are substituted by 8 inserted Aas) of Aas of the parvovirus structural protein.

In addition to an open reading frame beginning with a start codon close to its 5' end some further sequence requirements in the local environment of the start codon have to be fulfilled to initiate protein synthesis. One of these is the "Kozak sequence". The amount of protein synthesized from a given mRNA is dependent on the strength of the Kozak sequence. For a 'strong' consensus, relative to the translation initiation codon that is referred to as number 1 the nucleotides at positions +4 (i.e. G in the consensus) and −3 (i.e. either A or G in the consensus) must both match the consensus (there is no number 0 position). An 'adequate' consensus has only 1 of these sites, while a 'weak' consensus has neither. The cc at −1 and −2 are not as conserved, but contribute to the overall strength. There is also evidence that a G in the −6 position is important in the initiation of translation.

The term "percent identity" with respect to two sequences, particular amino acid sequences, indicates how many amino acids or bases are identical in an alignment of two sequences. For normalization, either the length of longer sequence, of shorter sequence or of columns of alignment occupied in both sequences, may be used. Usually, sequence alignment software is used in order to determine percent identity of sequences. Common software tools used for general sequence alignment tasks include for example ClustalW and T-coffee for alignment, and BLAST and FASTA3× for database searching. The skilled person will be able to select a suitable method or software and appropriate settings when assessing percent identity.

"Nucleic acid molecule" may be in the form of RNA, such as mRNA or cRNA, or in the form of DNA, including, for instance, cDNA and genomic DNA e.g. obtained by cloning or produced by chemical synthetic techniques or by a combination thereof. The DNA may be triple-stranded, double-stranded or single-stranded. Single-stranded DNA may be the coding strand, also known as the sense strand, or it may be the non-coding strand, also referred to as the anti-sense strand.

A "Rep-independent promoter" is a promoter which can be activated in the absence of the Rep protein, whereas in the context of this invention Rep stands for the non-structural protein(s) encoded by a parvovirus, particularly Rep40, Rep52, Rep68 and Rep78 as described by Muzyczka and Berns (2001). These promoters include for example heterologous constitutive promoters and inducible promoters.

"Gene expression" is the process by which inheritable information from a gene, such as the DNA sequence, is made into a functional gene product, such as protein or nucleic acid. Thus, gene expression always includes transcription, but not necessarily translation into protein. rRNA and tRNA genes are an example for non-protein coding genes that are expressed into rRNA and tRNA, respectively, and not translated into protein. In order for gene expression to take place a promoter preferably has to be present near the gene to provide (a) binding site(s) and recruit (an) enzyme(s) to start transcription.

"Shut off" of gene expression means that expression of a gene is blocked. It may be either through genetic modification (a change in the DNA sequence including mutation or deletion of the start codon, at least part of the cds or at least part of a sequence element necessary for its expression like e.g. the promoter), or by treatment with a reagent such as a short DNA or RNA oligonucleotide with a sequence complementary to either an mRNA transcript or a gene. Latter can preferably be used for transient shut off.

"Poly (A)" sites at the 3' end of the transcript signal the addition of a series of adenines during the RNA processing step before migration to the cytoplasm. These so-called poly(A) tails increase RNA stability.

The "sequence fragment Z" or "fragment Z" is a DNA fragment that comprises
(i) at least 44 nucleotides upstream of the VP3 start codon and
(ii) more than 242 nucleotides of the VP3 cds starting with the start codon,
derived from
(a) a parvovirus, or
(b) a nucleotide sequence that is at least 60%, preferably 80%, more preferably 90%, especially 99% and advantageously 100% identical to the nucleotide sequence of fragment Z derived from AAV2 (sequence 1, FIGS. 2A-2D), or
(c) a nucleic acid sequence that hybridizes in 4×SSC, 0.1% SDS at 65° C. to the complementary strand of the fragment Z DNA molecule of AAV2, or
(d) a nucleic acid sequence that can be used in trans-complementation assays to cause assembly of VP3 VLPs.

This means that the sequence of fragment Z at the same time represents part of the VP2 and VP3 cds, since the AAV capsid genes are encoded by overlapping sequences of the same ORF using alternative mRNA splicing and alternative translational start codons. Thus, the VP2 gene contains the whole VP3 gene sequence with a specific 5' region (schematic representation in FIG. 1).

A "functionally active variant" of the claimed polypeptide or a nucleic acid is a polypeptide or a nucleic acid that is referred to in the context of the present invention is a variant obtained by one or more mutations as detailed herein, which is functionally active in that the variant maintains its biological function, e.g. its capability to promote assembly of VP3. The biological activity may be determined in trans-complementation assays, where the expression of such polypeptide from such nucleic acid is able to promote assembly of VP3 VLPs from a VP3 coding construct whose expression under suitable conditions is insufficient for VP3 capsid assembly. Suitable insufficient AAV2 VP3 coding constructs are pCMV-VP3/2809 or pCI-VP3. A suitable test is described in the Examples, e.g. in Example 3. Preferably, maintenance of biological function is defined as having at least 50%, preferably at least 60%, more preferably at least 70%, 80% or 90%, still more preferably 95% of the activity of the natural occurring AAP.

Complementation assays can be performed as described in example 3 and either be analyzed by ELISA (example 1.5) or by immunofluorescence (1.6). Both assays are based on the detection of virus particles by the binding of a monoclonal antibody to the viral capsid in an assembled state. For example the monoclonal antibody A20 (Progen, Heidelberg, Germany) binds to the viral capsid of AAV2 and some other AAV serotypes, for more distantly related serotypes specific antibodies are commercially available. If no specific antibody is available, viral capsids can be detected by electron microscopy (for example see Hoque et al. (1999b)), or sucrose density gradient analysis (example 1.3.2.)

"Extended versions of VP3" comprise in general N-terminal extensions by several Aas. These N-terminal extensions represent the 3' part of the sequence coding for VP2 but not for VP3, since the AAV capsid genes are encoded by overlapping sequences of the same ORF using different start codons (FIG. 1). Thus, N-terminally extended VP3 is identical to N-terminally truncated VP2 meaning that parts of VP2 can be present within the N-terminal extension of VP3 but no complete and intact wildtype VP2 protein is expressed as e.g. given by Ruffing et al. (1994) and accessible from NCBI (number of entree: NC_001401. According to this invention the particles consist essentially of VP3 (as defined) and therefore extended versions of VP3 are very rare, whereas naturally occurring particles comprise VP1: VP2:VP3 in a ratio of 1:1:8 (Kronenberg et al., 2001).

To determine the composition of capsid proteins expressed in a given sample Western blot analysis can be used. The cell lysate or purified VLPs can be fractionated on a sucrose gradient and fractions analyzed upon gel electrophoresis and transfer to a nitrocellulose membrane, where they can be probed using binders specific to the target protein. The monoclonal antibody B1 reacts with all three capsid proteins and can be used to detect VP3, whereas the monoclonal antibody A69 reacts only with VP1 and VP2 and can be used to detect truncated VP2.

In the context of this invention "efficient particle formation" means that a high titer of particles is formed of about $10^{11}$, preferably of about $10^{12}$, and more preferably of about $10^{13}$ particles/ml in crude lysate (corresponding to about $10^5$, preferably about $10^6$, and more preferably about $10^7$ particles/transfected cell).

The term "about" means according to the invention a general error range of ±20%, especially ±10%, in particular ±5%.

Virus particle titers can be quantified from lysates of transfected cells (see above) in their undiluted form or in a dilution using a commercially available titration ELISA kit which is based on the binding of the monoclonal antibody A20 to the viral capsid in an assembled state to measure the virus concentration. As already described above, if the antibody A20 does not bind to the capsid of e.g. a different virus serotype, particle titers can be visualized by electron microscopy and quantified by counting (Grimm et al., 1999, Grimm and Kleinschmidt, 1999, Mittereder et al., 1996).

To analyze protein expression and estimate its amount cell lysates of identical portions of transfected cells can be processed for SDS-PAGE. Upon gel electrophoresis and transfer to a nitrocellulose membrane, proteins can be probed using binders specific to the target protein (e.g. monoclonal antibodies B1, A69, anti-GFP). The amount of protein translation can be estimated from the amount of binders that specifically bind to the protein. These complexes can be visualized and quantified by e.g. immunohistochemical staining, immunofluorescent staining or radioactive labeling.

The term "binder" refers to a molecule that specifically binds to its respective binding partner. Commonly used binders are antibodies, especially monoclonal antibodies, antibody derivatives such as single chain antibodies or antibody fragments. In principle all classes of antibodies can be used, preferred are IgG antibodies. Fragments or multimers of antibodies can equally be used. Commonly used fragments are single chain antibodies, Fab- or (Fab)$_2$-fragments. Examples of other suitable binders are protein scaffolds such as anticalins or lipocalins (Nygren and Skerra, 2004), receptors or parts thereof (e.g. soluble T-cell receptors), ankyrine, microbodies or aptamers.

The term "specifically binds" means that two molecules A and B, preferably proteins, bind to each other thereby generating complex AB with an affinity ($K_D=k_{off}/k_{on}$) of at least $K_D=1\times10^{-5}$ mol/l, preferably at least $1\times10^{-7}$ mol/l, more preferably at least $1\times10^{-8}$ mol/l, especially at least $1\times10^{-8}$ mold.

An "epitope" is the part of a macromolecule that is recognized by the immune system, specifically by antibodies, B-cells, or T-cells.

A "mimotope" is a non-linear structural epitope composed of several Aas derived from different regions of the linear sequence of the structural protein located in close neighborhood due to the overall tertiary structure of the capsid or from a non-peptide structure such as carbohydrate residues, nucleic acids or lipids, and such non-linear structural epitope is specifically bound by an antibody. Thus, by mimicking the structure of an epitope the mimotope causes an antibody response identical to the one elicited by the epitope. The mimotope in the context of the present invention might consist of (parts of) the inserted peptide sequence alone or might be composed of inserted peptide and parvovirus core particle AA residues.

As used herein the term "B-cell epitope" is meant to include also mimotopes. Therefore, the epitopes can be both linear and structural.

The term "antigen" in the context of the products, methods and uses of the present invention refers to any target antigen against which an immune reaction should be induced. Such target antigens are usually antigens that are susceptible to the humoral immune response. They are usually proteins that may be posttranslationally modified, as for example glycosylated proteins.

The term "Immunoglobulin" (abbr. Ig) refers to any of the glycoproteins naturally occurring in the blood serum that are induced in response to invasion by immunogenic antigens and that protect the host by eradicating pathogens. In total, there are five human antibody classes, known as IgM, IgG, IgA, IgD and IgE, which belong to this group of proteins.

In a first aspect, this invention relates to a nucleic acid encoding a polypeptide comprising an amino acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, and SEQ ID NO: 22, or encoding a polypeptide comprising a functionally active variant of any of these amino acid sequences, wherein the functionally active variant (i) has an amino acid sequence that is at least 60% identical to any of the amino acid sequences of SEQ ID NO: 1 to 22, and/oror (ii) is encoded by a cDNA that hybridizes in 6×SSC, 5×Denhardt's solution, 0.5% SDS at 40° C. for 2 to 12 hours to a nucleic acid sequence selected from the group consisting of SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, and SEQ ID NO: 44, or to a nucleic acid sequence complementary to any of the nucleic acid sequences of SEQ ID NO: 23 to SEQ ID NO: 44; and/oror (iii) is encoded by a part of a parvoviral genome comprising an open reading frame (ORF) not in frame with that encoding VP1, VP2 and VP3, that includes more than 378 nucleotides of the VP3 ORF, wherein the nucleic acid is incapable of expressing any of the functional Rep proteins, particularly incapable of expressing Rep40, Rep52, Rep68, Rep78, VP1, VP2 and VP3.

It was demonstrated that co-expression of a so far unidentified product of the AAV2 cap gene efficiently promotes assembly of VP3 into an icosahedral capsid. This protein, designated assembly activating protein or AAP is encoded by ORF2 of the cap gene (wherein the first ORF encodes VP1, VP2 and VP3) and has a molecular weight of approximately 23 kDa. The molecular weight of AAP estimated from Western blots was higher (about 30 kDa) maybe due to posttranslational modification(s). Its cellular localization is in the nucleolus and it targets the VP proteins to the nucleolus where capsid assembly takes place. However, nucleolar localization of VP3 alone is not sufficient for capsid formation, indicating that AAP provides an additional chaperon-type, scaffold and/oror nucleation function also within the full length AAV genome.

Homologous polypeptides can be identified for different parvoviruses. Such an alignment of predicted AAP protein sequences derived from ORF2 of the cap gene of different parvoviruses are shown in FIG. 28. Accordingly, the nucleic acid according to the invention is preferably characterized in that it encodes a polypeptide comprising the amino acid sequence of SEQ ID NO: 1 (AAV2), SEQ ID NO: 2 (AAV1), or the amino acid sequence of SEQ ID NO: 5 (AAV5).

It is envisaged by this invention that naturally occurring AAP may be modified but remains functionally active. Such functionally active variants may be generated e.g. in order to increase expression, stability and/oror activity, or in order to facilitate easier cloning of constructs. Accordingly, the invention also refers to an functionally active variant that has an amino acid sequence that is at least 65%, more preferably at least 70%, more preferably at least 75%, more preferably at least 80%, more preferably at least 85%, more preferably at least 90%, more preferably at least 95%, most preferably at least 99% and especially 100% identical to any of the amino acid sequences of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, and SEQ ID NO: 22 and/oror that is encoded by a cDNA that hybridizes in 6×SSC, 5×Denhardt's solution, 0.5% SDS at 45° C., more preferably at 50° C., more preferably at 55° C., more preferably at 60° C., especially at 65° C. and advantageously at 68° C. to a nucleic acid sequence complementary to any of the nucleic acid sequences of SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, and SEQ ID NO: 44. Preferably the functionally active variant is encoded by a cDNA that hybridizes at the conditions specified above in 6×SSC, 5×Denhardt's solution, 0.5% SDS to the nucleic acid sequence of SEQ ID NO: 23, or a nucleic acid sequence complementary to the nucleic acid sequence of SEQ ID NO: 23.

In a preferred embodiment of the invention, the nucleic acid encodes a polypeptide consisting of an amino acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, and SEQ ID NO: 22, or encodes a polypeptide consisting of a functionally active variant of any of these amino acid sequences, wherein the functionally active variant is defined above. More preferably the nucleic acid encodes a polypeptide consisting of an amino acid sequence selected from the group consisting of SEQ ID NO: 1, to SEQ ID NO: 22.

Due to N- and C-terminal truncation experiments with AAP it has been found that with respect to the 3'-end of AAP of AAV2 378 nt overlapping with the VP3 ORF starting at ATG$_{2809}$ are not able to support VP3 capsid assembly, whereas 445 nucleotides of the VP3 ORF are about equally efficient in yield of capsids as wt AAV. Accordingly, the nucleic acid of the invention is characterized in that it includes more than 378 nucleotides (such as more than 378, 379, 380, 381, 382, 383, 384, 385, 386, 387, 388, 389, 390, 391, 392, 393, 394, 395, 396, 397, 398, 399 nucleotides), preferable at least 400 nucleotides (such as at least 400, 401, 402, 403, 404, 405, 406, 407, 408, 409, 410, 411, 412, 413, 414, 415, 416, 417, 418, 419, 420, 421, 422, 423, 424 nucleotides), more preferably at least 425 nucleotides (such as at least 425, 426, 427, 428, 429, 430, 431, 432, 433, 434, 435, 436, 437, 438, 439, 440, 441, 442, 443, 444 or 445 nucleotides), and especially at least 445 nucleotides (such as 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487 or 488, 489, 490, 491, 492, 493, 494, 495, 496, 497, 498, 499, 500 or more nucleotides) of the VP3 ORF.

With respect to the 5'-end of AAP of AAV2 an N-terminally truncated AAP encoded by a nucleic acid with a 44 nucleotide extension upstream of the VP3 start codon is about equally efficient in yield of capsids as wt AAV, if translation is started by an ATG inserted in frame to ORF2, and with lower efficiency if no ATG start codon is inserted (data not shown). An N-terminally truncated AAP encoded by a nucleic acid starting with an ATG instead of the ACG at position 2858 did not lead to detectable capsid formation. For AAV4 and AAV9 it was shown that a VP3 cds expression construct starting at the respective VP3 start codon is sufficient for detectable capsid assembly, therefore still encoding functional AAP (variant) (data not shown).

Accordingly, the nucleic acid of the invention is characterized in that it includes at least 44 nucleotides (such as 44, 45, 46, 47, 48, 49, or 50 nucleotides), preferably at least 20 nucleotides (such as 20, 21, 22, 23, 24, 25, 26, 27, 28, 29, 30, 31, 32, 33, 34, 35, 36, 37, 38, 39, 40, 41, 42 or 43 nucleotides), more preferably at least 5 nucleotides (such as 5, 6, 7, 8, 9, 10, 11, 12, 13, 14, 15, 16, 17, 18 or 19 nucleotides) of the adjacent VP2-encoding nucleotides, which are located in direct succession of the 5' of the VP3 start codon.

The nucleic acid encoding AAP or variants thereof may even start 3' of the VP3 start codon, as can be seen from AAV4 and AAV9 (above). Therefore, in another preferred embodiment, the nucleic acid of the invention is characterized in that its start codon is an ATG at 4 nucleotides, preferably 24 nucleotides, and more preferably 44 nucleotides downstream of the VP3 start codon.

Therefore, in preferred embodiment the nucleic acid of the invention comprises nucleotides starting at least at 44 nucleotides upstream and 445 nucleotides downstream of the VP3 start codon (counting includes the ATG), preferably at least 20 nucleotides (such as 20, 21, 22, 23, 24, 25, 26, 27, 28, 29, 30, 31, 32, 33, 34, 35, 36, 37, 38, 39, 40, 41, 42, 43 or 44 nucleotides) upstream and 425 nucleotides (such as 425, 426, 427, 428, 429, 430, 431, 432, 433, 434, 435, 436, 437, 438, 439, 440, 441, 442, 443, 444 or 445 nucleotides) downstream of the VP3 start codon, and especially at least 5 nucleotides (such as 5, 6, 7, 8, 9, 10, 11, 12, 13, 14, 15, 16, 17, 18 or 19 nucleotides) upstream and 400 nucleotides (such as 400, 401, 402, 403, 404, 405, 406, 407, 408, 409, 410, 411, 412, 413, 414, 415, 416, 417, 418, 419, 420, 421, 422, 423 or 424 nucleotides) downstream of the VP3 start codon. Accordingly, total length of the nucleic acid of the invention is at least 489 nt (such as 489, 490, 491, 492, 493, 494, 495, 496, 497, 498, 499, 500 or more nt), preferably at least 445 nt (such as 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487 or 488 nt), and especially at least 405 nt (such as 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443 or 444 nt).

The nucleic acid of the invention is capable of expressing a protein promoting capsid assembly of VP3. It may be characterized in that it is derived from AAV2 and its translation start codon (found in wildtype AAV2 sequences) is $C_{2729}TG$, $A_{2735}CG$, $A_{2717}TT$ or $T_{2720}TG$ or that it is derived from another parvovirus and its translation start codon is at the homologous site to the translation start codons of AAV2. Homologous start codons for other parvoviruses can easily be identified by the given alignment (see FIGS. 27A and 27B) and looking for amino acids encoded by potential non-canonical start codons. Such potential non-canonical start codons can easily be verified by mutational analysis as done for AAV2 $C_{2729}TG$ in example 14. For parvoviruses not shown in FIGS. 27A and 27B such a sequence can easily be added to the given alignment.

In a preferred embodiment the AAP encoding ORF is mutated in a way in order to generate an ATG start codon allowing for improved translation of the open reading frame, whereas "improved" means higher expression of AAP or variants thereof compared to the respective wildtype sequence. Preferably one of the translation start codons of AAV2 or the homologous sites of other parvoviruses is mutated into an ATG start codon. Starting translation with the canonical start codon ATG generally leads to optimized expression of AAP or variants thereof and therefore, when AAP or variants thereof is suboptimal, leads to increased yield of capsid assembly. This becomes especially beneficial if expression systems are switched to cells that the respective virus is not adapted to. It can be assumed that expression of AAP or variants thereof in non-host cells will be suboptimal. For example, it is foreseen within this invention to manufacture capsids in insect cells or other cells suitable for infection by Baculovirus, in yeasts or bacteria, where optimized expression of AAP or variants thereof may be highly beneficial or crucial in order to get high capsid formation.

Whereas such mutation of the start codon of AAP into an ATG may reduce capsid formation in a cis situation (where AAP is encoded by an overlapping nucleic acid with ORF1 encoding VP3), such mutation is especially beneficial in a trans situation, where AAP is encoded independently from ORF1 encoding VP3 (example 14).

It is well known in the art and part of the invention that the nucleic acid is characterized in that the polypeptide coding sequence of the nucleic acid is followed by a poly(A) signal.

In one aspect of the invention the nucleic acid of the invention comprises a promoter driving transcription of the polypeptide-encoding sequence. In a preferred embodiment, a heterologous promoter, i.e. which is not present in the virus from which AAP-encoding nucleic acid is derived or preferably not present in any parvovirus wildtype genome, is used. The promoter which can be used in the method described herein is not limited to the examples described herein. It may be any known or subsequently discovered one. Constitutive promoters like e. g. the early cytomegalovirus (CMV) promoter (U.S. Pat. No. 4,168,062), that are continuously transcribed, are as useful in the invention as inducible promoters such as an antibiotic-specific or a cell-specific promoter. For expression in mammalian cell systems use of the CMV promoter is especially preferred, e.g. for use in manufacturing processes using transfection methods, whereas in insect cells use of the Polyhedrin promoter (PolH) is preferred. Inducible heterologous promoters are especially preferred, as they can be used to establish stable production cells for VP3.

Due to the high conservation of genome organization amongst the parvoviruses, the invention can easily be transferred to other parvovirus members. Within the parvoviruses preferred viruses, from which the nucleic acid of the invention is derived from, are adeno-associated virus (AAV), Goose parvovirus, Duck parvovirus, and Snake parvovirus. Preferred AAVs are selected from the group consisting of bovine AAV (b-AAV), canine AAV (CAAV), mouse AAV1, caprine AAV, rat AAV, avian AAV (AAAV), AAV1, AAV2, AAV3b, AAV4, AAV5, AAV6, AAV7, AAV8, AAV9, AAV10, AAV11, AAV12, and AAV13, especially AAV2.

In a further aspect the nucleic acid of the invention is comprised in an expression cassette, construct, vector or cell line. A construct, typically a plasmid, is generally a nucleic acid comprising the nucleic acid of the invention and additional sequences such as polycloning sites, origin of replication, selection marker genes etc. An expression cassette is generally a construct that, once it is inside a cell, is able to produce the protein encoded by the nucleic acid of the invention by the cellular transcription and translation machinery. The expression construct is engineered to contain regulatory sequences that act as enhancer or promoter regions and lead to efficient transcription of the nucleic acid of the invention. It further usually comprises a poly(A)-site that is later polyadenylated which is important for nuclear export, translation and stabilization of the mRNA. Vectors are constructs that are used to introduce the nucleic acid of the invention into cells. Dependent on the cells to be transfected they are constructed according to standard skills of the artisan. These can be plasmids for calcium phosphate transfection or liposomal transfection, or viral vectors, e.g. baculoviruses. Cell lines are laboratory cell lines suitable for the expression of AAP or variants thereof or the replication of AAP (variant) encoding plasmids.

A further aspect of the invention is a polypeptide encoded by a nucleic acid according to the invention. The underlying naturally occurring polypeptide is referred to as Assembly Activating Protein (AAP). Accordingly, variants of this polypeptide encoded by the nucleic acid of the present invention are referred to as APP variants. For example, a variant comprising the AAP protein and one or more further peptides would be referred to as an AAP-comprising polypeptide. The protein AAP is expressed from ORF2 (with the start codon for VP3 defining ORF1), has a calculated molecular weight of approximately 23 kDa and is able to provide capsid assembly of VP3 in the nucleolus. It is also essential for capsid formation within the whole AAV genome. It targets VP proteins to the nucleolus and exerts there an additional function in promoting the assembly reaction.

A further aspect of the invention is a method of producing the polypeptide of the invention, i.e. AAP or an AAP variant, by expressing a nucleic acid according to this invention in a host cell. Such production is suitable to promote capsid formation of parvoviruses in general and specifically of capsid comprising VP3, but no VP1 and VP2 and Rep proteins. Suitable host cells can be selected by the skilled person according to his needs and preferences. Preferred host cells selected from a list consisting of a mammalian cell line, especially a human cell line, a cell line used for baculovirus infection, a bacterial strain and a yeast strain.

A further aspect of the invention is an antibody or a binder in general that specifically binds AAP. Particularly, the antibody specifically binds to any of the sequences of SEQ ID NO: 1 to 22. Such antibodies can be used to further investigate the function of AAP or, when used as a trans-acting factor in heterologous expression systems, in order to verify and optimize AAP expression levels for commercial production of parvoviruses DNA or virus like particles. A preferred antibody is characterized in that it specifically binds AAP of AAV2 (SEQ ID NO:1). Antibodies according to this invention may be polyclonal or monoclonal. Further encompassed by the invention are corresponding antibody fragments like single chain antibodies, scF$_v$s, F$_{ab}$ fragments, nanobodies or alike, or antibody multimers.

A further aspect of the invention is the use of nucleic acid of the invention for the preparation of a polypeptide of the invention, including AAP and AAP variants.

A further aspect of the invention is the use of the nucleic acid or the polypeptide of the invention for the preparation of a parvovirus and parvoviral particle. The identification of AAP leads to previously unknown possibilities to manufacture such viruses as expression constructs can be optimized individually in order to increase yield or in order to generate inducible production systems using stable transfected producer cell lines. Expression can be increased through the use of heterologous promoters. Specifically, particles can be prepared in the absence of functional Rep and VP1 and VP2 encoding sequences enabling the manufacture of parvoviral particles not comprising any of the functional proteins VP1, VP2, Rep40, Rep52, Rep68 and Rep78. All these factors are important in the context of generating a robust, fast and cheap production system for such viruses and particles.

One aspect of the invention is a method of producing parvoviral particles consisting essentially of VP3, the method comprising the steps of (i) providing a cell capable of expressing VP3 from a VP3-coding sequence (cds) from a parvovirus, wherein the VP3 is under control of a rep-independent promoter and expressing a protein encoded by the nucleic acid according to the invention, (ii) incubating the cell at conditions conducive to the expression of VP3 and the protein from the nucleic acid according to the invention, thereby producing the parvoviral particle, and (iii) optionally purifying parvoviral particles from the cell, wherein at least $10^5$ virus particles are formed per cell and no functional VP1, VP2, Rep40, Rep52, Rep68 and Rep78 proteins are expressed. This method is equally applicable using fragment Z instead of the nucleic acid according to the invention.

In another aspect the invention provides a method of producing parvoviral particles essentially consisting of VP3, comprising the steps of i. expressing VP3 from a VP3 coding sequence (cds) from a parvovirus under control of a rep-independent promoter in a cell, ii. expressing a DNA sequence fragment (fragment Z) in the cell under control of a rep-independent promoter, that comprises
   (1) at least 44 nucleotides upstream of the VP3 start codon and
   (2) more than 242 nucleotides of the VP3 cds starting with the start codon
   derived from
   a) a parvovirus, or
   b) a nucleotide sequence that is at least 60%, preferably 80%, more preferably 90%, especially 99% and advantageously 100% identical to the nucleotide sequence of fragment Z derived from AAV2 (sequence 1, FIGS. 2A-2D), or
   c) a nucleic acid sequence that hybridizes in 4×SSC, 0.1% SDS at 65° C. to the complementary strand of the fragment Z DNA molecule of AAV2 (sequence 2), or
   d) a nucleic acid sequence that can be used in trans-complementation assays to cause assembly of VP3 VLPs.

iii. incubating the cell at conditions suitable for VP3 expression, and iv. purifying parvoviral particles from the cell, wherein approximately about $10^5$, preferably about $10^6$, and more preferably about $10^7$ virus particles are formed per cell and essentially no VP1, VP2 and Rep proteins (particularly Rep40, Rep52, Rep68 and Rep78) are expressed.

The invention of these methods is based on the generation of particles from a virus of the family of Parvoviridae wherein the wildtype expresses VP1, VP2 and VP3 as capsid proteins. Parvoviral particles consisting essentially of VP3 may be generated by expressing the parvoviral VP3 cds essentially in the absence of expression of functional VP1, VP2 and Rep proteins, particularly Rep40, Rep52, Rep68 and Rep78. As a result, the purified parvoviral particle consists essentially of only one capsid protein. Rep-mediated DNA packaging is completely avoided due to the absence of Rep in the particle. The invention provides high titers of parvoviral particles consisting essentially of VP3 which are amongst others suitable for vaccine development.

It is well known in the art that VP3 alone is not able to assemble into capsids. In the context of this invention a nucleic acid encoding a novel polypeptide designated AAP respectively a sequence element Z (fragment Z) was identified that, if expressed in the cell, mediates assembly of VP3 particles and that VP3 does not need additional viral proteins for capsid assembly.

Several lines of evidence led to the conclusion that VP3 requires RNA derived from the cap gene for capsid assembly. This factor required for VP3 capsid assembly could be provided in trans in a fragment of the cap gene fused to gfp (VP2N-gfp). Protein expression from the first ORF of this cap gene fragment (ORF that encodes VP1, VP2 and VP3) was not necessary as several constructs containing stop codons in the relevant region of the cap gene also provided helper function. Expression of VP2N-gfp from read-through transcripts could not be detected by Western blot analysis. Such protein expression, initiated at non-conventional translation start sites and followed by a stop codon is very unlikely and their amount would be very low. Such protein expression of VP2N-gfp is also not sufficient for stimulating capsid assembly of VP3. This has clearly been shown by expression of this protein using alternative codons which resulted in high VP2N-gfp protein levels but not in VP3 capsid assembly. Because such a change of the codons implicates a change of the nucleotide sequence it is clear that the correct nucleotide sequence is necessary for the assembly helper effect and not the expressed protein of the first ORF. Finally, providing the correct nucleotide sequence by a plasmid which could not be transcribed in the first ORF resulted also not in capsid assembly, arguing that transcription of the correct nucleotide sequence is necessary.

As shown in FIGS. 2A-2D, fragment Z comprises at least 44 nucleotides upstream and more than 242 nucleotides downstream of the VP3 start codon. Preferably, fragment Z does not comprise a full-length VP3 cds. The sequence of fragment Z can be derived from one of a number of different parvoviruses as listed in FIGS. 2A-2D where some examples for the nucleotide sequence of the respective region for fragment Z of parvoviruses AAV1, AAV2, AAV3b, AAV4, AAV5, AAV6, AAV7, AAV8, AAV10, AAV11, and b-AAV are given. This listing is not limited to the parvoviruses shown here. A further sequence can easily be aligned through its position of the VP3 start codon and selected as fragment Z. A nucleotide sequence can also be selected as fragment Z by its identity to the nucleotide sequence of fragment Z derived from AAV2 (SEQ ID NO: 45, see below) which is at least 60%, preferably 80%, more preferably 90%, especially 99% and advantageously 100%. Moreover, a nucleotide sequence hybridizing in 4×SSC, 0.1% SDS at 65° C. to the complementary strand of the fragment Z DNA molecule of AAV2 (SEQ ID NO: 46, see below) can also be used in trans-complementation assays as fragment Z to cause assembly of VP3 VLPs. It is especially preferred that fragment Z is derived from AAV2 and comprises SEQ ID NO: 45.

Nucleotide sequence of DNA sequence fragment Z derived from AAV2 (SEQ ID NO: 45, as also given in FIGS. 2A-2D):

```
  1 tcggacagcc accagcagcc ccctctggtc tgggaactaa tacgatggct
 51 acaggcagtg gcgcaccaat ggcagacaat aacgagggcg ccgacggagt
101 gggtaattcc tcgggaaatt ggcattgcga ttccacatgg atgggcgaca
151 gagtcatcac caccagcacc cgaacctggg ccctgcccac ctacaacaac
201 cacctctaca aacaaatttc cagccaatca ggagcctcga acgacaatca
251 ctactttggc tacagcaccc cttgggggta ttttgac
```

Reverse and complementary sequence of SEQ ID NO: 45, that can be used in hybridization experiments to identify an unknown DNA fragment as fragment Z (SEQ ID NO: 46):

```
  1 gtcaaaatac ccccaagggg tgctgtagcc aaagtagtga ttgtcgttcg
 51 aggctcctga ttggctggaa atttgtttgt agaggtggtt gttgtaggtg
101 ggcagggccc aggttcgggt gctggtggtg atgactctgt cgcccatcca
151 tgtggaatcg caatgccaat tcccgagga attacccact ccgtcggcgc
201 cctcgttatt gtctgccatt ggtgcgccac tgcctgtagc catcgtatta
251 gttcccagac cagagggggc tgctggtggc tgtccga
```

For initiation of transcription of the VP3 cds and the sequence of fragment Z or of the nucleic acid of the invention one or two "Rep-independent promoter(s)" is/are chosen. A rep-independent promoter is used in order to express VP3 and fragment Z in absence of the parvoviral factor Rep which is to be avoided as Rep is held responsible for packaging of virus genomes and unspecific DNA into parvoviral particles. For the purposes of this invention packaging of viral or unspecific DNA is to be avoided as the parvoviral particles could then unintentionally act as gene therapy vectors. By using a "Rep-independent promoter" for VP3 expression and transcription of fragment Z or the nucleic acid of the invention, RNA polymerase can initiate transcription in the absence of expression of Rep proteins enabling manufacture of capsids in the absence of Rep proteins, particularly Rep40, Rep52, Rep68 and Rep78. Rep-independent promoters are for example heterologous constitutive or inducible promoters.

Accordingly in one aspect of the invention the nucleic acid of the invention comprises a promoter driving transcription of the polypeptide-encoding sequence. In a preferred embodiment a heterologous promoter, which is not present in any parvovirus wildtype genome, is used. The promoter which can be used in the method described herein is not limited to the examples described herein. It may be any known or subsequently discovered one. Constitutive promoters like e. g. the early cytomegalovirus (CMV) promoter (U.S. Pat. No. 4,168,062), that are continuously transcribed, are as useful in the invention as inducible promoters such as an antibiotic-specific or a cell-specific promoter. For expression in mammalian cell systems use of the CMV promoter is especially preferred, e.g. for use in manufacturing processes using transfection methods, whereas in insect cells use of the Polyhedrin promoter (PolH) is preferred. Inducible heterologous promoters are especially preferred, as they can be used to establish stable production cells for VP3.

Suitable conditions for VP expression are well known in the art and can in principle be transferred to the expression of VP3 only. To produce parvoviruses or specifically parvoviral particles the respective DNA sequences have to be transfected into cells. One protocol is described within the examples. However, different transfection methods, different cells or stably transfected cells may be used instead. Different production methods are described for example by Grimm et al. (2002) and Grieger and Samulski (2005).

The methods of this invention lead to high yields of parvovirus particles, wherein about $10^5$, preferably about $10^6$, and more preferably about $10^7$ virus particles are formed per transfected cell. These numbers correspond to about $10^{11}$, preferably about $10^{12}$, and more preferably about $10^{13}$ particles/ml of crude lysate. The commercial use of VP3 particles requires an efficient method of production providing high yields of particles.

The particles can be purified by methods disclosed herein and the prior art.

It is especially preferred that the sequence of fragment Z or the nucleic acid according to the invention and the VP3 cds are arranged and expressed in such a way that parvoviral particles consisting only of VP3 are produced. "Consisting only" in this context means that no other proteinaceous molecules can be detected as part of the particles by common methods such as Western blotting. Such particles may comprise other molecules or salts such as water and other constituents of buffers. Additionally, the particle may comprise molecules that are incapsulated by chance during assembly of the particle within the cell.

According to one embodiment of the invention the sequence of fragment Z or the nucleic acid according to the invention do not overlap with the VP3 cds leading to parvoviral particles consisting only of VP3. This avoids the expression of a substoichiometrical number of N-terminally extended VP3 proteins present in the particles (see example 4). Such a small number of N-terminally extended VP3 proteins most likely would not affect activity or yield of the particles. However, under regulatory aspects of medicaments it is advantageous to have a one-protein product.

Accordingly, it is especially preferred that the parvoviral particles according to this invention are assembled only of VP3. For this purpose expression of VP1, VP2 and Rep, particularly Rep40, Rep52, Rep68 and Rep78, is shut off in the cell by a method well known to the skilled person, as for example deletion or mutation of the respective start codon, deletion (in whole or in part) of the cds specific for the protein, or mutation of the cds specific for the protein, avoiding expression of a functional gene product (examples are described for example in Warrington et al. (2004)).

Selection of the translational initiation site in most eukaryotic mRNAs appears to occur via a scanning mechanism which predicts that proximity to the 5' end plays a dominant role in identifying the start codon. This "position effect" causes that the first (most upstream) ATG start codon of a transcript initiates translation (Kozak, 2002).

Referring to the expression of parvovirus/AAV capsid proteins this means, that the minor spliced transcript mainly accounts for the synthesis of VP1 from the first ATG whereas translation of VP3 is primarily initiated from its ATG start codon which is the most upstream ATG of a major spliced transcript. This major spliced RNA also encodes the unusual ACG start codon of VP2 upstream of the VP3 start site. Therefore, in addition to VP3 that is effectively synthesized from the major spliced transcript, to a certain extent VP2 is expressed (Becerra et al., 1988, Becerra et al., 1985).

In general, the position effect is evident also in cases where a mutation inactivates or removes the normal start site and translation shifts to a downstream start site. Thus, a silent internal ATG codon can be activated and translational efficiency is increased, a problem well known in some disease states (Kozak, 2002).

Taken this knowledge into account, the mutagenesis of VP1 and VP2 start codons to inactivate their expression can activate translation of truncated proteins starting at downstream sites that are silent in the wildtype (as described by Warrington et al. (2004), and observed in example 2.2.).

Therefore, in addition to the main start codons known for capsid proteins such alternative start codons are preferably deleted or mutated to ensure that VP3 is the sole capsid protein to be expressed. Expression of VP3 only and shut off of any other capsid proteins may be controlled via Western blotting as described.

In a further preferred embodiment coding sequences for VP1 and VP2, which do not encode VP3 sequences, are completely deleted from the expression cassette encoding VP3. In such case fragment Z or the nucleic acid of the invention is provided in trans in order to enable production of VP3 capsids.

In a preferred embodiment of the invention the DNA sequence of fragment Z or the nucleic acid according to the invention is followed by a poly(A) signal. The poly(A) signal is able to recruit the polyadenylation machinery to add a stretch of adenines (the poly(A) tail) onto the RNA molecule once transcription of a gene has finished. This processing step increases stability of the factor transcribed from fragment Z within the cell. Poly(A) signals such as the poly(A) from SV40 large T-antigen are well known in the art and are regularly used in all kinds of expression cassettes and constructs.

Our analyses of a series of deletion mutants that started expression at different sites 5' of the VP3 start codon showed that the mutant pCMV-VP3/2765 is still able to cause capsid assembly (example 2.). Therefore, as already described above, fragment Z has to comprise at least 44 nucleotides upstream of the VP3 start codon. Since efficiency of particle formation was increased by using a fragment Z 5' extended by some nucleotides it is preferred that fragment Z comprises at least 113 nucleotides or especially at least 198 nucleotides upstream of the VP3 start codon, respectively. In our experiments we have chosen a construct providing a fragment Z of AAV2 that starts at nucleotide 2696 (corresponding to 113 nucleotides upstream of the VP3 start codon). In FIGS. 2A-2D the sequences of the different serotypes are listed relative to the VP3 start codon which is underlined. The sequences easily can be extended in the 5' or 3' direction according to the nucleotide sequences given in the respective NCBI entrees (compare legend of FIGS. 2A-2D).

If the 5' extended sequence of fragment Z comprises the translation start codon of VP1 and/oror VP2 or any other ATG start codon in ORF1, ORF2 or ORF3 they have to be inactivated by mutation or deletion to express VP3 as sole capsid protein.

Further, fragment Z has to comprise more than 242 nucleotides downstream of the VP3 start codon. It is preferred that fragment Z comprises more than about 275 nucleotides, more than about 300 nucleotides, more than about 325 nucleotides, more than about 350 nucleotides, more than about 375 nucleotides, more than about 400 nucleotides, more than about 425 nucleotides, and most preferably more than about 445 nucleotides of the VP3 cds starting with the start codon. An especially preferred fragment Z stops at about nucleotide 3254 (corresponding to about 445 nucleotides downstream of the VP3 start codon).

The active molecule encoded by fragment Z is most likely a diffusible molecule, i.e. a protein designated AAP. Based on the degenerated genetic code we optimized the sequence of fragment Z to get potentially higher expression of a putative diffusible protein possibly encoded within Z in the first reading frame (ORF1) that also encodes the capsid proteins VP1, VP2 and VP3, thereby leaving the AA sequence of proteins encoded in ORF1 unchanged but disturbing the protein sequence encoded by other ORFs by modifying the DNA sequence. This codon-optimized fragment, however, could not mediate particle formation as no virus particles could be detected anymore (example 5, FIGS. 6A-6D). On the other hand, insertion of stop codons into ORF1 within fragment Z, leading to shut off of protein synthesis from ORF1 but leading only to minor changes in the DNA sequence of ORF1 and not disrupting protein synthesis from ORF2, still enabled efficient particle formation (example 6, FIGS. 8A-8F).

It is especially preferred that the mutation of fragment Z comprises at least one stop codon for protein translation in the first or third reading frame. As a consequence no protein with a length of 18 AA or above can be translated from these reading frames of fragment Z in particular no VP2 protein or part of it can be generated. Therefore it is a main advantage that no VP2 or part of it is included in the particles.

As a preferred embodiment of this invention the main translation start codon ATG (AA 203, numbering according to VP1 of AAV2, (Girod et al., 1999)) of VP3 within fragment Z or the nucleic acid of the invention is mutated. It is further preferred that also one or both of the alternative minor start codons of VP3 (AA 211 and AA 235, (Warrington et al., 2004)) are mutated. In a more preferred embodiment all ATG codons that can be used for translational start of VP3 are mutated (a number of the possible ones are listed in Warrington et al., 2004) to completely avoid translation of VP3 from the expression construct providing fragment Z.

Since the product of fragment Z and the encoded function of the nucleic acid of the invention was characterized to be a trans-acting element meaning that fragment Z and the nucleic acid of the invention code for a diffusible molecule, the sequence of fragment Z or the nucleic acid of the invention can be provided on the same or a different nucleic acid molecule to the cell as the cap gene or part thereof, e.g. a VP3 cds.

In a preferred embodiment fragment Z or the nucleic acid of the invention is provided "in cis" relative to the VP3 cds. If fragment Z/the nucleic acid of the invention is provided "in cis" relative to an expression cassette coding for VP3 means that expression of fragment Z/the nucleic acid of the invention and VP3 are driven by the same one promoter. The sequence of fragment Z/the nucleic acid of the invention can be located upstream or downstream of the VP3 cds. The sequences coding for fragment Z and VP3 can be directly linked or separated by a variable number of nucleotides (FIG. 3, top right panel).

In a more specific embodiment of this invention fragment Z/the nucleic acid of the invention is located directly upstream of the VP3 cds. Since fragment Z/the nucleic acid of the invention comprises more than 242 nucleotides downstream of the VP3 start codon and this sequence has not to be present in duplicate, the directly following VP3 cds has only to provide the remaining DNA sequence of the VP3 ORF (a schema is given in FIG. 3, top right panel, see item "a)"). In this case substoichiometrical amounts of N-terminally extended VP3 are expressed and presented in the capsid (example 4). In order not to increase this part of N-terminally extended VP3 it is one important embodiment of this invention not to add new or delete existing start codon(s) respectively at the 5' end or upstream of fragment Z/the nucleic acid of the invention.

Moreover, only the VP3-specific cds that does not overlap with fragment Z/the nucleic acid of the invention can be mutated easily. Mutation of the VP3 cds that overlaps with fragment Z/the nucleic acid of the invention also possibly changes the sequence of the diffusible molecule coded by fragment Z/the nucleic acid of the invention. As a result, in some cases the diffusible molecule will not be active any more. Mutations in this context include silent mutations as well as e.g. insertion of epitopes. In order to increase possibilities to mutate the VP3 cds it is beneficial to minimize the overlap i.e. to separate fragment Z/the nucleic acid of the invention and the VP3 cds. This can be done in a cis situation where one promoter drives expression of a VP3 cds that does not contain the 44 nucleotides upstream of the VP3 start codon essential for fragment Z, and of a separate fragment Z place before such VP3 cds or thereafter.

It is especially preferred that fragment Z/the nucleic acid of the invention is provided "in trans" relative to the VP3 cds. If fragment Z/the nucleic acid of the invention is provided "in trans" relative to an expression cassette coding for VP3 it means that expression of fragment Z/the nucleic acid of the invention and VP3 are driven by separate promoters (in opposite to "in cis", see above). The sequence of fragment Z/the nucleic acid of the invention can be located upstream or downstream of the VP3 cds on the same construct, or on a different expression construct than the VP3 cds (examples are listed in FIG. 3, bottom right panel).

In this case fragment Z comprises only the 5' end of the VP3 cds and hence it is a main advantage that no N-terminally extended VP3 (see below) can be expressed and incorporated into the capsid. Therefore, if the sequence coding for VP3 and fragment Z are provided in trans, it is assumed that a more pure particle composition, preferably consisting only of the structural protein VP3, can be obtained.

It is one advantage of the in trans configuration that the VP3 cds can easily be modified e.g. to optimize its codon usage for the expression cell line in order to further increase the yield without changing the sequence of fragment Z/the nucleic acid of the invention. Also other modifications such as mutations, insertions, tags etc. can be done without affecting fragment Z/the nucleic acid of the invention. It can be assumed that during previous attempts to identify insertion sites within VP3 in overlapping sequences of fragment Z and the VP3 cds, potentially useful insertion sites were not identified as an insertion also interfered with expression of fragment Z or with the function of AAP. Accordingly, functional separation of these sequences either in a cis setting with no overlap or preferably in a trans setting enables independent mutagenesis of the VP3 coding sequence. Such mutagenesis has multiple commercial applicabilities. In the context of generation of novel gene therapy vectors limitations of generating chimeric parvovirus Cap sequences can be overcome. Several groups have tried direct evolution of AAV involving generation of randomly mutagenized viral libraries on one serotype (Koerber et al., 2008), by using STEP and shuffling methods to create multiple randomly recombined capsid species using known AAV serotype capsid sequences (Ward and Walsh, 2009, Li et al., 2008). In a similar way, independent expression of AAP can be used to identify further insertion sites that tolerate ligands (to be used for targeting to other cells), B-cell epitopes (to be used for generating epitope specific vaccines) or deletions/substitutions (to be used for detargeting of the virus or to reduce antigenicity of the virus).

A further advantage of the in trans configuration of fragment Z/the nucleic acid of the invention and the VP3 cds is that one construct can be stably transfected into a producer cell line whereas the other construct can be transiently transfected/transduced. For example an expression cassette comprising fragment Z/the nucleic acid of the invention can be stably transfected into a cell line suitable for efficient VP3 expression generating a single production cell line. Such production cell line then can be transiently transfected/transduced (e.g. infected with a virus) with a specific VP3 cds leading to expression of such VP3 and respective particle formation. Accordingly, one production cell line can be used for the production of different particles. Given the time and cost that is needed for qualification of production cell lines that are used for the manufacture of medicaments, this constitutes a considerable regulatory advantage. For this reason, it is especially preferred that fragment Z/the nucleic acid of the invention and the VP3 cds are provided on separate expression constructs.

This setup can additionally be used e.g. to generate AAV/parvovirus particles of a distinct serotype by providing an expression cassette coding for VP3 of a specific serotype in trans to the cells that have been stably transfected with fragment Z/the nucleic acid of the invention of one serotype. In general, a VP3 cds specific for an AAV serotype selected from the group consisting of AAV1, AAV2, AAV3b, AAV4, AAV5, AAV6, AAV7, AAV8, AAV9, AAV10, AAV11, AAV12 and AAV13 can be used for transfection of cells that have been stably transfected with fragment Z/the nucleic acid of the invention of only one serotype e.g. AAV2. Thereby, AAV particles consisting of VP3 of a selected serotype e.g. AAV1 particles can easily be generated. For AAV1 and AAV2 we could confirm that expression of fragment Z/the nucleic acid of the invention mediates capsid assembly of VP3 not only expressed from constructs cloned from the same serotype but also expressed from constructs cloned from the other serotype, namely AAV2 and AAV1, respectively (example 21). Nevertheless, it can not be generally expected that every serotype complements each other, but a person skilled in the art can easily identify the respective pairs of AAP from one parvovirus/serotype and VP3 from a different one to get assembly of VP3 VLPs in trans-complementation assays as described herein. Cross-complementation can be used for example if a stable cell line expressing a specific AAP has been obtained that can be used for the production of VP3 VLPs from different parvoviruses or AAV serotypes. The respective combinations can be chosen for time- and cost-effective VLP production at high titer.

Just as well the other way around is possible and one specific VP3 cds can be transfected in trans with an expression cassettes providing fragment Z/the nucleic acid of the invention chosen from a number of different sequences coding for fragment Z e.g. from different AAV serotypes/parvoviruses.

In another preferred embodiment of the invention the parvoviral particle does not contain Rep protein, particularly any functional Rep40, Rep52, Rep68 and Rep78 proteins. For details on this embodiment are given herein throughout the description.

In another preferred embodiment of the invention only/at most 1/50 of the expressed structural protein, preferably at most 1/100, more preferably at most 1/250 and essentially only/at most 1/500 of the structural proteins are N-terminally extended versions of VP3. Especially preferred are parvovirus particles that do not contain any structural proteins with N-terminally extended versions of VP3 or, vice e versa, none of the structural protein are N-terminally extended versions of VP3. If the sequences of fragment Z and VP3 cds overlap and are expressed under control of the same promoter (cis situation), the ATG start codon of the VP3 cds is mainly used as start for protein translation whereas only a very small proportion of protein translation starts upstream. The resulting small part of proteins contains in addition to the VP3 cds an N-terminal extension by several Aas corresponding to the 3' part of the sequence coding for VP2 but not for VP3. Taken together, expression of these 5' extended versions of VP3 was visible in Western blots (example 4) but accounted for only 1/50 of the structural proteins, preferably 1/100, more preferably 1/250 and essentially only 1/500 of the structural proteins of the parvovirus particle.

In another preferred embodiment of the invention only/at most 1/50 of the expressed structural protein, preferably at most 1/100, more preferably at most 1/250 and essentially only/at most 1/500 of the structural proteins is a polypeptide according to the invention, i.e. AAP or variants thereof. Whereas no specific influence of AAP has been shown on host cells that might have an impact on medical applications of parvovirus vectors or particles, it is in principle beneficial to have as little impurities as possible.

Viral Rep proteins bind to genomic and viral DNA and are discussed to play a role in DNA packaging. In order to use AAV as a vaccine and avoid unspecific reactions against the packaged DNA or an undesired gene transfer, parvoviral particles as free of DNA as possible are especially preferred. Therefore, parvoviral particles are produced in the absence of expression of Rep proteins in the cell. Hence, in still another preferred embodiment of the invention only 1/100 of the particles, preferably 1/1,000 and more preferably only ¹⁄₁₀,₀₀₀ of the particles contain DNA. Especially preferred is that none of the parvovirus particles contains DNA. Preferably at most ¹⁄₁₀₀, more preferably only/at most ¹⁄₁,₀₀₀, even more preferably only/at most ¹⁄₁₀,₀₀₀ of the particles contain any DNA. As a result, no inactivation step to destroy packaged DNA (e.g. gamma or UV-irradiation) is necessary prior to vaccination purposes.

The parvoviruses according to this invention are preferably selected from the group consisting of adeno-associated virus (AAV), bovine AAV (b-AAV), canine AAV (CAAV), and avian AAV (AAAV).

Especially preferred are AAVs selected from the group consisting of AAV-1, AAV-2, AAV-3b, AAV-4, AAV-5, AAV-6, AAV-7, AAV-8, AAV-9, AAV-10, AAV-11, AAV-12 and AAV13, especially AAV-2. AAV1 to AAV12 specify defined serotypes of adeno-associated virus (AAV).

As described herein in more detail, it is especially preferred that the VP3 cds further comprises at least one mutation. The mutation is in comparison to the respective wildtype parvoviral sequence, preferably selected from the group consisting of one or more deletion(s), one or more insertion(s), one or more substitution(s), and a combination of these mutations.

It is an embodiment of this invention that the VP3 cds comprises one or more silent mutation(s). By introducing DNA mutations that do not result in a change to the AA sequence of the VP3 protein it is possible to optimize the codon usage of the cds of VP3 e.g. to enhance its expression. Due to the degeneracy of the genetic code one AA may be specified by more then one codon, for example the AA glutamic acid is specified by GAA and GAG codons. Accordingly, for each AA of the structural protein VP3 one would select those codons that are translated with higher efficiency and mutate the cds respectively. As already discussed these mutations do not change the AA sequence of the protein, that is why they are called silent, but of course change the nucleotide sequence including the diffusible molecule coded by fragment Z/the nucleic acid of the invention. For this reason it is an especially preferred embodiment of this invention that only the part of the VP3 cds is modified by insertion or optimization of codon usage e.g. to get higher expression of VP3 in the chosen setup that does not overlap with the sequence of fragment Z, or in a trans situation as described above anywhere within the VP3 cds.

In a preferred embodiment, the one or more mutation(s) of the VP3 cds lead(s) to one or more mutations located on the surface of a VP3 VLP. The surface-located regions of the structural protein can be determined by analyzing the crystal structure, which is known for AAV2 (Xie et al., 2002). If the crystal structure is still not available for the chosen serotype the chosen VP3 sequence can be aligned to the VP3 sequence of at least one different serotype with an already known crystal structure to identify homologous regions of interest. The alignment can be done using a commercially available software like e.g. Multialign (Corpet, 1988) and standard parameters described there.

In a further preferred embodiment, the one or more mutation(s) of the VP3 cds lead(s) to one or more mutation (s) located at the N-terminus of VP3. Preferably, the N-terminus is defined as the N-terminal 10, preferably N-terminal 5, especially N-terminal 2 amino acids of the respective VP3. Especially preferred is an insertion at or corresponding to an insertion directly N- or C-terminal, preferably directly C-terminal of AA 203 (I-203).

It is preferred according to this invention that the insertion(s) is inserted into one or more positions selected from the group consisting of I-261, I-266, I-381, I-447, I-448, I-453, I-459, I-471, I-534, I-570, I-573, I-584, I-587, I-588, I-591, I-657, I-664, I-713 and I-716, preferably I-261, I-453, I-534, I-570, I-573 and I-587, especially I-587.

The used nomenclature I-### refers to the insertion site with ### naming the AA number relative to the VP1 protein of AAV-2, however meaning that the insertion may be located directly N- or C-terminal, preferably directly C-terminal of one AA in the sequence of 5 Aas N- or C-terminal of the given AA, preferably 3, more preferably 2, especially 1 AA(s)N- or C-terminal of the given AA. For parvoviruses other than AAV-2 the corresponding insertion sites can be identified by performing an AA alignment or by comparison of the capsid structures, if available. Such alignment has been performed for the parvoviruses AAV-1, AAV-2, AAV-3b, AAV-4, AAV-5, AAV-6, AAV-7, AAV-8, AAV-10, AAV-11, b-AAV, GPV, B19, MVM, FPV and CPV (FIG. 3 of WO 2008/145400).

The AA position after which the insertion was introduced and which named the site is underlined. It is also possible likewise to introduce an insertion into the five directly adjacent Aas located next to the underlined AA, because these are likewise located within a loop in the AAV2 capsid.

For example the insertion site I-587 corresponds to an insertion before and/or after one of the following Aas indicated by emphasis:

FQSSS TDPAT of AAV1 (SEQ ID NO:148),
LQRGN$_{587}$ RQAAT of AAV2 (SEQ ID NO:149),
LQSSN TAPTT of AAV-3b (SEQ ID NO:150),
LQSSS TDPAT of AAV-6 (SEQ ID NO:151),
LQAAN TAAQT of AAV-7 (SEQ ID NO:152),
LQQQN TAPQI of AAV-8 (SEQ ID NO:153),
LQQAN TGPIV of AAV10 (SEQ ID NO:154),
NQNAT TAPIT of AAV11 (SEQ ID NO:155), and
NQSST TAPAT of AAV-5 (SEQ ID NO:156).

Further, the insertion site I-453 corresponds to an insertion directly N- or C-terminal of the following ten Aas each, preferably directly C-terminal of the AA indicated by emphasis QNQSG SAQNK of AAV-1 (SEQ ID NO:157),
NTPSG453 TTTQS of AAV-2 (SEQ ID NO:158),
GTTSG TTNQS of AAV-3b (SEQ ID NO:159),
QNQSG SAQNK of AAV-6 (SEQ ID NO:160),
SNPGG TAGNR of AAV-7 (SEQ ID NO:161),
QTTGG TANTQ of AAV-8 (SEQ ID NO:162),
QSTGG TQGTQ of AAV-10 (SEQ ID NO:163),
SGETL NQGNA of AAV-11 (SEQ ID NO:164), and
FVSTN NTGGV of AAV-5 (SEQ ID NO:165).

Relating to the AAV2 sequence insertion sites for AAV and other parvoviruses encompassed by this invention are listed Table 1.

TABLE 1

Insertion sites for parvoviruses

| insertion site | corresponding AA/sequence of AAV2 | | references |
|---|---|---|---|
| I-261 | $S_{261}$ | YKQIS$_{261}$ SQSGA | (Girod et al., 1999) |
| I-266 | $A_{266}$ | SQSGA$_{266}$ SNDNH | (Wu et al., 2000) |
| I-381 | $N_{381}$ | YLTLN$_{381}$ NGSQA | (Girod et al., 1999) |
| I-447 | $R_{447}$ | YYLSR$_{447}$ TNTPS | (Girod et al., 1999, Wu et al., 2000) |
| I-448 | $T_{448}$ | YLSRT$_{448}$ NTPSG | (Grifman et al., 2001) |
| I-453 | $G_{453}$ | NTPSG$_{453}$ TTTQS | WO 2008/145400 |
| I-459 | $R_{459}$ | TTQSR$_{459}$ LQFSQ | (Shi et al., 2001, Arnold et al., 2006) |

TABLE 1-continued Insertion sites for parvoviruses

| insertion site | corresponding AA/sequence of AAV2 | | references |
|---|---|---|---|
| I-471 | $R_{471}$ | ASDIR$_{471}$ DQSRN | (Asokan and Samulski, 2006, Moskalenko et al., 2000) |
| I-534 | $F_{534}$ | EEKFF$_{534}$ PQSGV | (Girod et al., 1999) |
| I-570 | $P_{570}$ | RTTNP$_{570}$ VA$\underline{T}$EQ | |
| I-573 | $T_{573}$ | NPVAT$_{573}$ EQYGS | (Girod et al., 1999) |
| I-584 | $Q_{584}$ | STNLQ$_{584}$ RGNRQ | (Shi et al., 2001, Shi and Bartlett, 2003) |
| I-587 | $N_{587}$ | LQRGN$_{587}$ RQAAT | (Girod et al., 1999, Shi et al., 2001, Maheshri et al., 2006, Ried et al., 2002, Grifman et al., 2001, Nicklin et al., 2001, Arnold et al., 2006) |
| I-588 | $R_{588}$ | QRGNR$_{588}$ QAATA | (Shi and Bartlett, 2003) |
| I-591 | $A_{591}$ | NRQAA$_{591}$ TADVN | (Wu et al., 2000) |
| I-657 | $P_{657}$ | VPANP$_{657}$ STTFS | |
| I-664 | $A_{664}$ | TFSAA$_{664}$ KFASF | (Wu et al., 2000) |
| I-713 | $T_{713}$ | NVDFT$_{713}$ VDTNG | |
| I-716 | $T_{716}$ | FTVDT$_{716}$ NGVYS | (Maheshri et al., 2006) |

I-570 is especially suitable as an insertion site that goes along with a deletion of given Aas of the parvovirus structural protein at the site of insertion, leading to a complete substitution. In this case the Aas RTTNPVATEQ (SEQ ID NO:175) can be substituted by an epi- or mimotope.

Insertions have been successfully made into AAV-serotypes other than AAV2.

TABLE 2

Insertions into AAV-serotypes other than AAV2

| AAV serotype | sequence | insertion site/ AA relative to AAV2 | | references |
|---|---|---|---|---|
| AAV1 | FQSSS$_{588}$ TDPAT | I-587 | $N_{587}$ | own data |
| AAV1 | SSSTD$_{590}$ PATGD | I-589 | $Q_{589}$ | (Arnold et al., 2006, Stachler and Bartlett, 2006) |
| AAV-3 | NNLQS$_{586}$-SNTAP | I-585 | $R_{585}$ | (Arnold et al., 2006) |
| AAV-4 | GGDQS$_{584}$-NSNLP | I-585 | | (Arnold et al., 2006) |
| AAV-5 | TNNQS$_{575}$-STTAP | I-585 | | (Arnold et al., 2006) |

The most preferred insertion sites are:
i) I-587 as various insertions have been made in the AA stretch around $N_{587}$ (LQRGN$_{587}$ RQAAT (SEQ ID NO: 178)) of AAV2. Within this stretch insertions of various peptides were made C-terminal of Aas $Q_{584}$, $N_{587}$, $R_{588}$ and $A_{591}$ in AAV2 and C-terminal of Aas of other AAV-serotypes corresponding to $R_{585}$ and $Q_{589}$ of AAV2.
ii) I-453 as epitopes have been successfully inserted C-terminal of $G_{453}$ in AAV2.
iii) FQSSS$_{588}$ TDPAT (SEQ ID NO: 148) or SSSTD$_{590}$ PATGD (SEQ ID NO: 185) of AAV1.
iv) I-261 as according to this invention epitopes have been successfully inserted C-terminal of $S_{261}$ in AAV2.
v) I-534 as according to this invention epitopes have been successfully inserted C-terminal of $F_{53}4$ in AAV2.
vi) I-570 as according to this invention epitopes have been successfully inserted C-terminal of $P_{570}$ in AAV2.
vii) I-573 as according to this invention epitopes have been successfully inserted C-terminal of $T_{573}$ in AAV2.

Figure 3:
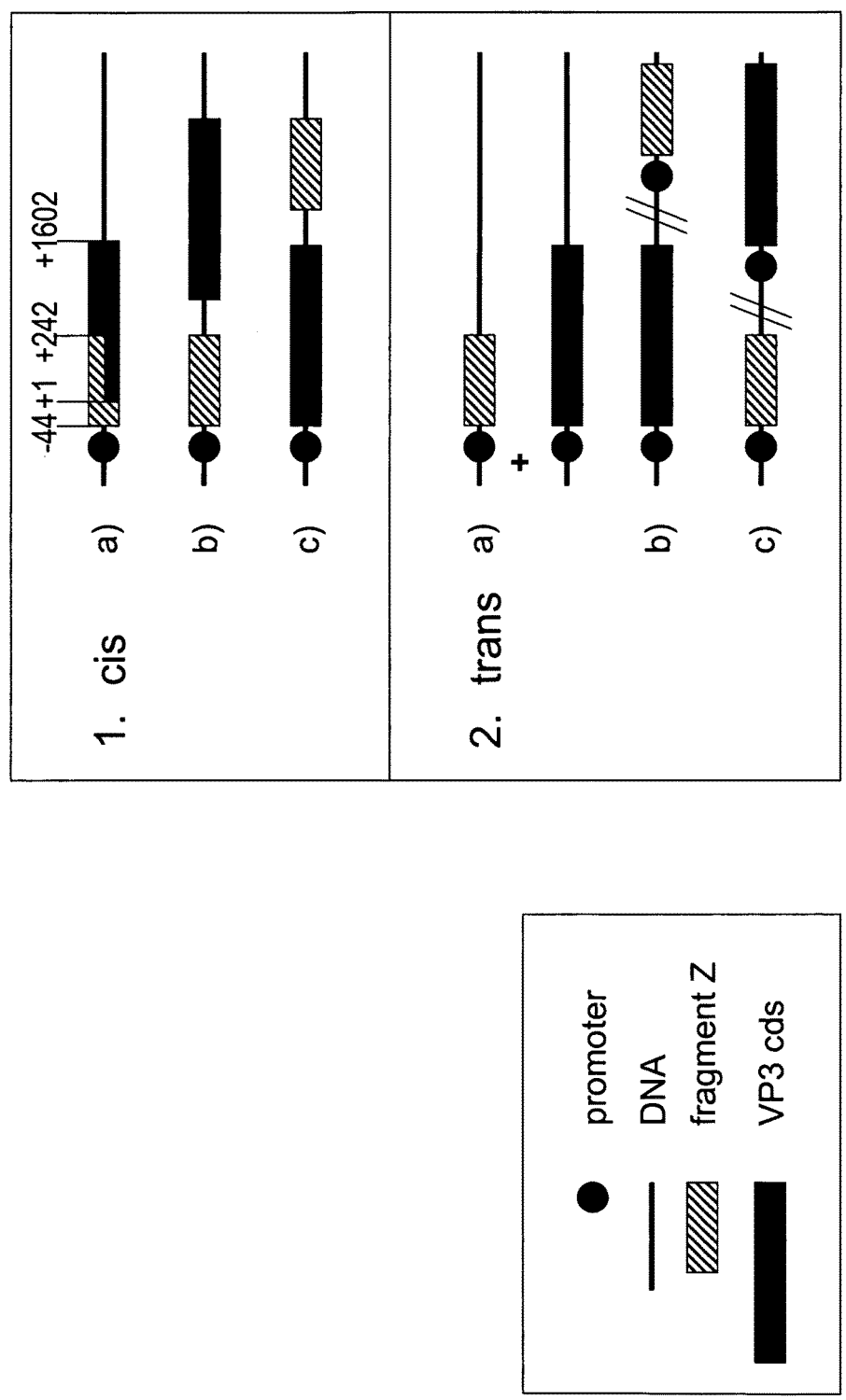

Corresponding Aas for all insertion sites specified herein for parvoviruses disclosed herein can be retrieved from the alignment in FIG. 3 of WO 2008/145400. For those parvoviruses not listed therein an alignment under standard parameters as used there can be performed with the provided AA sequence of such parvovirus and the corresponding AA can be retrieved from such alignment.

According to this invention two insertions may be preferred and are made into two positions selected from the group consisting of I-261, I-453, I-534, I-570, I-573 and I-587, preferably I-261 in combination with I-587, I-261 in combination with I-453 or I-453 in combination with I-587. With respect to triple insertions, preferred combinations are made into three positions of VP3, preferably an insertion in position 453 in combination with an insertion in position 587 and in combination with an additional mutation, more preferably in positions I-453, I-587 combined with one of the I-534, I-570 and I-573.

Particularly for vaccination applications AAV particles presenting the selected epitope have to be generated. Therefore, it is preferred that the VP3 cds comprises at least one epitope heterologous to the virus.

It is further preferred that the epitope of the VP3 protein is a B-cell epitope. Preferably the B-cell epitope is a part of an antigen. Preferred antigens are serum proteins, proteins that can be found at least under certain conditions (e.g. in a disease state) in the blood, membrane proteins, especially receptor proteins (e.g. CD20, acetylcholine receptors, IL13R, EGFR), and surface antigens of infectious agents, preferably not immuno-dominant epitopes of such surface antigens. Especially preferred antigens are IgE, tumor-antigens (e.g. Melan A, high molecular weight melanoma associated antigen (HMW MAA), CA125, IL13R, Her2/NEU, L1 cell adhesion molecule), VEGF, EGFR, CD20, IL1, IL4, IL5, IL6, IL9, IL13, IL17, IL18, IL33, TSLP (thymic stromal lymphopoietin), CETP (cholesterol ester transfer protein), TNF-family members (e.g. TNF-α), or β-amyloid.

In a further embodiment the VP3 comprises at least one B-cell epitope heterologous to the parvovirus, which is preferably not identical to a pathogen, particularly to a B-cell epitope of a pathogen, wherein the B-cell epitope is located on the surface of the virus. In a preferred embodiment the VP3 is capable of inducing an immunoglobulin capable of binding to the antigen the B-cell epitope is derived from.

In a preferred embodiment, the B-cell epitope is inserted into I-453 and/oror I-587, especially into I-453 and/oror I-587 of AAV1, AAV2 or AAV4.

It is especially preferred that an identical B-cell epitope is inserted at two or more different insertion sites, if it is key to have a large number of identical peptides being optimally presented on the surface of a capsid, especially in case direct B-cell receptor crosslinking should be required for T-cell independent priming of B-cells and breaking of B cell tolerance against self-antigens. A higher density of B-cell epitopes increases the likelihood of optimal peptide-specific B-cell receptor crosslinking which requires a defined distance between B-cell receptors, and therefore, respective B-cell epitopes being presented on a parvovirus capsid.

Moreover, a larger number of inserted B-cell epitopes decreases the probability for undesired immune reactions against the parvovirus backbone due to i) masking of natural parvovirus B-cell epi-/mimotopes and/oror ii) slight structural capsid changes rendering these natural B-cell epi-/mimotopes less immunogenic. Accordingly, parvovirus structural proteins comprising at least three insertions are especially preferred.

Taken together, preferred insertion sites for superficial presentation of epitopes are the positions following the amino acids that correspond to the AAV2 amino acids number I-261, I-266, I-381, I-447, I-448, I-453, I-459, I-471, I-534, I-570, I-573, I-584, I-587, I-588, I-591, I-657, 1-664, I-713 and I-716, especially I-261, I-453, I-534, I-570, I-573, I-587, and I-588, most preferably I-453 and I-587.

In a further embodiment the insertions, whether terminal or internal, are combined with the deletion of one or more amino acids, leading to a partial or 1:1 substitution of amino acids by different amino acids, wherein partial substitution means that e.g. 8 amino acids are substituted by 6 different amino acids, and a 1:1 substitution means that e.g. 8 amino acids are substituted by 8 different amino acids.

In one embodiment of this invention the VP3 is comprised in a fusion protein, e.g. fused to a second protein or peptide. In an especially preferred embodiment B-cell epitopes in particular epitopes larger than 20 amino acids are fused to the N-terminus of VP3.

In one specific embodiment the VP3 comprises at least one tag useful for binding to a ligand. In an especially preferred embodiment said tag is introduced in the parvovirus mutated structural protein by a further mutation. Such tags are well known in the art, Table 3.

TABLE 3

Tags and corresponding ligands

| Tag | Ligand |
|---|---|
| AU1 | Anti AU1 monoclonal antibody |
| HIS | Nickel |
| GST | Glutathione |
| Protein A | IgG |
| Biotin or Strep | Streptavidin |
| Calmodulin-binding peptide | Calmodulin |
| Fc-Peptide of IgG | Protein A |
| Flag | GLAG- or 3xFLAG peptide |
| HA (hem agglutinin) | HA peptide |

In another embodiment of the present invention the VP3 comprises at least one further mutation. The mutation may be any suitable mutation, such as any of those defined above.

For example, one or several further mutation(s) of the VP3 might be adequate to e.g. i) introduce additional or even identical B-cell epitopes of the same target antigen, and/oror ii) B-cell epitopes of one or more further target protein(s) (multi-target vaccine), T-cell epitope(s) to further promote the desired T-cell immune response, peptide sequence(s) to target and/oror activate antigen-presenting cells, or to obtain capsid mutants with reduced immunogenicity of the core particle. The latter might be one possibility to setup an efficient prime/boost regimen.

Besides, a further mutation of the parvovirus mutated structural protein at a different position can be used to compose more complex mimotopes, to modify certain properties of the virion, e.g. it can be used to modify its natural antigenicity (e.g. Huttner et al., 2003, and WO 01/05990), to modify its chromatographic properties (e.g. WO 01/05991), to insert a second B-cell epitope, to insert a T-helper epitope, or to insert a CTL epitope. Such further mutation is selected from a point mutation, an internal or terminal deletion, an insertion and a substitution. Preferably, the further (second) insertion is internally e.g. by an N- or C-terminal fusion.

Another aspect of the invention is a parvoviral particle obtainable from any of the methods disclosed above. Based upon the above described methods we were able to produce parvoviral particles which essentially consist only of VP3 and do not comprise a heterologous nuclear localization signal (NLS). Such particles do not contain Rep protein, particularly Rep40, Rep52, Rep68 and Rep78. The described methods enable the production of sufficient quantities/yields for the manufacture of medicaments in a commercial scale.

Another aspect of the invention relates to a parvoviral particle consisting essentially of VP3, wherein the VP3 optionally comprises one or more mutation(s) as compared to the corresponding wildtype VP3, and wherein the VP3 does not contain a heterologous nuclear localization signal (NLS), and wherein the particle does not contain Rep protein, particularly functional Rep40, Rep52, Rep68 and Rep78.

Especially preferred is a parvoviral particle wherein the capsid consists only of VP3.

With respect to the one or more mutations it is referred to the mutations as described before.

One further aspect of the invention is an expression cassette A comprising a VP3 cds as defined before and a heterologous promoter thereto, wherein transcription of VP3 is driven by the heterologous promoter, and wherein the expression cassette is capable of expressing essentially only VP3. Especially preferred are expression cassettes that express only VP3. The construct is used to express mutated VP3 according to this invention. The sequence of VP3 can be mutated as described. As understood by the skilled person the expression cassette further comprises a poly(A) sequence.

Another aspect of the invention is an expression cassette B comprising a fragment Z as defined before and a promoter heterologous thereto, wherein transcription of fragment Z is driven by the heterologous promoter. The construct is used to express fragment Z according to this invention. The sequence of fragment Z can be mutated as described. Optionally, this expression cassette further comprises a poly(A) sequence.

A further aspect of the invention is an expression cassette C comprising (i) a VP3 cds as defined before and fragment Z as defined before, and (ii) a promoter heterologous thereto, wherein the expression of VP3 and fragment Z is driven by this one heterologous promoter.

In a further aspect of the invention the expression cassette comprising a heterologous promoter, a VP3 cds as described above and the nucleic acid of the invention are combined, wherein the expression of VP3 and of the polypeptide encoded by the nucleic acid (AAP or AAP variant) is driven by this one heterologous promoter. Optionally, this expression cassette further comprises a poly(A) sequence.

It is one further aspect that at least one expression cassette A/VP3 expression cassette and at least one expression cassette B/expression cassette comprising the nucleic acid of the invention are combined in a kit. By combining expression of parvoviral VP3 from the VP3 cds and expression of fragment Z/the nucleic acid of the invention it is possible to generate particles consisting essentially only of VP3 according to this invention.

Another aspect relates to a kit comprising at least one VP3 expression cassette A and at least one nucleic acid of the invention or a kit comprising at least one expression cassette C for the combined and simultaneous expression of VP3 and fragment Z in the cell and generation of VP3 VLPs. Such kits preferably additionally contain a manual.

Still another aspect of the present invention relates to a medicament comprising the parvovirus particle according to the invention. Medicaments according to the present invention have numerous advantages over the prior art. The immune system of a mammal is specialized to generate strong antibody responses against viral capsid proteins due to the co-evolution of mammals and their immune system on one hand and viruses on the other hand. Strong antibody responses means titers of 1,000 to >100,000 measured in a standard ELISA. Virus-like particles are highly immunogenic due to resemblance of a virus, the repetitive and highly structural pattern of antigens, and efficient uptake of such particles by antigen-presenting cells. The size of the virion, the density and symmetric order of B-cell epitopes and the optimal distance of about 50 to 100 Å between any two B-cell epitopes plays a major role regarding very strong T-cell independent B-cell responses mediated by direct cross-linking of the respective B-cell receptor breaking even B-cell tolerance against self-antigens or tolerogens (Szomolanyi-Tsuda and Welsh, 1998, Szomolanyi-Tsuda et al., 1998, Szomolanyi-Tsuda et al., 2000, Szomolanyi-Tsuda et al., 2001, Zinkernagel, 2002, Bachmann et al., 1993).

Taken together, such medicaments are capable of inducing a polyclonal immune response against certain B-cell epitopes that leads to an active immune response resulting in high and long lasting antibody titers. The multimeric structure of the virion contains a large number of densely packed identical epitopes directly cross-linking the respective receptor on B-cells and, thereby, inducing a T-cell independent B-cell response. The particulate structure of the medicament further supports the immune response via efficient uptake by antigen-presenting cells which activate T-cells finally triggering IgG class switch and hypermutation of activated B-cells, leading to the persistent release of high-affinity IgG antibodies and differentiation of B-cells into memory cells.

Using the methods of the current invention such medicaments can easily be produced.

The medicament of the present invention may further additionally comprise one or more excipients. The excipient is a pharmaceutically acceptable carrier and/oror excipient. Excipients are conventional and may include buffers, stabilizers, diluents, preservatives, and solubilizers. Remington's Pharmaceutical Sciences, by E. W. Martin, Mack Publishing Co., Easton, Pa., 15th Edition (1975), describes compositions and formulations suitable for pharmaceutical delivery of the (parvo)viral particles herein disclosed. In general, the nature of the carrier or excipients will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e. g. powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

In a further embodiment the medicament is a vaccine. In general, a vaccine is a preparation consisting of antigens of a disease-causing agent which, when introduced into the body, stimulates the production of specific antibodies or altered cells. This produces generally an immune response as an active principle. Particularly, the parvovirus particles assembled of VP3 comprise at least one B-cell epitope heterologous to the parvovirus, preferably for preventing or treating an autoimmune disease (e.g. diabetes type 1), a tumor disease (examples are: melanoma: e.g. HMW MAA, glioblastome multiforme: e.g. CA125, anti-IL13R, colon cancer: e.g. CA125 or anti-EGF AND/OR, breast cancer: e.g. Her2/NEU, ovarian cancer: e.g. L1 adhesion molecule, B-cell lymphoma: e.g. CD20), an allergic disease (asthma, allergies such as allergic rhinitis, examples for targets are IgE, IL4, IL5, IL9, IL13, IL18, IL33, TSLP), a metabolic disease (e.g. high cholesterol, intervention into the cholesterol metabolism (target example: CETP), obesity, hypertension (target example angiotensin II), an inflammatory disease (e g. rheumatoid arthritis, Crohn's disease, target examples' IL6, IL17 and TNF-α), a neurological disease (e.g. Alzheimer's disease; target example: 3-Amyloid) or to be used in ophthalmology (e.g. AMD, target example VEGF).

Also encompassed by the present inventions are methods for vaccination and/oror for treating or preventing the diseases specified herein by administering to a patient an effective amount of parvovirus particles of the invention and/oror expression constructs coding for the VP3 VLP of the invention.

In a preferred embodiment the vaccine further comprises one or more adjuvants, particularly as an immunostimulatory substance. The adjuvant can be selected based on the method of administration and may include mineral oil-based adjuvants such as Freund's complete and incomplete adjuvant, Montanide incomplete Seppic adjuvant such as ISA, oil in water emulsion adjuvants such as the Ribi adjuvant system, syntax adjuvant formulation containing muramyl dipeptide, or aluminum salt adjuvants.

One embodiment of this invention is a medicament for the prevention or treatment of an autoimmune disease, an infectious disease, a tumor disease, an allergic disease, a metabolic disease, a (chronic) inflammatory disease, a neurological disease, addiction or to be used in ophthalmology. Preferred autoimmune diseases and/oror a chronic inflammatory diseases are rheumatoid arthritis, psoriasis and Crohn's disease. A preferred tumor disease is a disease eligible for treatment with a monoclonal antibody, e.g. trastuzumab. Preferred allergic diseases are asthma and allergies, e.g. allergic rhinitis. Examples for preferred allergens are birch pollen, house dust mite and grass pollen. A preferred neurological disease is Alzheimer's disease. A preferred metabolic disease is atherosclerosis. A preferred ophthalmological disease is age-related macular degeneration. In a further preferred embodiment the parvovirus particle or the medicament is used in a method of breaking B-cell tolerance, meaning inducing antibodies against a self-antigen.

In a further special embodiment the disease treated by the medicament is not an infectious disease.

Moreover, the parvovirus mutated structural protein of the medicament is not used as a vector in gene therapy.

In another embodiment the parvoviral particle of the invention is used for gene therapy.

According to this invention an embodiment is the use of a parvovirus particle as defined above, preferably the medicament as defined above, comprising at least one B-cell epitope heterologous to the parvovirus for the manufacture of a vaccine, preferably for preventing or treating an autoimmune disease and/oror a chronic inflammatory disease, preferably rheumatoid arthritis and/oror Crohn's disease, a tumor disease, an allergic disease, asthma, Alzheimer's disease, atherosclerosis, a metabolic disease, an inflammatory disease, a neurological disease or to be used in ophthalmology.

In this document, the content of all cited documents is included by reference.

The following examples and figures are intended to explain the invention in detail without restricting it.

FIGURES

FIG. 1: Schematic organization of the AAV capsid gene.

The coding DNA for the cap gene is shown in the first line, the Cap proteins VP1, VP2 and VP3 in the following ones. Nucleotide numbers correspond to the genome sequence of AAV-2 given by Ruffing et al. (1994) accessible from NCBI (number of entree: NC_001401). Numbering of amino acid (AA) sequences according to VP1 of AAV2 (Girod et al. 1999). EcoNI and BsiWI restriction sites are marked. Not to scale.

FIGS. 2A-2D: Nucleotide sequences of fragment Z of different AAVs.

The nucleotide sequences of fragment Z of the parvoviruses AAV1 (NC_002077), AAV2 (AF043303), AAV3b (AF028705), AAV4 (U89790), AAV5 (NC_006152), AAV6 (AF028704), AAV7 (AF513851), AAV8 (AF513852), AAV10 (AY631965), AAV11 (AY631966), and b-AAV (NC_005889) are given (numbers of nucleotide entrees according to NCBI are given in brackets). +1 indicates the position of the first nucleotide coding for the ATG start codon of VP3. The 44 nucleotides upstream and 242 nucleotides downstream of the +1 position are shown. The ATG start codon of VP3 is underlined.

FIG. 3: Schematic representation of the different expression constructs suitable for assembly of VP3 particles.

Six possible expression constructs differing in the set-up of the fragment Z sequence and VP3 cds are shown by different boxes as indicated. In the cis situation they are expressed under the same one promoter whereas in trans two separate promoters drive their expression, as indicated by the circle. +1 indicates the position of the first nucleotide coding for the ATG start codon of VP3. The DNA of fragment Z comprising at least 44 nucleotides upstream and more than 242 nucleotides downstream of the +1 position are boxed (compare FIGS. 2A-2D). +1602 marks the number of the last nucleotide of the TAA stop codon at the 3' end of the VP3 cds (as outlined in FIG. 1). An arbitrary number of nucleotides can separate the VP3 cds and fragment Z and is marked by //. Not to scale.

Figure 4:
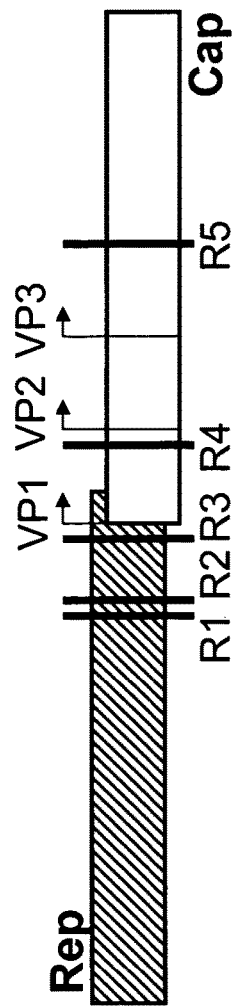

FIG. 4: Schematic organization of the rep and cap genes, as well as position of different restriction sites used for cloning of expression constructs.

Schematic representation of the rep and cap genes in the parvovirus genome. The position of the restriction sites R1 to R5 used for cloning of the different expression constructs, as well as the positions of the translation start codons of the three capsid proteins are marked. Not to scale FIGS. 5A-5D: Comparison of capsid assembly using different VP protein expression constructs.

Figure 5A:
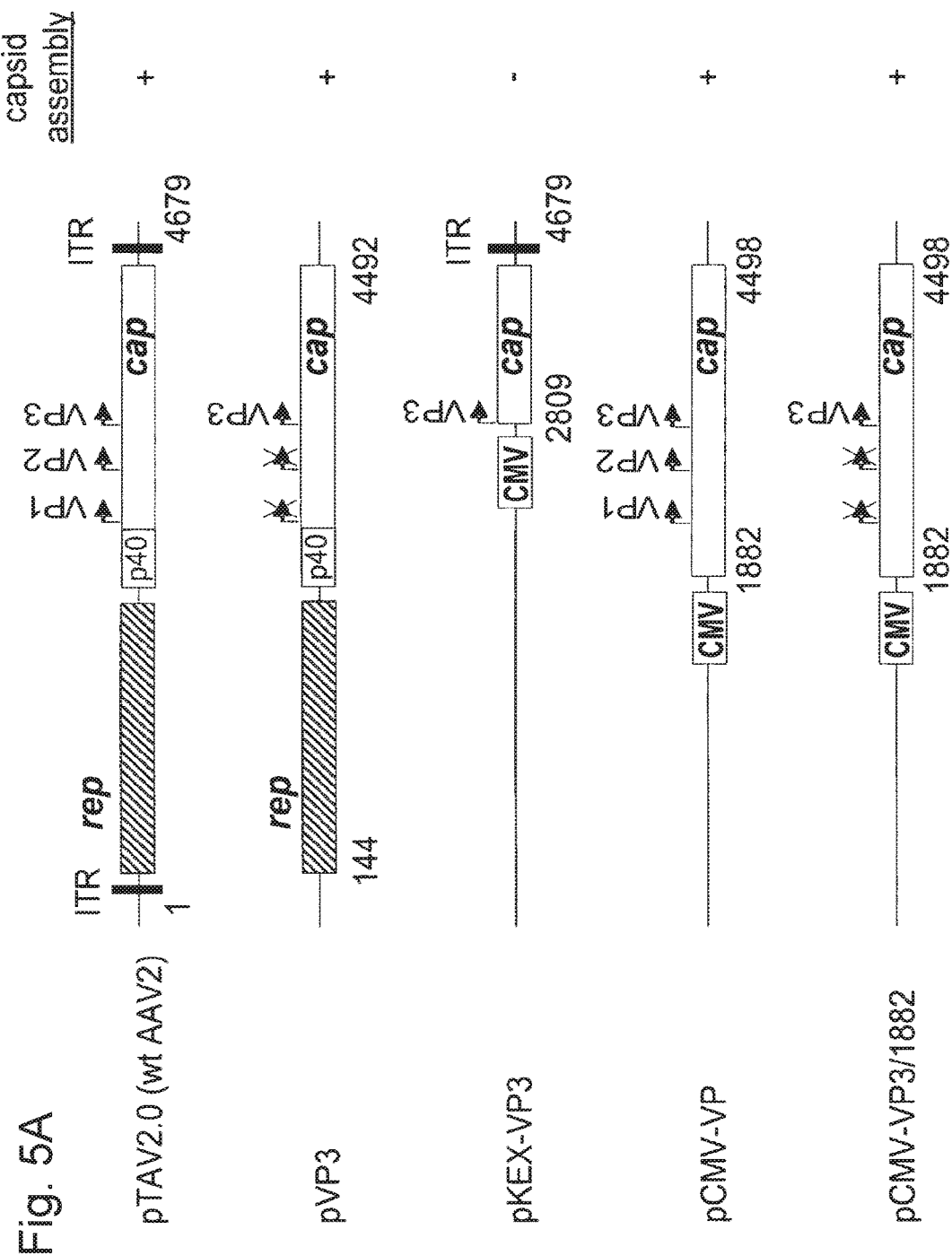
Figure 5B:
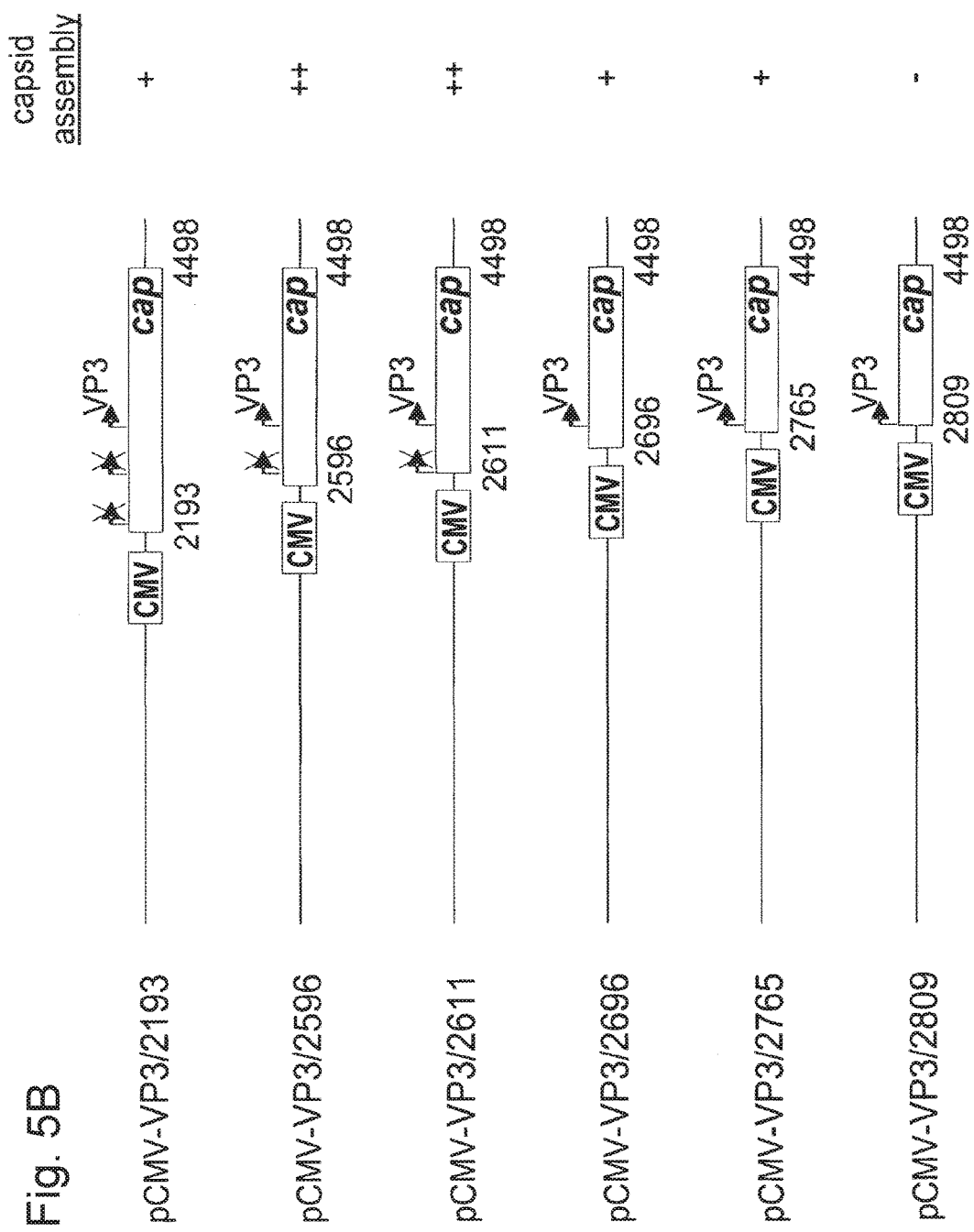
Figures 5C, 5D:
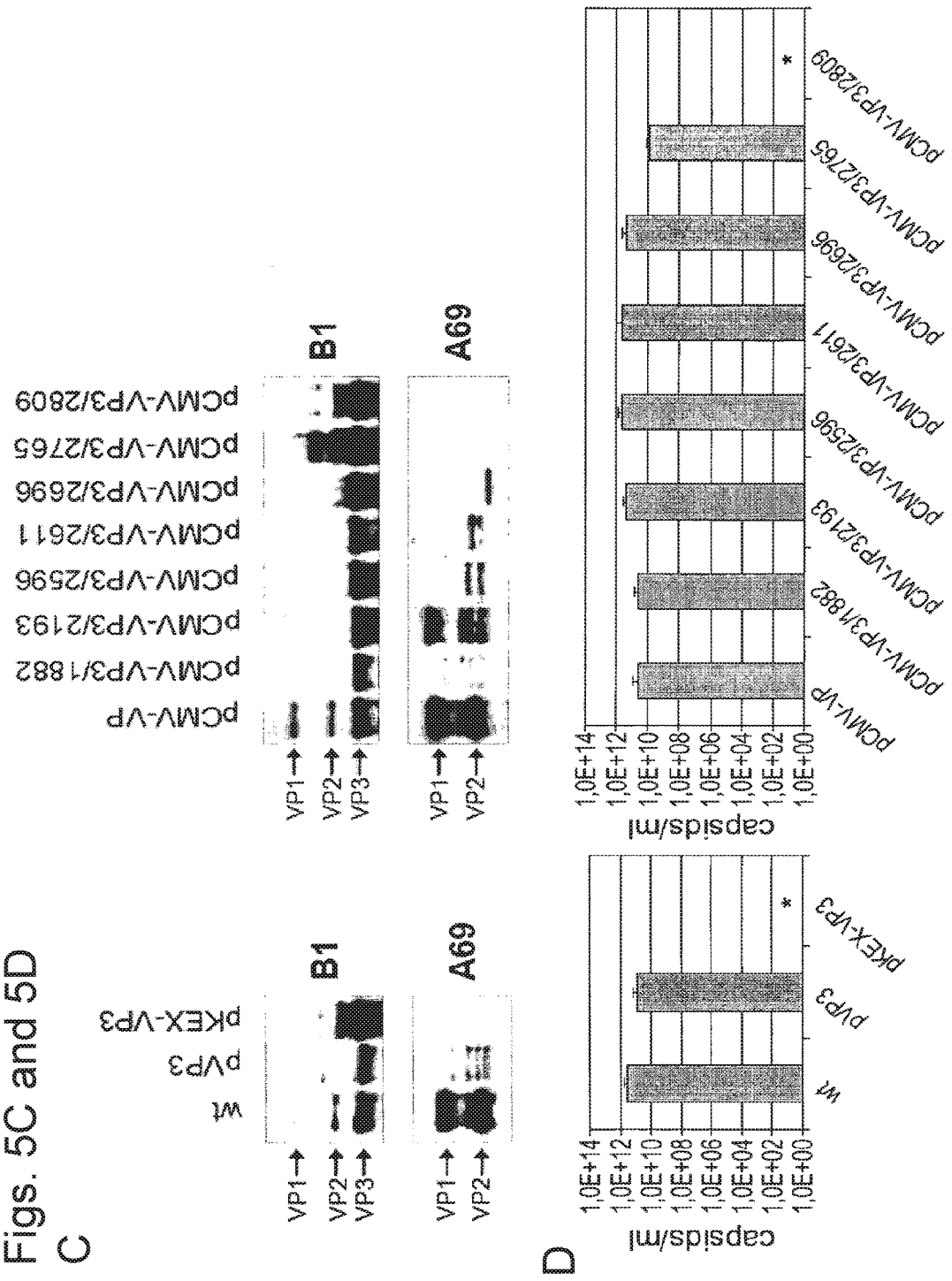

FIGS. 5A and 5B) Schematic representation of the cap gene expression constructs used for analysis of VP protein expression and to study capsid assembly. Plasmids pCMV-VP3/1882 to pCMV-VP3/2809 are derived from plasmid pVP3. Numbers indicate nucleotide positions in the AAV2 genome according to Ruffing et al., 1994 (supra). Arrows represent translation start sites of the VP proteins, mutated translation start sites are labeled with a cross. The ability of the proteins expressed from these expression constructs to assemble capsids is given in the right column (corresponding to the quantification in FIG. 5D, ++ corresponds to peak titer of capsids, − means that no capsids could be detected, + means that capsid assembly is detectable. FIG. 5C) Western blot analysis of expressed VP proteins was performed using antibody B1 which detects all three capsid proteins or antibody A69 which detects only VP1 and VP2. In each lane a different expression construct is separated, name according to FIGS. 5A and 5B. The position of the three capsid proteins is marked. FIG. 5D) Capsid formation was quantified by an ELISA based on monoclonal antibody A20. Means+/−standard deviations of at least three independent experiments are shown; asterisk indicates constructs for which no capsids could be detected.

FIGS. 6A-6D: Complementation of VP3 capsid assembly by VP2N-gfp.

Figures 6A, 6B, 6C:
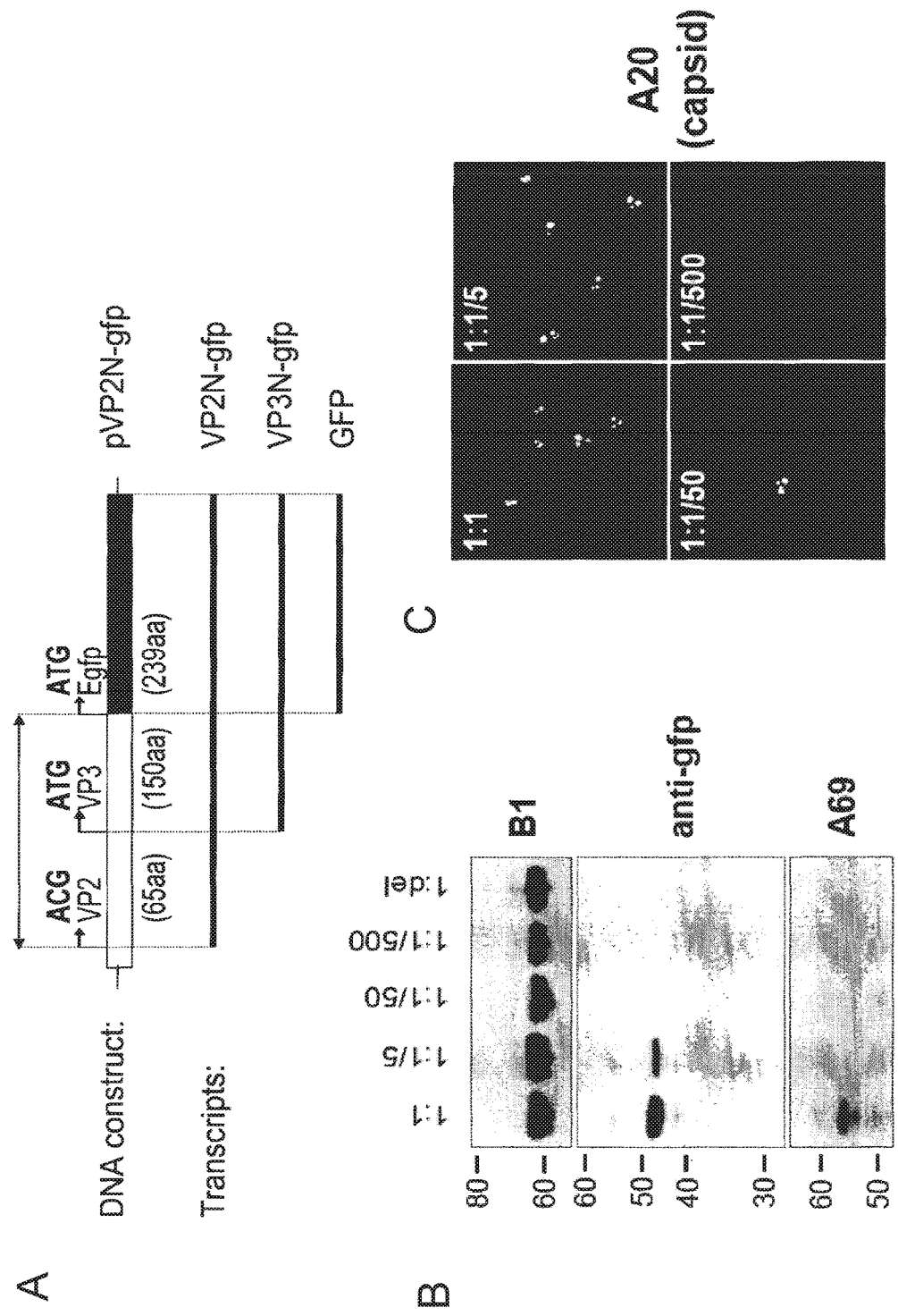

FIG. 6A) Schematic representation of the fusion construct, pVP2N-gfp, as well as of its transcripts VP2N-gfp, VP3N-gfp and GFP as indicated. FIG. 6B) Western blot detection of VP3 (B1 antibody), VP3N-gfp fusion protein (anti-gfp antibody) and VP2N-gfp (A69 antibody) expression in HeLa cells after co-transfection of pVP3/2809 (1) and decreasing amounts of pVP2N-gfp (1, ⅕, ⅕₀, ⅕₀₀, del meaning 0) as indicated. FIG. 6C) Detection of capsid formation by indirect immunofluorescence using antibody A20 in HeLa cells co-transfected with pVP3/2809 and pVP2N-gfp in different ratios as marked and shown in FIG. 6B. D) Quantification of capsid formation in HeLa cells co-transfected with pVP3/2809 and pVP2N-gfp in different ratios using the A20 based capsid ELISA. Again, the different plasmid ratios are marked and correspond to those shown in FIGS. 6B and 6C. For each experiment the mean concentration of capsids+/−standard deviations of at least two independent experiments are shown; asterisk indicates samples for which no capsids could be detected.

Figure 7:
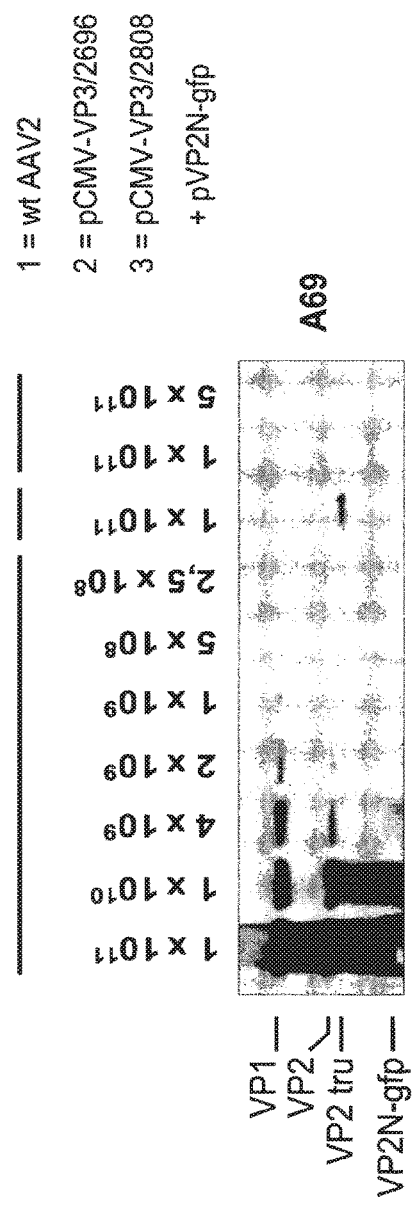

FIG. 7: Substoichiometric incorporation of truncated VP2 within VP3 particles in the cis situation.

Western blot analysis of purified wt AAV and capsids derived from pVP3/2696 or pVP3/2809 trans-complemented with pVP2N-gfp. Detection of VP1 and VP2 occurred with antibody A69. Different amounts of capsids as indicated were loaded to the gel for a qualitative estimation of the ratio of different signals (VP2tru=truncated VP2).

FIGS. 8A-8F: Characterization of helper plasmid pVP2Ncm-gfp with alternative codon usage.

FIGS. 8A-8C) Alignment of wt (VP2N, SEQ ID NO: 145) and codon modified VP2N (VP2Ncm, SEQ ID NO: 146) DNA sequences of the respective constructs pVP2N-gfp (details in FIG. 6A) and pVP2Ncm-gfp.

FIG. 8D) Western blot of 293-T cell extracts after transfection of the indicated plasmids with monoclonal antibody A69. FIG. 8E) Fluorescence images of HeLa cells transfected with pVP2N-gfp: The upper and lower left panels represent total GFP fluorescence. The upper and lower right panels show indirect immunofluorescence of the VP2 part within VP2N-gfp visualized by the A69 antibody and the respective secondary Cy3-labeled goat anti-mouse antibody. FIG. 8F) Quantification of capsid formation in 293-T cells co-transfected with pCMV-VP3/2809 and the indicated plasmids using the A20 based capsid ELISA. Means+/−standard deviations of at least three independent experiments are shown; asterisk indicates sample for which no capsids could be detected.

Figures 9A, 9B, 9C:
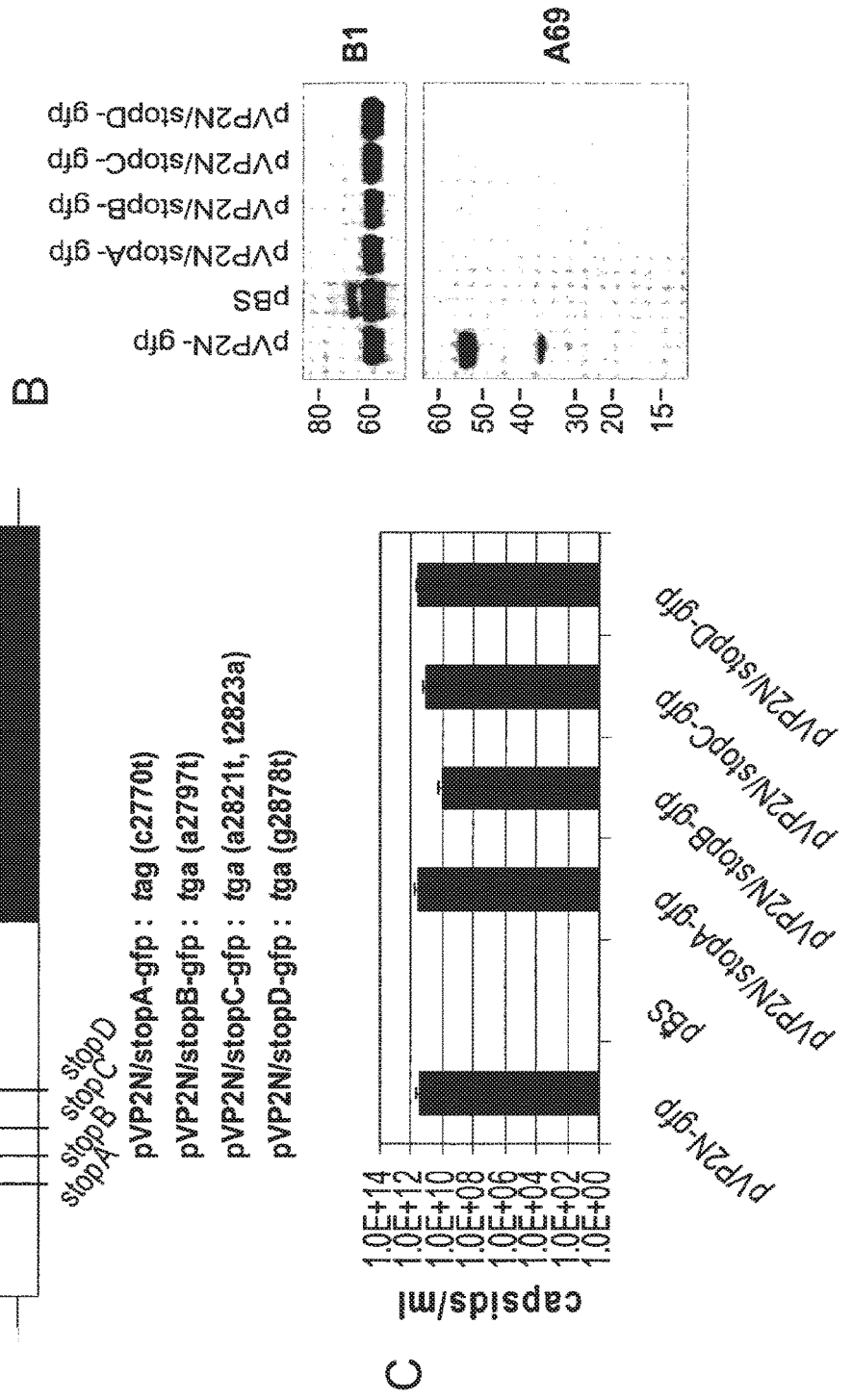

FIGS. 9A-9C: Stop codon mutagenesis within the trans-complementation construct

FIG. 9A) Schematic representation of pVP2N-gfp constructs with translation stop codons in the VP2N reading frame at four different positions. Numbers of the substituted nucleotides refer to the nucleotide positions of the AAV2 genome. In pVP2N/stopA the cag-codon starting at nucleotide 2770 and coding for glutamine has been mutated into tag, in pVP2N/stopB the gga-codon starting at nucleotide 2797 and coding for glycine has been mutated into tga, in pVP2N/stopC the agt-codon starting at nucleotide 2821 and coding for serine has been mutated into tga, and in pVP2N/stopD the gga-codon starting at nucleotide 2878 and coding for glycine has been mutated into tga. FIG. 9B) Western blot of 293-T cell extracts after co-transfection of pCMV-VP3/2809 and the indicated plasmids with monoclonal antibodies B1 and A69. FIG. 9C) Quantification of capsid formation in 293-T cells co-transfected with pCMV-VP3/2809 and the indicated plasmids using the A20 based capsid ELISA. Means+/−standard deviations of at least three independent experiments are shown; asterisk indicates sample for which no capsids could be detected.

Figure 10:
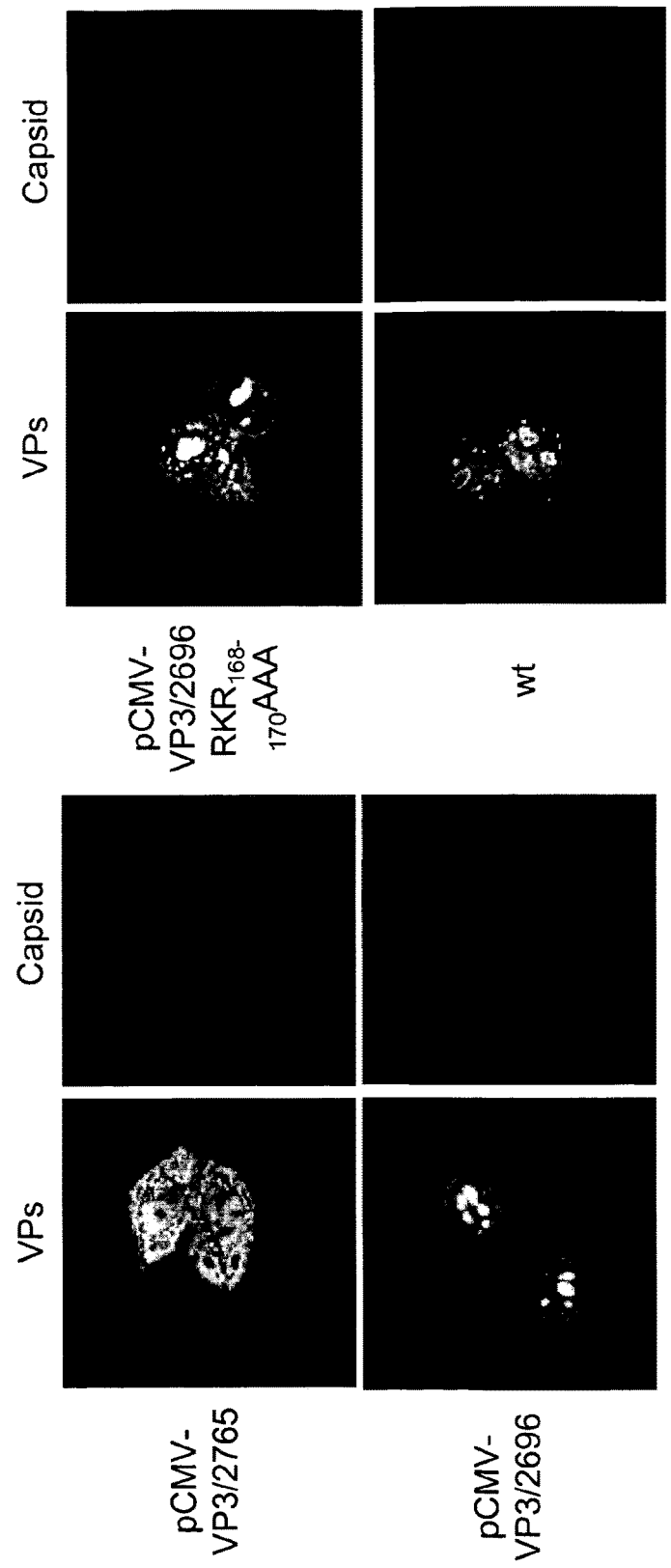

FIG. 10: Cellular localization of capsid proteins and capsids obtained by expression of different cap gene mutants.

Localization of capsid proteins expressed from different constructs in HeLa cells was visualized by double immunofluorescence using a polyclonal rabbit antiserum detecting total capsid proteins (VPs) and monoclonal antibody A20 detecting assembled capsids. The transfected plasmids are indicated at the left margin.

Immunofluorescence staining of transfected HeLa cells with the A20 antibody showed that the VP protein of mutant pCMV-VP3/2696RKR168-170AAA was as efficient in capsid assembly as wt AAV. For the construct pCMV-VP3/2696RKR168-170AAA the postulated NLS was mutated by converting the RKR peptide (AA 168-170).

Figure 11C:
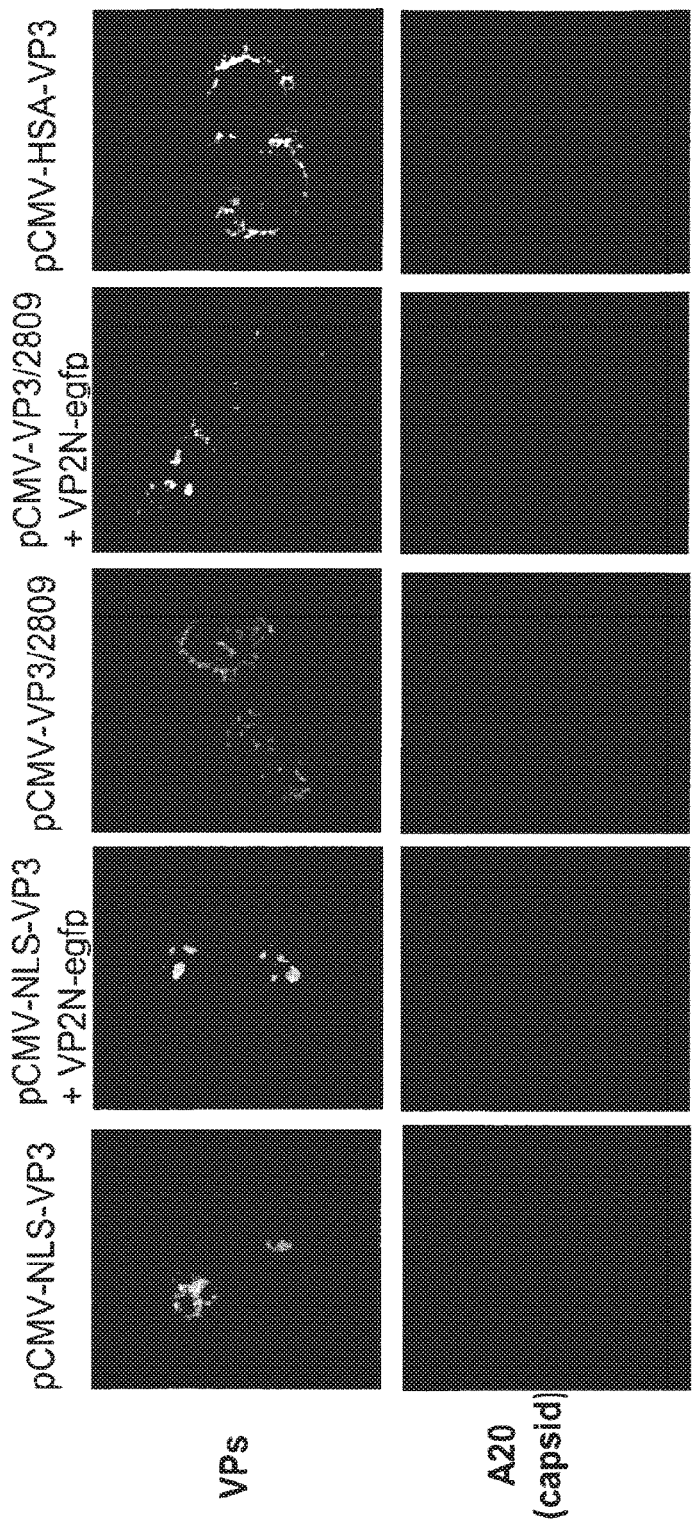

FIGS. 11A-11C: Capsid assembly of VP3 modified by a NLS or an N terminal extension of human serum albumin.

FIG. 11A) Schematic representation of NLS-VP3 and HSA-VP3 used for analysis of capsid assembly. FIG. 11B) Immuno dot blot analysis of fractions obtained from COS-1 cell extracts separated on sucrose gradients. The cells were harvested 48 h post transfection of the plasmids indicated in the left margin. Note that reaction with the A20 antibody was performed under non-denaturing conditions to detect assembled capsids, whereas reaction with B1 antibody was performed after denaturation of the capsids to detect single capsid proteins. The sedimentation constant of the viral capsid is indicated (60 S). FIG. 11C) Indirect double immunofluorescence of HeLa cells transfected with plasmids indicated above the images using a polyclonal VP antiserum (VPs) to localize total expressed capsid proteins (upper row) and antibody A20 to detect assembled capsids (lower row). VP2N-egfp is a synonym for pVP2N-gfp.

Figure 12B:
Figure 12C:
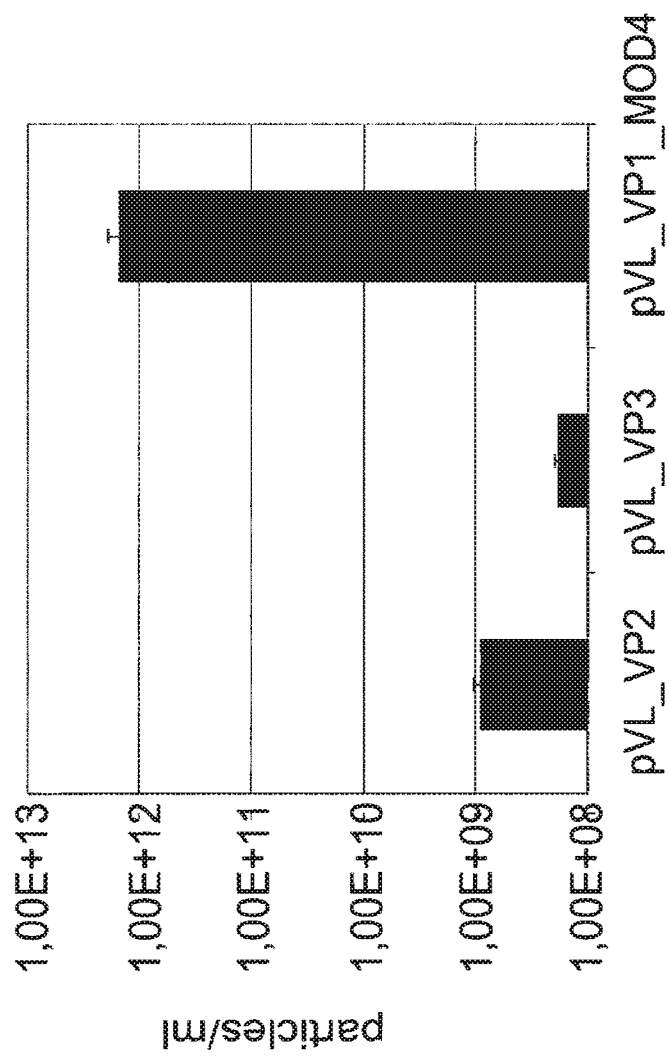

FIGS. 12A-12C: VP3 particle production in insect cells FIG. 12A) Schematic representation of constructs used for AAV production in insect cells. FIG. 12B) Western blot analysis of expressed VP proteins was performed using antibody SA7885 (1:10000 dilution) a polyclonal rabbit serum that detects all three capsid proteins and subsequent the secondary antibody anti rabbit IgG-HRP 1:2500 (Dianova, Hamburg, Germany).

FIG. 12C) Capsid formation was quantified by an ELISA based on monoclonal antibody A20. Means+/−standard deviations of 2 (VP2 construct) or 4 (VP3 and VP1_Mod4) independent experiments are shown.

Figures 13, 14:
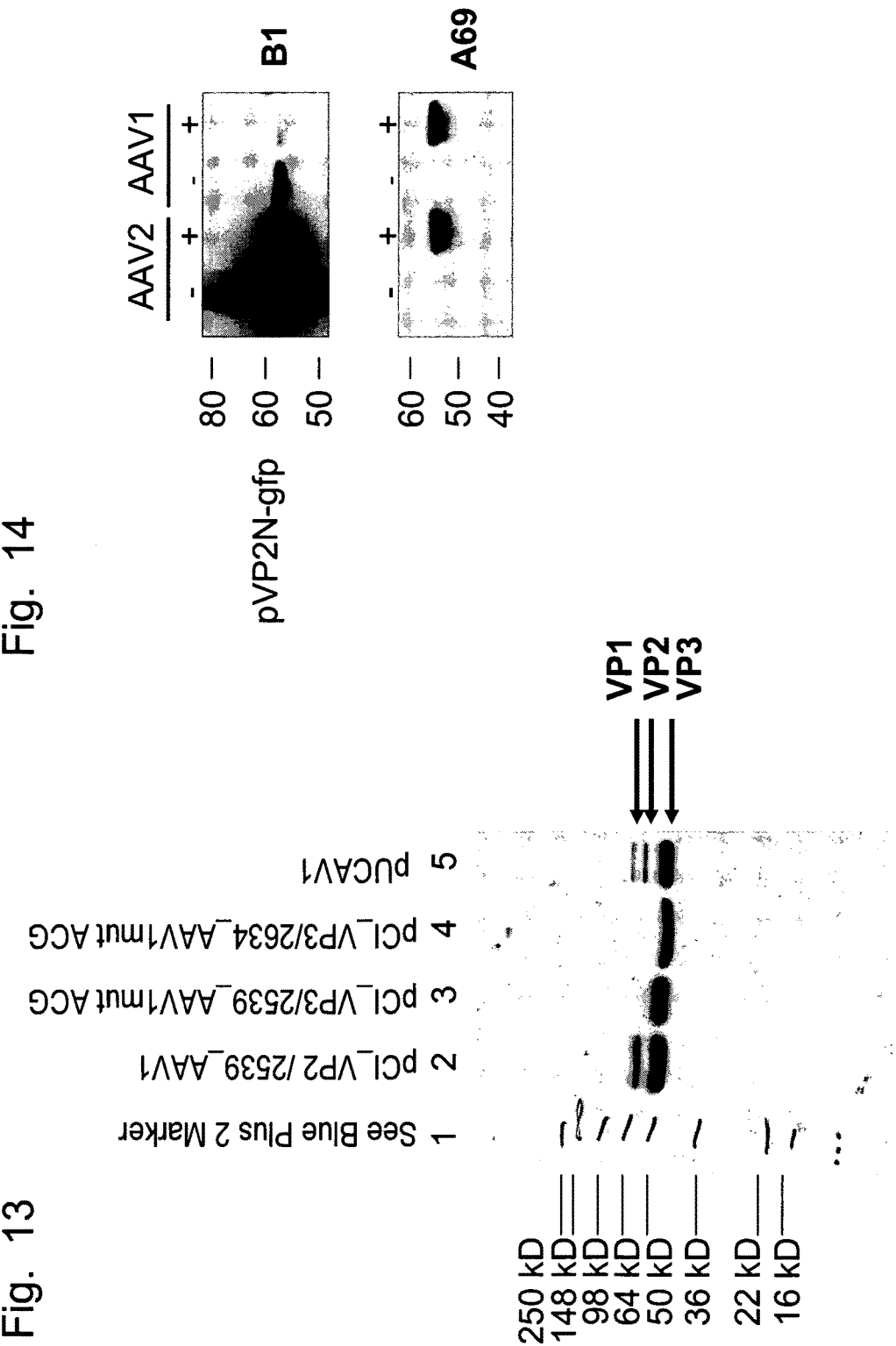

FIG. 13: Western Blot analyses of different AAV1 constructs Western blot analysis of expressed VP proteins in crude lysates of 293 cells transfected with different AAV1 constructs: pCI_VP2/2539 AAV1, pCI_VP3/2539 AAV1mutACG, pCI_VP3/2634 AAV1mutACG and pUCAV1. Detection of VP proteins was performed using the B1 antibody (dilution: 1:250) (Progen Heidelberg, Germany) and subsequent the secondary antibody anti mouse IgG-HRP 1:2500 (Dianova, Hamburg, Germany). 2E10 particles per construct were loaded according to AAV1 titration by an AAV1 capsid ELISA (Progen Heidelberg, Germany).

The Western Blot shows that construct pUCAV1 expresses the three capsid proteins VP1, VP2 and VP3 (lane 5) whereas pCI_VP2/2539_AAV1 leads to expression of VP2 and VP3 (lane 2) and within lysates of cells transfected with pCI_VP3/2539_AAV1mutACG and pCI_VP3/2634_AAV1mutACG only VP3 could be detected (lane 3 and 4).

FIG. 14: Trans-complementation of an AAV1 VP2 construct with pVP2N-gfp of AAV2

Western blot analysis of cell extracts transfected with VP3 expression construct of AAV2 pCMV-VP3/2809 or of AAV1 pCMV-AAV1VP3/2828 (indicated in the figure as AAV2 or AAV1, respectively) with or without cotransfection of pVP2N-gfp. AAV1 and AAV2 VP3 was detected by the antibody B1 (Progen, Heidelberg, Germany) which recognizes an epitope completely conserved between AAV1 and AAV2. The VP2N-gfp protein was detected by antibody A69 (Progen, Heidelberg, Germany).

Figure 15A:
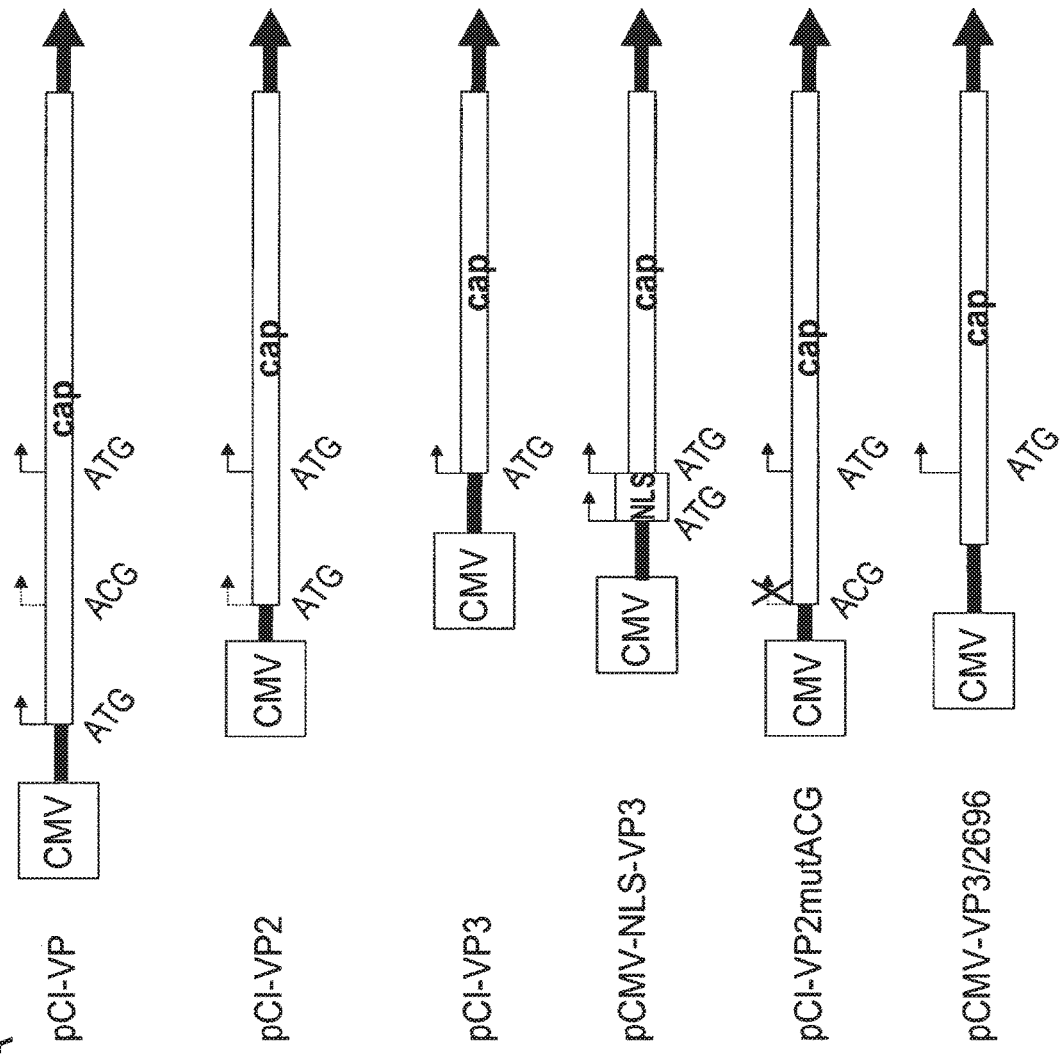
Figure 15C:
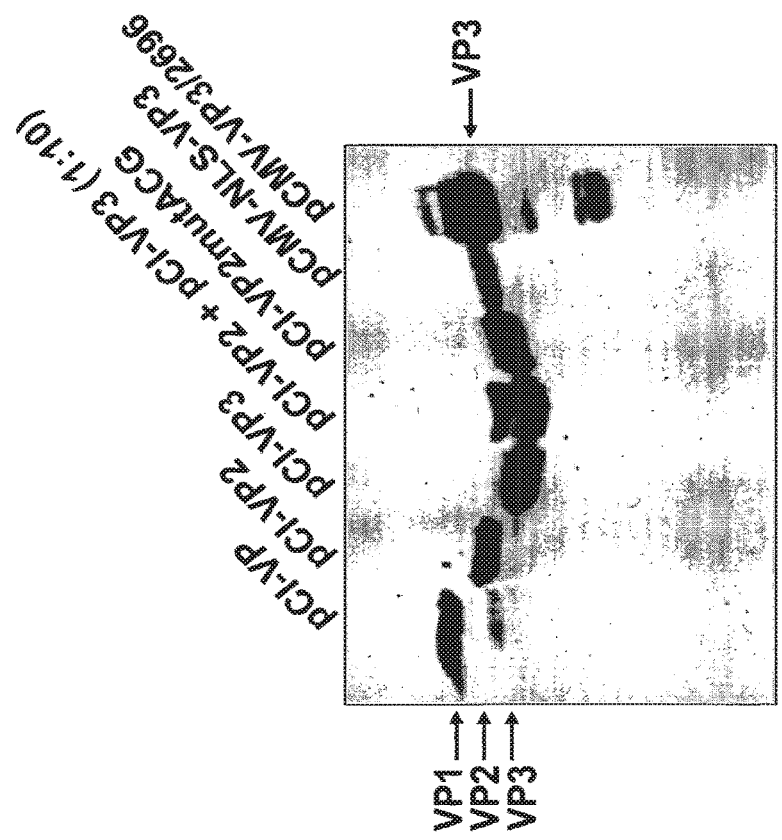

FIGS. 15A-15C: Comparison of particle production efficiency using different pCMV-VP expression vectors FIG. 15A) Schematic representation of constructs. pCI-VP, pCI-VP2 and pCI-VP3 were cloned by PCR amplification of the respective VP coding regions using primer with XhoI (5'-) and NotI (3'-) overhangs and subcloning of the XhoI-/NotI-digested PCR products into the XhoI-/NotI-digested vector pCI (PROMEGA). In case of pCI-VP2, the start codon for VP2 was changed from ACG to ATG at the same time.

For cloning of the constructs pCI-VP2mutACG, pCMV-NLS-VP3, and pCMV-VP3/2696 please refer to elsewhere.

FIG. 15B) For transfection 5.0E+05 293-T cells were seeded into each well of a 6-well cell culture plate in a total volume of 3 ml medium (DMEM containing 10% FCS and ABAM). Cells were cultivated at 37° C. and 5% $CO_2$ in a humidified atmosphere for 24 h. Subsequently cells were transfected using the calcium phosphate transfection protocol as disclosed in US 2004/0053410. Briefly, for transfection of one well with 293-T cells 6 µg of the indicated plasmids (pCI-VP, pCI-VP2, pCI-VP3, pCI-VP2 and pCI-VP3 in a 1:10 molar ratio, pCMV-NLS-VP3, pCI-VP2mutACG, and pCMV-VP3/2696, respectively) were mixed in 150 µl 270 mM $CaCl_2$). 150 µl 2×BBS (50 mM BES (pH 6.95), 280 mM NaCl and 1.5 mM $Na_2HPO_4$) was added to the mixture and the resulting solution was carefully mixed by pipetting. The solution was incubated for 20 min at room temperature and then added drop-wise to the cells. Cells were incubated at 35° C., 3% $CO_2$ in a humidified atmosphere for 18 h. After 18 h at 35° C. and 3% $CO_2$ cells were cultivated for an additional 3 d at 37° C., 5% $CO_2$ in a humidified atmosphere.

Subsequently, 293-T cells were lysed in the medium by three rounds of freeze (−80° C.) and thaw (37° C.) cycles. The lysate (3 ml total volume) was cleared by centrifugation and the VLP capsid titer was determined using a commercially available ELISA (AAV Titration ELISA, Progen). Average values of 4 to 6 independent transfections per construct are indicated with respective error bars.

Notably, particle production efficacy with construct pCMC-NLS-VP3 was below the detection limit (about 1E+09/ml) and, therefore, at least 3-4 logs lower compared to the best VP3 particle production vectors described in this invention (pCI-VP2mutACG and pCMV-VP3/2696).

FIG. 15C) For transfection 5.0E+05 293-T cells were seeded into each well of a 6-well cell culture plate in a total volume of 3 ml medium (DMEM containing 10% FCS and ABAM). Cells were cultivated at 37° C. and 5% $CO_2$ in a humidified atmosphere for 24 h. Subsequently cells were transfected using the calcium phosphate transfection protocol as disclosed in US 2004/0053410. Briefly, for transfection of one well with 293-T cells 6 μg of the indicated plasmids (pCI-VP, pCI-VP2, pCI-VP3, pCI-VP2 and pCI-VP3 in a 1:10 molar ratio, pCMV-NLS-VP3, pCI-VP2mutACG, and pCMV-VP3/2696, respectively) were mixed in 150 μl 270 mM $CaCl_2$). 150 μl 2×BBS (50 mM BES (pH 6.95), 280 mM NaCl and 1.5 mM $Na_2HPO_4$) was added to the mixture and the resulting solution was carefully mixed by pipetting. The solution was incubated for 20 min at room temperature and then added drop-wise to the cells. Cells were incubated at 35° C., 3% $CO_2$ in a humidified atmosphere for 18 h. After 18 h at 35° C. and 3% $CO_2$ cells were cultivated for an additional 3 d at 37° C., 5% $CO_2$ in a humidified atmosphere.

Subsequently, supernatant of 293-T cells was removed, cells were rinsed with PBS and finally lysed in 300 μl RIPA buffer (25 mM Tris.Cl pH 7.4, 150 mM NaCl, 1% IGEPAL, 1% Na.DOC, 0.1% SDS). 100 μl 3× Geba sample buffer (Gene Bio-Application Ltd) and 25 mM DTT were added, and samples were heated at 95° C. for 10 min. Samples were centrifuged and 30 μl cleared supernatant were subjected to SDS page (10% GeBa gels, Gene Bio-Application Ltd). Proteins were transferred to a nitrocellulose membrane (1 h, 230 mA) which was blocked for 1 h at RT subsequently. VP proteins were detected with the antibody B1 (Progen) by overnight incubation at 4° C. in blocking buffer (1:500 dilution), subsequent washing and incubation with secondary antibody (anti-mouse IgG-HRP; 1:2500 in blocking buffer). Finally, the membrane was rinsed again and incubated with super signal pico west substrate (Pierce) for 5 min at RT. AAV capsid proteins are expressed as expected from the different VP expression vectors.

Figure 16:
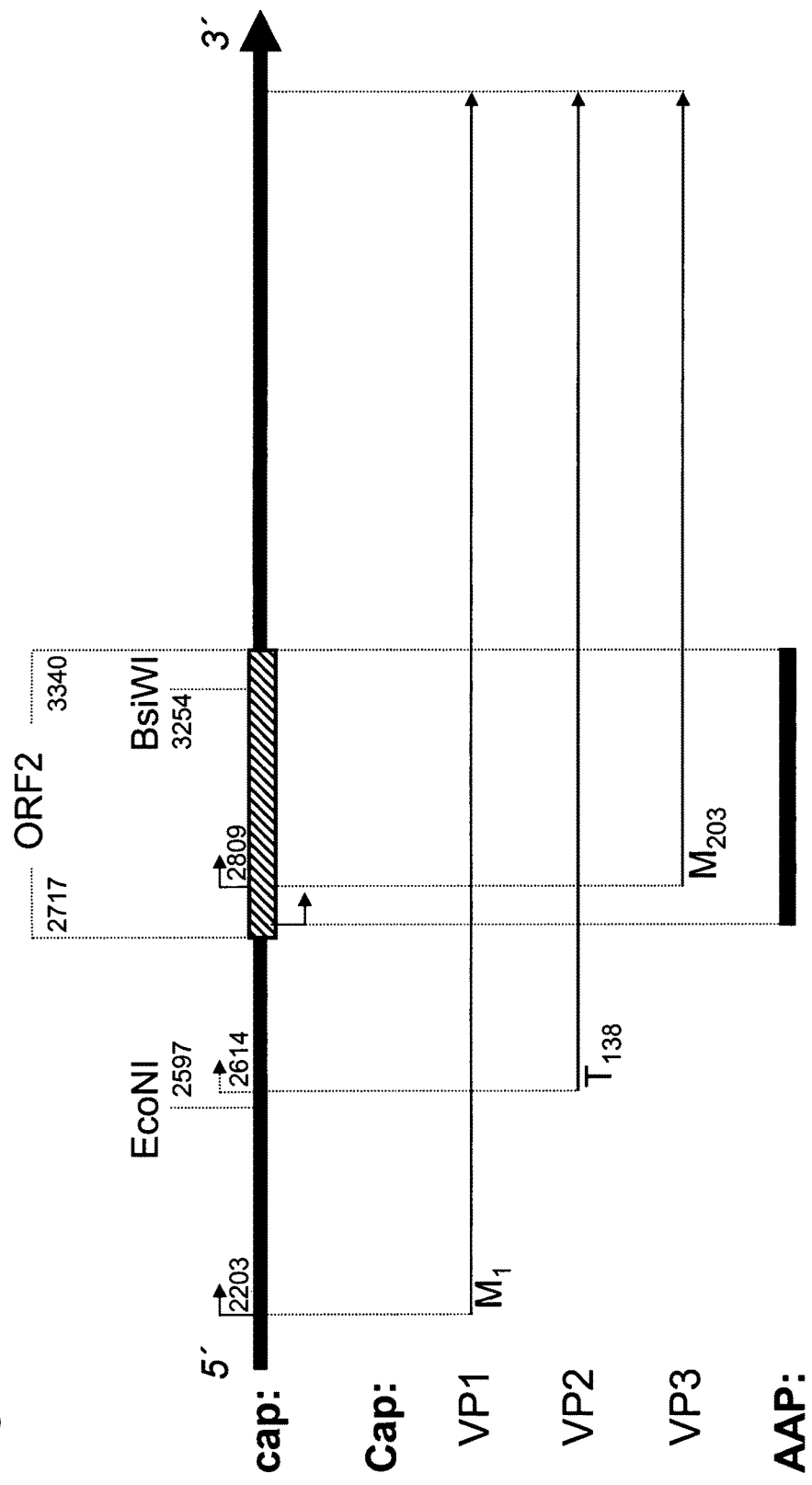

FIG. 16: Schematic organization of the AAV capsid gene.

The position of ORF2 and the encoded protein AAP is shown in relation to the position of translation start codons of the Cap proteins VP1, VP2 and VP3, as well as the EcoNI and BsiWI restriction sites (as given and described in more detail in FIG. 1). The arrows mark the translation start site and indicate that VP1, VP2 and VP3 are translated from the same one reading frame (named first ORF, ORF1, herein) of the cap gene, whereas AAP is translated from a different reading frame (ORF2). For VP1, VP2 and VP3 the well-defined numbers of the translation start points are given.

FIG. 17: Nucleotide sequence of ORF2 and protein sequence of AAP of AAV2.

The nucleotide sequence of ORF2 of AAV2 (NCBI entrée number NC_001401) from position 2717 to 3343 (including the tga stop codon), as well as the respective protein sequence of AAP obtained upon translation of ORF2 starting with the first nucleotide of ORF2 is given. 2809 marks the nucleotide position of the ATG start codon of VP3 which is underlined and given in bold. The predicted AAP translation initiation codon CTG coding for L (leucine) also is underlined and marked in bold.

FIGS. 18A and 18B: Sequence of ORF1 cm and ORF2 cm.

FIG. 18A) DNA sequence of the codon modified EcoNI-BsiWI restriction fragment ORF1 cm. FIG. 18B) DNA sequence of the codon modified EcoNI-BsiWI restriction fragment ORF2 cm. Translation start codons of VP2 and VP3 are underlined. Start of ORF2 is marked (↓) and position of the predicted non-canonical AAP translation initiation codon CTG intact in ORF2 cm is highlighted by a frame. And/orote that the translation start codon of AAP is mutated into CCG in ORF1 cm.

Figures 19A, 19B, 19C:
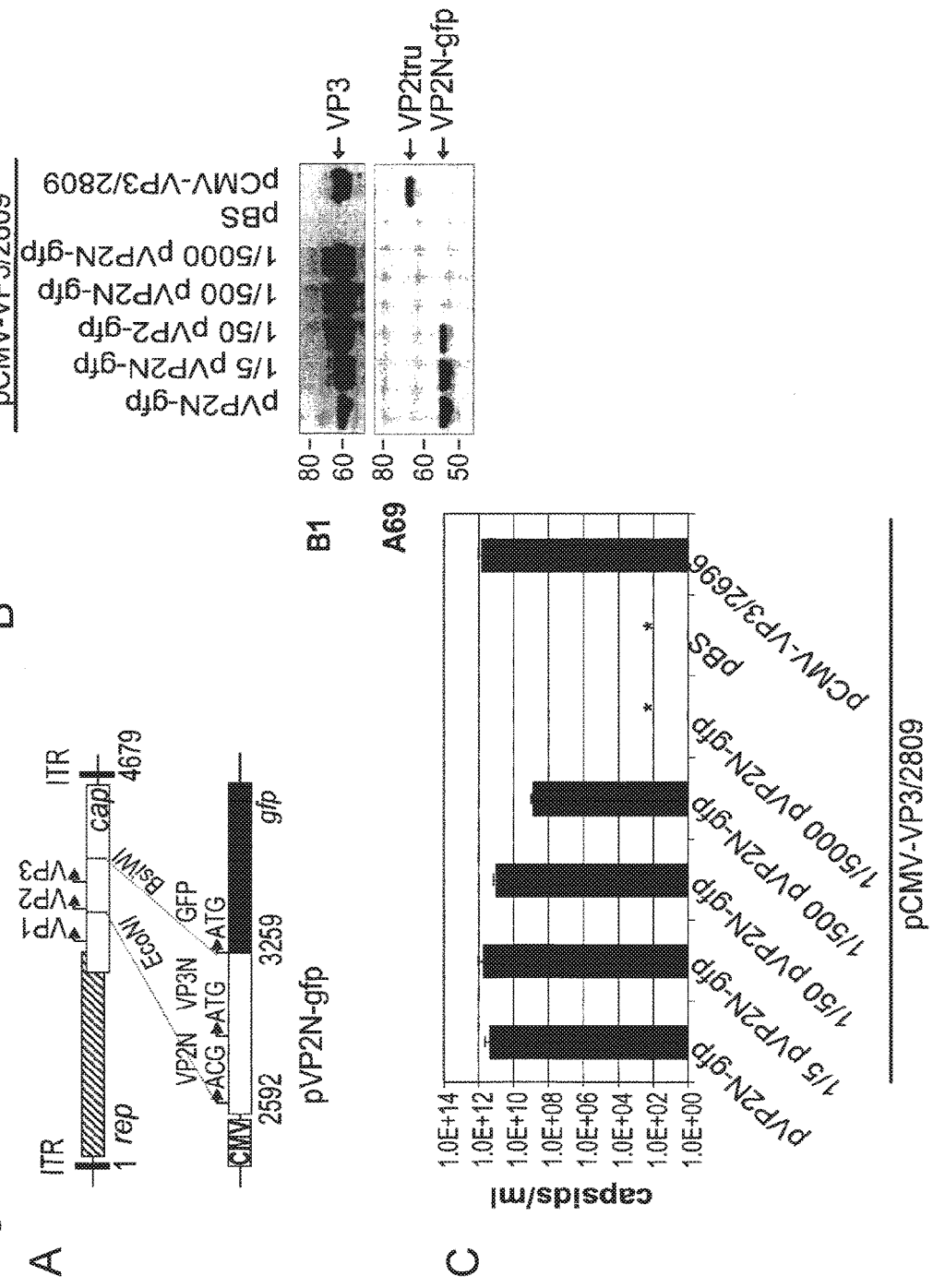

FIGS. 19A-19C: Trans-complementation of VP3 expressing plasmid with pVP2N-gfp.

FIG. 19A) Schematic representation of construct pVP2N-gfp, containing the EcoNI-BsiWI fragment derived of the AAV2 genome and a gfp-cassette, FIG. 19B). pVP2N-gfp was co-transfected with pCMV-VP3/2809 in decreasing amounts into 293-T cells, starting with equimolar ratios, in order to complement VP3 expression of plasmid pCMV-VP3/2809. For comparison empty vector pBS (commercially available Bluescript vector) or plasmid pCMV-VP3/2696 were transfected. Samples were analyzed by Western blot using monoclonal antibodies B1 for detection of VP3 and A69 for detection of VP2N-gfp and VP2tru (truncated VP2).

FIG. 19C) Capsid formation was quantified by an ELISA based on monoclonal antibody A20. Means+/−standard deviations of at least three independent experiments are shown; asterisks indicate samples for which no capsids could be detected.

Figures 20A, 20B, 20C:
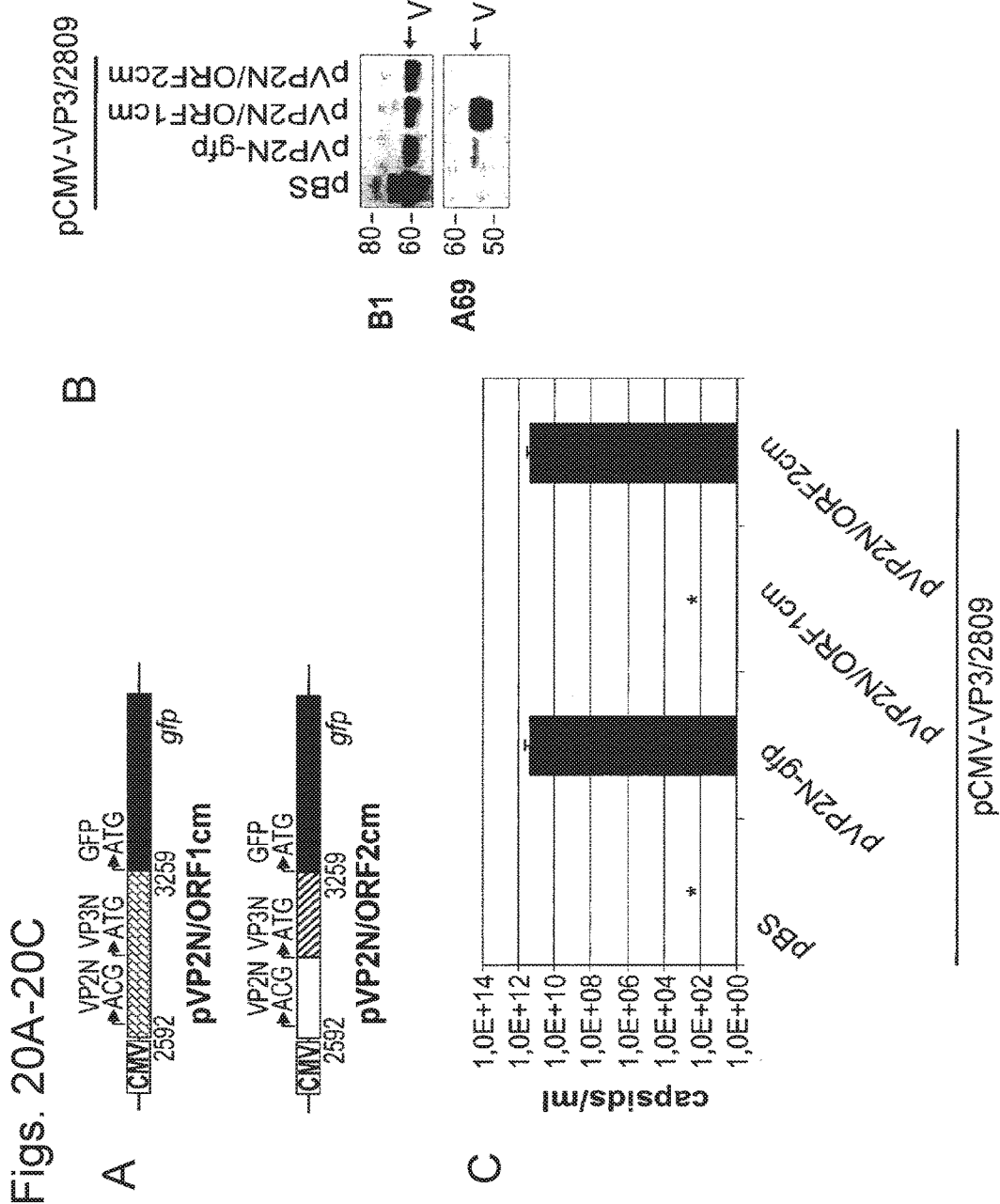

FIGS. 20A-20C: Trans-complementation of VP3 expressing plasmid with pVP2N/ORF1 cm and pVP2N/ORF2 cm.

Same experimental setup as described in FIGS. 19A-19C with the difference that the constructs pVP2N/ORF1 cm and pVP2N/ORF2 cm have been used for trans-complementation. Codon modified DNA sequences (detailed sequences are given in FIG. 18) are represented as shaded boxes in A).

FIGS. 21A-21C: Trans-complementation of VP3 expressing plasmid with pORF2/CTG-AU1, pORF2/ATG-AU1 and pORF2/TTG-AU1.

Same experimental setup as described in FIGS. 19A-19C with the difference that the constructs pORF2/CTG-AU1, pORF2/ATG-AU1 and pORF2/TTG-A have been used for trans-complementation. They comprise the entire ORF2 of the cap gene (as given in FIG. 17) fused to sequences coding for an AU1-tag. The predicted AAP translation initation codon (CTG) was additionally mutated to ATG and TTG Monoclonal antibody anti-AU1 for detection of AAP-AU1 or polyclonal anti-AAP serum for detection of AAP-AU1 or C-terminally truncated AAP (AAPtru).

Figures 22A, 22B, 22C:
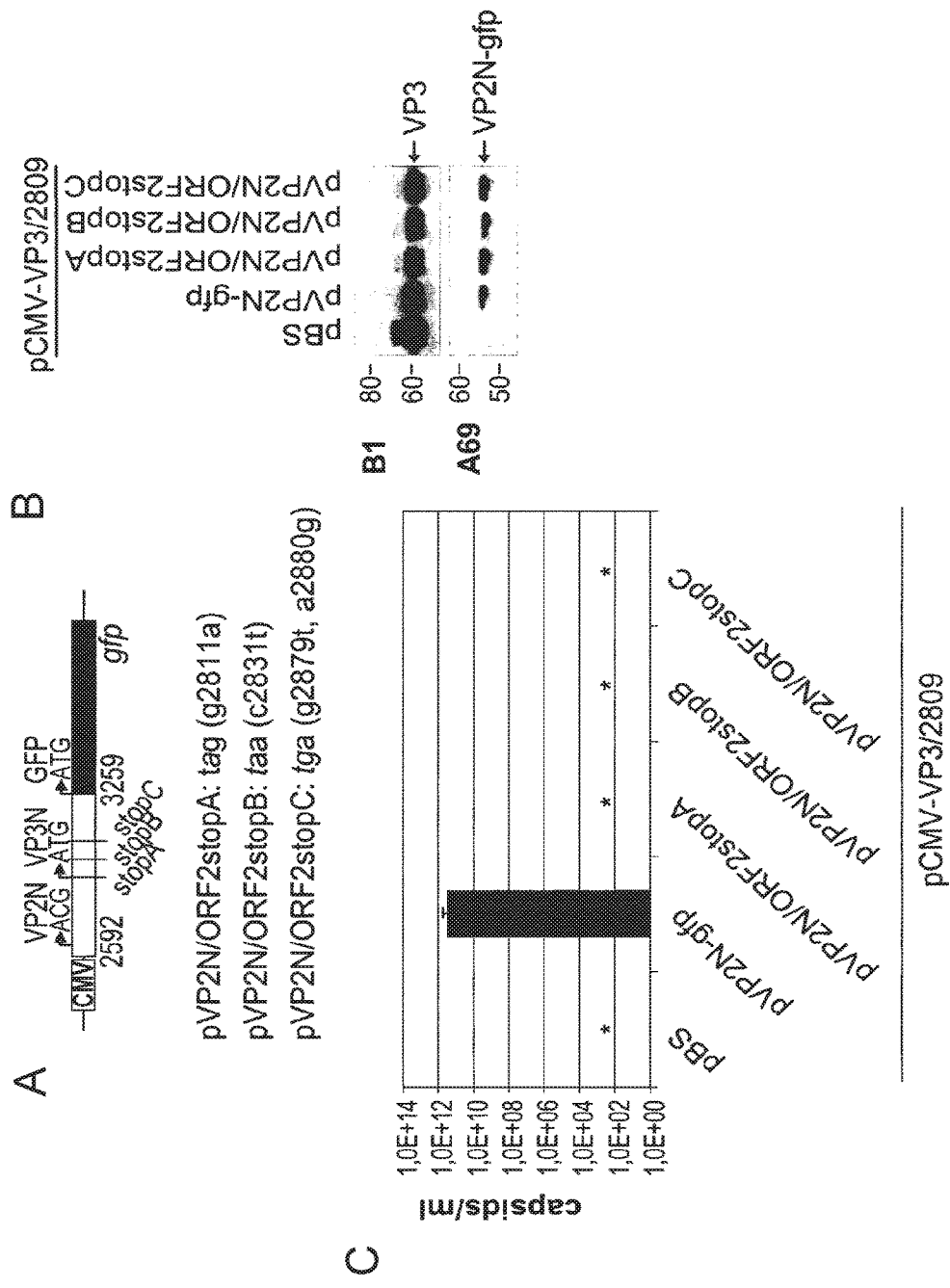

FIGS. 22A-22C: Trans-complementation of VP3 expressing plasmid with pVP2N/ORF2stopA, pVP2N/ORF2stopB, and pVP2N/ORF2stopC.

Derivates of pVP2N-gfp harbouring stop codons in ORF2 of the cap gene fragment were co-transfected with VP3 expression plasmid pCMV-VP3/2809 into 293-T cells.

FIG. 22A) Schematic representation of the constructs pVP2N/ORF2stopA, pVP2N/ORF2stopB, and pVP2N/ORF2stopC, respectively, containing stop codons in ORF2 of the cap gene fragment at the indicated positions. In pVP2N/ORF2stopA the tgg-codon starting at nucleotide 2810 has been mutated into tag, in pVP2N/ORF2stopB the caa-codon starting at nucleotide 2831 has been mutated into taa, and in pVP2N/ORF2stopC the gaa-codon starting at nucleotide 2879 has been mutated into tga. All mutations do not disrupt ORF1.

FIG. 22B) Samples were analyzed by Western blot using monoclonal antibodies B1 for detection of VP3 and A69 for detection of VP2N-gfp.

FIG. 22C) Capsid formation was quantified by an ELISA based on monoclonal antibody A20. Means+/−standard deviations of at least three independent experiments are shown; asterisks indicate samples for which no capsids could be detected.

FIGS. 23A-23D: Trans-complementation of full length AAV2 genome deficient in AAP expression with different constructs.

Figures 23A, 23B, 23C:
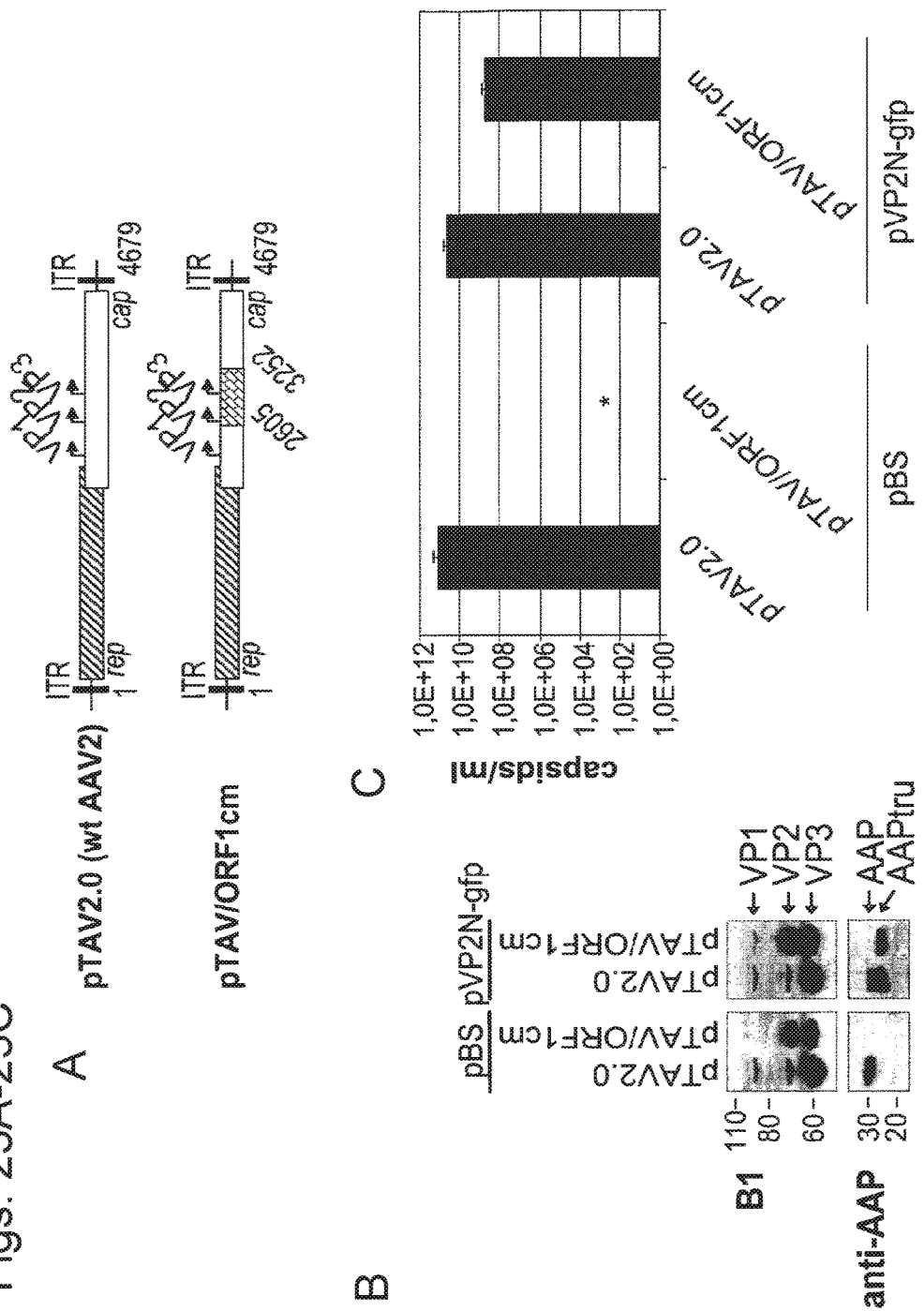

FIG. 23A) Schematic representation of plasmid pTAV2.0, harbouring the wildtype AAV2 genome and of plasmid pTAV/ORF1 cm, containing the ORF1 codon modified EcoNI/BsiWI fragment of the cap gene (shaded box).

FIG. 23B) Plasmids were co-transfected with the indicated constructs into 293-T cells. Western blot analysis of VP protein expression was performed using monoclonal antibody B1. AAP and truncated AAP (AAPtru) were detected with polyclonal anti-AAP serum.

Figure 23D:
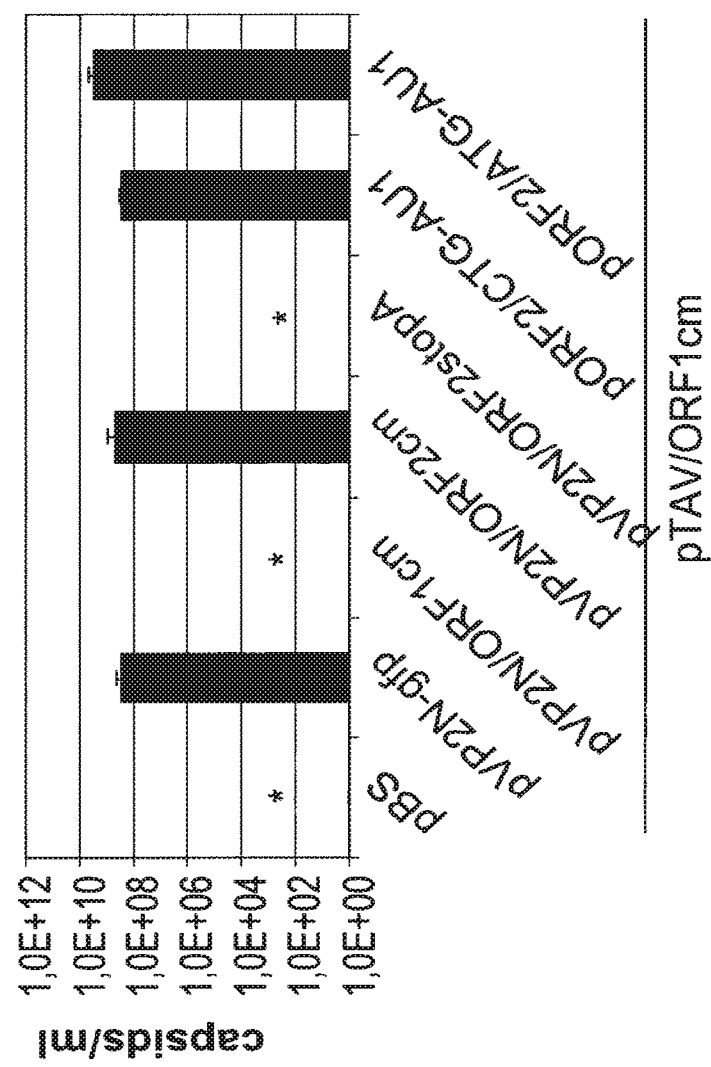

FIGS. 23C and 23D) Capsid formation upon co-transfection of plasmids as indicated in 293-T cells was quantified by an ELISA based on monoclonal antibody A20. Means+/− standard deviations of at least three independent experiments are shown; asterisks indicate samples for which no capsids could be detected.

Figures 24A, 24B, 24C:
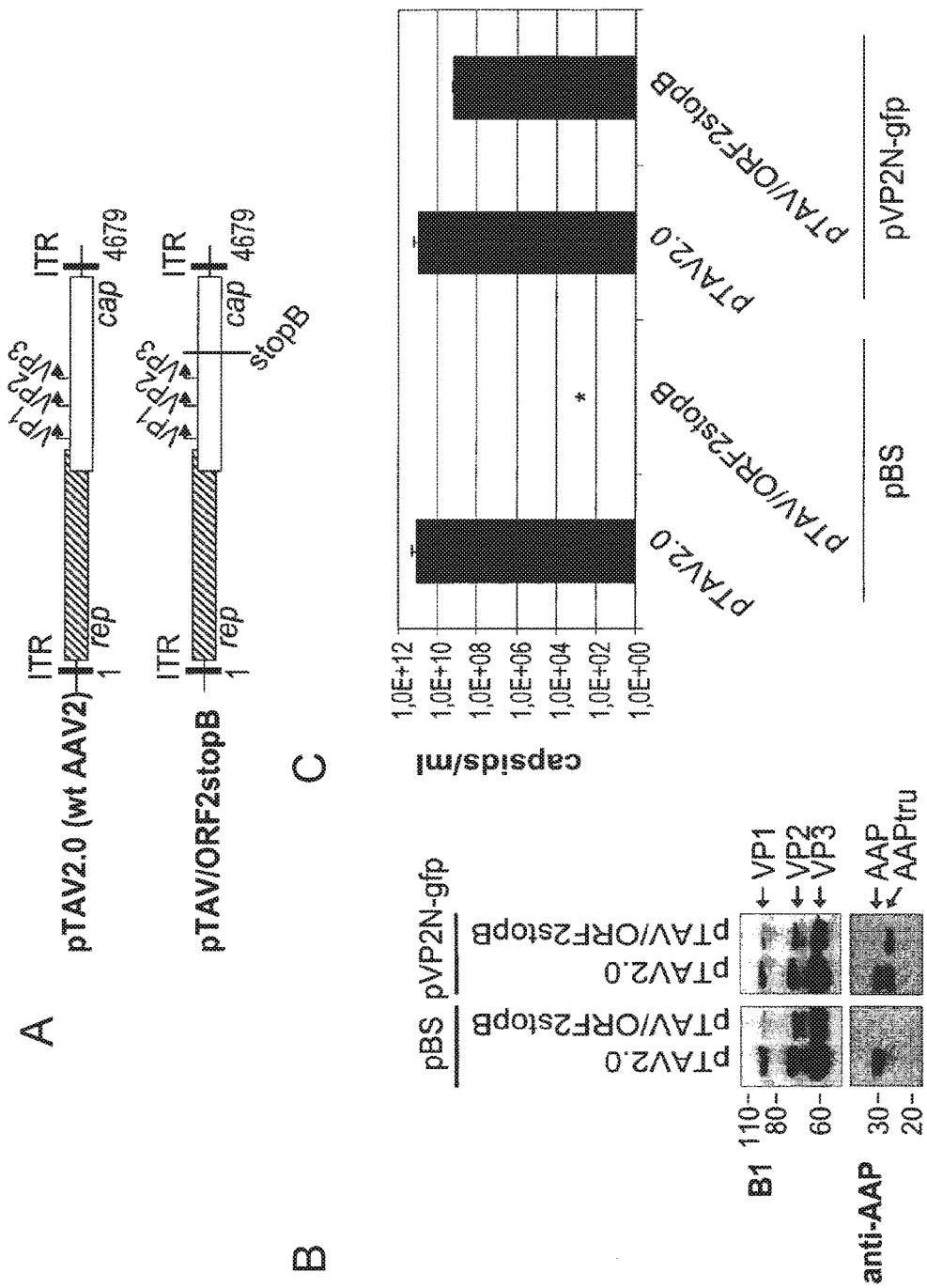

FIGS. 24A-24C: Trans-complementation of full length AAV2 genome containing a stop codon in ORF2 of the cap gene by wt genome.

FIG. 24A) Schematic representation of plasmid pTAV2.0, harbouring the wt AAV2 genome and of plasmid pTAV/ORF2stopB, containing a stop codon in ORF2 of the cap gene (equivalent position as in plasmid pVP2N/ORF2stopB, FIGS. 22A-22C).

FIG. 24B) Plasmids were co-transfected with empty vector pBS or with pVP2N-gfp (as indicated) into 293-T cells. Western blot analysis of VP protein expression was performed using monoclonal antibody B1. AAP and AAPtru were detected with polyclonal anti-AAP serum.

FIG. 24C) Capsid formation upon co-transfection of plasmids as indicated in 293-T cells was quantified by an ELISA based on monoclonal antibody A20. Means+/−standard deviations of three independent experiments are shown; asterisk indicates sample for which no capsids could be detected.

Figure 25A:
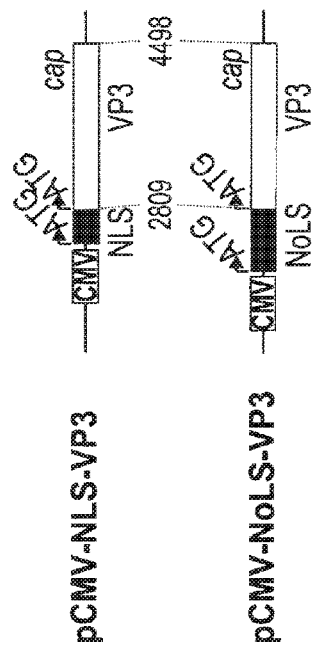
Figure 25B:
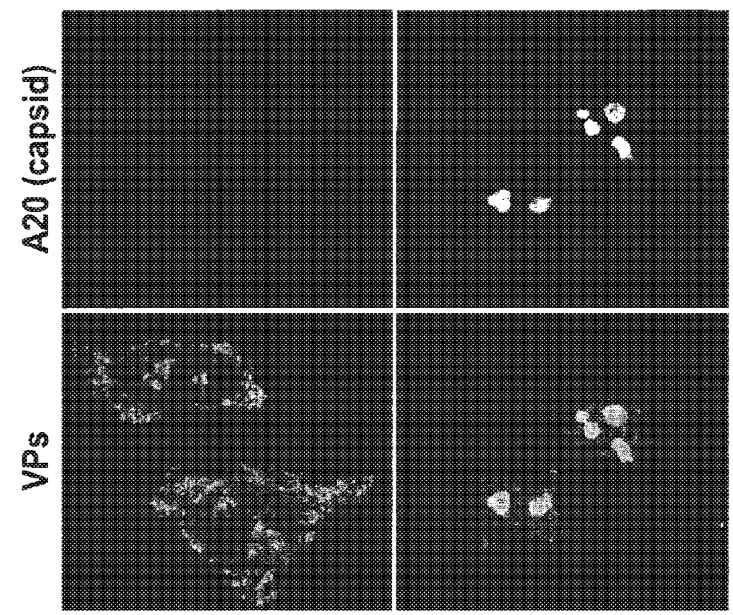

FIGS. 25A-25C: Immunofluorescence images for intracellular localization of VP3 and NoLS-VP3, as well as assembled capsids.

FIG. 25A) Schematic representation of the construct used for expression of VP3 fused to the nucleolar localization signal of HIV Rev (NoLS-VP3) in comparison to the construct expressing NLS-VP3 due to fusion of VP3 to the nuclear localization signal of the SV40 large T-antigen (as used in FIGS. 11A-11C).

FIG. 25B) Indirect double immunofluorescence of HeLa cells transfected with plasmids indicated at the left using a polyclonal VP antiserum (VPs) to localize total expressed capsid proteins (left images) and antibody A20 to detect assembled capsids (right images).

FIG. 25C) Indirect double immunofluorescence of HeLa cells transfected with plasmids indicated at the left using a monoclonal antibody against the AU1-tag (anti-AU1) to localize expressed AAP (left image) and polyclonal Fibrillarin antibody (anti-Fibrillarin) as a marker for nucleoli localization (middle image). On the right the phase contrast image of the same sector is shown.

Figure 26A:
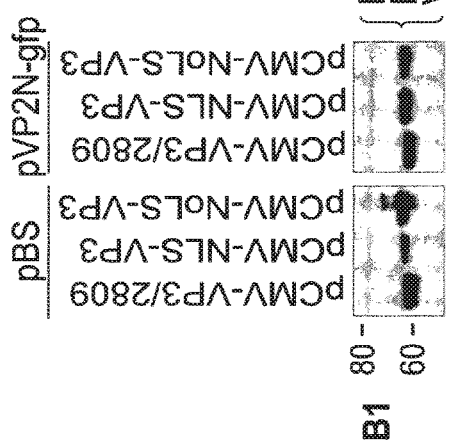
Figure 26B:
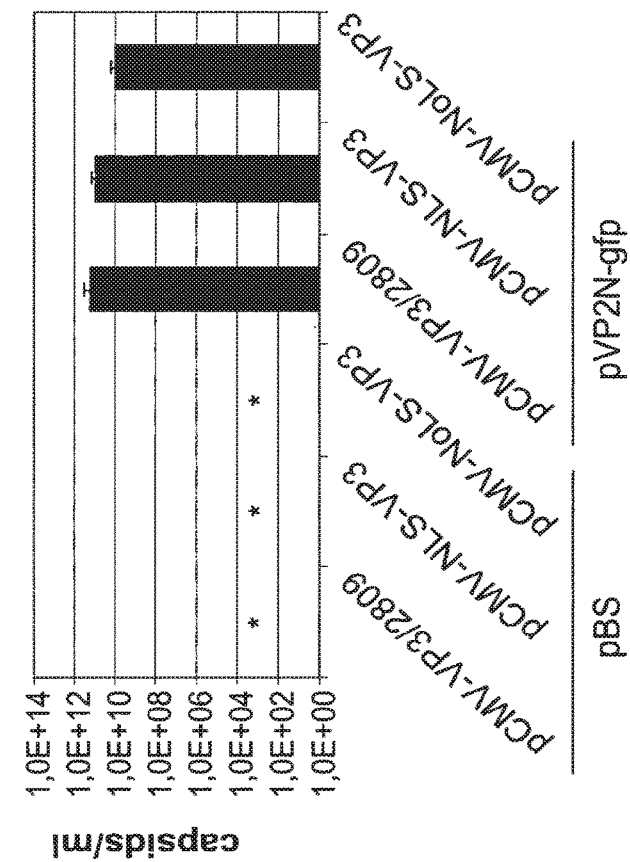

FIGS. 26A-26B: Expression and capsid assembly activity of VP3, NLS-VP3 and NoLS-VP3.

FIG. 26A) Western blot analysis of extracts of 293-T cells expressing VP3 or VP3 fusion proteins as indicated was performed using monoclonal antibody B1.

FIG. 26B) Capsid formation in 293-T cells was quantified by an ELISA based on monoclonal antibody A20. Means+/− standard deviations of at least three independent experiments are shown; asterisks indicate samples for which no capsids could be detected.

FIGS. 27A and 27B: Comparison of parvovirus AAP sequences.

Alignment of predicted AAP protein sequences derived from ORF2 of the cap gene of different parvoviruses. Conserved amino acids that are 100% identical in at least 60% of aligned sequences are represented as lines in the lower row. Position of the predicted AAV2 AAP translation start is highlighted by a frame. Non-translated sequences upstream of the potential translation initiation codons are included as well. NCBI entrée numbers of the corresponding DNA sequences are listed in table 8.

FIG. 28: EM analysis of AAV2 empty particle preparations

Virus-like particles assembled of VP1, VP2 and VP3 (VP1,2,3 VLP) or assembled only of VP3 (VP3 VLP) as indicated.

Figure 29:
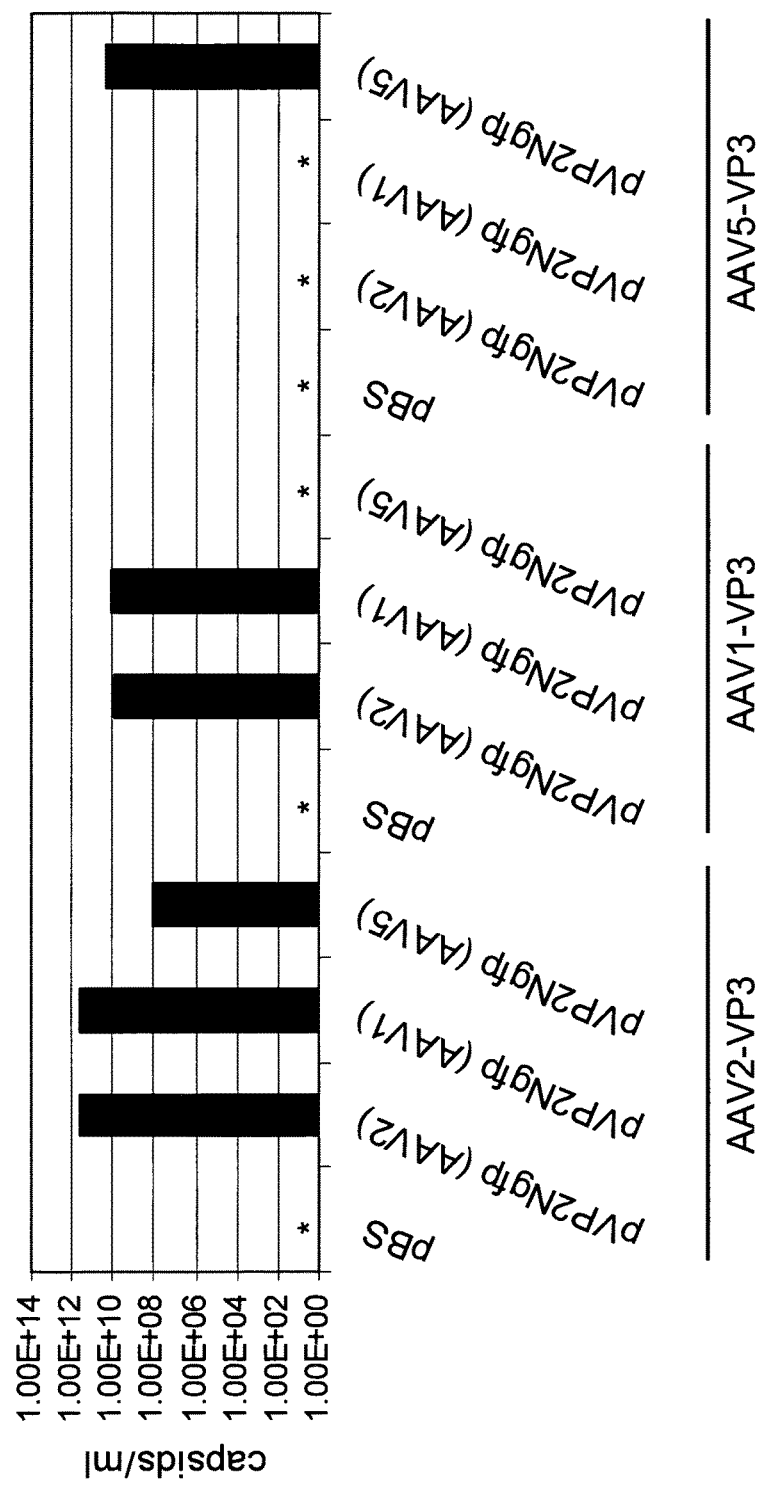

FIG. 29: Capsid assembly upon trans-complementation

Capsid formation in 293-T cells from constructs pCMV_VP3/2809 of AAV2 (AAV2-VP3), pCMV_AAV1VP3/2829 from AAV1 (AAV1-VP3) and a corresponding AAV5 VP3 construct (AAV5-VP3) co-transfected with pVP2N-gfp from AAV2, AAV1 and AAV5 as indicated was quantified by an ELISA based on monoclonal antibody A20. Bluescript vector (pBS) was used as negative control. Asterisks indicate samples for which no capsids could be detected.

Amino Acid Sequences

SEQ ID NO: 1

ILVRLETQTQ YLTPSLSDSH QQPPLVWELI RWLQAVAHQW QTITRAPTEW VIPREIGIAI

PHGWATESSP PAPEPGPCPP TTTTSTNKFP ANQEPRTTIT TLATAPLGGI LTSTDSTATF

HHVTGKDSST TTGDSDPRDS TSSSLTFKSK RSRRMTVRRR LPITLPARFR CLLTRSTSSR

TSSARRIKDA SRRSQQTSSW CHSMDTSP

SEQ ID NO: 2

SSRHKSQTPP RASARQASSP LKRDSILVRL ATQSQSPIHN LSENLQQPPL LWDLLQWLQA

VAHQWQTITK APTEWVMPQE IGIAIPHGWA TESSPPAPAP GPCPPTITTS TSKSPVLQRG

PATTTTTSAT APPGGILIST DSTATFHHVT GSDSSTTIGD SGPRDSTSNS STSKSRRSRR

MMASQPSLIT LPARFKSSRT RSTSFRTSSA LRTRAASLRS RRTCS

```
                                                           SEQ ID NO: 3
ISVRLATQSQ SQTLNLSENH QQPPQVWDLI QWLQAVAHQW QTITRVPMEW VIPQEIGIAI

PNGWATESSP PAPEPGPCPL TTTISTSKSP ANQELQTTTT TLATAPLGGI LTLTDSTATS

HHVTGSDSLT TTGDSGPRNS ASSSSTSKLK RSRRTMARRL LPITLPARFK CLRTRSISSR

TCSGRRTKAV SRRFQRTSSW SLSMDTSP

SEQ ID NO: 4
LNPPSSPTPP RVSAKKASSR LKRSSFSKTK LEQATDPLRD QLPEPCLMTV RCVQQLAELQ

SRADKVPMEW VMPRVIGIAI PPGLRATSRP PAPEPGSCPP TTTTSTSDSE RACSPTPTTD

SPPPGDTLTS TASTATSHHV TGDSSTTTG ACDPKPCGSK SSTSRSRRSR RRTARQRWLI

TLPARFRSLR TRRTNCRT

SEQ ID NO: 5
TTTFQKERRL GPKRTPSLPP RQTPKLDPAD PSSCKSQPNQ PQVWELIQCL REVAAHWATI

TKVPMEWAMP REIGIAIPRG WGTESSPSPP EPGCCPATTT TSTERSKAAP STEATPTPTL

DTAPPGGTLT LTASTATGAP ETGKDSSTTT GASDPGPSES KSSTFKSKRS RCRTPPPPSP

TTSPPPSKCL RTTTTSCPTS SATGPRDACR PSLRRSLRCR STVTRR

SEQ ID NO: 6
SSRHKSQTPP RALARQASSP LKRDSILVRL ATQSQSPTHN LSENLQQPPL LWDLLQWLQA

VAHQWQTITK APTEWVMPQE IGIAIPHGWA TESSPPAPEH GPCPPITTTS TSKSPVLQRG

PATTTTTSAT APPGGILIST DSTAISHHVT GSDSSTTIGD SGPRDSTSSS STSKSRRSRR

MMASRPSLIT LPARFKSSRT RSTSCRTSSA LRTRAASLRS RRTCS

SEQ ID NO: 7
SRHLSVPPTP PRASARKASS PPERDSISVR LATQSQSPTL NLSENLQQRP LVWDLVQWLQ

AVAHQWQTIT KVPTEWVMPQ EIGIAIPHGW ATESLPPAPE PGPCPPTTTT STSKSPVKLQ

VVPTTTPTSA TAPPGGILTL TDSTATSHHV TGSDSSTTTG DSGPRSCGSS SSTSRSRRSR

RMTALRPSLI TLPARFRYSR TRNTSCRTSS ALRTRAACLR SRRTSS

SEQ ID NO: 8
SHHPSVLQTP LRASARKANS PPEKDSILVR LATQSQFQTL NLSENLQQRP LVWDLIQWLQ

AVAHQWQTIT KAPTEWVVPR EIGIAIPHGW ATESSPPAPE PGPCPPTTTT STSKSPTGHR

EEPPTTTPTS ATAPPGGILT LTDSTATFHH VTGSDSSTTT GDSGPRDSAS SSSTSRSRRS

RRMKAPRPSP ITSPAPSRCL RTRSTSCRTF SALPTRAACL RSRRTCS

SEQ ID NO: 9
SSLLRNRTPP RVLANRVHSP LKRDSISVRL ATQSQSQTLN QSENLPQPPQ VWDLLQWLQV

VAHQWQTITK VPMEWVVPRE IGIAIPNGWG TESPPAPEP GPCPPTTITS TSKSPTAHLE

DLQMTTPTSA TAPPGGILTS TDSTATSHHV TGSDSTTTG DSGLSDSTSS SSTFRSKRLR

TTMESRPSPI TLPARSRSSR TQTISSRTCS GRLTRAASRR SQRTFS

SEQ ID NO: 10
TLGRLASQSQ SPTLNQSENH QQAPLVWDLV QWLQAVALQW QTITKAPTEW VVPQEIGIAI

PHGWATESSP PAPEPGPCPP TTTTSTSKSP TGHREEAPTT TPTSATAPPG GILTSTDSTA

TSHHVTGSDS STTTGDSGQK DSASSSSTSR SRRSRRMKAP RPSPITLPAR FRYLRTRNTS

CRTSSAPRTR AACLRSRRMS S

SEQ ID NO: 11
SHHKSPTPPR ASAKKANNQP ERGSTLKRTL EPETDPLKDQ IPAPCLQTLK CVQHRAEMLS

MRDKVPMEWV MPRVIGIAIP PGLRARSQQP RPEPGSCPPT TTTCTCVSEQ HQAATPTTDS

PPPGDILTST DSTVTSHHVT GKDSSTTTGD YDQKPCALKS SISKLRRSQR TARLRSLIT

LPARFRYLRT RRMSSRT
```

```
                                                SEQ ID NO: 12
KRLQIGRPTR TLGRPRPRKS KKTANQPTLL EGHSTLKTLE QETDPLRDHL PEKCLMMLRC

VRRQAEMLSR RDKVPMEWVM PPVIGIAIPP GQRAESPPPA PEPGSYPRTT TTCTCESEQR

PTATPTTDSP PPGDTLTLTA STATFPHATG SDSSTTTGDS GRNRCVLKSS TYRSRRSRRQ

TARLRSLITL PARFRSLRIR RMNSHT

SEQ ID NO: 13
SRVLKSQTPR AELARKANSL PERDSTLTTN LEPETGLPQK DHLPELCLLR LKCVQQLAEM

VAMRDKVPRE WVMPPVIGIA IPLGQRATSP PPQPAPGSCR PTTTTCTCGS ARATPATPST

DSPPPGDTLT LTASTATSRQ ETGKGSSTTT GDCAPKACKS ASSTSKLRRS RRLTGRRPYP

TTSPARSRSL RTARTSSRT

SEQ ID NO: 14
VKPSSRPKRG FSNPLVWWKT QRRLRPETSG KAKTNLVCPT LLHRLPRKTR SLARKDLPAG

QKIRAKAPLP TLEQQHPPLV WDHLSWLKEV AAQWAMQARV PMEWAIPPEI GIAIPNGWKT

ESSLEPPEPG SCPATTTTCT NESKDPAEAT TTTNSLDSAP PGDTLTTIDS TATFPRETGN

DSSTTTGASV PKRCALDSLT SRLKRSRSKT STPPSATTSP VRSRSLRTRT TNCRTSSDRL

PKAPSRRSQR ISTRSRSTGT AR

SEQ ID NO: 15
ILVRLATQSQ SQTLNHSDNL PQPPLVWDLL QWLQAVAHQW QTITRVPMEW VIPQEIGIAI

PNGWATESSP PAPAPGPCPP TTITSTSKSP ANQEPPTTTT TLATAPPGGI LTSTDSTATF

HHVTGKDSST TTGDSDPRDS TSSSLTFKSK RSRRMTVRRR LPITLPARFR CLLTPSTSSR

TSSARRIRDA SRRSQQTSSW SHSMDTSP

SEQ ID NO: 16
TRRTVSSLPL QRRPKLEALP PPAIWDLVRW LEAVARQSTT ARMVPMEWAM PREIGIAIPH

GWTTVSSPEP LGPGICQPTT TTSTNDSTER PPETKATSDS APPGDTLTST ASTVISPLET

GKDSSTITGD SDQRAYGSKS LTFKLKKSRR KTQRRSSPIT LPARFRYLRT RSTSSRT

SEQ ID NO: 17
LNNPTTRPGP GRSVPNASTT FSRKRRRPRP SKAKPLLKRA KTPEKEPLPT LDQAPPLVWD

HLSWLKEVAV QWAMQAKVPT EWAIPREIGI AIPNGWTTES LPEPLEPGSC PATTTTCTSG

SKDREEPTPT INSLDSAPPG GTLTTTDSTA TSPPETGNDS STTTGASDPK RCALDSLTSR

LKKSLSKTPT PPSPTTSPAR SKSLRTRTTS CRTSSDRLQR APSRRSQRIS TRSRSMVTAR

SEQ ID NO: 18
TTTFQKERRL GPKRTPSLPP RQTPKLDPAD PSSCKSQHNQ PQVWELIQCL REVAAHWATI

TKVPMEWAMP REIGIAIPRG WGTESSPSPP APGCCPATTT TSTERSKAAP STEATPTPTL

DTAPPGGTLT LTASTATGAP ETGKDSSTTI GASDPGLSES KSSTSKSKRS RCRTPPPPSP

TTSPPPSKCL RTTTTNSRTS SATGPRDACR PSPRRSLRCR STATRR

SEQ ID NO: 19
ASRSRSWLLQ SSVHTRPRKP QRTRRVSRDR IPGRRPRRGS SSPISLDLQQ TYLHPHNSPS

LPQGFPVWFL VRCLQEEALQ WTMLNKVPTE WAMPREIGIA IPNGWATEFS PDPPGPGCCP

ATTTTCTSRS QTPPACTASP GADTLATAPP GGTSTSIAST ATSRPETGSA SSITTGASDP

RDCESNSSTS RSRRSRLLIR RPRSPTTSRA RSRSSQTTST SCRTSAATPP RDACRRSPRT

SSRCRSTATR R
```

```
                                                        SEQ ID NO: 20
KTEEPPRRAP NLWQHLKWQR EEAELWATLQ GVPMEWVMPR EIGIAIPNGW ETQSSQRPPE

PGSCQATTTT STKQLPVEPL KMQMSSMQDT VPPGGTLIST ASTATSPLET GRDLSTTIGE

SDPNLLNSRS SMSKSKKSQR RIKQRPLQTI SPQRFKSLRM MSINSRMSWA RLRKAPCRRS

RRMSMPCRST GTAQCTPTRM EHGSMTVVHS TA

SEQ ID NO: 21
KSLNYLKKTL LHPVIVEEKQ VQLPPKAPNL WQHLTWQREE AELWATLQGV PMEWVMPQEI

GIAIPNGWET QSLPRLQEPG SCQATTTTST KPSQAEQTQT QIPNMLDTAP PGGTLISTDS

TAISLQETGR DSSTTIGGLD RKHSNSRYSM CKLKKSRRKT RQRLLLTTLP LQSRYSRIMN

TSCPMFWARP RRGRCHRSPQ MCMPCPSTAT AQCTPTRVEL DSMTEVPSIA

SEQ ID NO: 22
TNTILKLKRP NKACRYQLHL KAEKKKLHRH NLEGAQQVPI LAAHLSWLQE EAVRWQTITR

APREWVIPQV IGIAIPSGWE TTSLQSQPEL GCSPLTGIIS TGLSTLTAPQ VRVLMQPMQD

TRLPGGTLTS IDSIATSPPE TGKDSSTTTQ ASGRKDSKSK SLTSKSKKLQ HKIQRKQLPT

ISPAPYRSLR TRTTTYHMY

SEQ ID NO: 143
LNNPTTRPGP GRSVPNASTT FSRKRRRPRP SKAKPLLKRA KTPEKEPLPT LDQAPPLVWD

HLSWLKEVAV QWAMQAKVPT EWAIPREIGI AIPNGWTTES LPEPLEPGSC PATTTTCTSG

SKDREEPTPT INSLDSAPPG GTLTTTDSTA TSPPETGNDS STTTGASDPK RCALDSLTSR

LKKSLSKTPT PPSPTTSPAR SKSLRTRTTS CRTSSDRLQR APSRRSQRIS TRSRSMVTAR
```

Nucleic Acid Sequences

```
                                                        SEQ ID NO: 23
ATTTTGGTCA GACTGGAGAC GCAGACTCAG TACCTGACCC CCAGCCTCTC GGACAGCCAC

CAGCAGCCCC CTCTGGTCTG GAACTAATA CGATGGCTAC AGGCAGTGGC GCACCAATGG

CAGACAATAA CGAGGGCGCC GACGGAGTGG GTAATTCCTC GGGAAATTGG CATTGCGATT

CCACATGGAT GGGCGACAGA GTCATCACCA CCAGCACCCG AACCTGGGCC CTGCCCACCT

ACAACAACCA CCTCTACAAA CAAATTTCCA GCCAATCAGG AGCCTCGAAC ACAATCACT

ACTTTGGCTA CAGCACCCCT TGGGGGTATT TTGACTTCAA CAGATTCCAC TGCCACTTTT

CACCACGTGA CTGGCAAAGA CTCATCAACA ACAACTGGGG ATTCCGACCC AAGAGACTCA

ACTTCAAGCT CTTTAACATT CAAGTCAAAG AGGTCACGCA GAATGACGGT ACGACGACGA

TTGCCAATAA CCTTACCAGC ACGGTTCAGG TGTTTACTGA CTCGGAGTAC CAGCTCCCGT

ACGTCCTCGG CTCGGCGCAT CAAGGATGCC TCCCGCCGTT CCCAGCAGAC GTCTTCATGG

TGCCACAGTA TGGATACCTC ACCCTGA

SEQ ID NO: 24
AGCAGTCGCC ACAAGAGCCA GACTCCTCCT CGGGCATCGG CAAGACAGGC CAGCAGCCCG

CTAAAAAGAG ACTCAATTTT GGTCAGACTG GCGACTCAGA GTCAGTCCCC GATCCACAAC

CTCTCGGAGA ACCTCCAGCA ACCCCCGCTG CTGTGGGACC TACTACAATG GCTTCAGGCG

GTGGCGCACC AATGGCAGAC AATAACGAAG GCGCCGACGG AGTGGGTAAT GCCTCAGGAA

ATTGGCATTG CGATTCCACA TGGCTGGGCG ACAGAGTCAT CACCACCAGC ACCCGCACCT

GGGCCTTGCC CACCTACAAT AACCACCTCT ACAAGCAAAT CTCCAGTGCT TCAACGGGGG

CCAGCAACGA CAACCACTAC TTCGGCTACA GCACCCCCTG GGGGTATTTT GATTTCAACA

GATTCCACTG CCACTTTTCA CCACGTGACT GGCAGCGACT CATCAACAAC AATTGGGGAT

TCCGGCCCAA GAGACTCAAC TTCAAACTCT TCAACATCCA AGTCAAGGAG GTCACGACGA
```

-continued

```
ATGATGGCGT CACAACCATC GCTAATAACC TTACCAGCAC GGTTCAAGTC TTCTCGGACT

CGGAGTACCA GCTTCCGTAC GTCCTCGGCT CTGCGCACCA GGGCTGCCTC CCTCCGTTCC

CGGCGGACGT GTTCATGA
```

SEQ ID NO: 25
```
ATTTCGGTCA GACTGGCGAC TCAGAGTCAG TCCCAGACCC TCAACCTCTC GGAGAACCAC

CAGCAGCCCC CACAAGTTTG GGATCTAATA CAATGGCTTC AGGCGGTGGC GCACCAATGG

CAGACAATAA CGAGGGTGCC GATGGAGTGG GTAATTCCTC AGGAAATTGG CATTGCGATT

CCCAATGGCT GGGCGACAGA GTCATCACCA CCAGCACCAG AACCTGGGCC CTGCCCACTT

ACAACAACCA TCTCTACAAG CAAATCTCCA GCCAATCAGG AGCTTCAAAC GACAACCACT

ACTTTGGCTA CAGCACCCCT TGGGGGTATT TTGACTTTAA CAGATTCCAC TGCCACTTCT

CACCACGTGA CTGGCAGCGA CTCATTAACA ACAACTGGGG ATTCCGGCCC AAGAAACTCA

GCTTCAAGCT CTTCAACATC CAAGTTAAAG AGGTCACGCA GAACGATGGC ACGACGACTA

TTGCCAATAA CCTTACCAGC ACGGTTCAAG TGTTTACGGA CTCGGAGTAT CAGCTCCCGT

ACGTGCTCGG GTCGGCGCAC CAAGGCTGTC TCCCGCCGTT CCAGCGGAC GTCTTCATGG

TCCCTCAGTA TGGATACCTC ACCCTGA
```

SEQ ID NO: 26
```
TTGAATCCCC CCAGCAGCCC GACTCCTCCA CGGGTATCGG CAAAAAAGGC AAGCAGCCGG

CTAAAAAGAA GCTCGTTTTC GAAGACGAAA CTGGAGCAGG CGACGGACCC CCTGAGGGAT

CAACTTCCGG AGCCATGTCT GATGACAGTG AGATGCGTGC AGCAGCTGGC GGAGCTGCAG

TCGAGGGCGG ACAAGGTGCC GATGGAGTGG GTAATGCCTC GGGTGATTGG CATTGCGATT

CCACCTGGTC TGAGGGCCAC GTCACGACCA CCAGCACCAG AACCTGGGTC TTGCCCACCT

ACAACAACCA CCTCTACAAG CGACTCGGAG AGAGCCTGCA GTCCAACACC TACAACGGAT

TCTCCACCCC CTGGGGATAC TTTGACTTCA ACCGCTTCCA CTGCCACTTC TCACCACGTG

ACTGGCAGCG ACTCATCAAC AACAACTGGG GCATGCGACC CAAAGCCATG CGGGTCAAAA

TCTTCAACAT CCAGGTCAAG GAGGTCACGA CGTCGAACGG CGAGACAACG GTGGCTAATA

ACCTTACCAG CACGGTTCAG ATCTTTGCGG ACTCGTCGTA CGAACTGCCG TACGTGA
```

SEQ ID NO: 27
```
ACGACCACTT TCCAAAAAGA AAGAAGGCTC GGACCGAAGA GGACTCCAAG CCTTCCACCT

CGTCAGACGC CGAAGCTGGA CCCAGCGGAT CCCAGCAGCT GCAAATCCCA GCCCAACCAG

CCTCAAGTTT GGGAGCTGAT ACAATGTCTG CGGGAGGTGG CGGCCCATTG GGCGACAATA

ACCAAGGTGC CGATGGAGTG GGCAATGCCT CGGGAGATTG GCATTGCGAT TCCACGTGGA

TGGGGGACAG AGTCGTCACC AAGTCCACCC GAACCTGGGT GCTGCCCAGC TACAACAACC

ACCAGTACCG AGAGATCAAA AGCGGCTCCG TCGACGGAAG CAACGCCAAC GCCTACTTTG

GATACAGCAC CCCCTGGGGG TACTTTGACT TTAACCGCTT CCACAGCCAC TGGAGCCCCC

GAGACTGGCA AAGACTCATC AACAACTACT GGGGCTTCAG ACCCCGGTCC CTCAGAGTCA

AAATCTTCAA CATTCAAGTC AAAGAGGTCA CGGTGCAGGA CTCCACCACC ACCATCGCCA

ACAACCTCAC CTCCACCGTC CAAGTGTTTA CGGACGACGA CTACCAGCTG CCCTACGTCG

TCGGCAACGG GACCGAGGGA TGCCTGCCGG CCTTCCCTCC GCAGGTCTTT ACGCTGCCGC

AGTACGGTTA CGCGACGCTG A
```

SEQ ID NO: 28
```
AGCAGTCGCC ACAAGAGCCA GACTCCTCCT CGGGCATTGG CAAGACAGGC CAGCAGCCCG

CTAAAAAGAG ACTCAATTTT GGTCAGACTG GCGACTCAGA GTCAGTCCCC GACCCACAAC
```

-continued

```
CTCTCGGAGA ACCTCCAGCA ACCCCCGCTG CTGTGGGACC TACTACAATG GCTTCAGGCG

GTGGCGCACC AATGGCAGAC AATAACGAAG GCGCCGACGG AGTGGGTAAT GCCTCAGGAA

ATTGGCATTG CGATTCCACA TGGCTGGGCG ACAGAGTCAT CACCACCAGC ACCCGAACAT

GGGCCTTGCC CACCTATAAC AACCACCTCT ACAAGCAAAT CTCCAGTGCT TCAACGGGGG

CCAGCAACGA CAACCACTAC TTCGGCTACA GCACCCCCTG GGGGTATTTT GATTTCAACA

GATTCCACTG CCATTTCTCA CCACGTGACT GGCAGCGACT CATCAACAAC AATTGGGGAT

TCCGGCCCAA GAGACTCAAC TTCAAGCTCT TCAACATCCA AGTCAAGGAG GTCACGACGA

ATGATGGCGT CACGACCATC GCTAATAACC TTACCAGCAC GGTTCAAGTC TTCTCGGACT

CGGAGTACCA GTTGCCGTAC GTCCTCGGCT CTGCGCACCA GGGCTGCCTC CCTCCGTTCC

CGGCGGACGT GTTCATGA
```

SEQ ID NO: 29
```
AGCCGTCACC TCAGCGTTCC CCCGACTCCT CCACGGGCAT CGGCAAGAAA GGCCAGCAGC

CCGCCAGAAA GAGACTCAAT TTCGGTCAGA CTGGCGACTC AGAGTCAGTC CCCGACCCTC

AACCTCTCGG AGAACCTCCA GCAGCGCCCT CTAGTGTGGG ATCTGGTACA GTGGCTGCAG

GCGGTGGCGC ACCAATGGCA GACAATAACG AAGGTGCCGA CGGAGTGGGT AATGCCTCAG

GAAATTGGCA TTGCGATTCC ACATGGCTGG GCGACAGAGT CATTACCACC AGCACCCGAA

CCTGGGCCCT AACAACCACC TCTACAAGCA AATCTCCAGT GAAACTGCAG CCCACCTAC

GTAGTACCAA CGACAACACC TACTTCGGCT ACAGCACCCC CTGGGGGTAT TTTGACTTTA

ACAGATTCCA CTGCCACTTC TCACCACGTG ACTGGCAGCG ACTCATCAAC AACAACTGGG

GATTCCGGCC CAAGAAGCTG CGGTTCAAGC TCTTCAACAT CCAGGTCAAG GAGGTCACGA

CGAATGACGG CGTTACGACC ATCGCTAATA ACCTTACCAG CACGATTCAG GTATTCTCGG

ACTCGGAATA CCAGCTGCCG TACGTCCTCG GCTCTGCGCA CCAGGGCTGC CTGCCTCCGT

TCCCGGCGGA CGTCTTCATG A
```

SEQ ID NO: 30
```
AGCCATCACC CCAGCGTTCT CCAGACTCCT CTACGGGCAT CGGCAAGAAA GGCCAACAGC

CCGCCAGAAA AAGACTCAAT TTTGGTCAGA CTGGCGACTC AGAGTCAGTT CCAGACCCTC

AACCTCTCGG AGAACCTCCA GCAGCGCCCT CTGGTGTGGG ACCTAATACA ATGGCTGCAG

GCGGTGGCGC ACCAATGGCA GACAATAACG AAGGCGCCGA CGGAGTGGGT AGTTCCTCGG

GAAATTGGCA TTGCGATTCC ACATGGCTGG GCGACAGAGT CATCACCACC AGCACCCGAA

CCTGGGCCCT GCCCACCTAC AACAACCACC TCTACAAGCA AATCTCCAAC GGGACATCGG

GAGGAGCCAC CAACGACAAC ACCTACTTCG GCTACAGCAC CCCCTGGGGG TATTTTGACT

TTAACAGATT CCACTGCCAC TTTTCACCAC GTGACTGGCA GCGACTCATC AACAACAACT

GGGGATTCCG GCCCAAGAGA CTCAGCTTCA AGCTCTTCAA CATCCAGGTC AAGGAGGTCA

CGCAGAATGA AGGCACCAAG ACCATCGCCA ATAACCTCAC CAGCACCATC CAGGTGTTTA

CGGACTCGGA GTACCAGCTG CCGTACGTTC TCGGCTCTGC CCACCAGGGC TGCCTGCCTC

CGTTCCCGGC GGACGTGTTC ATGA
```

SEQ ID NO: 31
```
AGCAGTCTCC TCAGGAACCG GACTCCTCCG CGGGTATTGG CAAATCGGGT GCACAGCCCG

CTAAAAAGAG ACTCAATTTC GGTCAGACTG GCGACACAGA GTCAGTCCCA GACCCTCAAC

CAATCGGAGA ACCTCCCGCA GCCCCCTCAG GTGTGGGATC TCTTACAATG GCTTCAGGTG

GTGGCGCACC AGTGGCAGAC AATAACGAAG GTGCCGATGG AGTGGGTAGT TCCTCGGGAA

ATTGGCATTG CGATTCCCAA TGGCTGGGGG ACAGAGTCAT CACCACCAGC ACCCGAACCT
```

```
                                                         -continued
GGGCCCTGCC CACCTACAAC AATCACCTCT ACAAGCAAAT CTCCAACAGC ACATCTGGAG

GATCTTCAAA TGACAACGCC TACTTCGGCT ACAGCACCCC CTGGGGGTAT TTTGACTTCA

ACAGATTCCA CTGCCACTTC TCACCACGTG ACTGGCAGCG ACTCATCAAC AACAACTGGG

GATTCCGGCC TAAGCGACTC AACTTCAAGC TCTTCAACAT TCAGGTCAAA GAGGTTACGG

ACAACAATGG AGTCAAGACC ATCGCCAATA ACCTTACCAG CACGGTCCAG GTCTTCACGG

ACTCAGACTA TCAGCTCCCG TACGTGCTCG GGTCGGCTCA CGAGGGCTGC CTCCCGCCGT

TCCCAGCGGA CGTTTTCATG A

SEQ ID NO: 32
ACTTTGGGCA GACTGGCGAG TCAGAGTCAG TCCCCGACCC TCAACCAATC GGAGAACCAC

CAGCAGGCCC CTCTGGTCTG GGATCTGGTA CAATGGCTGC AGGCGGTGGC GCTCCAATGG

CAGACAATAA CGAAGGCGCC GACGGAGTGG GTAGTTCCTC AGGAAATTGG CATTGCGATT

CCACATGGCT GGGCGACAGA GTCATCACCA CCAGCACCCG AACCTGGGCC CTGCCCACCT

ACAACAACCA CCTCTACAAG CAAATCTCCA ACGGGACATC GGGAGGAAGC ACCAACGACA

ACACCTACTT CGGCTACAGC ACCCCCTGGG GGTATTTTGA CTTCAACAGA TTCCACTGCC

ACTTCTCACC ACGTGACTGG CAGCGACTCA TCAACAACAA CTGGGGATTC CGGCCAAAAA

GACTCAGCTT CAAGCTCTTC AACATCCAGG TCAAGGAGGT CACGCAGAAT GAAGGCACCA

AGACCATCGC CAATAACCTT ACCAGCACGA TTCAGGTATT TACGGACTCG AATACCAGC

TGCCGTACGT CCTCGGCTCC GCGCACCAGG GCTGCCTGCC TCCGTTCCCG GCGGATGTCT

TCATGA

SEQ ID NO: 33
AGTCACCACA AGAGCCCGAC TCCTCCTCGG GCATCGGCAA AAAGGCAAA CAACCAGCCA

GAAAGAGGCT CAACTTTGAA GAGGACACTG GAGCCGGAGA CGGACCCCCT GAAGGATCAG

ATACCAGCGC CATGTCTTCA GACATTGAAA TGCGTGCAGC ACCGGCGGA AATGCTGTCG

ATGCGGGACA AGGTTCCGAT GGAGTGGGTA ATGCCTCGGG TGATTGGCAT TGCGATTCCA

CCTGGTCTGA GGGCAAGGTC ACAACAACCT CGACCAGAAC CTGGGTCTTG CCCACCTACA

ACAACCACTT GTACCTGCGT CTCGGAACAA CATCAAGCAG CAACACCTAC AACGGATTCT

CCACCCCCTG GGGATATTTT GACTTCAACA GATTCCACTG TCACTTCTCA CCACGTGACT

GGCAAAGACT CATCAACAAC AACTGGGGAC TACGACCAAA AGCCATGCGC GTTAAAATCT

TCAATATCCA AGTTAAGGAG GTCACAACGT CGAACGGCGA GACTACGGTC GCTAATAACC

TTACCAGCAC GGTTCAGATA TTTGCGGACT CGTCGTATGA GCTCCCGTAC GTGA

SEQ ID NO: 34
AAAAGACTCC AAATCGGCCG ACCAACCCGG ACTCTGGGAA GGCCCCGGCC AAGAAAAAGC

AAAAAGACGG CGAACCAGCC GACTCTGCTA GAAGGACACT CGACTTTGAA GACTCTGGAG

CAGGAGACGG ACCCCCTGAG GGATCATCTT CCGGAGAAAT GTCTCATGAT GCTGAGATGC

GTGCGGCGCC AGGCGGAAAT GCTGTCGAGG CGGGACAAGG TGCCGATGGA GTGGGTAATG

CCTCCGGTGA TTGGCATTGC GATTCCACCT GGTCAGAGGG CCGAGTCACC ACCACCAGCA

CCCGAACCTG GGTCCTACCC ACGTACAACA ACCACCTGTA CCTGCGAATC GGAACAACGG

CCAACAGCAA CACCTACAAC GGATTCTCCA CCCCCTGGGG ATACTTTGAC TTTAACCGCT

TCCACTGCCA CTTTTCCCCA CGCGACTGGC AGCGACTCAT CAACAACAAC TGGGGACTCA

GGCCGAAATC GATGCGTGTT AAAATCTTCA ACATACAGGT CAAGGAGGTC ACGACGTCAA

ACGGCGAGAC TACGGTCGCT AATAACCTTA CCAGCACGGT TCAGATCTTT GCGGATTCGA

CGTATGAACT CCCATACGTG A
```

```
                                                            SEQ ID NO: 35
AGCAGAGTCC TCAAGAGCCA GACTCCTCGA GCGGAGTTGG CAAGAAAGGC AAACAGCCTG

CCAGAAAGAG ACTCAACTTT GACGACGAAC CTGGAGCCGG AGACGGGCCT CCCCCAGAAG

GACCATCTTC CGGAGCTATG TCTACTGAGA CTGAAATGCG TGCAGCAGCT GGCGGAAATG

GTGGCGATGC GGGACAAGGT GCCGAGGGAG TGGGTAATGC CTCCGGTGAT GGCATTGCG

ATTCCACTTG GTCAGAGAGC CACGTCACCA CCACCTCAAC CCGCACCTGG GTCCTGCCGA

CCTACAACAA CCACCTGTAC CTGCGGCTCG GCTCGAGCAA CGCCAGCGAC ACCTTCAACG

GATTCTCCAC CCCCTGGGGA TACTTTGACT TTAACCGCTT CCACTGCCAC TTCTCGCCAA

GAGACTGGCA AAGGCTCATC AACAACCACT GGGGACTGCG CCCCAAAAGC ATGCAAGTCC

GCATCTTCAA CATCCAAGTT AAGGAGGTCA CGACGTCTAA CGGGGAGACG ACCGTATCCA

ACAACCTCAC CAGCACGGTC CAGATCTTTG CGGACAGCAC GTACGAGCTC CCGTACGTGA

SEQ ID NO: 36
GTAAAGCCAT CTTCCAGGCC AAAAAGAGGG TTCTCGAACC CTTTGGTCTG GTGGAAGACT

CAAAGACGGC TCCGACCGGA GACAAGCGGA AAGGCGAAGA CGAACCTCGT TTGCCCGACA

CTTCTTCACA GACTCCCAAG AAAAACAAGA AGCCTCGCAA GGAAAGACCT TCCGGCGGGG

CAGAAGATCC GGGCGAAGGC ACCTCTTCCA ACGCTGGAGC AGCAGCACCC GCCTCTAGTG

TGGGATCATC TATCATGGCT GAAGGAGGTG GCGGCCCAGT GGGCGATGCA GGCCAGGGTG

CCGATGGAGT GGGCAATTCC TCCGGAAATT GGCATTGCGA TTCCCAATGG CTGGAAAACG

GAGTCGTCAC TCGAACCACC CGAACCTGGG TCTTGCCCAG CTACAACAAC CACCTGTACA

AACGAATCCA AGGACCCAGC GGAGGCGACA ACAACAACAA ATTCTTTGGA TTCAGCACCC

CCTGGGGATA CTTTGACTAC AATCGATTCC ACTGCCACTT TTCCCCGCGA GACTGGCAAC

GACTCATCAA CAACAACTGG GGCATCCGTC CCAAAGCGAT GCGCTTTAGA CTCTTTAACA

TCCAGGTTAA AGAGGTCACG GTCCAAGACT TCAACACCAC CATCGGCAAC AACCTCACCA

GTACGGTCCA GGTCTTTGCG GACAAGGACT ACCAACTGCC GTACGTCCTC GGATCGGCTA

CCGAAGGCAC CTTCCCGCCG TTCCCAGCGG ATATCTACAC GATCCCGCAG TACGGGTACT

GCACGCTAA

SEQ ID NO: 37
ATTTTGGTCA GACTGGCGAC ACAGAGTCAG TCCCAGACCC TCAACCACTC GGACAACCTC

CCGCAGCCCC CTCTGGTGTG GGATCTACTA CAATGGCTTC AGGCGGTGGC GCACCAATGG

CAGACAATAA CGAGGGTGCC GATGGAGTGG GTAATTCCTC AGGAAATTGG CATTGCGATT

CCCAATGGCT GGGCGACAGA GTCATCACCA CCAGCACCCG CACCTGGGCC CTGCCCACCT

ACAACAATCA CCTCTACAAG CAAATCTCCA GCCAATCAGG AGCCACCAAC GACAACCACT

ACTTTGGCTA CAGCACCCCC TGGGGGTATT TTGACTTCAA CAGATTCCAC TGCCACTTTT

CACCACGTGA CTGGCAAAGA CTCATCAACA ACAACTGGGG ATTCCGACCC AAGAGACTCA

ACTTCAAGCT CTTTAACATT CAAGTCAAAG AGGTCACGCA GAATGACGGT ACGACGACGA

TTGCCAATAA CCTTACCAGC ACGGTTCAGG TGTTTACTGA CTCCGAGTAC CAGCTCCCGT

ACGTCCTCGG CTCGGCGCAT CAGGGATGCC TCCCGCCGTT CCCAGCAGAC GTCTTCATGG

TCCCACAGTA TGGATACCTC ACCCTGA

SEQ ID NO: 38
ACGAGGAGGA CCGTGAGTTC GCTGCCGCTG CAGCGGAGAC CGAAACTGGA AGCGCTCCCC

CCACCGGCAA TTTGGGACCT GGTACGATGG CTGGAGGCGG TAGCGCGCCA ATCGACGACG

GCTCGTATGG TGCCGATGGA GTGGGCAATG CCTCGGGAGA TTGGCATTGC GATTCCACAT

GGCTGGACAA CTGTGTCATC ACCCGAACCA CTCGGACCTG GAATCTGCCA ACCTACAACA
```

-continued

```
ACCACATCTA CAAACGACTC AACGGAACGA CCTCCGGAGA CCAAAGCTAC TTCGGATTCA

GCACCCCCTG GGGATACTTT GACTTCAACC GCTTCCACTG TCATTTCTCC CCTCGAGACT

GGCAAAGACT CATCAACAAT AACTGGGGAC TCCGACCAAA GAGCCTACGG TTCAAAATCT

TTAACATTCA AGTTAAAGAA GTCACGACGC AAGACTCAAC GAAGATCATC TCCAATAACC

TTACCAGCAC GGTTCAGGTA TTTGCGGACA CGGAGTACCA GCTCCCGTAC GTGA
```

SEQ ID NO: 39
```
TTGAACAACC CGACAACACG GCCGGGACCG GGGAGAAGCG TCCCGAACGC GTCGACGACT

TTTTCCCGAA AAAGAAGAAG GCCAAGACCA AGCAAGGCAA AGCCCCTGCT CAAACGGGCG

AAGACCCCGG AGAAGGAACC TCTTCCAACG CTGGATCAAG CGCCCCCTCT AGTGTGGGAT

CATCTGTCAT GGCTGAAGGA GGTGGCGGTC CAATGGGCGA TGCAGGCCAA GGTGCCGACG

GAGTGGGCAA TTCCTCGGGA AATTGGCATT GCGATTCCCA ATGGCTGGAC AACGGAGTCG

TTACCCGAAC CACTCGAACC TGGGTCCTGC CCAGCTACAA CAACCACTTG TACAAGCGGA

TCCAAGGACC GGGAGGAACC GACCCCAACA ATAAATTCTT TGGATTCAGC ACCCCCTGGG

GGTACTTTGA CTACAACCGA TTCCACTGCC ACTTCTCCCC CCGAGACTGG CAACGACTCA

TCAACAACAA CTGGGGCATC CGACCCAAAG CGATGCGCTT TAGACTCTTT AACATCCAGG

TTAAAGAAGT CACTGTCCAA GACTCCAACA CCACCATCGC CAACAACCTC ACCAGCACGG

TCCAAGTCTT TGCGGACAAG GACTACCAGC TGCCGTACGT CCTCGGATCG GCTACAGAGG

GCACCTTCCC GCCGTTCCCA GCGGATATCT ACACGATCCC GCAGTATGGT TACTGCACGC

TAA
```

SEQ ID NO: 40
```
ACGACCACTT TCCAAAAAGA AAGAAGGCTC GGACCGAAGA GGACTCCAAG CCTTCCACCT

CGTCAGACGC CGAAGCTGGA CCCAGCGGAT CCCAGCAGCT GCAAATCCCA GCACAACCAG

CCTCAAGTTT GGGAGCTGAT ACAATGTCTG CGGGAGGTGG CGGCCCATTG GCGACAATA

ACCAAGGTGC CGATGGAGTG GGCAATGCCT CGGGAGATTG GCATTGCGAT TCCACGTGGA

TGGGGGACAG AGTCGTCACC AAGTCCACCG GCACCTGGGT GCTGCCCAGC TACAACAACC

ACCAGTACCG AGAGATCAAA AGCGGCTCCG TCGACGGAAG CAACGCCAAC GCCTACTTTG

GATACAGCAC CCCCTGGGGG TACTTTGACT TTAACCGCTT CCACAGCCAC TGGAGCCCCC

GAGACTGGCA AAGACTCATC AACAACTATT GGGGCTTCAG ACCCCGGTCT CTCAGAGTCA

AAATCTTCAA CATCCAAGTC AAAGAGGTCA CGGTGCAGGA CTCCACCACC ACCATCGCCA

ACAACCTCAC CTCCACCGTC CAAGTGTTTA CGGACGACGA C
```

SEQ ID NO: 41
```
GCGTCGAGGA GCCGGAGCTG GCTCCTCCAG TCAAGCGTCC ACACTCGCCC GAGAAAACCC

CAGAGAACCA GAAGGGTCAG CCGCGACCGG ATCCCCGGAC GCCGGCCAAG AAGAGGCTCG

AGTTCTCCGA TCAGCCTGGA TCTTCAGCAG ACTTACCTGC ATCCTCACAA CAGTCCCAGC

CTCCCGCAGG GGTTCCCGGT GTGGTTCCTG GTACGATGTC TGCAGGAGGA GGCGCTCCAG

TGGACGATGC TCAACAAGGT GCCGACGGAG TGGGCAATGC CTCGGGAGAT TGGCATTGCG

ATTCCAAATG GCTGGGCAAC CGAGTTCTCA CCCGATCCAC CCGGACCTGG GTGCTGCCCA

GCTACAACAA CCACCTGTAC AAGCAGATCT CAGACGCCTC CGGCGTGCAC AGCCTCCCCG

GGAGCCGATA CTTTGGCTAC AGCACCCCCT GGGGGTACTT CGACTTCAAT CGCTTCCACT

GCCACTTCTC GCCCAGAGAC TGGCAGCGCC TCGTCAATAA CCACTGGGGC TTCCGACCCA

AGAGACTGCG AGTCAAACTC TTCAACATCC AGGTCAAGGA GGTCACGACT ACTGATTCGA

CGACCACGGT CTCCAACAAC CTCACGAGCA CGGTCCAGGT CTTCACAGAC GACGAGTACC
```

```
AGCTGCCGTA CGTCTGCGGC AACGCCACCG AGGGATGCCT GCCGCCGTTC CCCCCGGACG

TCTTCACGCT GCCGCAGTAC GGCTACGCGA CGCTGA
```

SEQ ID NO: 42
```
AAGACGGAGG AGCCACCGCG GAGGGCACCG AACCTGTGGC AGCATCTGAA ATGGCAGAGG

GAGGAGGCGG AGCTATGGGC GACTCTTCAG GGGGTGCCGA TGGAGTGGGT AATGCCTCGG

GAAATTGGCA TTGCGATTCC CAATGGATGG GAAACACAGT CATCACAAAG ACCACCAGAA

CCTGGGTCCT GCCAAGCTAC AACAACCACA TCTACAAAGC AATTACCAGT GGAACCTCTC

AAGATGCAAA TGTCCAGTAT GCAGGATACA GTACCCCCTG GGGGTACTTT GATTTCAACC

GCTTCCACTG CCACTTCTCC CCTAGAGACT GGCAGAGACT TATCAACAAC CATTGGGGAA

TCCGACCCAA ATCTCTTAAA TTCAAGATCT TCAATGTCCA AGTCAAAGAA GTCACAACGC

AGGATCAAAC AAAGACCATT GCAAACAATC TCACCTCAAC GATTCAAGTC TTTACGGATG

ATGAGCATCA ACTCCCGTAT GTCCTGGGCT CGGCTACGGA AGGCACCATG CCGCCGTTCC

CGTCGGATGT CTATGCCCTG CCGCAGTACG GGTACTGCAC AATGCACACC AACCAGAATG

GAGCACGGTT CAATGACCGT AGTGCATTCT ACTGCTTAG
```

SEQ ID NO: 43
```
AAAAGCCTAA ATTATCTGAA GAAAACTCTC CTTCACCCAG TAATAGTGGA GGAGAAGCAA

GTGCAGCTGC CACCGAAGGC TCCGAACCTG TGGCAGCACC TAACATGGCA GAGGGAGGAA

GCGGAGCTAT GGGCGACTCT GCAGGGGGTG CCGATGGAGT GGGTAATGCC TCAGGAAATT

GGCATTGCGA TTCCCAATGG CTGGGAGACA CAGTCATTAC AAGACTACA AGAACCTGGG

TCCTGCCAAG CTACAACAAC CACATCTACA AAGCCATCAC AAGCGGAACA AACCCAGACA

CAAATACCCA ATATGCTGGA TACAGCACCC CCTGGGGGTA CTTTGATTTC AACAGATTCC

ACTGCCATTT CTCTCCAAGA GACTGGCAGA GACTCATCAA CAACCATTGG GGATTAGAC

CGAAAGCACT CAAATTCAAG ATATTCAATG TGCAAGTTAA AGAAGTCACG ACGCAAGACC

AGACAAAGAC TATTGCTAAC AACCTTACCT CTACAATCCA GATATTCACG ATAATGAAC

ACCAGCTGCC CTATGTTCTG GGCTCGGCCA CGGAGGGGAC GATGCCACCG TTCCCCTCAG

ATGTGTATGC CTTGCCCCAG TACGGCTACT GCACAATGCA CACCAACCAG AGTGGAGCTA

GATTCAATGA CAGAAGTGCC TTCTATTGCT TAG
```

SEQ ID NO: 44
```
ACGAATACTA TCCTAAAGCT AAAAAGGCCA AACAAGGCTT GCAGATACCA GCTCCACCTA

AAGGCGGAGA AGAAGAAGCT ACATCGTCAC AATCTGGAGG GAGCCCAGCA GGTTCCGATA

CTAGCGGCAC ATCTGTCATG GCTACAGGAG GAGGCGGTCC GATGGCAGAC GATAACCAGG

GCGCCGAGGG AGTGGGTAAT TCCTCAGGTG ATTGGCATTG CGATACCAAG TGGATGGGAG

ACCACGTCAT TACAAAGTCA ACCAGAACTT GGGTGCTCCC CACTTACGGG AATCATCTCT

ACGGGCCTAT CAACTTTGAC GGCACCACAG GTTCGGGTGC TAATGCAGCC TATGCAGGAT

ACAAGACTCC CTGGGGGTAC TTTGACTTCA ATCGATTCCA TTGCCACTTC TCCCCCCGAG

ACTGGCAAAG ACTCATCAAC AACCACACAG GCATCAGGCC GAAAGGACTC AAAATCAAAG

TCTTTAACGT CCAAGTCAAA GAAGTTACAA CACAAGATTC AACGAAAACA ATTGCCAACA

ATCTCACCAG CACCGTACAG ATCTTTGCGG ACGAGAACTA CGACTTACCA TATGTATTAG
```

SEQ ID NO: 142
```
TTGAACAACC CGACAACACG GCCGGGACCG GGGAGAAGCG TCCCGAACGC GTCGACGACT

TTTTCCCGAA AAAGAAGAAG GCCAAGACCG AGCAAGGCAA AGCCCCTGCT CAAACGGGCG

AAGACCCCGG AGAAGGAACC TCTTCCAACG CTGGATCAAG CGCCCCCTCT AGTGTGGGAT
```

```
                                    -continued
CATCTGTCAT GGCTGAAGGA GGTGGCGGTC CAATGGGCGA TGCAGGCCAA GGTGCCGACG

GAGTGGGCAA TTCCTCGGGA AATTGGCATT GCGATTCCCA ATGGCTGGAC AACGGAGTCG

TTACCCGAAC CACTCGAACC TGGGTCCTGC CCAGCTACAA CAACCACTTG TACAAGCGGA

TCCAAGGACC GGGAGGAACC GACCCCAACA ATAAATTCTT TGGATTCAGC ACCCCCTGGG

GGTACTTTGA CTACAACCGA TTCCACTGCC ACTTCTCCCC CCGAGACTGG CAACGACTCA

TCAACAACAA CTGGGGCATC CGACCCAAAG CGATGCGCTT TAGACTCTTT AACATCCAGG

TTAAAGAAGT CACTGTCCAA GACTCCAACA CCACCATCGC CAACAACCTC ACCAGCACGG

TCCAAGTCTT TGCGGACAAG GACTACCAGC TGCCGTACGT CCTCGGATCG GCTACAGAGG

GCACCTTCCC GCCGTTCCCA GCGGATATCT ACACGATCCC GCAGTATGGT TACTGCACGC

TAA
```

EXAMPLES

The following examples exemplify the invention for AAV, especially for AAV2. Due to the general similarities within the structures of the adeno-associated viruses and other parvoviruses the invention can be easily transferred to other parvoviruses encoding 3 viral capsid proteins.

1. General Methods 1.1. Production of AAV (Like Particles) in Insect Cells

For production of AAV particles in Sf9 cells (cultivated in Graces (JHR Bioscience, USA)/10 FCS) cells were transfected with the vector plasmid pVL_VP1_MOD4, pVL_VP2 or pVL_VP3, derivates of the pVL1393 Polyhedrin Promoter-Based Baculovirus Transfer Vector (BD Bioscience, San Jose, Calif., USA) harboring a modified AAV VP1 open reading frame. (Cloning of pVL_VP1_MOD4, pVL_VP2 and pVL_VP3 is described in example 9)

Transfection was performed using the BaculoGold™ Transfection Kit according to manufacturer's manual (BD Bioscience, San Jose, Calif., USA). Following transfection cells were incubated at 27° C. 5 days after transfection the supernatant was used for single clone separation via an end point dilution assay (EPDA). For that purpose Sf9 cells were cultivated in 96 well plates ($2 \times 10^4$ cells/well) and infected with serial dilutions of the transfection supernatant. 7 days after incubation at 27° C. the supernatant was transferred into a new 96 well plate (master plate) and stored at 2-8° C. The cells of the EPDA are lysed with sodium hydroxide, neutralized with sodium acetate and treated with Proteinase K. Following an Immune detection with the DIG-DNA wash and Block Buffer Kit (Roche, Mannheim, Germany) single clones could be detected.

To amplify single clones the according well from the master plate was used to infect Sf9 cells. Amplification of the recombinant Baculovirus was performed through several passages. Each passage was incubated for 3 days at 27° C. prior of use of the supernatant to infect cells for the next passage. In the first passage $1.2 \times 10^5$ Sf9 cells (12 well plates) were infected with 50 µl of the supernatant out of the according well of the master plate. Supernatant was used to infect $2 \times 10^6$ Sf9 (T25 Flask) (passage 1B). For passage $2.2 \times 10^7$ Sf9 (T175 Flasks) were infected with 1 ml supernatant from passage 1B.

The virus titer of supernatant of passage 2 (P2) was analyzed via an end point dilution assay. To produce AAV $1 \times 10^6$/well Sf9 (6 well plates) were infected with supernatant of P2 with a multiplicity of infection (MOI) of 1. Cultures were incubated at 27° C. for 2-3 days. Cells were harvested and disrupted by a freeze and thaw process and analyzed for AAV production. AAV2 titer was analyzed using a commercially available AAV2 titration ELISA kit (Progen, Heidelberg, Germany) according to the manufacturer's manual.

1.2. Production of AAV (Like Particles) in Mammalian Cells 1.2.1. Plasmids

Ad Helper Plasmid

An Ad helper plasmid encoding adenoviral proteins E2, E4 and VAI-VAII was used for AAV manufacturing in 293 or 293-T cells. The helper plasmid pUCAdE2/E4-VAI-VAII was constructed by subcloning the BamHI restriction fragment encoding the adenovirus (Ad) E2 and E4-ORF6 from pAdEasy-1 (Stratagene, La Jolla, USA) into the BamHI site of pUC19 (Fermentas, St. Leon-Rot, Germany). The resulting plasmid is referred to as pUCAdE2/E4. The VAI-VAII fragment from pAdVAntage™ (Promega, Mannheim, Germany) was amplified by PCR using the primers XbaI-VAI-780-3':
(SEQ ID NO: 59)
5'-TCT AGA GGG CAC TCT TCC GTG GTC TGG TGG-3',
and XbaI-VAII-1200-5':
(SEQ ID NO: 60)
5'-TCT AGA GCA AAA AAG GGG CTC GTC CCT GTT TCC-3' cloned into pTOPO (Invitrogen, Carlsbad, USA) and then subcloned into the XbaI site of pUCAdE2/E4. This plasmid was named pUCAdV.

AAV Encoding Plasmids

The construction of pUCAV2 is described in detail in U.S. Pat. No. 6,846,665. Plasmid pTAV2.0 is described in (Heilbronn et al., 1990), pVP3 is described in (Warrington et al., 2004). Further AAV viral protein encoding plasmids are described within the respective examples.

1.2.2. Transfection for Large Scale Virus Production

293-T cells (ATCC, Manassas, USA) ($7.5 \times 10^6$/dish) were seeded in 15 cm dishes (i.e. dish with a diameter of 15 cm) 24 h prior to transfection (cultivated in DMEM/10% FCS). Cells were transfected by calcium phosphate precipitation as described in US 2004/0053410.

In case of AAV promoter p40 dependent transcription a co-transfection with an adenoviral helper plasmid was performed. For co-transfection of the AAV encoding plasmid and pUCAdV a molar ratio of the plasmids of 1:1 was chosen. For transfection of one culture plate with 293-T cells the calcium phosphate transfection protocol was used as described above, 12 µg AAV Cap encoding plasmid (pU- CAV2, pTAV2.0, and pVP3, respectively) and 24 µg pUCAdV were used. In case of p40 independent transcription cells were transfected with the respective AAV VP1, VP2 and/oror VP3 encoding plasmid. For transfection of one culture plate of 293-T cells the calcium phosphate transfection protocol was used as disclosed in US 2004/0053410, 36 µg total DNA were mixed in 875 µl 270 mM $CaCl_2$). In brief, 875 µl 2×BBS (50 mM BES (N,N-Bis-(2-hydroxyethyl)-2-aminoethane sulfonic acid) (pH 6.95), 280 mM NaCl and 1.5 mM $Na_2HPO_4$) was added to the mixture and the resulting solution was carefully mixed by pipetting. The solution was incubated for 20 min at room temperature (RT) and then added drop-wise to the cell culture plate. After 18 h incubation of cells in a humidified atmosphere at 35° C. and 3% $CO_2$, medium was changed into a serum free DMEM (Invitrogen Carlsbad, USA) and cells were cultivated for an additional 3 d at 37° C., 5% $CO_2$ in a humidified atmosphere. 293-T cells were harvested with a cell lifter, transferred into 50 ml plastic tubes (Falcon) and centrifuged at 3000 g, 4° C. for 10 min. The cell pellet was resuspended in 0.5 ml lysis buffer (150 mM NaCl, 50 mM Tris, pH 8.5) per 15 cm dish and objected to three rounds of freeze and thaw cycles (liquid nitrogen/37° C.). The cell lysate was cleared by two centrifugation steps (3700 g, 4° C., 20 min) and the AAV-containing supernatant was used for further purification. Alternatively the whole dishes were objected to freeze and thaw cycles (−50° C./RT). The remaining supernatant was collected and further purified as described in 1.3.

1.2.3. Small Scale Transfection and Preparation of Virus Supernatants

Cells ($5×10^5$/dish) were seeded in 6 cm dishes 24 h prior to transfection. 293-T cells were transfected by calcium phosphate precipitation as described in US 2004/0053410. For HeLa and COS-1 cells transfections were performed using LIPOFECTAMINE® 2000 (Invitrogen, Carlsbad, USA) according to the manufacturer's manual. In case of promoter p40 dependent transcription of the cap gene (pTAV2.0, derivates thereof, and pVP3) cells were infected with adenovirus type 5 (Ad5) (MOI=10). After additional incubation for 24-48 h, cells were harvested in the medium and lysed by three freeze-thaw cycles (−80° C. and 37° C.). Lysates were incubated at 56° C. for 30 min to inactivate Ad5. Cell debris was removed by centrifugation at 10000 g for 5 min.

1.2.4. Cell Culture

HeLa and 293-T cells were maintained at 37° C. and 5% $CO_2$ in Dulbecco's modified Eagle's medium (DMEM) supplemented with 10% heat-inactivated fetal calf serum, 100 U/ml penicillin, 100 µg/ml streptomycin and 2 mM L-glutamine.

1.3. Purification 1.3.1 Tangential Cross Flow Filtration (TFF) and Benzonase Treatment After harvest the cleared cell culture medium was further concentrated using a Tangential Cross Flow Filtration Unit (SARTOFLOW® Slice 200 Benchtop Crossflow System, Sartorius Biotech GmbH, Gottingen, Germany) using a 100 kDa cut off membrane (SARTOCON® Slice 200). The resulting TFF concentrate was pooled with the supernatant (obtained as described in 1.2) and immediately treated with 100 U/ml BENZONASE® (Merck, Darmstadt, Germany) at 37° C. for 2 h. After BENZONASE® treatment the cell lysate was cleared by centrifugation at 3700 g, 4° C. for 20 min. Cleared supernatant was purified using size exclusion chromatography (ÄKTA explorer system, GE Healthcare, Munich, Germany).

1.3.2 Size Exclusion Chromatography (SEC)

Cleared supernatant was separated through a SUPERDEX™ 200 (prep grade) packed XK 50 chromatography column (250 mm in height and 50 mm in diameter; GE Healthcare, Munich, Germany). SEC fractions (5 ml each) were collected and the capsid titer was determined using the AAV2 capsid-specific A20 ELISA (Progen, Heidelberg, Germany, Cat. No: PRATV). SEC fractions containing AAV2 particles were pooled and further purified using iodixanol- or sucrose-density ultracentrifugation.

(i) Purification of AAV Particles by Density Gradient Centrifugation Using Iodixanol The virus-containing SEC pool was transferred to QUICK-SEAL® ultracentrifugation tubes (26×77 mm, Beckman Coulter, Marseille, France). Iodixanol solutions (purchased from Sigma, Deisenhofen, Germany) of different concentrations were layered beneath the virus containing lysate. By this an Iodixanol gradient was created composed of 6 ml 60% on the bottom, 5 ml 40%, 6 ml 25% and 9 ml 15% Iodixanol with the virus solution on top. The gradient was spun in an ultracentrifuge at 416000 g for 1 h at 18° C. The 40% phase containing the AAV particles was then extracted with a canula by puncturing the tube underneath the 40% phase and allowing the solution to drip into a collecting tube until the 25% phase was reached.

(ii) Sucrose Density Gradient Analysis $1.5×10^6$ cells were seeded in 10 cm dishes 24 h prior to transfection. They were harvested 48 h post transfection and lysed in 300 µl PBS-MK (phosphate-buffered saline: 18.4 mM $Na_2HPO_4$, 10.9 mM $KH_2PO_4$, 125 mM NaCl supplemented with 1 mM $MgCl_2$, 2.5 mM KCl) by five freeze-thaw cycles (−80° C. and 37° C.). After treatment with 50 U/ml BENZONASE® (Sigma, Deisenhofen, Germany) for 30 min at 37° C. and centrifugation at 3700 g for 20 min the supernatant was loaded onto a 11 ml 5-30% or 10-30% sucrose gradient (sucrose in PBS-MK, 10 mM EDTA, containing one tablet of COMPLETE™ mini EDTA free protease inhibitor (Roche, Mannheim, Germany)) in polyallomer centrifuge tubes (14 by 89 mm; Beckman Coulter, Marseille, France). After centrifugation at 160000 g for 2 h at 4° C. (SW41 rotor; Beckman), 500 µl fractions were collected from the bottom of the tubes. As reference empty AAV2 capsids (60 S) were analyzed in a separate gradient. For immuno dot blot assay 50 µl of heat denatured (99° C. for 10 min) or non denatured aliquots of the fractions were transferred to PROTRAN® nitrocellulose membranes (Schleicher & Schuell, Dassel, Germany) using a vacuum blotter. Membranes were blocked for 1 h in PBS containing 10% skim milk powder and then incubated for 1 h with monoclonal antibodies B1 (Progen, Heidelberg, Germany, Cat. No: 65158) to detect denatured capsid proteins or A20 to detect non denatured capsids. Antibodies B1 and A20 were applied in 1:10 dilutions. Membranes were washed several times with PBS and incubated for 1 h with a peroxidase-coupled goat anti-mouse antibody (1:5000 dilution) (Dianova, Hamburg, Germany). Then, membranes were washed again and the antibody reaction was visualized using an enhanced chemiluminescence detection kit (Amersham, Braunschweig, Germany). For Western blot analysis 15 µl per fraction were processed for SDS-PAGE and then probed with monoclonal antibodies A69 (Progen, Heidelberg, Germany, Cat. No: 65157) or B1.

(iii) Purification of AAV Particles by Chromatography

Purification of Empty wtVP3[#] and Modified AAVLPs[*]

Indices [#] and [*] refer to slight differences in the purification protocol between wtAAV[#] and modified AAVLPs[*]. Buffer ingredients are marked correspondingly.

Cation Exchange Chromatography (ÄKTA™ Explorer System)

Total lysate containing empty wtVP3# and modified AAV-LPs* was obtained by performing three freeze thaw cycles (−54° C./37° C.). Total lysate was cleared by centrifugation at 4100 rpm, 4° C., 20 min (MULTIFUGE L-R; Heraeus, Hanau, Germany). The pH of the resulting cleared supernatant was adjusted to 6. In addition, the conductivity of salt was reduced to approximately 10 mS/cm by adding sterile water.

A FRACTOGEL® EMD $SO_3^-$ (M) chromatography column (100 mm in height; 15 mm in diameter, XK16, GE Healthcare, Munchen, Germany) was packed and equilibrated using 5 CV running buffer consisting of 80 mM NaCl, 2% sucrose, 50 mM HEPES (pH 6.0), 2.5 mM $MgCl_2$.

After equilibration, cleared supernatant was separated through the FRACTOGEL® EMD 503 (M) packed chromatography column (flow rate 10 ml/min). After separation, column was washed using 5 CV running buffer mentioned above. Bound particles (wtVP3 or modified AAVLPs) were effectively eluted at a sodium chloride concentration of 350 mM (peak 1≈45 ml).

Buffer Exchange (ÄKTA™ Explorer System)

To adjust the pH and the salt concentration of the eluted proteins (peak 1) for successive anion exchange chromatography, buffer exchange was performed using a Sephadex G25 packed chromatography column (500 mm in height; 15 mm in diameter, XK26, GE Healthcare, München, Germany) (flow rate 10 ml/min). After column equilibration using 3 CV SOURCE 15Q running buffer consisting of 25 mM Tris (pH 8.2), 150 mM NaCl#/100 mM NaCl*, 2.5 mM $MgCl_2$ peak 1 was separated through the column. Protein fraction (≈120 ml) was collected.

Anion Exchange Chromatography (ÄKTA™ Explorer System)

A SOURCE 15Q chromatography column (80 mm in height; 15 mm in diameter, XK16, GE Healthcare, Munchen, Germany) was equilibrated using 5 CV SOURCE 15Q running buffer consisting of 25 mM Tris (pH 8.2), 150 mM NaCl#/100 mM NaCl*, 2.5 mM $MgCl_2$. After equilibration, the protein fraction obtained after buffer exchange (appr. 120 ml) was loaded and separated through the chromatography column (flow rate 10 ml/min). Flow-through containing 90% of the particles (appr. 120 ml) was collected.

Particle Concentration Using Centrifugal Filter Devices

Flow-through containing wtVP3# or modified AAVLPs* was concentrated using CENTRICON® Plus-70 (cut off 100 kDa) centrifugal filter devices (Millipore). Concentration was carried out using a swinging-bucket rotor (MULTIFUGE™ L-R; Heraeus, Hanau, Germany) at 3500 g, 20° C. for 15 min. Resulting concentrate (appr. 45 ml) was immediately separated through a size exclusion chromatography.

Size Exclusion Chromatography (ÄKTA™ Explorer System)

A SUPERDEX® 200 (prep grade) chromatography column (500 mm in height; 50 mm in diameter, XK50, GE Healthcare, München, Germany) was packed and equilibrated using 2 CV running buffer consisting of 200 mM NaCl, 2% sucrose, 50 mM HEPES (pH 6.0), 2.5 mM $MgCl_2$. The concentrate mentioned above (appr. 45 ml) was separated through the column (flow-rate 10 ml/min). Particles eluted first (SEC fraction no. 1-13; each 5 ml). SEC fractions with a particle purity of greater than 95% were pooled, sterile filtered (0.2 µm) (MINISART®; Sartoriusstedim) and stored at −84° C.

1.4. Analysis of Protein Expression by Western Blot

Identical portions of harvested cells or identical amounts of purified particles were processed for SDS-PAGE. Protein expression was analyzed by Western blot assay using monoclonal antibodies A69, B1 (Progen, Heidelberg, Germany), anti-AU1 (Covance, Emeryville, USA), anti-GFP (clone B-2; Santa Cruz Biotechnology, Santa Cruz, USA) or polyclonal antibody anti-AAP (see 1.7.) as described previously (Wistuba et al., 1995). Variations of the protocols are indicated within the description of the respective examples.

1.5. Titer Analysis

Capsid titers were determined using a commercially available AAV2 titration ELISA kit (Progen, Heidelberg, Germany Cat. No: PRATV) or the respective AAV1 titration ELISA kit (Progen, Heidelberg, Germany Cat. No: PRAAV1) according to the manufacturer's manual.

1.6. Immunofluorescence Analysis

For immunofluorescence analysis HeLa cells were cultivated for 24 h on coverslips, transfected and in case of promoter p40 dependent transcription of the cap gene (pTAV2.0 and pVP3) infected with Ad5 (MOI=4). After 20-48 h cells were fixed with 100% methanol (10 min, −20° C.) and washed with PBS (phosphate-buffered saline: 18.4 mM $Na_2HPO_4$, 10.9 mM $KH_2PO_4$, 125 mM NaCl). Incubation with primary antibodies was performed for 1 h at RT or over night at 4° C. As primary antibodies hybridoma supernatants A20 or A69 were used to detect assembled capsids or VP2 respectively. A20 and A69 were used undiluted (Progen, Heidelberg, Germany). For detection of unassembled capsids a rabbit polyclonal serum was used in a 1:500 dilution to label all three free VP proteins. Coverslips were washed three times with PBS and thereafter incubated with appropriate secondary antibodies (Cy 3 labeled goat anti mouse in 1:400 dilution or FITC labeled goat anti rabbit 1:150 purchased from Dianova, Hamburg, Germany or Molecular Probes, Leiden, The Netherlands) for 1 h at RT. Coverslips were washed again, dipped into 100% ethanol and embedded in PERMAFLUOR™ mounting medium (Beckman Coulter, Marseille, France). Confocal images (0.3 µm sections) were obtained with a Leica TCS SP2 laser scanning microscope and further processed using ADOBE® PHOTOSHOP® CS software. Variations of the protocols are indicated within the description of the respective examples.

To visualize GFP expression, cells were fixed with 2% paraformaldehyde for 15 min, quenched twice with 50 mM $NH_4Cl$ for 5 min, and permeabilized with 0.2% Triton X-100 for 10 min.

1.7. Preparation of Polyclonal Antibody

The polyclonal AAP antiserum (anti-AAP) was generated by immunization of a guinea pig with a peptide comprising the sequence GKDSSTTTGDSDPRDSTS (SEQ ID NO: 61) conjugated to KLH (Keyhole Limpet Hemocyanin) following standard procedures.

1.8. Negative Staining of Virus Particles for Electron Microscopy

For electron microscopy according to (Grimm et al., 1999, Grimm and Kleinschmidt, 1999, Mittereder et al., 1996), negative staining of virus particles was performed as described in detail below.

Five µl of sample (about $5 \times 10^{10}$ virus particles) were applied onto the freshly air-glow discharged carbon coated side of a grid and incubated for 2 min. Excess solution was removed by blotting the edge of the grid onto Whatman filter paper. To avoid salt precipitates, the grid was washed with 3 drops of water followed by four drops of 2% (w/v) uranyl acetate solution. The last droplet of staining solution was allowed to sit on the grid for 5 min before blotting and air drying. Electron micrographs were taken with a Morgagni 268D FEI microscope at 100 kV.

2. Analysis of VLP Formation by N-Terminal Deletion Analysis of VP2

Our as well as previous studies (compare above) reported a lack of capsid assembly when VP3 is expressed from constructs comprising the cds of VP3 alone. Since expression of VP3 is not sufficient for VLP formation, we tried to identify further sequences which could overcome this defect. In this experiment we checked whether a sequence upstream of the VP3 cds was necessary for VLP formation. If yes, the sequence should be characterized.

2.1. Cloning of Deletion Mutants

Plasmids pTAV2.0 (Heilbronn et al., 1990), pVP3 (Warrington et al., 2004), pCMV-VP (Wistuba et al., 1997) and pKEX-VP3 (Ruffing et al., 1992) have been described previously. The deletion mutants pCMV-VP3/1882, pCMV-VP3/2193, pCMV-VP3/2596, pCMV-VP3/2611, pCMV-VP3/2696, pCMV-VP3/2765 and pCMV-VP3/2809 were cloned from plasmid pVP3. Numbers behind the name of the pCMV-VP3 plasmid indicate the nucleotide position in the AAV2 genome according to Ruffing et al. (1994). Constructs are schematically shown in FIGS. 5A and 5B.

For cloning of deletion mutants, the HindIII/BsiWI fragment of pVP3 (with mutated VP1 and VP2 translation start codons) was subcloned into the HindIII/BsiWI backbone of pCMV-VP resulting in the construct pCMV-VP3/1882 (FIGS. 5A-5D). Constructs pCMV-VP3/2193 and pCMV-VP3/2596 were generated by subcloning of the DraI/BsiWI or the EcoNI (blunted)/BsiWI fragment from pVP3 into the HindIII (blunted)/BsiWI backbone of pCMV-VP (EcoNI and HindIII sites were blunted by digestion of the single stranded overhang) (the position of the different restriction sites used for cloning relative to the genomic sequence is shown in FIG. 4). For further deletions pVP3 was used as a template for site-directed mutagenesis reactions. Mutagenesis was performed using a QUICKCHANGE® site-directed mutagenesis kit (Stratagene, Amsterdam, The Netherlands) according to the manufacturer's manual. For each mutation, two complementary PCR primers were designed to generate a new HindIII restriction site at the designated area. Primer sequences:

(SEQ ID NO: 62)
5'-CCTCTGGTCTGGGAACTAAGCTTATGGCTACAGGCAGTGGCG-3'

(SEQ ID NO: 63)
5'-CGCCACTGCCTGTAGCCATAAGCTTAGTTCCCAGACCAGAGG-3'

HindIII/BsiWI fragments from mutated plasmids were then subcloned into the HindIII/BsiWI backbone of pCMV-VP resulting in constructs pCMV-VP3/2611, pCMV-VP3/2696, pCMV-VP3/2765 and pCMV-VP3/2809 (FIGS. 5A and 5B).

2.2. Analyses of Constructs by Western Blot and ELISA

For analysis of protein expression identical portions of harvested cells were processed for SDS-PAGE.

As shown in FIG. 5C, transfection of 293-T cells with all constructs listed in FIGS. 5A and 5B except pTAV2.0 (wt AAV) and pCMV-VP resulted in expression of only VP3 when analyzed by Western blotting using antibody B1 which reacts with all three capsid proteins. In contrast cells transfected with pTAV2.0 (wt AAV) or pCMV-VP, a plasmid in which the corresponding translation start sites were not mutated, VP1 and VP2 were well detected in addition to VP3. Antibody B1 reacted with two polypeptide bands migrating slower than VP3 e.g. for mutated plasmids pKEX-VP3, pCMV-VP3/2765 and pCMV-VP3/2809. At least for plasmids pKEX-VP3 and pCMV-VP3/2809 the corresponding polypeptides cannot contain VP1 or VP2 amino acid sequences since the nucleotide sequences coding for VP1 or VP2 were completely deleted. Moreover, VP1 and VP2 could not be detected upon expression of all three mutant plasmids, using the antibody A69. Hence, the presence of VP1 and VP2 in these samples could clearly be excluded. We concluded that the two polypeptide bands migrating slower than VP3 were a consequence of higher VP3 levels, which were not completely denatured.

When, however, extracts of cells transfected with pVP3 were probed with antibody A69 which detects only VP1 and VP2, thus omitting the reaction with the abundant VP3, one could detect faint bands in the region of VP1 and VP2 which were absent in extracts of cells transfected with pKEX-VP3. This result suggests that transfection of the pVP3 construct leads to the expression of small amounts of VP1 and VP2 or VP1- and VP2-like proteins. They are possibly translated from alternative translation initiation codons or by unscheduled initiation at the mutated VP1 and VP2 translation initiation sites.

Antibody A69 revealed in all deletion mutants of pVP3 up to pCMV-VP3/2696 one or several polypeptide band(s), only Western blots with extracts of cells transfected with pCMV-VP3/2765 and pCMV-VP3/2809 showed no reaction with A69 because the antibody epitope was already deleted in these proteins.

Capsid assembly was confirmed by an antibody A20 based capsid ELISA (FIG. 5D). In contrast, expression of VP3 by pKEX-VP3 did not yield detectable amounts of capsids (FIG. 5D), although the amount of expressed VP3 protein was even higher compared to pVP3 (FIG. 5C).

In agreement with our previous results, expression of VP3 alone by transfecting pCMV-VP3/2809—which is equivalent to pKEX-VP3—did not lead to detectable capsid formation (FIG. 5D). The formation of capsids which might not react with the A20 ELISA was excluded by analysis of cell extracts on sucrose gradients followed by Western blotting with the B1 antibody (data not shown). Interestingly, analyzing the capsid assembly efficiency of the different deletion mutants it was detected that the capsid assembly efficiency increased from one deletion mutant to the next, before decreasing upon a certain extent of deletion. Peak efficiencies in capsid assembly were seen for mutants pCMV-VP3/2596 and pCMV-VP3/2611 (FIGS. 5A, 5B, and 5D).

2.3 Conclusion

This result shows a clear correlation between the presence of N-terminally extended VP3 sequence (due to the presence of DNA sequence upstream of the VP3 start codon) and capsid assembly. We identified a DNA sequence of about 44 nucleotides upstream of the VP3 cds that has to be present in addition to the VP3 cds for VP3 VLP formation. This 44 nt confers to construct pCMV-VP3/2765 which still is able to cause capsid assembly.

The presence of some more DNA sequence upstream of the 2765' site increases efficiency of capsid assembly which is in line with ORF2 starting at nucleotide position 2717 and the putative start of the full-length AAP possibly located between nucleotide 2717 and 2765.

3. Sequence Fragment of the Cap Gene is Able to Induce Capsid Assembly in Trans

In example 2, we identified some sequence upstream of the VP3 start codon (comprised by fragment Z) that has to be present in addition to the VP3 cds for particle formation. To prove the hypothesis that the product of fragment Z functions transiently and in trans, we tested whether a capsid sequence fragment comprising the EcoNI/BsiWI restriction fragment fused to the cds of GFP can rescue the capsid assembly deficiency of VP3.

3.1. Cloning of pVP2N-Gfp for Trans-Complementation

For generation of construct pVP2N-gfp, EcoNI and BsiWI restriction sites were introduced into the multiple cloning site of the vector pEGFP-N1 (BD Biosciences, Erembodegem, Belgium). Afterwards the EcoNI/BsiWI fragment from pTAV2.0 (position of restriction sites is given in FIG. 4) was inserted downstream of a CMV promoter and upstream of the GFP cds and its poly(A) signal. Expression of this fusion construct pVP2N-gfp results in three transcripts VP2N-gfp, VP3N-gfp and GFP, depending on the initiation of transcription at one of the three existing start codons for VP2, VP3 or GFP as schematically shown in FIG. 6A.

A number of derivates containing e.g. codon modifications or stop codons originated from pVP2N-gfp as schematically indicated in the respective figures. They always include the GFP cds and were named accordingly (with the addition -gfp). To simplify matters this appendix (-gfp) is missing to names of the respective constructs in some figures (e.g. FIGS. 20, 22, 23).

3.2. Analysis of Functional Substitution in Trans

Figure 6D:
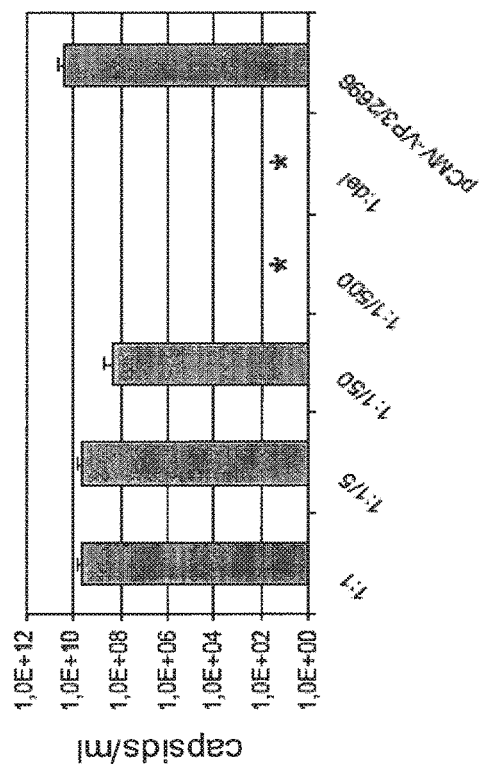

The following experiments were performed in HeLa cells. Plasmids pCMV-VP3/2809 and pVP2N-gfp were co-transfected in different molar ratios and analyzed for gene expression and capsid assembly (FIGS. 6A-6D). While Western blot analysis confirmed that the amount of VP3 was the same in cell extracts transfected in each molar ratio of the two plasmids (detection with antibody B1, FIG. 6B upper part), VP2N-gfp (detection with antibody A69, FIG. 6B lower part) could only be detected after transfection in a 1:1 or 1:1/5 ratio, respectively. In the 1:1 or 1:1/5 ratio, antibody anti-gfp (FIG. 6B, middle) additionally detects all three transcripts resulting from expression of the fusion construct pVP2N-gfp as schematically shown in FIG. 6A, namely VP2N-gfp, VP3N-gfp and GFP. Due to the strong start codon of VP3 and corresponding to the in vivo situation the transcript of VP3N-gfp dominates. Surprisingly, capsid assembly could be observed by immunofluorescence up to a pCMV-VP3/2809 to GFP-fusion-plasmid ratio of 1:1/50 (FIG. 6C). Quantification of capsid formation using the antibody A20 based capsid ELISA showed that capsid formation of mutant pCMV-VP3/2809 supplemented with pVP2N-gfp was similarly efficient as mutant pCMV-VP3/2696 where the N terminally extended VP3 was co-expressed (FIG. 6D).

3.3. Conclusion

This result shows that presence of an EcoNI-BsiWI restriction fragment of the cap gene in trans rescues capsid assembly of constructs expressing VP3 as only capsid protein. Since assembly could be detected even at a 50-fold reduced amount of pVP2N-gfp plasmid co-transfected, a substoichiometric action of the helper factor for VP3 capsid assembly can be assumed.

4. C-Terminally Truncated VP2 Proteins are Expressed in Substoichometric Amounts and Become Incorporated into Capsids Here it was investigated if the generated AAV like particles consist of VP3 only. Empty particles were produced from plasmid pCMV-VP3/2696 or in a trans-complementation assay of cotransfection of pCMV-VP/2809 and pVP2N-GFP Particles were purified via sucrose cushion according to Steinbach et al. (1997) with modification described by Kronenberg et al. (2001) and with the modification that the 293 cells were transfected without adenoviral infection and cells were harvested after 48 h. Incorporation of truncated VP2 protein was analyzed by Western blot (FIG. 7).

pVP2N-GFP could not be detected within maximal loading of $5 \times 10^{11}$ particles. But transfecting pCMV-VP3/2696 an A69 signal was detected which shows that a truncated VP2 is incorporated into the capsids substoichiometrically.

4.1. Result

In conclusion VP3 only particles are generated within the trans situation. In contrast in the cis situation a truncated VP2 is incorporated substochiometrically. From Western blot the signal intensity of VP1 from $2 \times 10^9$ wt AAV particles is about the same as the signal from $1 \times 10^{11}$ particles generated from pCMV-VP3/2696. This means the amount of truncated VP2 is about 50 fold lower than the amount of VP1. Assuming a stoichiometric ratio of VP1:VP2:VP3 of 1:1:10 within a wt capsid there is approximately 500-fold less truncated VP2 than VP3. Since one capsid is composed of 60 VP subunits also capsids must exist that are composed of VP3 only.

4.2. Conclusion

This result strengthens the conclusion that the truncated VP2 protein itself is not required for the capsid itself.

5. Codon Modification of the Construct Used for Trans-Complementation can Inhibit the Trans-Complementation Process To investigate the nature of the trans-complementing agent of the fragment Z, the VP2N part (part between restriction sites EcoNI and BsiWI) within pVP2N-gfp was codon modified. That means the DNA sequence was altered without changing the amino acid sequence of the first ORF. Codon modification was performed by GENEART® (Regensburg, Germany). Codons were modified for codons preferentially used in mammalian cells. Sequence is shown in FIGS. 8A-8C. Identity of the DNA sequence of pVP2N-gfp versus pVP2N-gfp codon modified (cm, pVP2Ncm-gfp) is 71% while protein identity is 100%.

Protein expression of pVP2Ncm-gfp was compared in Western blot analysis (FIG. 8D) and by immunoflourescence within transfected 293 cells (FIG. 8E). The ability to rescue capsid formation of pCMV-VP3/2809 was tested in trans-complementation assays as described in example 3 (FIG. 8F). Plasmids were cotransfected in a molar ratio of 1:1.

Result and Conclusion

Western blot showed that the protein expression from the codon modified construct (pVP2Ncm-gfp) was even higher than protein expression from the non-modified construct (pVP2N-gfp), not unexpected since the codon modification was optimized for mammalian cells (FIG. 8D). Also the localization within the cells of the codon modified protein did not differ from the non-modified protein (FIG. 8E). Surprisingly the pVP2Ncm-gfp lost its ability to rescue capsid formation of pCMV-VP3/2809 (FIG. 8F).

To exclude a negative effect of the large amounts of pVP2Ncm-gfp protein on capsid assembly, we co-transfected the codon modified pVP2Ncm-gfp with pCMV-VP3/2696. In this combination capsid assembly was normal, showing that the assembly activity was not suppressed by the high amount of pVP2Ncm-gfp (data not shown). Also expression of lower amounts of pVP2Ncm-gfp by transfection of reduced amounts of plasmid pVP2Ncm-gfp together with pCMV-VP3/2809 did not rescue capsid assembly (data not shown).

This result strengthens the hypothesis that no protein translated from the first ORF is responsible for the trans-complementing activity.

6. Insertion of Stop Codons into the Construct Used for Trans-Complementation Does not Inhibit the Trans-Complementation Process To further analyze the nature of the trans-complementing agent stop codons were inserted within the EcoNI-BsiWI restriction fragment. To insert Stop codons point mutations were performed.

6.1. Insertion of Stop Codons into pVP2N-Gfp

For construction of pVP2N/stopA-gfp (also named pVP2N/ORF1stopA-gfp), pVP2N/stopB-gfp (identical to pVP2N/ORF1stopB-gfp), pVP2N/stopC-gfp (also named pVP2N/ORF1stopC-gfp) and pVP2N/stopD-gfp (identical to pVP2N/ORF1stopD-gfp) site-directed mutagenesis reactions (QUICKCHANGE® site-directed mutagenesis kit, Stratagene) were performed using template pVP2N-gfp and two complementary PCR primers which included the desired substitutions. In each case the EcoNI/BsiWI fragment was then cloned into the EcoNI/BsiWI backbone of pVP2N-gfp.

For generation of StopA cytosine at nucleotide position 2770 were substituted to thymine resulting in a tag stop codon. For generation of StopB adenine at nucleotide position 2797 was substituted to thymine resulting in a tga stop codon. Stop C was generated by substituting adenine at nucleotide position 2821 to thymine and thymine at position 2823 to adenine, resulting in a tga stop codon. Stop D was created by substituting guanine at nucleotide position 2878 to thymine resulting in a tga stop codon. Positions are according to Ruffing et al. (1994).

Further protein expression of the Stop constructs was tested by Western blot analysis using the A69 antibody.

6.2. Result and Conclusion

Western blot analysis confirmed that VP3 is expressed in all samples (detected by monoclonal antibody B1 in FIG. 9B). As expected Bluescript vector (pBS) did not cause capsid assembly in the trans-complementation assay and therefore served as a negative control (FIG. 9C). Interestingly, although no protein expression was detected for the pVP2N/stop-gfp constructs in contrast to the pVP2N-gfp construct (FIG. 9B), the insertion of stop codons did not influence the trans-complementing activity of the EcoNI-BsiWI restriction fragment of the cap gene. VP3 particles could easily be assembled (FIG. 9C). The reduction in capsid titers obtained with mutants pVP2N/stopB-gfp and pVP2N/stopC-gfp could be due to the nucleotide changes introduced by generating the respective mutations (stopB in ORF1 led to a Trp→Cys mutation in ORF2, stopC in ORF1 led to a Val→Glu mutation in ORF2). These experiments together show that the nucleic acid sequence of the EcoNI-BsiWI fragment is the basis for the capsid assembly helper activity and not an expressed protein from the first ORF, since all mutants contain stop codons in the first ORF. Although the substitutions resulting in stop codons in ORF 1 did not stop amino acid synthesis of AAP from ORF2, differences in capsid titers indicated that the functionality of AAP was influenced.

Primer pairs used for insertion of Stop codons at four different sites within the pVP2N-gfp

| | | |
|---|---|---|
| StopA | 5'-CCA GCC TCT CGG ATA GCC ACC AGC AGC C-3' | (SEQ ID NO: 64) |
| i-StopA | 5'-GGC TGC TGG TGG CTA TCC GAG AGG CTG G-3' | (SEQ ID NO: 65) |
| StopB | 5'-GCC CCC TCT GGT CTG TGA ACT AAT ACG ATG GC-3' | (SEQ ID NO: 66) |
| i-StopB | 5'-GCC ATC GTA TTA GTT CAC AGA CCA GAG GGG GC-3' | (SEQ ID NO: 67) |
| StopC | 5'-CGA TGG CTA CAG GCT GAG GCG CAC CAA TGG C-3' | (SEQ ID NO: 68) |
| i-StopC | 5'-GCC ATT GGT GCG CCT CAG CCT GTA GCC ATC G-3' | (SEQ ID NO: 69) |
| StopD | 5'-GGA GTG GGT AAT TCC TCG TGA AAT TGG CAT TGC G-3' | (SEQ ID NO: 70) |
| i-StopD | 5'-CGC AAT GCC AAT TTC ACG AGG AAT TAC CCA CTC C-3' | (SEQ ID NO: 71) |

Schematic presentation of the inserted stop codons is depicted in FIG. 9A. In pVP2N/stopA-gfp nucleotide c2770 has been mutated into t, therefore the cag-codon encoding glutamine is changed into tag (silent mutation in ORF2), in pVP2N/stopB-gfp nucleotide g2797 has been mutated into t, hence the gga-codon encoding glycine is changed into tga (Trp→Cys mutation in ORF2), in pVP2N/stopC-gfp nucleotide $a_{282}$, has been mutated into t (silent in ORF2) and nucleotide $t_{2823}$ has been mutated into a, therefore the agt-codon encoding serine is changed into tga (Val→Glu mutation in ORF2), and in pVP2N/stopD-gfp nucleotide g2878 has been mutated into t, hence the gga-codon encoding glycine is changed into tga (silent in ORF2). Positions are according to Ruffing et al. (1994). All substitutions do not disrupt ORF2. The resulting pVP2N-gfp stop constructs were used for trans-complementation of the construct pCMV-VP3/2809 as described in example 3. Plasmids pCMV-VP3/2809 and the respective pVP2N/stop-gfp construct were cotransfected in a molar ratio of 1:1.

7. The Postulated NLS is not Necessary for VLP Formation

While mutant pCMV-VP3/2696 formed high capsid levels, the slightly shorter mutant pCMV-VP3/2765 assembled to clearly reduced amounts of capsids (FIG. 5D). This shorter mutant had lost a group of AA which had been suggested to function as a NLS for AAV VP2 proteins (Hogue et al., 1999a) and showed reduced nuclear transport of the VP protein (FIG. 10) To test whether the postulated NLS is responsible for this difference, we substituted the respective sequence element by converting the RKR peptide (AA 168-170) into AAA in the construct pCMV-VP3/2696 in order to destroy the proposed NLS activity by site directed mutagenesis according to standard procedures using two complementary PCR primers which included the desired substitutions. Primers used for substitution of RKR by AAA:

BC3-ala forward:

(SEQ ID NO: 72)
5'-GGC GGG CCA GCA GCC TGC AGC AGC AGC ATT GAA TTT TGG TCA GAC TGG-3'

BC3-ala reverse:

(SEQ ID NO: 73)
5'-CCA GTC TGA CCA AAA TTC AAT GCT GCT GCT GCA GGC TGC TGG CCC GCC-3'

Immunofluorescence of transfected HeLa cells with the A20 antibody (FIG. 10) and the capsid ELISA (data not shown) showed that the VP protein of mutant pCMV-VP3/2696RKR168-170AAA was as active in capsid assembly as wt AAV.

This supports the interpretation that the sequence element comprising RKR168-170 does not act as a NLS in this context and might play a different role in capsid assembly.

8. Nuclear Localization (and N Terminal Extension) of VP Proteins is not Sufficient for Capsid Assembly It has been reported that fusion of an NLS derived from the SV40 large T antigen to VP3 translocates VP3 into the nucleus and leads to capsid assembly (Hogue et al., 1999a). We repeated this experiment and observed efficient nuclear accumulation of VP3 protein, however, there was no capsid assembly detectable with antibody A20 (FIGS. 11A, 11B and 15B).

Further, a heterologous N terminal extension upstream of VP3 (HSA) was tested to restore assembly competence to VP3.

Further several constructs were transfected in 293 cells to compare protein expression and assembly efficiency.

8.1. Cloning of Constructs pCI-VP, pCI-VP2 and pCI-VP3 were cloned by PCR amplification of the respective VP coding regions using primer with XhoI (5'-) and NotI (3'-) overhangs and subcloning of the XhoI-/NotI-digested PCR products into the XhoI-/NotI-digested vector pCI (PROMEGA). In case of pCI-VP2, the start codon for VP2 was changed from ACG to ATG at the same time Cloning of the construct pCMV-NLS-VP3 was carried out by site-directed mutagenesis reaction using the construct pCMV-VP3/2809 as template and the complementary PCR primers (SEQ ID NO: 74)
5'-GGAAT TCGAT ATCAA GCTTG CCATG GCACC ACCAA AGAAG AAGCG AAAGG TTATG GCTAC AGGCA GTGG-3'
and (SEQ ID NO: 75)
5'-CCACT GCCTG TAGCC ATAAC CTTTC GCTTC TTCTT TGGTG GTGCC ATGGC AAGCT TGATA TCGAA TTCC-3'.

Then the HindIII/BsiWI fragment was subcloned from the amplicon into the HindIII/BsiWI backbone of pCMV-VP3/2809. The cap gene product NLS-VP3 contains the amino acid sequence of SV40 NLS MAPPKKKRKV at the N-terminus of VP3.

The construct pCMV-HSA-VP3 is also based on pCMV-VP3/2809 and contains a nucleic acid sequence coding for amino acids 25-58 of human serum albumin (HSA) directly upstream of the VP3 cds. Fragment (SEQ ID NO: 76)
5'-GGTAC CAAGC TTACG GACGC CCACA AGAGC GAGGT GGCCC ACCGG TTCAA GGACC TGGGC GAGGA AAACT TCAAG GCCCT GGTGC TGATC GCCTT CGCCC AGTAC CTGCA GCAGT GCAAG CTTGA GCTC-3'

(with a HindIII restriction site at both ends) was obtained via gene synthesis (GENEART®, Regensburg, Germany). After HindIII digestion of the corresponding vector the resulting 111 bp fragment was subcloned into the HindIII linearized pCMV-VP3/2809 backbone. Translation of VP3 is initiated at a standard ATG start codon whereas translation of HSA-VP3 (with 37 Aas elongation at VP3 N-terminus) is initiated at an ACG start codon.

8.2. Analyses of Constructs by Immunofluorescence and Sucrose Gradient

We transfected HeLa cells with the different constructs: pCMV-NLS-VP3 or pCMV-VP3/2809 either alone or in a co-transfection with pVP2N-GFP. Further pCMV-HSA-VP3 was transfected. Expression of capsid proteins and formation of capsids was analyzed by immunofluorescence as described above using a polyclonal VP antiserum or the monoclonal A20 antibody. Further capsid formation was analyzed within following a sucrose gradient.

Results

Just as Hoque et al. (1999a) and comparable to the wildtype (wt) and the proteins expressed from the N-terminally truncated construct pCMV/2696, we could express VP3 from the construct pCMV-NLS-VP3 and observed efficient nuclear accumulation of VP3 protein. However, in contrast to the wt and the N-terminally truncated construct pCMV/2696 we could not detect capsid assembly using the antibody A20 (FIG. 11C).

As expected, expression of the VP3 protein with a prolonged N-terminus consisting of 36 AA of human serum albumin (HSA-VP3), equivalent in length to the VP3 N-terminal extension of mutant pCMV-VP3/2696 could be detected by antibody staining (FIG. 11C). In comparison to the expression product of pCMV-NLS-VP3 those of the mutant pCMV-HSA-VP3 showed a much higher fraction of cytoplasmic staining. Again, we could not detect capsid assembly using the antibody A20 (FIG. 11C).

Co-transfection of pVP2N-gfp induced capsid assembly, readily detectable by antibody A20 (FIG. 11C).

Analysis of possible assembly products—not reacting with the A20 antibody—by sucrose density gradient sedimentation showed very low amounts of VP protein containing material (sedimenting over the whole range of the gradient) which reacted with antibody B1 (FIG. 11B). This indicates the formation of incorrectly assembled or aggregated VP protein in rather low, hardly detectable quantities.

8.3. Analyses of Constructs by Western Blot and ELISA

A set of different constructs was analyzed for gene expression in Western Blot and in ELISA for capsid assembly (FIG. 15A):

pCI-VP2: The VP2 sequence of AAV2 was cloned into the multiple cloning site of pCI (Promega, Mannheim, Germany). The VP2 start codon ACG was changed into an ATG.

pCI-VP3: The wildtype VP3 sequence was cloned into pCI.

pCI-VP: The complete cap ORF was cloned into pCI. The start codons of VP2 and VP3 were not mutated.

pCMV-NLS-VP3: (described in example 8 and by Hoque et al. (1999a))

pCI-VP2mutACG: This is a modification of the pCI_VP2: the VP2 start-codon is destroyed and replaced by a GAG codon pCMV-VP3/2696 (described in example 2)

Results

Western Blot analysis showed similar capsid protein expression of the different constructs with the expected size of the VP proteins (FIG. 15C). The efficiency in capsid assembly however was quite different (FIG. 15B). Particle titer obtained with the construct cloned analogue to Hoque et al (pCMV-NLS-VP3) was below detection limit. That also means that the favorised constructs pCI-VP2mutACG or pCMV-VP3/2696 are more than 3 log more efficient in VP3 particle formation efficiency when compared to the Hoque construct pCMV-NLS-VP3. The construct pCI-VP2 corresponds to pCMV-VP3/2611 except for a mutation of the minor ACG start codon to an ATG in pCI-VP2 whereas the ACG codon is completely deleted in pCMV-VP3/2611. Capsid formation efficiency of the pCI-VP2 construct is strongly reduced (FIG. 15B). We did not analyze whether the particles obtained from pCI-VP2 are mainly composed of VP2, VP3 or a mixture of both proteins. FIG. 15C shows that VP3 is still expressed from this construct even though with significantly (about 10 fold) lower efficiency compared to VP2. We hypothesize that the particles obtained mainly consist of VP3. The low titer is explained by i) 10-fold reduced amounts of VP3 from pCI-VP2 compared to pCMV-VP3/2611. Furthermore, we speculate that the ATG start codon in pCI-VP2 interferes with AAP expression as the ATG probably dominates the non-canonical start codon of AAP. pCI-VP3 showed only low capsid formation efficiency as expected. Efficiency of particle assembly could partially be rescued by co-transfection of pCI-VP3 with pCI-VP2 (FIG. 15B) in a ratio of 10:1. However, the overall particle formation is still reduced by 1-2 log compared to pCI-VP2mutACG or pCMV-VP3/2696 supporting our hypothesis that the ATG start codon in the VP2 coding region of pCI-VP2 interferes with AAP expression. Particle formation from pCI-VP is much lower when compared to pCMV-VP (FIGS. 5A-5D). This is explained as follows: pCI-VP differs from pCMV-VP by lack of the splice donor site. Therefore, only one messenger RNA is transcribed from pCI-VP expressing mainly VP1, whereas two messenger RNAs are transcribed from pCMV-VP. The minor transcript mainly expresses VP1, whereas the major transcript encodes VP2 and VP3 in a ration of 1:8. Therefore, pCMV-VP expresses VP1:VP2:VP3 in the expected ratio of 1:1:8, whereas VP2 and VP3 can hardly if at all be detected with construct pCI-VP.

Conclusion

The results show that nuclear accumulation of VP3 alone is not sufficient for capsid assembly and that a heterologous N-terminal extension upstream of VP3 is not able to bring about assembly competence to VP3.

Further our favored constructs pCI-VP2mutACG or pCMV-VP3/2696 lead to more than 3 log higher VP3 particle titers when compared to the NLS-VP3 fusion construct described by Hogue et al. (1999a). These experiments also demonstrate that VP3 N-terminal fusion constructs can assemble into VLPs. Therefore I-203 is a suitable insertion site for foreign peptide sequences.

9. VP3 Capsid Assembly can be Achieved in Insect Cells 9.1. Cloning of the VP1 Mutant "Modification 4"

The construct pVL_VP1_MOD4 was generated to produce viral particles consisting essentially of the capsid protein VP3 in the absence of any Rep expression.

In detail, pUC19AV2 (described in detail in U.S. Pat. No. 6,846,665) was used as template to amplify VP1 according to standard PCR conditions in the presence of the following primers:

```
Insect_mod_4_s:
                                        (SEQ ID NO: 77)
5'-CAC CCG CGG GGA TCC GCC GCT GCC GAC GGT TAT CTA CCC GAT TGG CTC-3',
and E_VP2_rev:
                                        (SEQ ID NO: 78)
5'-CGC GAA TTC CTA TTA CAG ATT ACG AGT CAG G-3'
```

Thereby, the wildtype translation start codon ATG (coding for Methionin) of VP1 was changed into GCC (Alanin) and inactivated. The resulting EcoRI/BamHI fragment was cloned into pBSIIKS (Stratagene, La Jolla, Calif., USA). This vector was used to inactivate the translation start codon of VP2 by site directed mutagenesis according to the instructions of the QUICKCHANGE® II Site directed mutagenesis kit (Stratagene) using the following primers:

```
Insect-muta_4_s:
                                        (SEQ ID NO: 79)
5'-ACC TGT TAA GAC AGC TCC GGG AAA AAA G-3'

Insect-muta_4_as:
                                        (SEQ ID NO: 80)
5'-CTT TTT TCC CGG AGC TGT CTT AAC AGG T-3'
```

Thereby, the wildtype translation start codon ACG of VP2 was changed into ACA (both coding for Threonin). The resulting construct was digested with restriction enzymes BamHI and EcoRI and cloned into the baculo transfer vector pVL1393. As a result, the construct contained the complete AAV cap gene with mutations of the VP1 and VP2 start codons but no rep cds. (FIGS. 12A-12C)

9.2. cloning of pVL_VP2

AAV2 VP2 was amplified using the primers E_VP2_for and E_VP2_rev listed below. Thereby, the wildtype VP2 translation start codon ACG (coding for Threonine) was changed into ATG (Methionine). Primers:

```
E_VP2_for:
                                        (SEQ ID NO: 81)
5'-CAC CCG CGG GGA TCC ACT ATGGCT CCG GGA AAA AAG

AGG-3'

E_VP2_rev:
                                        (SEQ ID NO: 82)
5'-CGC GAA TTC CTA TTA CAG ATT ACG AGT CAG G-3'
```

The resulting construct was cloned into the baculo transfer vector pVL1393.

9.3. Cloning of pVL_VP3

AAV2 VP3 was amplified using the primers E_VP3_for and E_VP3_rev listed below. Primers:

```
E_VP3_for:
                                        (SEQ ID NO: 83)
5'-CAC CCG CGG GGA TCC ACT ATG GCT ACA GGC AGT GGC
GCA C-3'

E_VP2_rev:
                                        (SEQ ID NO: 84)
5'-CGC GAA TTC CTA TTA CAG ATT ACG AGT
CAG G-3'
```

The resulting construct was cloned into the baculo transfer vector pVL1393.

9.4. Analysis of Particle Production

AAV particles were produced as described in 1.1. Cell lysates were investigated by Western blot analysis for protein expression. pVL_VP1_MOD4 showed only VP3 expression, pVL_VP2 VP2 expression, while pVL_VP3 showed in addition to VP3 smaller degradation signals (FIG. 12B). Titers were obtained by an A20 ELISA. A titer of $1 \times 10^{12}$ particles/ml was observed for the modification 4 construct while VP2 pVL_VP2 showed a titer of $9 \times 10^8$ particles/ml and pVL_VP3 only a titer of $1 \times 10^8$ particles/ml (FIG. 12C).

Conclusion

This result shows that AAV VLPs can be produced in insect cells as efficiently as in mammalian cells. The data show that in insect cells the N-terminal sequence of VP3 also seems to be required and sufficient for efficient VP3 capsid assembly. Further a change of the VP2 start codon from ACG into ATG comes along with loss of efficiency in capsid assembly (FIG. 12C). We speculate that particle assembly from pVL_VP2 goes along with minor VP3 expression initiated from a VP3 ATG which was left intact in the construct.

10. Capsids Composed Essentially of VP3 Tolerate Insertions of Polypeptides

10.1. Generation of Virus-Like Particles (VLP) Containing Epitopes at Position I-587

For cloning of expression vectors encoding VLPs composed of VP3 capsid proteins containing a particular epitope sequence at position I-587, the epitope sequence was first cloned into the VP coding sequence of pUCAV2 at the site corresponding to I-587 (amino acid number relative to the VP1 protein of AAV-2) and was subsequently sub-cloned into the vector pCIVP2mutACG.

Generation of vector pUCAV2 is described in detail in U.S. Pat. No. 6,846,665. Basically, this vector contains the complete AAV2 genome (BglII fragment) derived from pAV2 (Laughlin et al., 1983) cloned into the BamHI restriction site of pUC19. pUCAV2 was further modified by introduction of a NotI and AscI restriction site allowing the insertion of epitope sequences at position I-587 of the AAV2 capsid (PCT/EP2008/004366). In addition, an FseI restriction site located between position 453 (amino acid number relative to the VP1 protein of AAV-2) and I-587 was introduced in-frame into the VP coding sequence of the vector by site directed mutagenesis.

For cloning of epitope sequences into modified pUCAV2 sense- and anti-sense oligonucleotides were designed that encode the respective epitope with an alanine or glycine adaptor sequence and contain a 5'-site extension. The 5'-site extension of the oligonucleotides was designed so that annealing of the sense and anti-sense oligonucleotides results in a dsDNA with 5'-site and 3'-site overhangs compatible with overhangs generated by NotI and AscI restriction of the modified pUCAV2. The sequences of the oligonucleotides and the respective epitope sequences are summarized in Table 4. Each of the inserted epitopes is flanked by an adaptor according to the following scheme ($X_n$ represents the epitope sequence):

Type I adaptor: $(Ala)_2$-$(Gly)_3$-$X_n$-$(Gly)_4$-Ala
Type II adaptor: $(Ala)_2$-$(Gly)_4$-$X_n$-$(Gly)_4$-Ala
Type III adaptor: $(Ala)_3$-$(Gly)_5$-$X_n$-$(Gly)_5$-$(Ala)_2$
Type IV adaptor: $(Ala)_5$-$X_n$-$(Ala)_5$ To anneal the oligonucleotides 50.0 µg of the sense oligonucleotide and 50.0 µg of the anti-sense oligonucleotide were mixed in a total volume of 200 µl 1×PCR-Buffer (Qiagen) and incubated for 3 min at 95° C. in a thermomixer. After 3 min at 95° C. the thermomixer was switched off and the tubes were left in the incubator for an additional 2 h to allow annealing of the oligonucleotides during the cooling down of the incubator. To clone the annealed oligonucleotides into pUCAV2 at I-587 the vector was linearized by restriction with NotI and AscI and the cloning reaction was performed using the Rapid DNA Ligation Kit (Roche). Briefly, the annealed oligonucleotides were diluted 10-fold in 1×DNA Dilution Buffer and incubated for 5 min at 50° C. 100 ng of the annealed oligonucleotides and 50 ng of the NotI/AscI linearized vector pUCAV2 were used in the ligation reaction, which was performed according to the instructions of the manufacturer of the Rapid DNA Ligation Kit (Roche). E. coli XL1 blue or DH5a were transformed with an aliquot of the ligation reaction and plated on LB-Amp agar plates. Plasmids were prepared according to standard procedures and were analyzed by sequencing.

For generation of empty VLPs composed of VP3 proteins containing an epitope sequence at I-587 the BsiWI/XcmI restriction fragment of pUCAV2 containing the epitope at I-587 was sub-cloned into the vector pCIVP2mutACG according to standard procedures. The vector pCIVP2mutACG contains the overlapping AAV2 VP2 and VP3 coding sequences cloned into the XhoI/NotI site of pCI (Promega). In pCIVP2mutACG the ACG start-codon of VP2 is destroyed and replaced by a GAG codon. Substitution was performed by PCR amplification of the AAV2 VP2 and VP3 coding sequences using VP2 specific primers and the plasmid pCIVP2 as template (the vector pCIVP2 contains the wildtype VP2 and VP3 coding sequence cloned into the polylinker of pCI). The forward primer used for PCR anneals to the 5' site of the VP2 coding sequence and contains the substitution of the VP2 ACG start codon by a GAG codon. In addition, the forward primer contains an XhoI recognition sequence at the 5'-site. The reverse primer annealed to the 3' end of the VP2/VP3 coding sequence and contained a NotI recognition sequence at its 5'-site. The resulting PCR product was cloned into the XhoI/NotI site of pCI.

The resulting vectors were used for production of VLPs by transfection of 293-T cells. Cells ($5 \times 10^5$/dish) were seeded in 6 cm dishes 24 h prior to transfection. 293-T cells were transfected by calcium phosphate precipitation as described in US 2004/0053410. Subsequently, 293-T cells were lysed in the medium by three rounds of freeze (−80° C.) and thaw (37° C.) cycles. The lysate (3 ml total volume) was cleared by centrifugation and the VLP capsid titer was determined using a commercially available ELISA (AAV Titration ELISA; Progen, Heidelberg, Germany). VLP titers ranged between 2.1 E+12 and 9.8 E+12 capsids/ml (Table 5). The VLP TP18 clone was directly used for large scale packaging (as described in example 1). It contained 1.2E+13 capsids/ml within the crude lysate (Table 5).

10.2. Generation of Virus-Like Particles (VLP) Containing Epitopes at Position I-587 and I-453 of the Capsid For cloning of expression vectors encoding VLPs composed of VP3 capsid proteins containing epitope sequences at position I-453 and I-587 (amino acid number relative to the VP1 protein of AAV-2), the first epitope sequence was cloned into pCIVP2mutACG at the site corresponding to I-587 as described above.

The second epitope sequence was initially cloned into the NotI/AscI restriction site of the vector pCIVP2-I453-NotI-AscI (described in: WO 2008/145400). Briefly, the vector pCI-VP2-I453-Not-AscI was created by PCR amplification of the AAV2 VP2 gene and cloning of the respective PCR product into the XhoI/NotI site of vector pCI (Promega). The resulting vector pCIVP2 was modified by destruction of the NotI restriction site of the cloning site by site-directed mutagenesis. The vector was further modified by introduction of a novel singular NotI and AscI restriction site allowing the insertion of epitope sequences at position I-453 of the AAV2 capsid. In addition, an FseI site located between I-453 and I-587 was introduced in-frame into the VP coding sequence of pCIVP2-I453-NotI-AscI by site directed mutagenesis. For cloning of epitope sequences into the NotI/AscI site of the vector sense- and anti-sense oligonucleotides were designed that encode the respective epitope with a alanine/glycine adaptor sequence and contain a 5'-site extension. The 5'-site extension of the oligonucleotides was designed so that annealing of the sense and anti-sense oligonucleotides results in a dsDNA with 5'-site and 3'-site overhangs compatible with overhangs generated by NotI and AscI restriction of pCIVP2-I453-Not-AscI. Cloning of the annealed oligonucleotides was performed as described above.

The sequences of the oligonucleotides and the respective epitope sequences are summarized in Table 6. Each of the inserted epitopes is flanked by an adaptor according to the following scheme ($X_n$ represents the epitope sequence):

$(Ala)_2$-$(Gly)_3$-$X_n$-$(Gly)_4$-Ala

For generation of bivalent VLPs displaying epitopes (murine TNFα or IL-17 epitope) at I-453 and I-587 the BsiWI/FseI fragment of pCIVP2-I453-NotI-AscI containing a given epitope inserted at I-453 was subcloned into the vector pCIVP2mutACG containing a particular epitope inserted into I-587 (described above). The resulting vector was used for production of bivalent VLPs by transfection of 293-T cells as described above (example 1.2) (6-well plate scale). Particle production was analyzed by ELISA (AAV2 Titration ELISA; Progen). Results are shown in Table 7. These data demonstrate that VLPs composed of VP3 proteins with epitope insertions at I-453 and I-587 can be produced with high capsid titers.

TABLE 4

Oligonucleotides used for cloning of epitope sequences into I-587

| Name/ Peptide Seq. | Type | sense Oligonucleotide | anti-sense Oligonucleotide | Adaptor |
|---|---|---|---|---|
| CETP TP18 DISVTGAPVIT ATYL | Rabbit CETP epitope | 5'GGCCGGCGGAGGTGACAT CAGCGTGACCGGTGCACCCG TGATCACCGCCACCTACCTG GGGGGTGGCGGTG 3' (SEQ ID NO: 85) | 5'CGCGCACCGCCACCCCC CAGGTAGGTGGCGGTGATC ACGGGTGCACCGGTCACGC TGATGTCACCTCCGCC 3' (SEQ ID NO: 86) | Type I |
| 3Depi-3 DSNPRGVSAY LSR | Human IgE epitope | 5'GGCCGGCGGAGGTGGTGA CAGCAACCCTAGAGGCGTGA GCGCCTACCTGAGCAGAGGG GGTGGCGGTG 3' (SEQ ID NO: 87) | 5'CGCGCACCGCCACCCCC TCTGCTCAGGTAGGCGCTC ACGCCTCTAGGGTTGCTGT CACCACCTCCGCC 3' (SEQ ID NO: 88) | Type II |
| Kricek VNLTWSRASG | Human IgE epitope | 5'GGCCGCAGCGGCGGTGAA CCTGACCTGGAGCAGAGCCT CCGGCGCGGCGGCGGCGG 3' (SEQ ID NO: 89) | 5'CGCGCCGCCGCCGCCGC GCCGGAGGCTCTGCTCCAG GTCAGGTTCACCGCCGCTG C3' (SEQ ID NO: 90) | Type IV |
| TNFα-V1 SSQNSSDKPV AHVVANHQVE | Murine TNFα epitope | 5'GGCCGGCGGAGGTAGCAG CCAGAACAGCAGCGACAAGC CCGTGGCCCACGTGGTGGCT AACCACCAGGTGGAGGGGGG TGGCGGTG 3' (SEQ ID NO: 91) | 5'CGCGCACCGCCACCCCC CTCCACCTGGTGGTTAGCC ACCACGTGGGCCACGGGCT TGTCGCTGCTGTTCTGGCT GCTACCTCCGCC 3' (SEQ ID NO: 92) | Type I |
| IL-17-V1 NAEGKLDHH MNSVL | Murine IL-17 epitope | 5'GGCCGGCGGAGGTAACGC CGAGGGCAAGCTTGACCACC ACATGAACAGCGTGCTGGGG GGTGGCGGTG 3' (SEQ ID NO: 93) | 5'CGCGCACCGCCACCCCC CAGCACGCTGTTCATGTGG TGGTCAAGCTTGCCCTCGG CGTTACCTCCGCC 3' (SEQ ID NO: 94) | Type I |
| IL-6-V2 LEEFLKVTLRS | Murine IL-6 epitope | 5'GGCCGGCGGAGGTCTGGA GGAATTCCTGAAGGTGACCC TGAGAAGCGGGGGTGGCGGT G 3' (SEQ ID NO: 95) | 5'CGCGCACCGCCACCCCC GCTTCTCAGGGTCACCTTC AGGAATTCCTCCAGACCTC CGCC 3' (SEQ ID NO: 96) | Type I |
| Aβ(1-9) DAEFRHDSG | Human amyloid-β epitope | 5'GGCCGCAGGCGGAGGGGG AGGCGACGCCGAGTTCAGAC ACGACAGCGGCGGCGGAGGG GGAGGCGCGG 3' (SEQ ID NO: 97) | 5'CGCGCCGCGCCTCCCCC TCCGCCGCCGCTGTCGTGT CTGAACTCGGCGTCGCCTC CCCTCCGCCTGC 3' (SEQ ID NO: 98) | Type III |

TABLE 5

Small scale production of different VLPs

| Name | Epitope at I-587 | Titer (capsids/ml) |
|---|---|---|
| VLP-TP18 | CETP TP18 DISVTGAPVITATYL (SEQ ID NO: 99) | 1.2E+13(*) |
| VLP-3Depi3 | 3Depi-3 DSNPRGVSAYLSR (SEQ ID NO: 100) | 2.1E+12 |
| VLP-Kricek | Kricek VNLTWSRASG (SEQ ID NO: 101) | 2.6E+12 |
| VLP-TNFα | TNFα-V1 SSQNSSDKPVAHVVANHQVE (SEQ ID NO: 102) | 9.8E+12 |
| VLP-IL-17 | IL-17-V1 NAEGKLDHHMNSVL (SEQ ID NO: 103) | 5.6E+12 |
| VLP-IL-6 | IL-6-V2 LEEFLKVTLRS (SEQ ID NO: 104) | 5.6E+12 |
| VLP-Aβ | Aβ(1-9) DAEFRHDSG (SEQ ID NO: 105) | 6.2E+12 |

(*)Large-scale packaging

TABLE 6

Oligonucleotides used for cloning of epitope sequences into I-453

| Name/Peptide Seq. | Type | sense Oligonucleotide | anti-sense Oligonucleotide |
|---|---|---|---|
| TNFα-V1 SSQNSSDKPVA HVVANHQVE | Murine TNFα epitope | 5'GGCCGCCGGTGGAGGCAG CAGCCAGAACAGCAGCGACA AGCCCGTGGCCCACGTGGTG GCTAACCACCAGGTGGAGGG CGGTGGAGGG 3' (SEQ ID NO: 106) | 5'CGCGCCCTCCACCGCCCTCCAC CTGGTGGTTAGCCACCACGTGGGC CACGGGCTTGTCGCTGCTGTTCTG GCTGCTGCCTCCACCGGC 3' (SEQ ID NO: 107) |
| IL-17-V1 NAEGKLDHHMN SVL | Murine IL-17 epitope | 5'GGCCGCCGGTGGAGGCAA CGCCGAGGGCAAGCTTGACC ACCACATGAACAGCGTGCTG GGCGGTGGAGGG 3' (SEQ ID NO: 108) | 5'CGCGCCCTCCACCGCCCAGCAC GCTGTTCATGTGGTGGTCAAGCTT GCCCTCGGCGTTGCCTCCACCGGC 3' (SEQ ID NO: 109) |
| IL-6-V2 LEEFLKVTLRS | Murine IL-6 epitope | 5'GGCCGCCGGTGGAGGCCT GGAGGAATTCCTGAAGGTGA CCCTGAGAAGCGGCGGTGGA GGG 3' (SEQ ID NO: 110) | 5'CGCGCCCTCCACCGCCGCTTCT CAGGGTCACCTTCAGGAATTCCTC CAGGCCTCCACCGGC 3' (SEQ ID NO: 111) |

TABLE 7

Production of VLPs carrying epitopes at I-453 and I-587

| combination | Epitope at I-453 | Epitope at I-587 | Titer (capsids/ml) |
|---|---|---|---|
| TNF-α/IL-17 | TNF α-V1 SSQNSSDKPVAHVVANHQVE (SEQ ID NO: 112) | IL-17-V1 NAEGKLDHHMNSVL (SEQ ID NO: 113) | 7.9E+12 |
| TNF-α/IL-6 | TNF α-V1 SSQNSSDKPVAHVVANHQVE (SEQ ID NO: 114) | IL-6-V2 LEEFLKVTLRS (SEQ ID NO: 115) | 8.5E+12 |
| IL-17/TNF-α | IL-17-V1 NAEGKLDHHMNSVL (SEQ ID NO: 116) | TNFα-V1 SSQNSSDKPVAHVVAN TABLE 7-continued Production of VLPs carrying epitopes at I-453 and I-587

| combination | Epitope at I-453 | Epitope at I-587 | Titer (capsids/ml) |
|---|---|---|---|
| IL-6/TNF-α | IL-6-V2 LEEFLKVTLRS (SEQ ID NO: 118) | TNFα-V1 SSQNSSDKPVAHVVANHQVE (SEQ ID NO: 119) | 1.0E+13 |
| IL-17/IL-6 | IL-17-V1 NAEGKLDHHMNSVL (SEQ ID NO: 120) | IL-6-V2 LEEFLKVTLRS (SEQ ID NO: 121) | 3.9E+12 |
| IL-6/IL-17 | IL-6-V2 LEEFLKVTLRS (SEQ ID NO: 122) | IL-17-V1 NAEGKLDHHMNSVL (SEQ ID NO: 123) | 8.9E+12 |

10.3. Conclusion

VP3 particles tolerate insertions and can therefore be used as a medicament such as a vaccine for example by insertion of B-Cell epitopes.

11. VP3 Capsid Assembly of Different AAV Serotypes 11.1. AAV1 Deletion Constructs To analyze whether these findings can be conferred to other serotypes an analogue setting of constructs for AAV1 were tested.

Following constructs were cloned:

pCI_VP2/2539_AAV1: The complete AAV1 VP2 plus 95 bp of VP1 were cloned into pCI (Promega, Mannheim, Germany). The VP2 ACG start codon was not mutated.

pCI_VP3/2539_AAV1mutACG: The complete AAV1 VP2 plus 95 bp of VP1 were cloned into pCI. The VP2 ACG start codon was mutated to ACC.

pCI_VP3/2634_AAV1mutACG: The VP1 part was deleted completely and the VP2 ACG start codon was mutated into an ACC.

Cloning

Cloning of all constructs was performed by site directed mutagenesis standard procedures using modified primers (primers used for site directed mutagenesis are listed below). pCI_VP2/2539_AAV1 was generated by inserting a NheI site 95 bp upstream of the VP2 ACG start codon and a XmaI site downstream of the VP3 stop codon. Mutations were generated within pUCrep/fs/cap_AAV1_I588 (described within PCT/EP2008/004366). The resulting plasmid was digested with NheI and XmaI. The generated fragment was cloned into the pCI-VP2 Vector (described in PCT/EP2008/004366). Primers:

AAV1 NheI VP2plus95bp:
(SEQ ID NO: 124)
5'-GAG CGT CTG CTA GCA GAT ACC TCT TTT GGG G-3'

AAV1 VP3 Xma rev:
(SEQ ID NO: 125)
5'-GAA ACG AAT CAC CCG GGT TAT TGA TTA AC-3' pCI_VP3/2539_AAV1mutACG was generated by mutating the ACG start codon to ACC within pCIVP2/2539_AAV1. Primer:

AAV1 VP2ko for:
(SEQ ID NO: 126)
5'-GGC GCT AAG ACC GCT CCT GGA AAG-3'

AAV1 VP2ko rev:
(SEQ ID NO: 127)
5'-CTT TCC AGG AGC GGT CTT AGC GCC-3' pCI_VP3/2634_AAV1mutACG was generated by deleting the 95 bp directly upstream of the VP2 ACG start codon and mutating by the same step the ACG start codon to ACC within pCIVP2_AAV1. Primer:

AAV1 VP2ko_VP1del for:
(SEQ ID NO: 128)
5'-ACG ACT CAC TAT AGG CTA GCA GGC GCT AAG ACC GCT CCT GGA AAG-3'

AAV1 VP2ko_VP1del rev:
(SEQ ID NO: 129)
5'-CTT TCC AGG AGC GGT CTT AGC GCC TGC TAG CCT ATA GTG AGT CGT-3'

Assembly of AAV1 capsids was controlled within crude lysates after transfection of 293 cells with the respective plasmid. The capsid titer was determined by an AAV1 titration ELISA (Progen, Heidelberg, Germany) according to manufacturer's manual. The assembly efficiency of the three AAV1 constructs was comparable. The construct pCI_VP3/2634_AAV1mutACG gave a titer of $10^{13}$ particles/ml, confirming the fact that capsid generation of AAV1 particles is generally more efficient than of AAV2 particles. In Western blot analyses VP2 and VP3 proteins were detectable for construct pCI_VP2/2539_AAV1 and only VP3 was detectable for pCI_VP3/2539_AAV1mutACG and pCI_VP3/2634_AAV1mutACG respectively (FIG. 13). As a control for capsid protein expression, pUCAV1 was transfected. pUCAV1 contains the complete AAV1 Cap open reading frame encoding VP1, VP2 and VP3 of AAV1. pUCAV1 is described in detail in the PCT submission PCT/EP2008/004366 (there referred to as "pUCAV1_AgeI").

11.2. Trans-Complementation of pCMV Driven AAV1 VP3 Constructs

To see whether trans-complementation experiments described in example 5 can be conferred to other serotypes analogue constructs of pCMV-VP3/2809 (AAV2) were cloned for AAV1.

11.2.1. Cloning pCMV_AAV1VP3/2829 was cloned as following: By mutagenesis a HindIII restriction site was introduced directly before the VP3 ATG start codon of plasmid pUCrep/ fs/cap_AAV1 (described within PCT/EP2008/004366) using the primers indicated below. The resulting plasmid was digested with AgeI. The Age I site was blunt ended with Klenow polymerase and the construct was subsequently digested with HindIII. The generated fragment was cloned into the HindIII/HincII-digested pBSCMV backbone. pBSCMV was generated by insertion of a 650 bp BamHI CMV promoter fragment into the BamHI site of BlueskriptII SK+ vector (Stratagene, Amsterdam, Netherlands) described by Wistuba et al, 1997. Primer Hind III mutagenesis:

Forward:
(SEQ ID NO: 130)
5'-CGC TGC TGT GGG ACC TAA GCT TAT GGC TTC AGG CGG TGG CG-3'

Reverse:
(SEQ ID NO: 131)
5'-CGC CAC CGC CTG AAG CCA TAA GCT TAG GTC CCA CAG CAG CG-3'

11.2.2. Trans-Complementation Assay

Trans-complementation was performed with the pVP2N-gfp construct from AAV2 as described in example 3. Cells were transfected with plasmid pCMV-VP3 of either AAV2 pCMV_VP3/2809) or AAV1 (pCMV_AAV1VP3/2829) with or without cotransfection of pVP2N-gfp (FIG. 14). Same molar ratios of VP3 construct and pVP2N-gfp were transfected. Protein expression was analyzed by Western blot and particle formation efficiency was measured by ELISA.

11.2.3. Result and Conclusion

Particle assembly of AAV1 analyzed by an AAV1 ELISA (Progen, Heidelberg) was rescued by trans-complementation with pVP2N-gfp derived from AAV2. Rescue efficiency cannot be indicated as we did not compare cotransfection of pCMV_AAV1VP3/2829 and pVP2N-gfp with transfection of pCIVP3/2634_AAV1mutACG (see chapter 11.1 above). Also, we did not yet clone and test an AAV1 trans-complementation plasmid pVP2N-Gfp Particle titer measured for trans-complemented AAV2 VP3 was 2.1E11. For AAV1 VP3 the titer obtained was 3.4E10 (a direct comparison of AAV1 and AAV2 titers is not possible due to the use of different ELISAs).

The results indicate that AAV1 makes use of the same mechanism for capsid assembly as AAV2 and that fragment Z and VP3 are interchangeable with different AAV serotypes.

11.3. Insertion of Polypeptides within AAV1 I588 is Tolerated

Here it was investigated whether empty AAV1 essentially VP3 particles tolerate insertions within amino-acid position 588.

For cloning of epitope sequences into pUCAV1-AgeI-I588 (described in PCT/EP2008/004366), sense- and antisense oligonucleotides were designed that encode the respective epitope with a glycine adaptor sequence. Upon hybridization of both oligonucleotides, 5'- and 3'-overhangs are generated that are compatible with overhangs generated by NotI and AscI restriction of the pUCAV1-AgeI-I588. The sequences of the oligonucleotides and the respective epitope sequences investigated are summarized in Table 4. Each of the inserted epitopes is flanked by an adaptor according to the following scheme ($X_n$ represents the epitope sequence): Ser(588)-(Ala)$_2$-(Gly)$_5$-$X_n$-(Gly)$_5$-Thr(589)

Oligo nucleotides for cloning the human IgE epitope "Kricek"

Amino acid sequence:
VNLTWSRASG
Sense oligo:
(SEQ ID NO: 132)
5'-g gcc gca gcc gca gtg aac ctg acc tgg agc aga gcc tcc ggc gcg gca gct gca gct-3' antisense oligo:
(SEQ ID NO: 133)
5'-g gcg agc tgc agc tgc cgc gcc gga ggc tct gct cca ggt cag gtt cac tgc ggc tgc-3'

Oligo nucleotides for cloning the human IgE epitope "3Depi-3"

Amino acid sequence:
DSNPRGVSAYLSR
Sense oligo:
(SEQ ID NO: 134)
5'-GGCC GGC GGT GGA GGC GGT GAC AGC AAC CCT AGA GGC GTG AGC GCC TAC CTG AGC AGA GGA GGC GGT GGA GGG-3' antisense oligo:
(SEQ ID NO: 135)
5'-CGCG CCC TCC ACC GCC TCC TCT GCT CAG GTA GGC GCT CAC GCC TCT AGG GTT GCT GTC ACC GCC TCC ACC GCC-3'

The precise cloning procedure used corresponds to the protocol used for insertion of epitopes into AAV2 1587 described in example 10.

For generation of empty AAV1 VLPs composed of essentially VP3 proteins containing an epitope sequence at I-588 the BsiWI/SphI restriction fragment of pUCAV1-AgeI-I588 carrying the epitope at I-588 was sub-cloned into the vector pCIVP3/2634 AAV1mutACG (described in example 11.1) according to standard procedures.

The resulting vectors were used for production of AAV1 VLPs by transfection of 293-T cells as described above (example 1.2.)

Titers were determined by a commercial AAV1 ELISA (Progen, Heidelberg, Germany). High titers of 3.6E13/ml (Kricek) and 9.2E13/ml (3Depi-3) were obtained, indicating that insertions within AAV1 588 (being homologous to AAV2 587) are well tolerated and that AAV1 VP3 particles can be used as vaccine carrier.

12. ORF2 Comprises Fragment Z and Encodes AAP.

Detailed sequence analysis revealed that fragment Z encodes a significant part of the new "assembly activating protein" (AAP). FIG. 16 gives an overview and FIG. 17 shows in more detail the position of ORF2 and the encoded protein AAP in relation to the cap gene and the position of the translation start codons of the Cap proteins VP1, VP2 and VP3, as well as the location of fragment Z and EcoNI and BsiWI restriction sites. The three Cap proteins VP1, VP2 and VP3 are translated from the same one ORF of the cap gene (also named the first ORF, ORF1), whereas AAP is translated from a different reading frame (named the second ORF, ORF2). For VP1, VP2 and VP3 numbers of the well-defined translation start points are given, whereas for AAP it is not definitely known.

In FIG. 17 the sequence of ORF2 (627 nucleotides, SEQ ID NO: 23) and the respective AAP protein sequence (208 amino acids, SEQ ID NO: 1) is given for AAV2 as extracted from NCBI entrée number NC_001401.

The sequences of the respective open reading frames and proteins of some other parvoviruses were extracted from the capsid gene sequences available in the NCBI database and given in detail in SEQ ID Nos 2-44 as listed in table 8.

TABLE 8

NCBI entrée numbers and numbers of corresponding SEQ IDs of AAP encoding nucleotide and protein sequences from different parvoviruses.

| parvovirus | No. of nt entrée at NCBI | respective ORF2 | Length of ORF2/nt | encoded protein AAP | Length of AAP/AA |
|---|---|---|---|---|---|
| AAV2 | NC_001401 | SEQ ID NO: 23 | 627 | SEQ ID NO: 1 | 208 |
| AAV1 | NC_002077 | SEQ ID NO: 24 | 678 | SEQ ID NO: 2 | 225 |
| AAV3b | AF028705 | SEQ ID NO: 25 | 627 | SEQ ID NO: 3 | 208 |
| AAV4 | NC_001829 | SEQ ID NO: 26 | 597 | SEQ ID NO: 4 | 198 |
| AAV5 | NC_006152 | SEQ ID NO: 27 | 681 | SEQ ID NO: 5 | 226 |
| AAV6 | AF028704 | SEQ ID NO: 28 | 678 | SEQ ID NO: 6 | 225 |
| AAV7 | NC_006260 | SEQ ID NO: 29 | 681 | SEQ ID NO: 7 | 226 |
| AAV8 | NC_006261 | SEQ ID NO: 30 | 684 | SEQ ID NO: 8 | 227 |
| AAV9 | AY530579 | SEQ ID NO: 31 | 681 | SEQ ID NO: 9 | 226 |
| AAV10 | AY631965 | SEQ ID NO: 32 | 606 | SEQ ID NO: 10 | 201 |
| AAV11 | AY631966 | SEQ ID NO: 33 | 594 | SEQ ID NO: 11 | 197 |
| AAV12 | DQ813647 | SEQ ID NO: 34 | 621 | SEQ ID NO: 12 | 206 |
| b-AAV (bovine) | NC_005889 | SEQ ID NO: 35 | 600 | SEQ ID NO: 13 | 199 |
| Avian AAV ATCC VR-865 | AY186198 | SEQ ID NO: 36 | 789 | SEQ ID NO: 14 | 262 |
| Avian AAV strain DA-1 | AY629583 | SEQ ID NO: 142 | 723 | SEQ ID NO: 143 | 240 |
| AAV13 | EU285562 | SEQ ID NO: 37 | 627 | SEQ ID NO: 15 | 208 |
| Mouse AAV1 | DQ100362 | SEQ ID NO: 38 | 534 | SEQ ID NO: 16 | 177 |
| Avian AAV strain DA-1 | AY629583 | SEQ ID NO: 39 | 723 | SEQ ID NO: 17 | 240 |
| Caprine AAV1 isolate AAV-Go. 1 | AY724675 | SEQ ID NO: 40 | 581 | SEQ ID NO: 18 | 226 |
| Rat AAV1 | DQ100363 | SEQ ID NO: 41 | 756 | SEQ ID NO: 19 | 251 |
| Goose parvovirus strain DB3 | EU088102 | SEQ ID NO: 42 | 639 | SEQ ID NO: 20 | 212 |
| Duck parvovirus strain 90-0219 | AY382892 | SEQ ID NO: 43 | 693 | SEQ ID NO: 21 | 230 |
| Snake parvovirus 1 | AY349010 | SEQ ID NO: 44 | 600 | SEQ ID NO: 22 | 199 |

For sequence comparison an alignment of the predicted AAP protein sequences derived from ORF2 of the cap gene of some parvoviruses is given in FIGS. 27A and 27B.

In construct pVP2N-gfp the EcoNI/BsiWI fragment from pTAV2.0 was inserted downstream of a CMV promoter and upstream of the GFP cds of vector pEGFP-N1 (example 3.1/FIG. 6A and example 13/FIG. 19A). Since the BsiWI site is located about 90 nucleotides upstream of the 3' end of ORF2, the vector pVP2N-gfp encodes C-terminally truncated AAP (named AAPtru) that is as active in trans-complementation as AAP expressed from full-length ORF2 (see e.g. FIGS. 21A-21C).

13. Codon Modification Confirms that Expression of Functional Protein from ORF2 is Necessary for Trans-Complementation To investigate the nature of the trans-complementing activity of ORF2, the sequence between the EcoNI/BsiWI restriction fragment was codon modified (cm).

The first mutant DNA sequence was named ORF1 cm. The DNA sequence of the mutant was altered in such a way that the first reading frame coding for the capsid protein remained intact whereas the second reading frame coding for AAP was changed. As a result the sequence encodes wildtype capsid protein but no functionally active AAP any more. Identity of the DNA sequence of pVP2N-gfp versus pVP2N/ORF1 cm-gfp is 71% while protein identity in the first reading frame is 100%.

The second mutant DNA sequence was named ORF2 cm and altered in the first reading frame meaning that it did not code for a functionally active capsid protein any more but functionally intact AAP could be expressed. Identity of the DNA sequence of pVP2N-gfp versus pVP2N/ORF2 cm-gfp is 79% while protein identity in the second reading frame is 100%. The sequences of ORF1 cm and ORF2 cm are given in FIGS. 18A and 18B, respectively. As already described in example 5, codon modification was performed by GENEART® (Regensburg, Germany). Codons were modified for codons preferentially used in mammalian cells.

As described in example 3.1, pVP2N-gfp was generated by inserting the EcoNI/BsiWI restriction fragment of pTAV2.0 into the multiple cloning site of pEGFP-N1. Constructs pVP2N/ORF1 cm-gfp and pVP2N/ORF2 cm-gfp were generated in the same way with the difference that the codon modified EcoNI/BsiWI fragments were inserted into the corresponding vector backbone.

Protein expression of pVP2N/ORF1 cm-gfp and pVP2N/ORF2 cm-gfp (FIG. 20A) was compared with that of unmodified pVP2N-gfp (FIG. 20B) in Western blot analysis. The ability to rescue capsid formation of pCMV-VP3/2809 was tested in trans-complementation assays as described in example 3. Plasmids were cotransfected in a molar ratio of 1:1 (FIG. 20C).

Result and Conclusion

As already described in example 3 and shown in FIGS. 6A-6D, Western blot analysis using monoclonal antibody A69 confirmed expression of a capsid protein comprising the VP2 N-terminus (VP2N-gfp, FIG. 19B) in the GFP fusion construct pVP2N-gfp (FIG. 19A). Complementation of plasmid pCMV-VP3/2809 with different molar ratios of pVP2N-gfp in 293-T cells corresponding to decreasing amounts of co-transfected pVP2N-gfp showed decreasing capsid assembly upon its quantification (FIG. 19C). Determination of the number of assembled capsids also revealed that deletion mutant pCMV-VP3/2809 co-transfected with pVP2N-gfp was nearly as efficient in capsid assembly as mutant pCMV-VP3/2696, the deletion mutant that showed normal capsid formation (FIGS. 5A-5D). Assembly could be detected even at a 500-fold reduced amount of co-transfected pVP2N-gfp plasmid.

Hence it was clear, that the assembly promoting activity associated with the constructs containing cap sequences upstream of the VP3 translation start site can be provided in trans.

As already described for example 5, FIG. 8D codon-modified construct pVP2N/ORF1 cm protein expression from codon-modified constructs was even higher than protein expression from the non-modified construct pVP2N-gfp, since the codon modification was optimized for mammalian cells. VP3 levels from co-expressed pCMV-VP3/2809 were normal. However, capsid assembly was not detected when using the helper construct pVP2N/ORF1 cm (FIG. 20C). Also reduced expression of the respective protein by transfecting lower amounts of pVP2N/ORF1 cm did not support capsid formation of VP3 (data not shown).

In contrast, assembled capsid could be detected using the helper construct pVP2N/ORF2 cm (FIG. 20C). As described above, only ORF2 cm expresses functionally intact AAP, whereas in pVP2N/ORF1 cm the sequence of AAP is non-functional and this codon-modified construct encodes solely capsid protein. Accordingly, only pVP2N/ORF2 cm rescued capsid assembly in trans-complementation.

This result clearly indicates, that the trans-complementing activity of fragment Z is mediated by its encoded protein AAP in ORF2. Codon modification experiments confirmed that expression of functional capsid protein in ORF1 is not necessary for trans-complementation but expression of functional AAP in ORF2.

14. Mutation of the Predicted Translation Start Codon of AAP

The sequence of ORF2 as given in FIG. 17 was analyzed in detail to further characterize AAP mediating capsid assembly. ORF2 does not contain an ATG prior to the VP3 start codon. It has to be assumed that a non-canonical start codon is utilized which is upstream of the defined minimal 5'-end of fragment Z at nt 2765. Taken into account the sequence requirements in the local environment of a start codon i.a. as defined by Kozak (2002) we predict the fifth codon at position 2729-2731, which is CTG and encodes a leucine (underlined in FIG. 17), to be the non-canonical start codon for translation of AAP. To observe its influence on expression efficiency, the site was mutated into ATG and TTG.

Protein expression of AU1 tagged versions of ORF2, namely pORF2/CTG-AU1, pORF2/ATG-AU1 and pORF2/TTG-AU1 (FIG. 21A), was compared with that of unmodified pVP2N-gfp in Western blot analysis (FIG. 21B). The ability to rescue capsid formation of pCMV-VP3/2809 was tested in trans-complementation assays as described in example 3. Plasmids were cotransfected in a molar ratio of 1:1 (FIG. 21C).

Constructs pORF2/CTG-AU1, pORF2/ATG-AU1 and pORF2/TTG-AU1 comprise the entire ORF2 of the cap gene (AAV2 nt 2717-3340) fused to sequences coding for an AU1-tag (FIG. 21A).

For generation of constructs pORF2/CTG-AU1, pORF2/ATG-AU1 and pORF2/TTG-AU1 PCRs were performed with template pTAV2.0 and forward primer

```
                                        (SEQ ID NO: 136)
5'-GGATCGCAAGCTTATTTTGGTCAGACTGGAGACGCAGACTCAGTACC

TGACCC-3', (SEQ ID NO: 137)
5'-GGATCGCAAGCTTATTTTGGTCAGAATGGAGACGCAGACTCAG-3',
``` or

```
                                        (SEQ ID NO: 138)
5'-GGATCGCAAGCTTATTTTGGTCAGATTGGAGACGCAGACTCAG-3'
``` and reverse primer

```
                                        (SEQ ID NO: 139)
5'-GCGGTGTCTCGAGTTATATATAGCGATAGGTGTCGGGTGAGGTATCC

ATACTGTGGCACCATGAAGAC-3'.
```

The HindIII/XhoI digested amplification products were inserted into the HindIII/XhoI backbone of pBS-CMV sense, which was generated by insertion of a 560 bp BamHI human cytomegalo-virus (CMV) promoter fragment from pHCMV-Luci (kindly provided by K. Butz, Germen Cancer Research Center, Heidelberg, Germany) into the BamHI site of plasmid Bluescript II SK+(pBS, Stratagene, La Jolla, Calif., USA).

Results and Conclusion

The expression of the postulated proteins could be demonstrated using a monoclonal antibody against the AU1-tag (anti-AU1) for the constructs pORF2/CTG-AU1 and pORF2/ATG-AU1 (FIG. 21B), whereas expression from construct pORF2/TTG was below the detection level. Co-transfection of the ORF2 containing plasmids pORF2/CTG-AU1, pORF2/ATG-AU1 and pORF2/TTG-AU1 with the VP3 expression plasmid pCMV-VP3/2809 yielded capsid formation (FIG. 21C) wherein the number of assembled capsids measured per volume correlated with the amount of expressed protein estimated from the Western blot. Capsid titers obtained after transfection of pORF2/ATG-AU1 with pCMV-VP3/2809 were comparable to those obtained after co-transfection of pVP2N-gfp with pCMV-VP3/2809. In contrast, the TTG start codon encoding plasmid stimulated capsid assembly by a factor of approximately $10^3$ fold less compared to the pVP2N-gfp plasmid. A polyclonal antiserum directed against a peptide of ORF2 clearly indicated expression of AAP and detected in addition to the AU1-tagged full length AAP also the C-terminally truncated AAP (AAPtru) expressed from pVP2N-gfp (FIG. 21B).

Taken together, mutation of the putative non-canonical CTG start codon into a strong ATG start codon enhanced protein synthesis and capsid assembly whereas mutation into a codon which normally is not preferred as initiation codon for protein synthesis significantly reduces protein levels and the number of assembled capsids. This result not only corroborates our conclusion that the protein product of ORF2 promotes the capsid assembly process. The results further indicate that the non-canonical CTG start codon is likely used as a start for translation, as its mutation into TTG leads to a significant reduction of AAP expression.

15. Insertion of Stop Codons in ORF2 Confirm that Expression of Functional AAP is Necessary for Trans-Complementation Additionally, mutations were performed in the AAP encoding reading frame by introduction of stop codons into ORF2 in order to confirm that expression of functional AAP is necessary for trans-complementation.

Plasmids pVP2N/ORF2stopA-gfp, pVP2N/ORF2stopB-gfp, and pVP2N/ORF2stopC-gfp were created by site-directed mutagenesis (QUICKCHANGE® site-directed mutagenesis kit, Stratagene) of template pVP2N-gfp using two complementary PCR primers which included the desired substitutions. In pVP2N/ORF2stopA-gfp codon $tgg_{2811}$ has been mutated into tag, in pVP2N/ORF2stopB-gfp codon $c_{2831}aa$ has been mutated into taa, and in pVP2N/ORF2stopC-gfp codon $g_{2879}aa$ has been mutated into tga (FIG. 22A). Positions are according to Ruffing et al. (1994). All mutations do not disrupt ORF1. In each case the EcoNI/BsiWI fragment was then cloned into the EcoNI/BsiWI backbone of pVP2N-gfp.

Results and Conclusion

Western blot analysis confirmed that VP3 is expressed in all samples (detected by monoclonal antibody B1 in FIG. 22B). Again, Bluescript vector (pBS) did not cause capsid assembly in the trans-complementation assay (FIG. 22C). Introduction of stop codons into ORF2 of the cap gene at the three different sites (as indicated in FIG. 22A) did not influence expression of VP2N-gfp (FIG. 22B), whereas all mutants harboring stop codons in ORF2 did not show any activity in capsid assembly (FIG. 22C).

Accordingly, Cap expression from pVP2n-gfp is not sufficient for capsid assembly in the trans-complementation assay. This result clearly supports the existence of AAP expressed from a different reading frame (ORF2) overlapping with the cap gene, which provides the capsid assembly helper function.

16. Expression of Functional AAP Rescues Capsid Assembly in the Context of the AAV Genome Next we wanted to analyze whether expression of the newly discovered "assembly activating protein" AAP is necessary for capsid assembly in the context of the whole AAV genome. Therefore, construct pTAV/ORF1 cm was created by cloning the EcoNI/BsiWI fragment of pVP2N/ORF1 cm-gfp (example 13) into the EcoNI/BsiWI backbone of pTAV2.0 (example 1.2.1.). Hence, plasmid pTAV/ORF1 cm (schematically shown in FIG. 23A) encodes the known AAV2 capsid and Rep proteins but should be deficient in the synthesis of AAP, because the codons of the cap gene were modified in the second reading frame (ORF2) without changing the first one encoding the Cap proteins (ORF1).

Results and Conclusion

Indeed, the four Rep proteins (Rep40, Rep52, Rep68, and Rep78) were correctly expressed (data not shown). Western blot analysis showed that the expression pattern of the three VP proteins was slightly altered. Expression of endogenous AAP from wildtype plasmid pTAV2.0 but not from the codon modified one pTAV/ORF1 cm was directly proven using polyclonal anti-AAP serum (FIG. 23B). As expected, truncated AAP is detectable upon co-expression of pVP2N-gfp.

Capsid assembly of the two constructs was compared after co-transfection of wildtype plasmid pTAV2.0 and codon modified plasmid pTAV/ORF1 cm with empty Bluescript vector (pBS) or with pVP2N-gfp. As expected, transfection of pTAV/ORF1 cm with pBS showed no detectable capsid formation, since pTAV/ORF1 cm expresses all three capsid proteins but neither pTAV/ORF1 cm nor pBS express functionally active AAP. In contrast, transfection of pTAV/ORF1 cm with pVP2N-gfp restored capsid assembly at least partially (FIG. 23C), since C-terminally truncated but active AAP is expressed from pVP2N-gfp.

Complementation of pTAV/ORF1 cm that is deficient in expression of functional active AAP with mutant plasmids like pVP2N/ORF1 cm-gfp (as described in example 13) and pVP2N/ORF2stopA-gfp (see example 15) which both were unable to express the AAP protein (due to codon modification or introduction of a stop codon, respectively) also did not lead to capsid formation. In contrast, in addition to pVP2N-gfp functionally active AAP can be expressed from plasmids pVP2N/ORF2 cm-gfp (described in example 13), pORF2/CTG-AU1 and pORF2/ATG-AU1 (see example 14) and rescued capsid assembly in trans-complementation (FIG. 23D).

Taken together, capsid formation in the context of the complete viral genome is dependent on the expression of endogenous or complemented AAP.

17. Expression of Functional AAP is Necessary for Capsid Assembly in the Context of the AAV Genome To further prove that AAP is necessary for capsid assembly in the context of the whole AAV genome, a stop codon was introduced in ORF2 disrupting AAP amino acid sequence.

Therefore, construct pTAV/ORF2stopB was created by cloning the EcoNI/BsiWI fragment of pVP2N/ORF2stopB-gfp (for details see example 15) into the EcoNI/BsiWI backbone of pTAV2.0. (example 1.2.1). In pVP2N/ORF2stopB-gfp the caa codon starting at nucleotide 2831 was mutated into a taa stop codon. Hence, plasmid pTAV/ORF2stopB (schematically shown in FIG. 24A) encodes the known AAV2 capsid and Rep proteins but should be deficient in the synthesis of AAP, because of the inserted stop codon.

Results and Conclusion

Again, correct expression of the four Rep proteins could be detected in Western blot analysis (data not shown), as well as a slightly altered expression pattern of the three VP proteins. Expression of endogenous AAP from wildtype plasmid pTAV2.0 but not from the one containing the stop codon was directly proven using polyclonal anti-AAP serum (FIG. 24B).

Capsid assembly of the two constructs was compared after co-transfection of wildtype plasmid pTAV2.0 and mutant plasmid pTAV/ORF2stopB with empty Bluescript vector (pBS) or with pVP2N-gfp. As expected, transfection of pTAV/ORF2stopB with pBS showed no detectable capsid formation, since pTAV/ORF2stopB expresses all three capsid proteins but neither pTAV/ORF2stopB nor pBS express functionally active AAP. In contrast, transfection of pTAV/ORF2stopB with pVP2N-gfp restored capsid assembly at least partially (FIG. 24C), since C-terminally truncated but active AAP is expressed from pVP2N-gfp.

This result further confirmed that capsid formation in the context of the complete viral genome is dependent on the expression of functional AAP.

18. The "Assembly Activating Protein" AAP Targets VP Proteins to the Nucleolus.

In addition to example 8, several constructs were transfected in 293-T cells to compare the location of expressed proteins within the transfected cell and assembly efficiency.

18.1. Cloning of Constructs

Cloning of construct pCMV-NLS-VP3 is described in example 8.1. The approach for generation of pCMV-NoLS- VP3 was concordant to that of pCMV-NLS-VP3 with the difference that the complementary primer pair

```
                                          (SEQ ID NO: 140)
5'-GGAAT TCGAT ATCAA GCTTG CCATG GCACG GCAGG CCCGG

CGGAA TAGAC GGAGA CGGTG GCGGG AACGG CAGCG GATGG

CTACA GGCAG TGG-3',
```
and

```
                                          (SEQ ID NO: 141)
5'-CCACT GCCTG TAGCC ATCCG CTGCC GTTCC CGCCA CCGTC

TCCGT CTATT CCGCC GGGCC TGCCG TGCCA TGGCA AGCTT

GATAT CGAAT TCC-3'
``` was used. Accordingly, the cap gene product NoLS-VP3 contains the amino acid sequence of the nucleolar localization signal of HIV Rev MARQARRNRRRRWRERQR at the N terminus of VP3. Both constructs are schematically shown in FIG. 25A.

18.2. Analyses of Constructs by Immunofluorescence

Analogous to the experimental setup described in example 8, HeLa cells were transfected with the different constructs as indicated. Expression of capsid proteins and formation of capsids was analyzed by immunofluorescence as described above using a polyclonal VP antiserum or the monoclonal A20 antibody.

18.3. Results and Conclusion

From literature analyzing productive AAV infection (e.g. Wistuba et al., 1997) it is known that capsid assembly can first be detected in the nucleoli of infected cells. Capsid protein VP3 expressed from pCMV-VP3/2809 in HeLa cells was distributed throughout the cell nucleus and the cytoplasm and excluded from nucleoli (as shown in FIG. 11C) and no capsids were detectable in these cells upon staining with capsid specific monoclonal antibody A20. But if AAP is co-expressed by co-transfecting pVP2N-gfp, translocation of a significant part of the VP3 protein to nucleoli and the formation of capsids could be detected.

As described in example 8, we expressed the construct pCMV-NLS-VP3 and observed strong nuclear accumulation of VP3 fused to the nuclear localization signal (NLS) of SV40, which however was excluded from nucleoli and did not cause capsid assembly (FIG. 11C). Co-expression of AAP from plasmid pVP2N-gfp however again targeted a portion of NLS-VP3 proteins to the nucleoli where capsid formation was detectable.

Interestingly, AAP protein expressed from pORF2/ATG-AU1 (described in example 14) and stained with anti-AU1 antibody co-located with Fibrillarin to the nucleoli (FIG. 25C, the phase contrast image on the right confirms location of nucleoli at the site of staining).

This result suggested that AAP co-transports VP proteins to the nucleoli, which is a prerequisite for subsequent capsid assembly.

When expressing the construct pCMV-NoLS-VP3 we observed at least partially nucleolar localization of VP3 fused to the nucleolar localization signal derived from HIV REV, but surprisingly no capsid assembly could be detected (FIG. 25B). Therefore it seemed that the transfer of VP proteins to nucleoli is not sufficient for capsid formation. Again, co-expression of AAP from pVP2N-gfp promoted capsid formation, substantiating that AAP not only targets VP proteins to the nucleoli but plays an additional positive role in the assembly reaction. This example also shows that VP3 N-terminal insertions (I-203) are tolerated even if a highly positively charged 17mer NoLS-sequence seems to partially interfere with VLP titers.

19. Expression of Functional AAP is Necessary for Capsid Assembly.

In addition to the immunofluorescence images seen in example 18 we analyzed protein expression of the respective mutant constructs pCMV-NLS-VP3 and pCMV-NoLS-VP3 on Western blots. Moreover, we quantified capsid assembly activity of the respective constructs by monoclonal antibody A20 capsid ELISA.

Results and Conclusion

Western blot analysis confirmed expression of VP3 from pCMV-VP3/2809 and the slightly longer proteins NLS-VP3 and NoLS-VP3 from pCMV-NLS-VP3 and pCMV-NoLS-VP3, respectively (FIG. 26A).

As already observed in example 18, neither NLS-VP3 nor NoLS-VP3 rescue capsid formation upon cotransfection with Bluescript vector (pBS), whereas in the presence of AAP expression (from pVP2N-gfp) capsid formation was detectable (FIG. 26B).

This result confirms that AAP not only targets VP proteins to the nucleoli (which is also accomplished by the NoLS-VP3 fusion construct not leading to capsid assembly) but also plays an essential role in the assembly reaction itself.

20. Assembly of Wildtype and VP3 VLPs

To compare the morphology of virus-like particles assembled of VP1, VP2 and VP3 (VP1,2,3 VLP) with that of VLPs assembled only of VP3 (VP3 VLP) the respective samples have been investigated by electron microscopy after negative staining using 2% uranylacetate as described above.

Virus-like particles assembled of VP1, VP2 and VP3 corresponding to the wildtype capsid were produced in 293-T cells by expression of the complete cap gene. VLPs assembled only of VP3 were produced by co-transfection of pCMV-VP3/2809 and pVP2N-gfp (VP3 VLP).

Results and Conclusion

Electron microscopic images confirmed that the morphology of virus-like particles assembled of VP1, VP2 and VP3 (VP1,2,3 VLP) is comparable to that of VLPs assembled only of VP3 (VP3 VLP, FIG. 28). In both images, no staining of the interior is visible, therefore clearly confirming that all particles are empty. An image of full (DNA-containing) particles in comparison to empty particles is shown e.g. in Xie et al. (2004).

21. Trans-Complementation of AAP and VP3 Cloned from Different Serotypes

To confirm that expression of AAP from one parvovirus is capable of mediating capsid assembly of VP3 from another parvovirus, we used the respective sequences of AAV1, AAV2 and AAV5 in trans-complementation assays.

Cloning of pVP2N-gfp of AAV1 and AAV5 was performed analogous to that of AAV2 (compare 3.1) with the difference that primer pairs were selected to amplify the respective sequences for AAV1 and AAV5 as given in SEQ ID NO: 24 and SEQ ID NO: 27 respectively. For trans-complementation cells were transfected with plasmid pCMV-VP3 of either AAV2 (pCMV_VP3/2809), AAV1 (pCMV_AAV1VP3/2829) as described above or a corresponding AAV5 VP3 expression construct with or without cotransfection of pVP2N-gfp of the respective AAV serotype (FIG. 29). Same molar ratios of VP3 construct and pVP2N-gfp were transfected. Particle formation efficiency was measured by ELISA Results and Conclusion Capsid assembly of VP3 cloned from AAV1, AAV2 and AAV5, respectively, was compared after co-transfection of pVP2N-gfp cloned from AAV2 and AAV1, respectively, or Bluescript vector (pBS) (see FIG. 29). As expected, expression of VP3 in the absence of any other viral protein (pBS control) showed no detectable capsid formation, irrespective of its origin. In contrast, expression of AAP (expressed from the respective pVP2N-gfp construct) from serotype AAV1 completely restored AAV2 VP3 assembly (compared to assembly mediated by AAP from AAV2). Also vice e versa, AAP from AAV2 completely restored AAV1 VP3 assembly (compared to assembly mediated by AAP from AAV1). AAP from AAV5 was only partially able to complement AAV2 VP3 assembly and failed to complement AAV1 VP3 assembly. Further, AAV2 and AAV1 AAP failed to complement AAV5 VP3 assembly. The failure of trans-complementation with respect to AAV5 constructs may be due to the fact that AAPs in these experiments were fused to GFP leading to a short C-terminal deletion of AAP which might interfere with the complementation of more distant parvoviruses while activity is sufficient for closely related serotypes. A further likely explanation is that more distant AAV serotypes are only partially able to complement each other with respect to VP3 assembly. Whereas AAP from AAV1 and AAV2 have a 71.5% identity and 81.0% similarity (Smith-Waterman Alignment), AAV2 and AAV5 only have a 56.2% identity and 60.8% similarity. These numbers are even lower with respect to AAV1 compared to AAV5 (53.8% identity and 58.1% similarity). Accordingly, the skilled artisan will be able to select functionally active AAPs from different serotypes and/oror other functionally active variants by looking at identities/similarities of AAP.

Still, in addition to example 11 these result confirm that parvoviruses other than AAV2 encode functional AAP and make use of the same mechanism for capsid assembly. Further, AAP and VP3 are in principal interchangeable between different parvoviruses, especially between closely related viruses.

LITERATURE

ARNOLD, G. S., SASSER, A. K., STACHLER, M. D. & BARTLETT, J. S. (2006) Metabolic biotinylation provides a unique platform for the purification and targeting of multiple AAV vector serotypes. *Mol Ther*, 14, 97-106.

ASOKAN, A. & SAMULSKI, R. J. (2006) AAV does the shuffle. *Nat Biotechnol*, 24, 158-60.

BACHMANN, M. F., ROHRER, U. H., KUNDIG, T. M., BURKI, K., HENGARTNER, H. & ZINKERNAGEL, R. M. (1993) The influence of antigen organization on B cell responsiveness. *Science*, 262, 1448-51.

BECERRA, S. P., KOCZOT, F., FABISCH, P. & ROSE, J. A. (1988) Synthesis of adeno-associated virus structural proteins requires both alternative mRNA splicing and alternative initiations from a single transcript. *J Virol*, 62, 2745-54.

BECERRA, S. P., ROSE, J. A., HARDY, M., BAROUDY, B. M. & ANDERSON, C. W. (1985) Direct mapping of adeno-associated virus capsid proteins B and C: a possible ACG initiation codon. *Proc Natl Acad Sci USA*, 82, 7919-23.

CORPET, F. (1988) Multiple sequence alignment with hierarchical clustering. *Nucleic Acids Res*, 16, 10881-90.

GIROD, A., RIED, M., WOBUS, C., LAHM, H., LEIKE, K., KLEINSCHMIDT, J., DELEAGE, G. & HALLEK, M. (1999) Genetic capsid modifications allow efficient re-targeting of adeno-associated virus type 2. *Nat Med*, 5, 1438.

GRIEGER, J. C., JOHNSON, J. S., GURDA-WHITAKER, B., AGBANDJE-MCKENNA, M. & SAMULSKI, R. J. (2007) Surface-exposed adeno-associated virus Vp1-NLS capsid fusion protein rescues infectivity of noninfectious wild-type Vp2/Vp3 and Vp3-only capsids but not that of fivefold pore mutant virions. *J Virol*, 81, 7833-43.

GRIEGER, J. C. & SAMULSKI, R. J. (2005) Adeno-associated virus as a gene therapy vector: vector development, production and clinical applications. *Adv Biochem Eng Biotechnol*, 99, 119-45.

GRIFMAN, M., TREPEL, M., SPEECE, P., GILBERT, L. B., ARAP, W., PASQUALINI, R. & WEITZMAN, M. D. (2001) Incorporation of tumor-targeting peptides into recombinant adeno-associated virus capsids. *Mol Ther*, 3, 964-75.

GRIMM, D. (2002) Production methods for gene transfer vectors based on adeno-associated virus serotypes. *Methods*, 28, 146-57.

GRIMM, D., KERN, A., PAWLITA, M., FERRARI, F., SAMULSKI, R. & KLEINSCHMIDT, J. (1999) Titration of AAV-2 particles via a novel capsid ELISA: packaging of genomes can limit production of recombinant AAV-2. *Gene Ther*, 6, 1322-30.

GRIMM, D. & KLEINSCHMIDT, J. A. (1999) Progress in adeno-associated virus type 2 vector production: promises and prospects for clinical use. *Hum Gene Ther*, 10, 2445-50.

HEILBRONN, R., BURKLE, A., STEPHAN, S. & ZUR HAUSEN, H. (1990) The adeno-associated virus rep gene suppresses herpes simplex virus-induced DNA amplification. *J Virol*, 64, 3012-8.

HOQUE, M., ISHIZU, K., MATSUMOTO, A., HAN, S. I., ARISAKA, F., TAKAYAMA, M., SUZUKI, K., KATO, K., KANDA, T., WATANABE, H. & HANDA, H. (1999a) Nuclear transport of the major capsid protein is essential for adeno-associated virus capsid formation. *J Virol*, 73, 7912-5.

HOQUE, M., SHIMIZU, N., ISHIZU, K., YAJIMA, H., ARISAKA, F., SUZUKI, K., WATANABE, H. & HANDA, H. (1999b) Chimeric virus-like particle formation of adeno-associated virus. *Biochem Biophys Res Commun*, 266, 371-6.

HUTTNER, N. A., GIROD, A., PERABO, L., EDBAUER, D., KLEINSCHMIDT, J. A., BUNING, H. & HALLEK, M. (2003) Genetic modifications of the adeno-associated virus type 2 capsid reduce the affinity and the neutralizing effects of human serum antibodies. *Gene Ther*, 10, 2139-47.

KING, J. A., DUBIELZIG, R., GRIMM, D. & KLEINSCHMIDT, J. A. (2001) DNA helicase-mediated packaging of adeno-associated virus type 2 genomes into preformed capsids. *Embo J*, 20, 3282-91.

KOERBER, J. T., JANG, J. H. & SCHAFFER, D. V. (2008) DNA shuffling of adeno-associated virus yields functionally diverse viral progeny. *Mol Ther*, 16, 1703-9.

KOZAK, M. (2002) Pushing the limits of the scanning mechanism for initiation of translation. *Gene*, 299, 1-34.

KRONENBERG, S., KLEINSCHMIDT, J. A. & BOTTCHER, B. (2001) Electron cryo-microscopy and image reconstruction of adeno-associated virus type 2 empty capsids. *EMBO Rep*, 2, 997-1002.

LAUGHLIN, C. A., TRATSCHIN, J. D., COON, H. & CARTER, B. J. (1983) Cloning of infectious adeno-associated virus genomes in bacterial plasmids. *Gene*, 23, 65-73.

LI, W., ASOKAN, A., WU, Z., VAN DYKE, T., DIPRIMIO, N., JOHNSON, J. S., GOVINDASWAMY, L.,

AGBANDJE-MCKENNA, M., LEICHTLE, S., REDMOND, D. E., JR., MCCOWN, T. J., PETERMANN, K. B., SHARPLESS, N. E. & SAMULSKI, R. J. (2008) Engineering and selection of shuffled AAV genomes: a new strategy for producing targeted biological nanoparticles. *Mol Ther,* 16, 1252-60.

MAHESHRI, N., KOERBER, J. T., KASPAR, B. K. & SCHAFFER, D. V. (2006) Directed evolution of adeno-associated virus yields enhanced gene delivery vectors. *Nat Biotechnol,* 24, 198-204.

MITTEREDER, N., MARCH, K. L. & TRAPNELL, B. C. (1996) Evaluation of the concentration and bioactivity of adenovirus vectors for gene therapy. *J Virol,* 70, 7498-509.

MOSKALENKO, M., CHEN, L., VAN ROEY, M., DONAHUE, B. A., SNYDER, R. O., MCARTHUR, J. G. & PATEL, S. D. (2000) Epitope mapping of human anti-adeno-associated virus type 2 neutralizing antibodies: implications for gene therapy and virus structure. *J Virol,* 74, 1761-6.

MUZYCZKA, N. & BERNS, K. I. (2001) Parvoviridae: the viruses and their replication. IN KNIPE, T. M. & HOWLEY, P. M. (Eds.) Fields Virology. Fourth Edition ed. Philadelphia, Lippincott-Raven.

NICKLIN, S. A., BUENING, H., DISHART, K. L., DE ALWIS, M., GIROD, A., HACKER, U., THRASHER, A. J., ALI, R. R., HALLEK, M. & BAKER, A. H. (2001) Efficient and selective AAV2-mediated gene transfer directed to human vascular endothelial cells. *Mol Ther,* 4, 174-81.

NYGREN, P. A. & SKERRA, A. (2004) Binding proteins from alternative scaffolds. *J Immunol Methods,* 290, 3-28.

RABINOWITZ, J. E., XIAO, W. & SAMULSKI, R. J. (1999) Insertional mutagenesis of AAV2 capsid and the production of recombinant virus. *Virology,* 265, 274-85.

RIED, M. U., GIROD, A., LEIKE, K., BUNING, H. & HALLEK, M. (2002) Adeno-associated virus capsids displaying immunoglobulin-binding domains permit antibody-mediated vector retargeting to specific cell surface receptors. *J Virol,* 76, 4559-66.

RUFFING, M., HEID, H. & KLEINSCHMIDT, J. A. (1994) Mutations in the carboxy terminus of adeno-associated virus 2 capsid proteins affect viral infectivity: lack of an RGD integrin-binding motif. *J Gen Virol,* 75 (Pt 12), 3385-92.

RUFFING, M., ZENTGRAF, H. & KLEINSCHMIDT, J. A. (1992) Assembly of viruslike particles by recombinant structural proteins of adeno-associated virus type 2 in insect cells. *J Virol,* 66, 6922-30.

SHI, W., ARNOLD, G. S. & BARTLETT, J. S. (2001) Insertional mutagenesis of the adeno-associated virus type 2 (AAV2) capsid gene and generation of AAV2 vectors targeted to alternative cell-surface receptors. *Hum Gene Ther,* 12, 1697-711.

SHI, W. & BARTLETT, J. S. (2003) RGD inclusion in VP3 provides adeno-associated virus type 2 (AAV2)-based vectors with a heparan sulfate-independent cell entry mechanism. *Mol Ther,* 7, 515-25.

STACHLER, M. D. & BARTLETT, J. S. (2006) Mosaic vectors comprised of modified AAV1 capsid proteins for efficient vector purification and targeting to vascular endothelial cells. *Gene Ther,* 13, 926-31.

STEINBACH, S., WISTUBA, A., BOCK, T. & KLEINSCHMIDT, J. A. (1997) Assembly of adeno-associated virus type 2 capsids in vitro. *J Gen Virol,* 78 (Pt 6), 1453-62.

SZOMOLANYI-TSUDA, E., BRIEN, J. D., DORGAN, J. E., GARCEA, R. L., WOODLAND, R. T. & WELSH, R. M. (2001) Antiviral T-cell-independent type 2 antibody responses induced in vivo in the absence of T and NK cells. *Virology,* 280, 160-8.

SZOMOLANYI-TSUDA, E., BRIEN, J. D., DORGAN, J. E., WELSH, R. M. & GARCEA, R. L. (2000) The role of CD40-CD154 interaction in antiviral T cell-independent IgG responses. *J Immunol,* 164, 5877-82.

SZOMOLANYI-TSUDA, E., LE, Q. P., GARCEA, R. L. & WELSH, R. M. (1998) T-Cell-independent immunoglobulin G responses in vivo are elicited by live-virus infection but not by immunization with viral proteins or virus-like particles. *J Virol,* 72, 6665-70.

SZOMOLANYI-TSUDA, E. & WELSH, R. M. (1998) T-cell-independent antiviral antibody responses. *Curr Opin Immunol,* 10, 431-5.

WARD, P. & WALSH, C. E. (2009) Chimeric AAV Cap sequences alter gene transduction. *Virology,* 386, 237-48.

WARRINGTON, K. H., JR., GORBATYUK, O. S., HARRISON, J. K., OPIE, S. R., ZOLOTUKHIN, S. & MUZYCZKA, N. (2004) Adeno-associated virus type 2 VP2 capsid protein is nonessential and can tolerate large peptide insertions at its N terminus. *J Virol,* 78, 6595-609.

WISTUBA, A., KERN, A., WEGER, S., GRIMM, D. & KLEINSCHMIDT, J. A. (1997) Subcellular compartmentalization of adeno-associated virus type 2 assembly. *J Virol,* 71, 1341-52.

WISTUBA, A., WEGER, S., KERN, A. & KLEINSCHMIDT, J. A. (1995) Intermediates of adeno-associated virus type 2 assembly: identification of soluble complexes containing Rep and Cap proteins. *J Virol,* 69, 5311-9.

WU, P., XIAO, W., CONLON, T., HUGHES, J., AGBANDJE-MCKENNA, M., FERKOL, T., FLOTTE, T. & MUZYCZKA, N. (2000) Mutational analysis of the adeno-associated virus type 2 (AAV2) capsid gene and construction of AAV2 vectors with altered tropism. *J Virol,* 74, 8635-47.

XIE, Q., BU, W., BHATIA, S., HARE, J., SOMASUNDARAM, T., AZZI, A. & CHAPMAN, M. S. (2002) The atomic structure of adeno-associated virus (AAV-2), a vector for human gene therapy. *Proc Natl Acad Sci USA,* 99, 10405-10.

XIE, Q., HARE, J., TURNIGAN, J. & CHAPMAN, M. S. (2004) Large-scale production, purification and crystallization of wild-type adeno-associated virus-2. *J Virol Methods,* 122, 17-27.

ZINKERNAGEL, R. M. (2002) Uncertainties—discrepancies in immunology. *Immunological Reviews,* 185, 103-125.

What is claimed is:

1. A parvoviral particle assembled to at least 98% VP3,
   i) wherein the VP3 optionally comprises one or more mutation(s),
   ii) wherein the VP3 does not contain a heterologous nuclear localization signal, and
   iii) wherein the particle does not contain any Rep proteins functional for packaging of virus genomes and unspecific DNA into preformed capsids.

2. The parvoviral particle according to claim 1, wherein the capsid consists only of VP3.

3. The parvoviral particle according to claim 1, wherein the mutation(s) of VP3 is/are:
   a) one or more mutation(s) selected from the group consisting of one or more deletion(s), one or more insertion(s), one or more substitution(s), and a combination thereof;
   b) one or more silent mutation(s);
   c) one or more mutations located on the surface of a VP3 virus-like particle (VLP);
   d) one or more mutation(s) located at the N-terminus of VP3;
   e) one or more insertions at one or more positions selected from the group consisting of I-261, I-266, I-381, I-447, I-448, I-453, I-459, I-471, I-534, I-570, I-573, I-584, I-587, I-588, I-591, I-657, I-664, I-713, and I-716; or wherein two insertions are made at two positions selected from the group consisting of I-261, I-453, I-534, I-570, I-573, and I-587, wherein mutations are made into position 453 in combination with an insertion in position 587 and in combination with an additional mutation;
   f) at least one epitope heterologous to the virus, wherein the heterologous epitope is a B-cell epitope and/or wherein the heterologous epitope is inserted into I-453 and/or I-587 of AAV1, AAV2 or AAV4;
   g) wherein the VP3 is included in a fusion protein:
   h) at least one tag useful for binding to a ligand; and/or
   i) at least one further mutation.

4. A pharmaceutical composition comprising the parvoviral particle of claim 1.

5. The pharmaceutical composition of claim 4, further comprising one or more excipients.

6. The pharmaceutical composition of claim 4, wherein the pharmaceutical composition is a vaccine.

7. The pharmaceutical composition of claim 6, wherein the vaccine further comprises one or more adjuvants.

8. The parvoviral particle of claim 1, wherein the Rep proteins functional for packaging of virus genomes and unspecific DNA into preformed capsids include Rep40, Rep52, Rep68, and Rep78.

* * * * *